(12) United States Patent
La Greca et al.

(10) Patent No.: US 7,271,262 B2
(45) Date of Patent: Sep. 18, 2007

(54) PYRROLOPYRIMIDINE DERIVATIVES

(75) Inventors: Susan D. La Greca, Old Lyme, CT (US); Joel T. Arcari, Groton, CT (US); Jinshan Chen, Clinton, CT (US); Matthew A. Marx, Waterford, CT (US); Matthew D. Wessel, Ledyard, CT (US)

(73) Assignee: Pfizer Inc, New York, NY (US)

( * ) Notice: Subject to any disclaimer, the term of this patent is extended or adjusted under 35 U.S.C. 154(b) by 175 days.

(21) Appl. No.: 10/732,509

(22) Filed: Dec. 10, 2003

(65) Prior Publication Data

US 2005/0037999 A1 Feb. 17, 2005

Related U.S. Application Data

(60) Provisional application No. 60/434,568, filed on Dec. 19, 2002.

(51) Int. Cl.
C07D 487/04 (2006.01)
C07F 9/32 (2006.01)
A61P 35/00 (2006.01)

(52) U.S. Cl. ...................... 544/280; 544/244
(58) Field of Classification Search .............. 544/280, 544/244; 514/265.1, 81
See application file for complete search history.

(56) References Cited

U.S. PATENT DOCUMENTS

| 6,001,839 A | 12/1999 | Calderwood | |
|---|---|---|---|
| 6,051,577 A | 4/2000 | Altmann | |
| 2003/0207870 A1 | 11/2003 | Dumas et al. | ............ 514/227.5 |

FOREIGN PATENT DOCUMENTS

| DE | 3145287 | | 5/1983 |
|---|---|---|---|
| GB | 981458 | * | 1/1965 |
| WO | 9732879 | | 9/1997 |
| WO | 0017202 | | 3/2000 |
| WO | 0017203 | | 3/2000 |
| WO | 0172751 | | 3/2000 |
| WO | 0200651 | | 1/2002 |

OTHER PUBLICATIONS

West, Anthony R., Solid State Chemistry and its Applications, Wiley, New York, 1988, pp. 358 & 365.*
Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Burchat, A. F.; Calderwood, D. J.; Hirst, G. C.; Holman, N. J.; Johnston, D. N.; Munschauer, R.; Rafferty, P.; Tometzki, G. B., Bioorganic & Medicinal Chemistry Letters, 10(19), 2171-2174 (English) 2000.*
Newman et. al. (DDT; 2003; 8(19); 898-905).*
Renau T. E. et al., Journal of Medicinal Chemistry, vol. 39, No. 4, pp. 873-880 (1996).
Abdelhamid A. O. et al., Heterocycles, vol. 27, No. 8, pp. 1861-1866 (1988).
Steinhilber D. et al., Pharmaceutical Research, vol. 3, No. 5, pp. 271-277 (1986).
Folkers G. et al., Journal of Molecular Graphics, vol. 3, No. 4, pp. 146-150 (1985).
Mueller, C. E. et al., Journal of Medicinal Chemistry, vol. 33(10), pp. 2822-2828 (1990).
Renau, T. E. et al., Bioorganic & Medicinal Chemistry Letters, vol. 2, No. 12, pp. 1755-1760 (1992).
Taylor E. C. et al., Journal of the American Chemical Society, vol. 87(9), pp. 1995-2003 (1965); and.
Daly J. W. et al., Biochemical Pharmacology, vol. 37, No. 19, pp. 3749-3753 (1988).

* cited by examiner

*Primary Examiner*—Mark L. Berch
*Assistant Examiner*—Susanna Moore
(74) *Attorney, Agent, or Firm*—Steve T. Zelson; Sandra Kim

(57) ABSTRACT

The invention relates to compounds of the formula 1

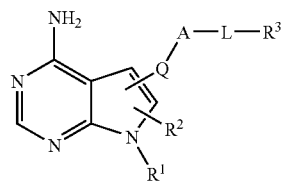

or a pharmaceutically acceptable salt, prodrug or hydrates thereof, wherein Q, A, L, $R^1$, $R^2$ and $R^3$ are as defined herein. The invention also relates to pharmaceutical compositions containing the compounds of formula 1 and to methods of treating hyperproliferative disorders in a mammal by administering the compounds of formula 1.

61 Claims, No Drawings

PYRROLOPYRIMIDINE DERIVATIVES

This application claims the benefit of U.S. Provisional Application No. 60/434,568, filed Dec. 19, 2002, which is incorporated in its entirety herein by reference.

BACKGROUND OF THE INVENTION

This invention relates to novel pyrrolopyrimidine derivatives that are useful in the treatment of hyperproliferative diseases, such as cancers, in mammals. This invention also relates to a method of using such compounds in the treatment of hyperproliferative diseases in mammals, especially humans, and to pharmaceutical compositions containing such compounds.

Compounds that are useful in the treatment of hyperproliferative diseases are referred to the following patent applications: PCT international patent application number PCT/IB97/00675 (filed Jun. 11, 1997), U.S. provisional patent application No. 60/041,846 (filed Apr. 9, 1997), U.S. provisional patent application No. 60/031,862 (filed Nov. 27, 1996), U.S. provisional patent application No. 60/028,881 (filed Oct. 17, 1996), PCT international patent application number PCT/IB97/00584 (filed May 22, 1997), U.S. patent application Ser. No. 08/653,786 (filed May 28, 1996), PCT international patent application publication number WO 96/40142 (published Dec. 19, 1996), PCT international patent application publication number WO 97/13771 (published Apr. 17, 1997), PCT international patent application publication number WO 95/23141 (published Aug. 31, 1995) and United States patent application having attorney reference number PC9882B (filed Feb. 10, 2000). Each of the foregoing United States and PCT international patent applications is incorporated herein by reference in its entirety.

It is known that a cell may become cancerous by virtue of the transformation of a portion of its DNA into an oncogene (i.e. a gene that upon activation leads to the formation of malignant tumor cells). Many oncogenes encode proteins which are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are large enzymes that span the cell membrane and possess an extracellular binding domain for growth factors such as epidermal growth factor, a transmembrane domain, and an intracellular portion that functions as a kinase to phosphorylate specific tyrosine residue in proteins and hence to influence cell proliferation. The foregoing tyrosine kinases may be classified as growth factor receptor (e.g. TIE-2, TrkA, EGFR, PDGFR, FGFR and erbB2) or non-receptor (e.g. c-src and bcr-abl) kinases. It is known that such kinases are often aberrantly expressed in common human cancers such as breast cancer, gastrointestinal cancer such as colon, rectal or stomach cancer, leukemia, and ovarian, bronchial or pancreatic cancer. Aberrant erbB2 activity has been implicated in breast, ovarian, non-small cell lung, pancreatic, gastric and colon cancers. It has also been shown that epidermal growth factor receptor (EGFR) is mutated or overexpressed in many human cancers such as brain, lung, squamous cell, bladder, gastric, breast, head and neck, oesophageal, gynecological and thyroid cancers. Thus, it is believed that inhibitors of receptor tyrosine kinases, such as the compounds of the present invention, are useful as selective inhibitors of the growth of mammalian cancer cells.

Tie-2 (TEK) is a member of a recently discovered family of endothelial cell specific receptor tyrosine kinases which is involved in critical angiogenic processes, such as vessel branching, sprouting, remodeling, maturation and stability. Tie-2 is the first mammalian receptor tyrosine kinase for which both agonist ligand(s) (e.g., Angiopoietin1 ("Ang1"), which stimulates receptor autophosphorylation and signal transduction), and antagonist ligand(s) (e.g., Angiopoietin2 ("Ang2")), have been identified. Knock-out and transgenic manipulation of the expression of Tie-2 and its ligands indicates tight spatial and temporal control of Tie-2 signaling is essential for the proper development of new vasculature. The current model suggests that stimulation of Tie-2 kinase by the Ang1 ligand is directly involved in the branching, sprouting and outgrowth of new vessels, and recruitment and interaction of periendothelial support cells important in maintaining vessel integrity and inducing quiescence. The absence of Ang1 stimulation of Tie-2 or the inhibition of Tie-2 autophosphorylation by Ang2, which is produced at high levels at sites of vascular regression, may cause a loss in vascular structure and matrix contacts resulting in endothelial cell death, especially in the absence of growth/survival stimuli.

The situation is however more complex, since at least two additional Tie-2 ligands (Ang3 and Ang4) have recently been reported, and the capacity for heterooligomerization of the various agonistic and antagonistic angiopoietins, thereby modifying their activity, has been demonstrated. Targeting Tie-2 ligand-receptor interactions as an antiangiogenic therapeutic approach is thus less favored and a kinase inhibitory strategy preferred.

The soluble extracellular domain of Tie-2 ("ExTek") can act to disrupt the establishment of tumor vasculature in a breast tumor xenograft and lung metastasis models and in tumor-cell mediated ocular neovasculatization. By adenoviral infection, the in vivo production of mg/ml levels ExTek in rodents may be achieved for 7-10 days with no adverse side effects. These results suggest that disruption of Tie-2 signaling pathways in normal healthy animals may be well tolerated. These Tie-2 inhibitory responses to ExTek may be a consequence sequestration of ligand(s) and/or generation of a nonproductive heterodimer with full-length Tie-2.

Recently, significant upregulation of Tie-2 expression has been found within the vascular synovial pannus of arthritic joints of humans, consistent with a role in the inappropriate neovascularization. This finding suggests that Tie-2 plays a role in the progression of rheumatoid arthritis. Point mutations producing constitutively activated forms of Tie-2 have been identified in association with human venous malformation disorders. Tie-2 inhibitors are, therefore, useful in treating such disorders, and in other situations of inappropriate neovascularization. The identification of effective small compounds which specifically inhibit signal transduction and cellular proliferation by modulating the activity of receptor and non-receptor tyrosine and serine/threonine kinases to regulate and modulate abnormal or inappropriate cell proliferation, differentiation, or metabolism is therefore desirable. Agents, such as the compounds of the present invention, that are capable of binding to or modulating the Tie-2 receptor may be used to treat disorders related to vasculogenesis or angiogenesis such as diabetes, diabetic retinopathy, hemangioma, glioma, melanoma, Kaposi's sarcoma and ovarian, breast, lung, pancreatic, prostate, colon and epidermoid cancer.

It is known that growth factors such as the neurotrophin family activate receptor tyrosine kinases such as trks. The neurotrophin family of growth factors includes nerve growth factor (NGF), brain derived neurotrophic factor (BDNF), neurotrophin-3 (NT-3) and neurotrophin 4/5 (NT-4/5). These basic proteins are approximately 120 amino acids in length, share approximately 50% sequence homology, and are highly conserved among mammalian species (Issackson et al., FEBS Lett. 285:260-64, 1991). NGF was the first growth factor discovered and remains the best characterized neurotrophin. NGF is required for normal development of sensory and sympathetic neurons and for normal function of these cells in adult life (Levi-Montalcini, Annu. Rev. Neurosci. 5:341-362, 1982; Yankner et al., Annu. Rev. Biochem 51:845-868,1982).

Neurotrophin binding and activation of a set of high affinity receptors (trks) is necessary and sufficient to mediate most of the biological effects of the neurotrophins. The trks are transmembrane proteins that contain an extracellular ligand binding domain, a transmembrane sequence, and a cytoplasmic tyrosine kinase domain. The trks comprise a family of structurally related proteins with preferential binding specificities for the individual neurotrophins. TrkA, which is sometimes referred to as trk, is a high-affinity receptor for NGF, but it can also mediate biological responses to NT-3 under particular conditions (Kaplan et al. Science 252:554-558, 1991; Klein et al., Cell 65, 189-197, 1991; Cordon-Cardo et al., Cell 66:173-183, 1991). TrkB binds and mediates functions of BDNF, NT-3, and NT4/5 (Klein et al. Cell 66:395-403, 1991; Squinto et al., Cell 65:885-893, 1991; Klein et al. Neuron 8:947-956, 1992). TrkC is relatively specific for NT-3 (Lamballe et al., Cell 66:967-979, 1991).

The Trk family of receptor tyrosine kinases is frequently expressed in lung, breast, pancreatic and prostate cancers. See, Endocrinol. 141: 118, 2000; Cancer Res., 59: 2395, 1999; Clin. Cancer Res. 5: 2205, 1999; and Oncogene 19: 3032, 2000. The tyrosine kinas activity of Trk is believed to promote the unregulated activation of cell proliferation machinery. Recent pre-clinical data suggests that Trk inhibitors suppress the growth of breast, pancreatic and prostate tumor xenografts. Furthermore, it is believed that Trk inhibition may be tolerated in cancer patients. It is also believed by those in the art that inhibitors of either TrkA or TrkB kinases have utility against some of the most common cancers, such as brain, melanoma, squamous cell, bladder, gastric, pancreatic, breast, head, neck, oesophageal, prostate, colorectal, lung, renal, kidney, ovarian, gynecological, and thyroid cancer. It is further believed that additional therapeutic uses of Trk inhibitors include pain, neurapthay and obesity.

SUMMARY OF THE INVENTION

The present invention relates to compounds of the formula 1

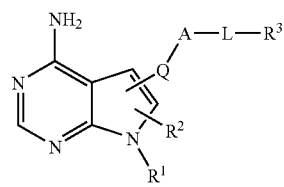

1 or a pharmaceutically acceptable salt, prodrug, solvate or hydrate thereof, wherein:

Q is selected from the group consisting of CO, $CR^{11}R^{12}$, $NR^{11}$ and $S(O)_n$, wherein n is an integer from 0 to 2;

A is a bond, $C_6$-$C_{10}$ aryl, 5 to 13 membered heteraromatic ring, $C_3$-$C_8$ alkyl, and 3 to 8 membered heteroalkyl ring and each of the foregoing A groups is optionally substituted with 1 to 5 $R^5$ groups;

L is —$(CH_2)_p$— wherein p is an integer from 0 to 5; —O—; —S—; —S(O)—; —S(O)$_2$; —N(R)—; N(C(O)OR)—; —N(C(O)R)—; —N(SO$_2$R); —CH$_2$O—; —CH$_2$S—; —CH$_2$N(R)—; —C(NR)—; —CH$_2$N(C(O)R))—; —CH$_2$N(C(O)OR)—; —CH$_2$N(SO$_2$R)—; —CH(NHR)—; —CH(NHC(O)R)—; —CH(NHSO$_2$R)—; —CH(NHC(O)OR)—; —CH(OC(O)R)—; —CH(OC(O)NHR)—; —CH=CH—; —C(=NOR)—; —C(O)—; —CH(OR)—; —C(O)N(R)—; —N(R)C(O)—; —N(R)S(O)—; —N(R)S(O)$_2$—; OC(O)N(R)—; —N(R)C(O)N(R)—; —NRC(O)O—; —S(O)N(R)—; —S(O)$_2$N(R)—; —N(C(O)R)S(O)—; —N(C(O)R)S(O)$_2$—; —N(R)S(O)N(R)—; —N(R)S(O)$_2$N(R)—; —C(O)N(R)C(O)—; —S(O)N(R)C(O)—; —S(O)$_2$N(R)C(O)—; —OS(O)N(R)—; —OS(O)$_2$N(R)—; —N(R)S(O)O—; —N(R)S(O)$_2$O—; —N(R)S(O)C(O)—; —N(R)S(O)$_2$C(O)—; —SON(C(O)R)—; —SO$_2$N(C(O)R)—; —N(R)SON(R)—; —N(R)SO$_2$N(R)—; —C(O)O—; —N(R)P(OR$^X$)O—; —N(R)P(OR$^X$)—; —N(R)P(O)(OR$^X$)O—; —N(R)P(O)(OR$^X$)—; —N(C(O)R)P(OR$^X$)O—; —N(C(O)R)P(OR$^X$)—; —N(C(O)R)P(O)(OR$^X$)O—; —N(C(O)R)P(OR$^X$)—; —CH(R)S(O)—; —CH(R)S(O)$_2$—; —CH(R)N(C(O)OR$^X$)—; —CH(R)N(C(O)R)—; —CH(R)N(SO$_2$R)—; —CH(R)O—; —CH(R)S—; —CH(R)N(R)—; —CH(R)N(C(O)R))—; —CH(R)N(C(O)OR)—; —CH(R)N(SO$_2$R)—; —CH(R)C(=NOR)—; —CH(R)C(O)—; —CH(R)CH(OR)—; —CH(R)C(O)N(R)—; —CH(R)N(R)C(O)—; —CH(R)N(R)S(O)—; CH(R)N(R)S(O)$_2$; —CH(R)OC(O)N(R)—; —CH(R)N(R)C(O)N(R)—; —CH(R)N(R)C(O)O—; —CH(R)S(O)N(R)—; —CH(R)S(O)$_2$N(R)—; —CH(R)N(C(O)R)S(O)—; —CH(R)N(C(O)R)S(O)$_2$—; —CH(R)N(R)S(O)N(R)—; —CH(R)N(R)S(O)$_2$N(R)—; —CH(R)C(O)N(R)C(O)—; —CH(R)S(O)N(R)C(O)—; CH(R)S(O)$_2$N(R)C(O)—; —CH(R)OS(O)N(R)—; —CH(R)OS(O)$_2$N(R)—; CH(R)N(R)S(O)O—; —CH(R)N(R)S(O)$_2$O—; —CH(R)N(R)S(O)C(O)—; —CH(R)N(R)S(O)$_2$C(O)—; —CH(R)SON(C(O)R)—; —CH(R)S(O)$_2$N(C(O)R)—; —CH(R)N(R)SON(R)—; —CH(R)N(R)S(O)$_2$N(R)—; —CH(R)C(O)O—; —CH(R)N(R)P(OR')O—; —CH(R)N(R)P(OR$^X$)—; —CH(R)N(R)P(O)(OR$^X$)O—; —CH(R)N(R)P(O)(OR$^X$)—; —CH(R)N(C(O)R)P(OR$^X$)O—; —CH(R)N(C(O)R)P(OR$^X$)—; —CH(R)N(C(O)R)P(O)(OR$^X$)O— or —CH(R)N(C(O)R)P(OR$^X$)—, wherein each R and $R^X$ is independently selected from H, $C_1$-$C_6$ acyl, $C_1$-$C_6$ alkyl, $C_6$-aromatic group and 5 or 6 membered heteroaromatic group, wherein each of the foregoing R and $R^X$ groups are independently optionally substituted with 1-3 halo atoms, $C_1$-$C_6$ alkyl and $C_1$-$C_6$ alkoxy;

$R^1$ is H, $C_1$-$C_6$ alkyl, $C_3$-$C_8$ cycloalkyl, substituted bicycloalkyl, 5 to 8 membered cycloalkenyl, 6 to 10 membered aromatic group, 5 to 13 membered heteroaromatic group, 3 to 8 membered heterocycloalkyl group, and heterobicycloalkyl group, and each of the foregoing $R^1$ groups is optionally substituted with 1 to 5 $R^{10}$ groups;

$R^2$ is H, halo, $C_1$-$C_6$ alkyl, $C_3$-$C_8$ cycloalkyl, 6 to 10 membered aromatic group, 5 to 13 membered heteroaromatic group, 3 to 8 membered heterocycloalkyl, —$(CH_2)_{0-3}NR^6R^7$, and —$(CH_2)_{0-3}C(O)NR^6R^7$, and each of the foregoing $R^2$ groups is optionally substituted with 1 to 5 $R^5$ groups;

$R^3$ is H, $C_1$-$C_6$ alkyl, $C_3$-$C_8$ cycloalkyl, —$(CH_2)_t C_6$-$C_{10}$ aromatic group, —$(CH_2)_t$(5 to 13 membered heteroaromatic group), and 3 to 8 membered heterocycloalkyl, and each of the foregoing $R^3$ groups is optionally substituted with 1 to 5 $R^5$ groups;

each $R^5$ is independently selected from the group consisting of halo, cyano, trifluoromethoxy, trifluoromethyl, —C(O)$R^8$, —$NR^6C(O)R^7$, —C(O)$NR^6R^7$, —$NR^6R^7$, —$OR^9$, —$SO_2NR^6R^7$, —$SO_2R^6$, —$NR^6SO_2R^7$, $C_1$-$C_6$ alkyl, $C_2$-$C_6$ alkenyl, $C_2$-$C_6$ alkynyl, —$(CH_2)_t O(CH_2)_q NR^6R^7$, —$(CH_2)_t O(CH_2)_q OR^9$, —$(CH_2)_t OR^9$, —$S(O)_j(C_1$-$C_6$ alkyl), —$(CH_2)_t(C_6$-$C_{10}$ aryl), —$(CH_2)_t$(5 to 10 membered heterocyclic), —$(CH_2)_t O(CH_2)_q$ (5 to 10 membered heterocyclic), —C(O)$(CH_2)_t$(5 to 10 membered heterocyclic), —$(CH_2)_j NR^7(CH_2)_q NR^6R^7$, —$(CH_2)_j NR^7 CH_2C(O)NR^6R^7$, —$(CH_2)_j NR^7(CH_2)_q NR^9C(O)R^8$, —$(CH_2)_j NR^7(CH_2)_t O(CH_2)_q OR^9$, —$(CH_2)_j NR^7(CH_2)_q S(O)_j(C_1$-$C_6$ alkyl), —$(CH_2)_j NR^7(CH_2)_t R^6$, —$SO_2(CH_2)_t(C_6$-$C_{10}$ aryl), and —$SO_2(CH_2)_t$(5 to 10 membered heterocyclic), wherein j is an integer from 0 to 2, t is an integer from 0 to 6, q is an integer from 2 to 6, the —$(CH_2)_q$— and —$(CH_2)_t$— moieties of the foregoing $R^5$ groups optionally include a carbon-carbon double or triple bond where t is an integer from 2 to 6, and the alkyl, aryl and heterocyclic moieties of the foregoing $R^5$ groups are optionally substituted by 1 to 3 substituents independently selected from halo, cyano, trifluoromethyl, —C(O)$R^8$, —$NR^6C(O)R^7$, —C(O)$NR^6R^7$, —$(CH_2)_t NR^6R^7$, —$SO_2R^6$, —$SO_2NR^6R^7$, $C_1$-$C_6$ alkyl, —$(CH_2)_t$(5 to 10 membered heterocyclic), —$(CH_2)_t O(CH_2)_q OR^9$, and —$(CH_2)_t OR^9$, wherein t is an integer from 0 to 6 and q is an integer from 2 to 6;

each $R^6$ and $R^7$ is independently selected from H, $C_1$-$C_6$ alkyl, —$(CH_2)_t(C_6$-$C_{10}$ aryl), —$(CH_2)_t$(5 to 10 membered heterocyclic), —$(CH_2)_t O(CH_2)_q OR^9$, and —$(CH_2)_t OR^9$, wherein t is an integer from 0 to 6 and q is an integer from 2 to 6, and the alkyl, aryl and heterocyclic moieties of the foregoing $R^6$ and $R^7$ groups are optionally substituted by 1 to 3 substituents independently selected from halo, cyano, trifluoromethyl, —C(O)$R^8$, —$NR^9C(O)R^{10}$, —C(O)$NR^9R^{10}$, —$NR^9R^{10}$, $C_1$-$C_6$ alkyl, —$(CH_2)_t(C_6$-$C_{10}$ aryl), —$(CH_2)_t$(5 to 10 membered heterocyclic), —$(CH_2)_t O(CH_2)_q OR^9$, and —$(CH_2)_q OR^9$, wherein t is an integer from 0 to 6 and q is an integer from 2 to 6, with the proviso that where $R^6$ and $R^7$ are both attached to the same nitrogen, then $R^6$ and $R^7$ are not both bonded to the nitrogen directly through an oxygen;

each $R^8$ is independently selected from H, $C_1$-$C_{10}$ alky, —$(CH_2)_t(C_6$-$C_{10}$ aryl), and —$(CH_2)_t$(5 to 10 membered heterocyclic), wherein t is an integer from 0 to 6;

each $R^9$ and $R^{10}$ is independently selected from H and $C_1$-$C_6$ alkyl; and $R^{11}$ and $R^{12}$ are independently selected from the group consisting of H, $C_1$-$C_6$ alkyl, $C_3$-$C_6$ cycloalkyl, $C_1$-$C_6$ alkoxy or $R^{11}$ and $R^{12}$ taken together form a 3 to 7 membered alkyl or heteroalkyl ring.

Specific embodiments of the compounds of formula 1 include those wherein Q is selected from the group consisting of CO, $CR^{11}R^{12}$ and $NR^{11}$.

Other specific embodiments of the compounds of formula 1 include those wherein Q is selected from the group consisting of CO and $CR^{11}R^{12}$.

One preferred embodiment of the compounds of formula 1, include those wherein Q is CO.

One preferred embodiment of the compounds of formula 1, include those wherein Q is $CR^{11}R^{12}$.

One preferred embodiment of the compounds of formula 1, include those wherein Q is $NR^{11}$.

One preferred embodiment of the compounds of formula 1, include those wherein Q is $S(O)_n$.

Other specific embodiments of the compounds of formula 1 include those wherein A is $C_6$-$C_{10}$ aryl, 5 to 13 membered heteraromatic ring, $C_3$-$C_8$ alkyl, and 3 to 8 membered heteroalkyl ring and each of the foregoing A groups is optionally substituted with 1 to 5 $R^5$ groups.

Other specific embodiments of the compounds of formula 1 include those wherein A is $C_6$-$C_{10}$ aryl or 5 to 13 membered heteraromatic ring and each of the foregoing A groups is optionally substituted with 1 to 5 $R^5$ groups.

In one preferred embodiment of the present invention the compounds of formula 1 include those wherein A is $C_6$-$C_{10}$ aryl, wherein said aryl ring is optionally substituted with 1 to 5 $R^5$ groups.

In another preferred embodiment of the present invention the compounds of formula 1 include those wherein A is 5 to 13 membered heteraromatic ring, wherein said ring is optionally substituted with 1 to 5 $R^5$ groups.

Specific embodiments of the compounds of formula 1 include those wherein each $R^5$ is independently selected from the group consisting of halo, cyano, trifluoromethoxy, trifluoromethyl, —C(O)$R^8$, —$NR^6C(O)R^7$, —C(O)$NR^6R^7$, —$NR^6R^7$, —$OR^9$, $SO_2NR^6R^7$, —$SO_2R^6$, —$NR^6SO_2R^7$, $C_1$-$C_6$ alkyl, —$(CH_2)_t OR^9$, —$(CH_2)_j NR^7(CH_2)_q NR^6R^7$, —$(CH_2)_j NR^7 CH_2C(O)NR^6R^7$, —$(CH_2)_j NR^7(CH_2)_q NR^9C(O)R^8$, —$(CH_2)_j NR^7(CH_2)_t O(CH_2)_q OR^9$, —$(CH_2)_j NR^7(CH_2)_t R^6$, wherein j is an integer from 0 to 2, t is an integer from 0 to 6, q is an integer from 2 to 6, the —$(CH_2)_q$— and —$(CH_2)_t$— moieties of the foregoing $R^5$ groups optionally include a carbon-carbon double or triple bond where t is an integer from 2 to 6, and the alkyl, aryl and heterocyclic moieties of the foregoing $R^5$ groups are optionally substituted by 1 to 3 substituents independently selected from halo, cyano, trifluoromethyl, —C(O)$R^8$, —$NR^6C(O)R^7$, —C(O)$NR^6R^7$, —$(CH_2)_t NR^6R^7$, —$SO_2R^6$, —$SO_2NR^6R^7$, $C_1$-$C_6$ alkyl, —$(CH_2)_t$(5 to 10 membered heterocyclic), —$(CH_2)_t O(CH_2)_q OR^9$, and —$(CH_2)_t OR^9$, wherein t is an integer from 0 to 6 and q is an integer from 2 to 6.

Other specific embodiments of the compounds of formula 1 include those wherein each $R^5$ is independently selected from the group consisting of halo, cyano, trifluoromethoxy, trifluoromethyl, —C(O)$R^8$, —$NR^6C(O)R^7$, —C(O)$NR^6R^7$, —$NR^6R^7$, $SO_2NR^6R^7$, —$SO_2R^6$, —$NR^6SO_2R^7$, $C_1$-$C_6$ alkyl, —$(CH_2)_t OR^9$, and the alkyl moieties of the foregoing $R^5$ groups are optionally substituted by 1 to 3-substituents independently selected from halo, cyano, trifluoromethyl, —C(O)$R^8$, —$NR^6C(O)R^7$, —C(O)$NR^6R^7$, —$(CH_2)_t NR^6R^7$, —$SO_2R^6$, —$SO_2NR^6R^7$, $C_1$-$C_6$ alkyl, —$(CH_2)_t$(5 to 10 membered heterocyclic), —$(CH_2)_t O(CH_2)_q OR^9$, and —$(CH_2)_t OR^9$, wherein t is an integer from 0 to 6 and q is an integer from 2 to 6; and each $R^6$ and $R^7$ is independently selected from H, $C_1$-$C_6$ alkyl, and the alkyl, moieties of the foregoing $R^6$ and $R^7$ groups are optionally substituted by 1 to 3 substituents independently selected from halo, cyano, trifluoromethyl, —C(O)$R^8$, —$NR^9C(O)R^{10}$, —C(O)$NR^9R^{10}$, —$NR^9R^{10}$, $C_1$-$C_6$ alkyl.

Other specific embodiments of the compounds of formula 1 include those wherein each $R^5$ is independently selected from the group consisting of halo, trifluoromethoxy, trifluoromethyl, $C_1$-$C_6$ alkyl and —$(CH_2)_t OR^9$ and the alkyl moieties of the foregoing $R^5$ groups are optionally substituted by 1 to 3 substituents independently selected from halo, cyano, trifluoromethyl, —C(O)$R^8$, —$NR^6C(O)R^7$, —C(O)$NR^6R^7$, —$(CH_2)_t NR^6R^7$, —$SO_2R^6$, —$SO_2NR^6R^7$, $C_1$-$C_6$ alkyl, —$(CH_2)_t$(5 to 10 membered heterocyclic), —$(CH_2)_tO(CH_2)_qOR^9$, and —$(CH_2)_tOR^9$, wherein t is an integer from 0 to 6 and q is an integer from 2 to 6.

In one preferred specific embodiments of the compounds of formula 1 include those wherein L is —$(CH_2)_p$— wherein p is an integer from 0 to 5; —O—; —S—; —S(O)—; —S(O)$_2$; —N(R)—; N(C(O)OR)—; —N(C(O)R)—; —N(SO$_2$R); —N(R)C(O)—; —N(R)S(O)—; —N(R)S(O)$_2$—; OC(O)N(R)—; —N(R)C(O)N(R)—; —NRC(O)O—; —S(O)N(R)—; —S(O)$_2$N(R)—; —N(C(O)R)S(O)—; N(C(O)R)S(O)$_2$—; —N(R)S(O)N(R)—; —N(R)S(O)$_2$N(R)—; —C(O)N(R)C(O)—; —S(O)N(R)C(O)—; —S(O)$_2$N(R)C(O)—; —OS(O)N(R)—; —OS(O)$_2$N(R)—; —N(R)S(O)O—; —N(R)S(O)$_2$O—; —N(R)S(O)C(O)—; N(R)S(O)$_2$C(O)—; —SON(C(O)R)—; —SO$_2$N(C(O)R)—; —N(R)SON(R)—; —N(R)SO$_2$N(R)—; —C(O)O—, and wherein each R is independently selected from H, $C_1$-$C_6$ acyl, $C_1$-$C_6$ alkyl, $C_6$-aromatic group and 5 or 6 membered heteroaromatic group, and wherein each of the foregoing R groups is independently optionally substituted with 1-3 halo atoms, $C_1$-$C_6$ alkyl and $C_1$-$C_6$ alkoxy.

Other preferred specific embodiments of the compounds of formula 1 include those wherein L is —O—; —S—; —S(O)$_2$; —N(R)—; —N(C(O)R)—; —N(SO$_2$R); —N(R)C(O)—; —N(R)S(O)$_2$—; —N(R)C(O)N(R)—; —S(O)$_2$N(R)—; —N(C(O)R)S(O)$_2$; —N(R)S(O)$_2$N(R)—; —C(O)N(R)C(O)—; —S(O)$_2$N(R)C(O)—; —OS(O)$_2$NR—; —N(R)S(O)$_2$O—; N(R)S(O)$_2$C(O)—; —SO$_2$N(C(O)R)—; —N(R)SO$_2$N(R)—; —C(O)O—, and wherein each R is independently selected from H, $C_1$-$C_6$ acyl, $C_1$-$C_6$ alkyl, $C_6$-aromatic group and 5 or 6 membered heteroaromatic group, and wherein each of the foregoing R groups is independently optionally substituted with 1-3 halo atoms, $C_1$-$C_6$ alkyl and $C_1$-$C_6$ alkoxy.

Other preferred specific embodiments of the compounds of formula 1 include those wherein L is —N(SO$_2$R)— or —N(R)C(O)N(R)— and wherein each R is independently selected from H, $C_1$-$C_6$ acyl, $C_1$-$C_6$ alkyl, $C_6$-aromatic group and 5 or 6 membered heteroaromatic group, and wherein each of the foregoing R groups is independently optionally substituted with 1-3 halo atoms, $C_1$-$C_6$ alkyl and $C_1$-$C_6$ alkoxy.

Other more preferred specific embodiments of the compounds of formula 1 include those wherein L is —N(R)C(O)N(R)— and wherein each R is independently selected from the group consisting of H or $C_1$-$C_6$ alkyl.

Other more preferred specific embodiments of the compounds of formula 1 include those wherein L is —N(SO$_2$R)— and wherein each R is independently selected from the group consisting of H or $C_1$-$C_6$ alkyl.

Other more preferred specific embodiments of the compounds of formula 1 include those wherein substituent Q is attached to the pyrrolopyrimidine ring at the 5-position.

Other preferred specific embodiments of the compounds of formula 1 include those wherein $R^1$ is selected from the group consisting of H, $C_1$-$C_6$ alkyl, $C_3$-$C_8$ cycloalkyl, and 3 to 8 membered heterocycloalkyl group and each of the foregoing $R^1$ groups is optionally substituted with 1 to 5 $R^5$ groups.

Other more preferred specific embodiments of the compounds of formula 1 include those wherein $R^1$ is selected from the group consisting of H, $C_1$-$C_6$ alkyl, and $C_3$-$C_8$ cycloalkyl and each of the foregoing $R^1$ groups is optionally substituted with 1 to 5 $R^5$ groups.

Other more preferred specific embodiments of the compounds of formula 1 include those wherein $R^1$ is selected from the group consisting of $C_1$-$C_6$ alkyl and $C_3$-$C_8$ cycloalkyl and each of the foregoing $R^1$ groups is optionally substituted with 1 to 5 $R^5$ groups.

Other most preferred specific embodiments of the compounds of formula 1 include those wherein $R^5$ is $C_3$-$C_8$ cycloalkyl and said $C_3$-$C_8$ cycloalkyl group is optionally substituted with 1 to 5 $R^5$ groups.

Other preferred specific embodiments of the compounds of formula 1 include those wherein each $R^5$ is independently selected from the group consisting of halo, cyano, trifluoromethoxy, trifluoromethyl, —C(O)$R^8$, —$NR^6C(O)R^7$, —C(O)$NR^6R^7$, —$NR^6R^7$, —$OR^9$, $SO_2NR^6R^7$, —$SO_2R^6$, —$NR^6SO_2R^7$, $C_1$-$C_6$ alkyl, —$(CH_2)_tOR^9$, —$(CH_2)_jNR^7(CH_2)_qNR^6R^7$, —$(CH_2)_jNR^7CH_2C(O)NR^6R^7$, $(CH_2)_jNR^7(CH_2)_qNR^9C(O)R^8$, —$(CH_2)_jNR^7(CH_2)_tO(CH_2)_qOR^9$, —$(CH_2)_jNR^7(CH_2)_tR^6$, wherein j is an integer from 0 to 2, t is an integer from 0 to 6, q is an integer from 2 to 6, the —$(CH_2)_q$— and —$(CH_2)_t$— moieties of the foregoing $R^5$ groups optionally include a carbon-carbon double or triple bond where t is an integer from 2 to 6, and the alkyl, aryl and heterocyclic moieties of the foregoing $R^5$ groups are optionally substituted by 1 to 3 substituents independently selected from halo, cyano, trifluoromethyl, —C(O)$R^8$, —$NR^6C(O)R^7$, —C(O)$NR^6R^7$, —$(CH_2)_tNR^6R^7$, —$SO_2RO$, —$SO_2NR^6R^7$, $C_1$-$C_6$ alkyl, —$(CH_2)_t$(5 to 10 membered heterocyclic), —$(CH_2)_tO(CH_2)_qOR^9$, and —$(CH_2)_tOR^9$, wherein t is an integer from 0 to 6 and q is an integer from 2 to 6.

Other preferred specific embodiments of the compounds of formula 1 include those wherein each $R^5$ is independently selected from the group consisting of halo, cyano, trifluoromethoxy, trifluoromethyl, —C(O)$R^8$, —$NR^6C(O)R^7$, —C(O)$NR^6R^7$, —$NR^6R^7$, $SO_2NR^6R^7$, —$SO_2R^6$, —$NR^6SO_2R^7$, $C_1$-$C_6$ alkyl, —$(CH_2)_tOR^9$, and the alkyl moieties of the foregoing $R^5$ groups are optionally substituted by 1 to 3 substituents independently selected from halo, cyano, trifluoromethyl, —C(O)$R^8$, —$NR^6C(O)R^7$, —C(O)$NR^6R^7$, —$(CH_2)_tNR^6R^7$, —$SO_2R^6$, —$SO_2NR^6R^7$, $C_1$-$C_6$ alkyl, —$(CH_2)_t$(5 to 10 membered heterocyclic), —$(CH_2)_tO(CH_2)_qOR^9$, and —$(CH_2)_tOR^9$, wherein t is an integer from 0 to 6 and q is an integer from 2 to 6; and each $R^6$ and $R^7$ is independently selected from H, $C_1$-$C_6$ alkyl, and the alkyl, moieties of the foregoing $R^6$ and $R^7$ groups are optionally substituted by 1 to 3 substituents independently selected from halo, cyano, trifluoromethyl, —C(O)$R^8$, —$NR^9C(O)R^{10}$, —C(O)$NR^9R^{10}$, —$NR^9R^{10}$, $C_1$-$C_6$ alkyl.

Other preferred specific embodiments of the compounds of formula 1 include those wherein each $R^5$ is independently selected from the group consisting of halo, trifluoromethoxy, trifluoromethyl, $C_1$-$C_6$ alkyl and —$(CH_2)_tOR^9$ and the alkyl moieties of the foregoing $R^5$ groups are optionally substituted by 1 to 3 substituents independently selected from halo, cyano, trifluoromethyl, —C(O)$R^8$, —$NR^6C(O)R^7$, —C(O)$NR^6R^7$, —$(CH_2)_tNR^6R^7$, —$SO_2R^6$, —$SO_2NR^6R^7$, $C_1$-$C_6$ alkyl, —$(CH_2)_t$(5 to 10 membered heterocyclic), —$(CH_2)_tO(CH_2)_qOR^9$, and —$(CH_2)_tOR^9$, wherein t is an integer from 0 to 6 and q is an integer from 2 to 6.

Other preferred specific embodiments of the compounds of formula 1 include those wherein $R^2$ is H, halo, $C_1$-$C_6$ alkyl, $C_3$-$C_8$ cycloalkyl, —$(CH_2)_{0-3}NR^6R^7$, and —$(CH_2)_{0-3}C(O)NR^6R^7$ and each of the foregoing $R^2$ groups is optionally substituted with 1 to 5 $R^5$ groups.

Other more preferred specific embodiments of the compounds of formula 1 include those wherein $R^2$ is H, halo, and $C_1$-$C_6$ alkyl and each of the foregoing $R^2$ groups is optionally substituted with 1 to 5 $R^5$ groups;

Other most preferred specific embodiments of the compounds of formula 1 include those wherein $R^2$ substituent is attached to the pyrrolopyrimidine ring at the 6-position.

Other preferred specific embodiments of the compounds of formula 1 include those wherein $R^3$ is $C_3$-$C_8$ cycloalkyl, —$(CH_2)_tC_6$-$C_{10}$ aryl, —$(CH_2)_t$(5 to 13 membered heteroaromatic group), and 3 to 8 membered heterocycloalkyl, and each of the foregoing $R^3$ groups is optionally substituted with 1 to 5 $R^5$ groups.

Other more preferred specific embodiments of the compounds of formula 1 include those wherein $R^3$ is $C_3$-$C_8$ cycloalkyl, —$(CH_2)_tC_6$-$C_{10}$ aryl, and —$(CH_2)_t$(5 to 13 membered heteroaromatic group) and each of the foregoing $R^3$ groups is optionally substituted with 1 to 5 $R^5$ groups.

Other most preferred specific embodiments of the compounds of formula 1 include those wherein $R^3$ is —$(CH_2)_tC_6$-$C_{10}$ aryl, and —$(CH_2)_t$(5 to 13 membered heteroaromatic group) and each of the foregoing $R^3$ groups is optionally substituted with 1 to 5 $R^5$ groups.

Other more preferred specific embodiments of the compounds of formula 1 include those wherein Q is selected from the group consisting of CO, $CR^{11}R^{12}$ and $NR^{11}$; and A is $C_6$-$C_{10}$ aryl, 5 to 13 membered heteroaromatic ring, $C_3$-$C_8$ alkyl, and 3 to 8 membered heteroalkyl ring and each of the foregoing A groups is optionally substituted with 1 to 5 $R^5$ groups.

Other more preferred specific embodiments of the compounds of formula 1 include those wherein L is —$(CH_2)_p$— wherein p is an integer from 0 to 5; —O—; —S—; —S(O)—; —$S(O)_2$; —N(R)—; N(C(O)OR)—; —N(C(O)R)—; —N($SO_2$R); —N(R)C(O)—; —N(R)S(O)—; —N(R)$S(O)_2$—; OC(O)N(R)—; —N(R)C(O)N(R)—; —NRC(O)O—; —S(O)N(R)—; —$S(O)_2$N(R)—; —N(C(O)R)S(O)—; N(C(O)R)$S(O)_2$—; —N(R)S(O)N(R)—; —N(R)$S(O)_2$N(R)—; —C(O)N(R)C(O)—; —S(O)N(R)C(O)—; —$S(O)_2$N(R)C(O)—; —OS(O)N(R)—; —OS$(O)_2$N(R)—; —N(R)S(O)O—; —N(R)$S(O)_2$O—; —N(R)S(O)C(O)—N(R)$S(O)_2$C(O)—; —SON(C(O)R)—; —$SO_2$N(C(O)R)—; —N(R)SON(R)—; —N(R)$SO_2$N(R)—; —C(O)O—, and wherein each R is independently selected from H, $C_1$-$C_6$ acyl, $C_1$-$C_6$ alkyl, $C_6$-aromatic group and 5 or 6 membered heteroaromatic group, and wherein each of the foregoing R groups is independently optionally substituted with 1-3 halo atoms, $C_1$-$C_6$ alkyl and $C_1$-$C_6$ alkoxy.

Other more preferred specific embodiments of the compounds of formula 1 include those wherein $R^1$ is selected from the group consisting of H, $C_1$-$C_6$ alkyl, $C_3$-$C_8$ cycloalkyl, and 3 to 8 membered heterocycloalkyl group and each of the foregoing $R^1$ groups is optionally substituted with 1 to 5 $R^5$ groups.

Other more preferred specific embodiments of the compounds of formula 1 include those wherein $R^2$ is H, halo, $C_1$-$C_6$ alkyl, $C_3$-$C_8$ cycloalkyl, —$(CH_2)_{0-3}NR^6R^{7\prime}$ and —$(CH^2)_{0-3}C(O)NR^6R^7$ and each of the foregoing $R^2$ groups is optionally substituted with 1 to 5 $R^5$ groups.

Other preferred specific embodiments of the compounds of formula 1 include those wherein $R^3$ is $C_3$-$C_8$ cycloalkyl, —$(CH_2)_tC_6$-$C_{10}$ aryl, —$(CH_2)_t$(5 to 13 membered heteroaromatic group), and 3 to 8 membered heterocycloalkyl, and each of the foregoing $R^3$ groups is optionally substituted with 1 to 5 $R^5$ groups.

Other preferred specific embodiments of the compounds of formula 1 include those wherein each $R^5$ is independently selected from the group consisting of halo, cyano, trifluoromethoxy, trifluoromethyl, —C(O)$R^8$, —$NR^6C(O)R^7$, —C(O)$NR^6R^7$, —$NR^6R^7$, —$OR^9$, $SO_2NR^6R^7$, —$SO_2R^6$, —$NR^6SO_2R^6$, $C_1$-$C_6$ alkyl, —$(CH_2)_tOR^9$, —$(CH_2)_jNR^7(CH_2)_qNR^6R^7$, —$(CH_2)_jNR^7CH_2C(O)NR^6R^7$, —$(CH_2)_jNR^7(CH_2)_qNR^9C(O)R^8$, —$(CH_2)_jNR^7(CH_2)_tO(CH_2)_qOR^9$, —$(CH_2)_jNR^7(CH_2)_tR^6$, wherein j is an integer from 0 to 2, t is an integer from 0 to 6, q is an integer from 2 to 6, the —$(CH_2)_q$— and —$(CH_2)_t$— moieties of the foregoing $R^5$ groups optionally include a carbon-carbon double or triple bond where t is an integer from 2 to 6, and the alkyl, aryl and heterocyclic moieties of the foregoing $R^5$ groups are optionally substituted by 1 to 3 substituents independently selected from halo, cyano, trifluoromethyl, —C(O)$R^8$, —$NR^6C(O)R^7$, —C(O)$NR^6R^7$, —$(CH_2)_tNR^6R^7$, —$SO_2R^6$, —$SO_2NR^6R^7$, $C_1$-$C_6$ alkyl, —$(CH_2)_t$(5 to 10 membered heterocyclic), —$(CH_2)_tO(CH_2)_qOR^9$, and —$(CH_2)_tOR^9$, wherein t is an integer from 0 to 6 and q is an integer from 2 to 6.

Other more preferred specific embodiments of the compounds of formula 1 include those wherein Q is selected from the group consisting of CO, $CR^{11}R^{12}$ and $NR^{11}$; A is $C_6$-$C_{10}$ aryl or 5 to 13 membered heteroaromatic ring and each of the foregoing A groups is optionally substituted with 1 to 5 $R^5$ groups; L is —$(CH_2)_p$— wherein p is an integer from 0 to 5; —O—; —S—; —S(O)—; —$S(O)_2$; —N(R)—; N(C(O)OR)—; —N(C(O)R)—; —N($SO_2$R); —N(R)C(O)—; —N(R)S(O)—; —N(R)$S(O)_2$—; OC(O)N(R)—; —N(R)C(O)N(R)—; —NRC(O)O—; —S(O)N(R)—; —$S(O)_2$N(R)—; —N(C(O)R)S(O)—; N(C(O)R)$S(O)_2$—; —N(R)S(O)N(R)—; —N(R)$S(O)_2$N(R)—; —C(O)N(R)C(O)—; —S(O)N(R)C(O)—; —$S(O)_2$N(R)C(O)—; —OS(O)N(R)—; —OS$(O)_2$N(R)—; —N(R)S(O)O—; —N(R)$S(O)_2$O—; —N(R)S(O)C(O)—; N(R)$S(O)_2$C(O)—; —SON(C(O)R)—; —$SO_2$N(C(O)R)—; —N(R)SON(R)—; —N(R)$SO_2$N(R)—; —C(O)O—, and wherein each R is independently selected from H, $C_1$-$C_6$ acyl, $C_1$-$C_6$ alkyl, $C_6$-aromatic group and 5 or 6 membered heteroaromatic group, and wherein each of the foregoing R groups is independently optionally substituted with 1-3 halo atoms, $C_1$-$C_6$ alkyl and $C_1$-$C_6$ alkoxy.

Other preferred specific embodiments of the compounds of formula 1 include those wherein A is $C_6$-$C_{10}$ aryl, wherein said aryl ring is optionally substituted with 1 to 5 $R^5$ groups.

Other more preferred specific embodiments of the compounds of formula 1 include those wherein A is $C_6$-$C_8$ aryl, wherein said aryl ring is optionally substituted with 1 to 5 $R^5$ groups.

Other most preferred specific embodiments of the compounds of formula 1 include those wherein A is $C_6$-aryl, wherein said aryl ring is optionally substituted with 1 to 5 $R^5$ groups.

Other more preferred specific embodiments of the compounds of formula 1 include those wherein A is 5 to 13 membered heteroaromatic ring, wherein said ring is optionally substituted with 1 to 5 $R^5$ groups.

Other preferred specific embodiments of the compounds of formula 1 include those wherein R is selected from the group consisting of H, $C_1$-$C_6$ alkyl, $C_3$-$C_8$ cycloalkyl, and 3 to 8 membered heterocycloalkyl group and each of the foregoing $R^1$ groups is optionally substituted with 1 to 5 $R^5$ groups.

Other more preferred specific embodiments of the compounds of formula 1 include those wherein $R^2$ is H, halo, $C_1$-$C_6$ alkyl, $C_3$-$C_8$ cycloalkyl, —$(CH_2)_{0-3}NR^6R^7$, and —$(CH^2)_{0-3}C(O)NR^6R^7$ and each of the foregoing $R^2$ groups is optionally substituted with 1 to 5 $R^5$ groups.

Other more preferred specific embodiments of the compounds of formula 1 include those wherein $R^3$ is $C_3$-$C_8$ cycloalkyl, —$(CH_2)_tC_6$-$C_{10}$ aryl, —$(CH_2)_t$(5 to 13 membered heteroaromatic group), and 3 to 8 membered heterocycloalkyl, and each of the foregoing $R^3$ groups is optionally substituted with 1 to 5 $R^5$ groups.

Other most preferred specific embodiments of the compounds of formula 1 include those wherein $R^3$ is $C_3$-$C_8$ cycloalkyl, —$(CH_2)_t C_6$-$C_{10}$ aryl, —$(CH_2)_t$(5 to 13 membered heteroaromatic group), and 3 to 8 membered heterocycloalkyl, and each of the foregoing $R^3$ groups is optionally substituted with 1 to 5 $R^5$ groups.

Other preferred specific embodiments of the compounds of formula 1 include those wherein each $R^5$ is independently selected from the group consisting of halo, cyano, trifluoromethoxy, trifluoromethyl, —$C(O)R^8$, —$NR^6C(O)R^7$, —$C(O)NR^6R^7$, —$NR^6R^7$, —$OR^9$, $SO_2NR^6R^7$, —$SO_2R^6$, —$NR^6SO_2R^7$, $C_1$-$C_6$ alkyl, —$(CH_2)_t OR^9$, —$(CH_2)_j NR^7(CH_2)_q NR^6R^7$, —$(CH_2)_j NR^7 CH_2 C(O)NR^6R^7$, —$(CH_2)_j NR^7 (CH_2)_q NR^9 C(O)R^8$, —$(CH_2)_j NR^7(CH_2)_t O(CH_2)_q OR^9$, —$(CH_2)_j NR^7(CH_2)_t R^6$, wherein j is an integer from 0 to 2, t is an integer from 0 to 6, q is an integer from 2 to 6, the —$(CH_2)_q$— and —$(CH_2)_t$— moieties of the foregoing $R^5$ groups optionally include a carbon-carbon double or triple bond where t is an integer from 2 to 6, and the alkyl, aryl and heterocyclic moieties of the foregoing $R^5$ groups are optionally substituted by 1 to 3 substituents independently selected from halo, cyano, trifluoromethyl, —$C(O)R^8$, —$NR^6C(O)R^7$, —$C(O)NR^6R^7$, —$(CH_2)_t NR^6R^7$, —$SO_2R^6$, —$SO_2NR^6R^7$, $C_1$-$C_6$ alkyl, —$(CH_2)_t$(5 to 10 membered heterocyclic), —$(CH_2)_t O(CH_2)_q OR^9$, and —$(CH_2)_t OR^9$, wherein t is an integer from 0 to 6 and q is an integer from 2 to 6.

Other more preferred specific embodiments of the compounds of formula 1 include those wherein each $R^5$ is independently selected from the group consisting of halo, cyano, trifluoromethoxy, trifluoromethyl, —$C(O)R^8$, —$NR^6C(O)R^7$, —$C(O)NR^6R^7$, —$NR^6R^7$, —$OR^9$, $SO_2NR^6R^7$, —$SO_2R^6$, —$NR^6SO_2R^7$, $C_1$-$C_6$ alkyl, —$(CH_2)_t OR^9$, —$(CH_2)_j NR^7(CH_2)_q NR^6R^7$, —$(CH_2)_j NR^7 CH_2 C(O)NR^6R^7$, —$(CH_2)_j NR^7(CH_2)_q NR^9 C(O)R^8$, —$(CH_2)_j NR^7(CH_2)_t O(CH_2)_q OR^9$, —$(CH_2)_j NR^7(CH_2)_t R^6$, wherein j is an integer from 0 to 2, t is an integer from 0 to 6, q is an integer from 2 to 6, the —$(CH_2)_q$— and —$(CH_2)_t$— moieties of the foregoing $R^5$ groups optionally include a carbon-carbon double or triple bond where t is an integer from 2 to 6, and the alkyl, aryl and heterocyclic moieties of the foregoing $R^5$ groups are optionally substituted by 1 to 3 substituents independently selected from halo, cyano, trifluoromethyl, —$C(O)R^8$, —$NR^6C(O)R^7$, —$C(O)NR^6R^7$, —$(CH_2)_t NR^6R^7$, —$SO_2R^6$, —$SO_2NR^6R^7$, $C_1$-$C_6$ alkyl, —$(CH_2)_t$(5 to 10 membered heterocyclic), —$(CH_2)_t O(CH_2)_q OR^9$, and —$(CH_2)_t OR^9$, wherein t is an integer from 0 to 6 and q is an integer from 2 to 6.

Other more preferred specific embodiments of the compounds of formula 1 include those wherein Q is selected from the group consisting of CO and $CR^{11}R^{12}$; A is $C_6$-$C_{10}$ aryl or 5 to 13 membered heteroaromatic ring and each of the foregoing A groups is optionally substituted with 1 to 5 $R^5$ groups; L is —$N(SO_2R)$— or —$N(R)C(O)N(R)$— and wherein each R is independently selected from H, $C_1$-$C_6$ acyl, $C_1$-$C_6$ alkyl, $C_6$-aromatic group and 5 or 6 membered heteroaromatic group, and wherein each of the foregoing R groups is independently optionally substituted with 1-3 halo atoms, $C_1$-$C_6$ alkyl and $C_1$-$C_6$ alkoxy, $R^1$ is selected from the group consisting of $C_1$-$C_6$ alkyl and $C_3$-$C_8$ cycloalkyl and each of the foregoing $R^1$ groups is optionally substituted with 1 to 5 $R^5$ groups; $R^2$ is H, halo, and $C_1$-$C_6$ alkyl and each of the foregoing $R^2$ groups is optionally substituted with 1 to 5 $R^5$ groups; and $R^3$ is $C_3$-$C_8$ cycloalkyl, —$(CH_2)_t C_6$-$C_{10}$ aryl, and —$(CH_2)_t$(5 to 13 membered heteroaromatic group) and each of the foregoing $R^3$ groups is optionally substituted with 1 to 5 $R^5$ groups.

Other preferred specific embodiments of the compounds of formula 1 include those wherein L is —N(R)C(O)N(R)— and wherein each R is independently selected from the group consisting of H or $C_1$-$C_6$ alkyl.

Other more preferred specific embodiments of the compounds of formula 1 include those wherein substitutent Q is attached to the pyrrolopyrimidine ring at the 5-position.

Other specific embodiments of the compounds of formula 1 include those selected from the group consisting of:

1-[3-(4-Amino-7-isopropyl-7H-pyrrolo[2,3-d]pyrimidine-5-carbonyl)-phenyl]-3-(2-chloro-phenyl)-urea;

1-[3-(4-Amino-7-isopropyl-7H-pyrrolo[2,3-d]pyrimidine-5-carbonyl)-phenyl]-3-(2-methoxy-5-methyl-phenyl)-urea;

1-[3-(4-Amino-7-isopropyl-7H-pyrrolo[2,3-d]pyrimidine-5-carbonyl)-phenyl]-3-(2-fluoro-5-methyl-phenyl)-urea;

1-[3-(4-Amino-7-isopropyl-7H-pyrrolo[2,3-d]pyrimidine-5-carbonyl)-phenyl]-3-m-tolyl-urea;

1-[3-(4-Amino-7-isopropyl-7H-pyrrolo[2,3-d]pyrimidine-5-carbonyl)-phenyl]-3-(3-ethyl-phenyl)-urea;

N-[3-(4-Amino-7-isopropyl-7H-pyrrolo[2,3-d]pyrimidine-5-carbonyl)-phenyl]-3-chloro-4-methyl-benzenesulfonamide;

N-[3-(4-Amino-7-isopropyl-7H-pyrrolo[2,3-d]pyrimidine-5-carbonyl)-phenyl]-3,5-dichloro-benzenesulfonamide;

N-[3-(4-Amino-7-isopropyl-7H-pyrrolo[2,3-d]pyrimidine-5-carbonyl)-phenyl]-2,4-dichloro-benzenesulfonamide;

1-[3-(4-Amino-7-isopropyl-7H-pyrrolo[2,3-d]pyrimidine-5-carbonyl)-phenyl]-3-(2-fluoro-phenyl)-urea;

1-[3-(4-Amino-7-isopropyl-7H-pyrrolo[2,3-d]pyrimidine-5-carbonyl)-phenyl]-3-(2,4-difluoro-phenyl)-urea;

1-[3-(4-Amino-7-isopropyl-7H-pyrrolo[2,3-d]pyrimidine-5-carbonyl)-phenyl]-3-(2,6-difluoro-phenyl)-urea;

1-[3-(4-Amino-7-isopropyl-7H-pyrrolo[2,3-d]pyrimidine-5-carbonyl)-phenyl]-3-(3,4-difluoro-phenyl)-urea;

1-[3-(4-Amino-7-isopropyl-7H-pyrrolo[2,3-d]pyrimidine-5-carbonyl)-phenyl]-3-(3-fluoro-phenyl)-urea;

1-[3-(4-Amino-7-isopropyl-7H-pyrrolo[2,3-d]pyrimidine-5-carbonyl)-phenyl]-3-(5-fluoro-2-methyl-phenyl)-urea;

1-[3-(4-Amino-7-isopropyl-7H-pyrrolo[2,3-d]pyrimidine-5-carbonyl)-phenyl]-3-(4-fluoro-phenyl)-urea;

1-[3-(4-Amino-7-isopropyl-7H-pyrrolo[2,3-d]pyrimidine-5-carbonyl)-phenyl]-3-(3-fluoro-4-methyl-phenyl)-urea;

1-[3-(4-Amino-7-isopropyl-7H-pyrrolo[2,3-d]pyrimidine-5-carbonyl)-phenyl]-3-(3,5-difluoro-phenyl)-urea;

1-[3-(4-Amino-7-isopropyl-7H-pyrrolo[2,3-d]pyrimidine-5-carbonyl)-phenyl]-3-(2,5-difluoro-phenyl)-urea;

1-[3-(4-Amino-7-isopropyl-7H-pyrrolo[2,3-d]pyrimidine-5-carbonyl)-phenyl]-3-(3-chloro-phenyl)-urea;

1-[3-(4-Amino-7-isopropyl-7H-pyrrolo[2,3-d]pyrimidine-5-carbonyl)-phenyl]-3-(4-chloro-phenyl)-urea;

1-[3-(4-Amino-7-isopropyl-7H-pyrrolo[2,3-d]pyrimidine-5-carbonyl)-phenyl]-3-p-tolyl-urea;

1-[3-(4-Amino-7-isopropyl-7H-pyrrolo[2,3-d]pyrimidine-5-carbonyl)-phenyl]-3-(2-ethyl-phenyl)-urea;

1-[3-(4-Amino-7-isopropyl-7H-pyrrolo[2,3-d]pyrimidine-5-carbonyl)-phenyl]-3-(2-isopropyl-phenyl)-urea;

1-[3-(4-Amino-7-isopropyl-7H-pyrrolo[2,3-d]pyrimidine-5-carbonyl)-phenyl]-3-(4-isopropyl-phenyl)-urea;

1-[3-(4-Amino-7-isopropyl-7H-pyrrolo[2,3-d]pyrimidine-5-carbonyl)-phenyl]-3-(4-methoxy-phenyl)-urea;
1-[3-(4-Amino-7-isopropyl-7H-pyrrolo[2,3-d]pyrimidine-5-carbonyl)-phenyl]-3-(2-methoxy-phenyl)-urea;
1-[3-(4-Amino-7-isopropyl-7H-pyrrolo[2,3-d]pyrimidine-5-carbonyl)-phenyl]-3-(2-ethoxy-phenyl)-urea;
1-[3-(4-Amino-7-isopropyl-7H-pyrrolo[2,3-d]pyrimidine-5-carbonyl)-phenyl]-3-(4-methylsulfanyl-phenyl)-urea;
1-[3-(4-Amino-7-isopropyl-7H-pyrrolo[2,3-d]pyrimidine-5-carbonyl)-phenyl]-3-(3-methylsulfanyl-phenyl)-urea;
1-[3-(4-Amino-7-isopropyl-7H-pyrrolo[2,3-d]pyrimidine-5-carbonyl)-phenyl]-3-(3-cyano-phenyl)-urea;
1-[3-(4-Amino-7-isopropyl-7H-pyrrolo[2,3-d]pyrimidine-5-carbonyl)-phenyl]-3-(3,5-dimethyl-phenyl)-urea;
1-[3-(4-Amino-7-isopropyl-7H-pyrrolo[2,3-d]pyrimidine-5-carbonyl)-phenyl]-3-(3,4-dimethyl-phenyl)-urea;
1-[3-(4-Amino-7-isopropyl-7H-pyrrolo[2,3-d]pyrimidine-5-carbonyl)-phenyl]-3-(2,5-dimethyl-phenyl)-urea;
1-[3-(4-Amino-7-isopropyl-7H-pyrrolo[2,3-d]pyrimidine-5-carbonyl)-phenyl]-3-(2,3-dimethyl-phenyl)-urea;
1-[3-(4-Amino-7-isopropyl-7H-pyrrolo[2,3-d]pyrimidine-5-carbonyl)-phenyl]-3-(2,4-dimethyl-phenyl)-urea;
1-[3-(4-Amino-7-isopropyl-7H-pyrrolo[2,3-d]pyrimidine-5-carbonyl)-phenyl]-3-thiophen-2-yl-urea;
1-[3-(4-Amino-7-isopropyl-7H-pyrrolo[2,3-d]pyrimidine-5-carbonyl)-phenyl]-3-thiophen-3-yl-urea;
1-[3-(4-Amino-7-isopropyl-7H-pyrrolo[2,3-d]pyrimidine-5-carbonyl)-phenyl]-3-cyclohexyl-urea;
1-[3-(4-Amino-7-isopropyl-7H-pyrrolo[2,3-d]pyrimidine-5-carbonyl)-phenyl]-3-o-tolyl-urea;
1-[3-(4-Amino-7-isopropyl-7H-pyrrolo[2,3-d]pyrimidine-5-carbonyl)-phenyl]-3-(4-ethyl-phenyl)-urea;
1-(3-Acetyl-phenyl)-3-[3-(4-amino-7-isopropyl-7H-pyrrolo[2,3-d]pyrimidine-5-carbonyl)-phenyl]-urea;
1-(4-Acetyl-phenyl)-3-[3-(4-amino-7-isopropyl-7H-pyrrolo[2,3-d]pyrimidine-5-carbonyl)-phenyl]-urea;
1-[3-(4-Amino-7-isopropyl-7H-pyrrolo[2,3-d]pyrimidine-5-carbonyl)-phenyl]-3-(4-dimethylamino-phenyl)-urea;
1-[3-(4-Amino-7-isopropyl-7H-pyrrolo[2,3-d]pyrimidine-5-carbonyl)-phenyl]-3-(4-ethoxy-phenyl)-urea;
1-[3-(4-Amino-7-isopropyl-7H-pyrrolo[2,3-d]pyrimidine-5-carbonyl)-phenyl]-3-(4-methoxy-2-methyl-phenyl)-urea;
4-{3-[3-(4-Amino-7-isopropyl-7H-pyrrolo[2,3-d]pyrimidine-5-carbonyl)-phenyl]-ureido}-benzoic acid methyl ester
1-[3-(4-Amino-7-isopropyl-7H-pyrrolo[2,3-d]pyrimidine-5-carbonyl)-phenyl]-3-(2-methylsulfanyl-phenyl)-urea;
1-[3-(4-Amino-7-isopropyl-7H-pyrrolo[2,3-d]pyrimidine-5-carbonyl)-phenyl]-3-(2-chloro-benzyl)-urea;
1-[3-(4-Amino-7-isopropyl-7H-pyrrolo[2,3-d]pyrimidine-5-carbonyl)-phenyl]-3-(2-chloro-5-methyl-phenyl)-urea;
1-[3-(4-Amino-7-isopropyl-7H-pyrrolo[2,3-d]pyrimidine-5-carbonyl)-phenyl]-3-(3-chloro-2-methyl-phenyl)-urea;
1-[3-(4-Amino-7-isopropyl-7H-pyrrolo[2,3-d]pyrimidine-5-carbonyl)-phenyl]-3-(2-chloro-6-methyl-phenyl)-urea;
1-[3-(4-Amino-7-isopropyl-7H-pyrrolo[2,3-d]pyrimidine-5-carbonyl)-phenyl]-3-(5-chloro-2-methyl-phenyl)-urea;
1-[3-(4-Amino-7-isopropyl-7H-pyrrolo[2,3-d]pyrimidine-5-carbonyl)-phenyl]-3-(3-chloro-4-methyl-phenyl)-urea;
1-[3-(4-Amino-7-isopropyl-7H-pyrrolo[2,3-d]pyrimidine-5-carbonyl)-phenyl]-3-(4-chloro-2-methyl-phenyl)-urea;
1-[3-(4-Amino-7-isopropyl-7H-pyrrolo[2,3-d]pyrimidine-5-carbonyl)-phenyl]-3-(3-chloro-4-fluoro-phenyl)-urea;
1-[3-(4-Amino-7-isopropyl-7H-pyrrolo[2,3-d]pyrimidine-5-carbonyl)-phenyl]-3-(4-tert-butyl-phenyl)-urea;
1-[3-(4-Amino-7-isopropyl-7H-pyrrolo[2,3-d]pyrimidine-5-carbonyl)-phenyl]-3-isopropyl-urea;
1-[3-(4-Amino-7-isopropyl-7H-pyrrolo[2,3-d]pyrimidine-5-carbonyl)-phenyl]-3-phenyl-urea;
N-[3-(4-Amino-7-isopropyl-7H-pyrrolo[2,3-d]pyrimidine-5-carbonyl)-phenyl]-2-methyl-benzenesulfonamide;
N-[3-(4-Amino-7-isopropyl-7H-pyrrolo[2,3-d]pyrimidine-5-carbonyl)-phenyl]-4-methyl-benzenesulfonamide;
N-[3-(4-Amino-7-isopropyl-7H-pyrrolo[2,3-d]pyrimidine-5-carbonyl)-phenyl]-4-fluoro-benzenesulfonamide;
2-Phenyl-ethenesulfonic acid[3-(4-amino-7-isopropyl-7H-pyrrolo[2,3-d]pyrimidine-5-carbonyl)-phenyl]-amide;
N-[3-(4-Amino-7-isopropyl-7H-pyrrolo[2,3-d]pyrimidine-5-carbonyl)-phenyl]-4-ethyl-benzenesulfonamide;
N-[3-(4-Amino-7-isopropyl-7H-pyrrolo[2,3-d]pyrimidine-5-carbonyl)-phenyl]-3-chloro-2-methyl-benzenesulfonamide;
Naphthalene-2-sulfonic acid[3-(4-amino-7-isopropyl-7H-pyrrolo[2,3-d]pyrimidine-5-carbonyl)-phenyl]-amide;
N-[3-(4-Amino-7-isopropyl-7H-pyrrolo[2,3-d]pyrimidine-5-carbonyl)-phenyl]-4-tert-butyl-benzenesulfonamide;
N-[3-(4-Amino-7-isopropyl-7H-pyrrolo[2,3-d]pyrimidine-5-carbonyl)-phenyl]-5-chloro-2-methoxy-benzenesulfonamide;
N-[3-(4-Amino-7-isopropyl-7H-pyrrolo[2,3-d]pyrimidine-5-carbonyl)-phenyl]-4-butoxy-benzenesulfonamide;
N-[3-(4-Amino-7-isopropyl-7H-pyrrolo[2,3-d]pyrimidine-5-carbonyl)-phenyl]-2,4-dichloro-5-methyl-benzenesulfonamide;
N-[3-(4-Amino-7-isopropyl-7H-pyrrolo[2,3-d]pyrimidine-5-carbonyl)-phenyl]-3-fluoro-benzenesulfonamide;
N-[3-(4-Amino-7-isopropyl-7H-pyrrolo[2,3-d]pyrimidine-5-carbonyl)-phenyl]-2-fluoro-benzenesulfonamide;
N-[3-(4-Amino-7-isopropyl-7H-pyrrolo[2,3-d]pyrimidine-5-carbonyl)-phenyl]-3,4-difluoro-benzenesulfonamide;
N-[5-(4-Amino-7-isopropyl-7H-pyrrolo[2,3-d]pyrimidine-5-carbonyl)-2-methoxy-phenyl]-3,5-dichloro-benzenesulfonamide;
1-[5-(4-Amino-7-isopropyl-7H-pyrrolo[2,3-d]pyrimidine-5-carbonyl)-2-methoxy-phenyl]-3-(2-fluoro-5-methyl-phenyl)-urea;
1-[5-(4-Amino-7-isopropyl-7H-pyrrolo[2,3-d]pyrimidine-5-carbonyl)-2-methoxy-phenyl]-3-(2-chloro-phenyl)-urea;
1-[5-(4-Amino-7-isopropyl-7H-pyrrolo[2,3-d]pyrimidine-5-carbonyl)-2-methoxy-phenyl]-3-(3,5-dichloro-phenyl)-urea;
1-[5-(4-Amino-7-isopropyl-7H-pyrrolo[2,3-d]pyrimidine-5-carbonyl)-2-methoxy-phenyl]-3-m-tolyl-urea;
1-[5-(4-Amino-7-isopropyl-7H-pyrrolo[2,3-d]pyrimidine-5-carbonyl)-2-methoxy-phenyl]-3-(3,5-difluoro-phenyl)-urea;
1-[5-(4-Amino-7-isopropyl-7H-pyrrolo[2,3-d]pyrimidine-5-carbonyl)-2-methoxy-phenyl]-3-(2,4-dichloro-phenyl)-urea;

N-[5-(4-Amino-7-isopropyl-7H-pyrrolo[2,3-d]pyrimidine-5-carbonyl)-2-methoxy-phenyl]-2-chloro-benzenesulfonamide;

N-[5-(4-Amino-7-isopropyl-7H-pyrrolo[2,3-d]pyrimidine-5-carbonyl)-2-methoxy-phenyl]-2,4-dichloro-benzenesulfonamide;

1-[5-(4-Amino-7-isopropyl-7H-pyrrolo[2,3-d]pyrimidine-5-carbonyl)-2-methyl-phenyl]-3-(2,4-dichloro-phenyl)-urea;

N-[5-(4-Amino-7-isopropyl-7H-pyrrolo[2,3-d]pyrimidine-5-carbonyl)-2-methyl-phenyl]-3-chloro-4-fluoro-benzenesulfonamide;

1-[5-(4-Amino-7-isopropyl-7H-pyrrolo[2,3-d]pyrimidine-5-carbonyl)-2-methyl-phenyl]-3-(2-chloro-phenyl)-urea;

1-[5-(4-Amino-7-isopropyl-7H-pyrrolo[2,3-d]pyrimidine-5-carbonyl)-2-methyl-phenyl]-3-m-tolyl-urea;

1-[5-(4-Amino-7-isopropyl-7H-pyrrolo[2,3-d]pyrimidine-5-carbonyl)-2-methyl-phenyl]-3-(2-fluoro-5-methyl-phenyl)-urea;

1-[5-(4-Amino-7-isopropyl-7H-pyrrolo[2,3-d]pyrimidine-5-carbonyl)-2-methyl-phenyl]-3-cyclohexyl-urea;

1-[5-(4-Amino-7-isopropyl-7H-pyrrolo[2,3-d]pyrimidine-5-carbonyl)-2-methyl-phenyl]-3-(2,4-dichloro-benzyl)-urea;

1-[5-(4-Amino-7-isopropyl-7H-pyrrolo[2,3-d]pyrimidine-5-carbonyl)-2-methyl-phenyl]-3-(3,5-difluoro-phenyl)-urea;

1-[5-(4-Amino-7-isopropyl-7H-pyrrolo[2,3-d]pyrimidine-5-carbonyl)-2-methyl-phenyl]-3-(4-chloro-phenyl)-urea;

1-[3-(4-Amino-7-isopropyl-7H-pyrrolo[2,3-d]pyrimidine-5-carbonyl)-2-methyl-phenyl]-3-(2-chloro-phenyl)-urea;

N-[3-(4-Amino-7-isopropyl-7H-pyrrolo[2,3-d]pyrimidine-5-carbonyl)-2-methyl-phenyl]-3,5-dichloro-benzenesulfonamide;

1-[3-(4-Amino-7-isopropyl-7H-pyrrolo[2,3-d]pyrimidine-5-carbonyl)-2-methyl-phenyl]-3-(2,4-dichloro-phenyl)-urea;

1-[3-(4-Amino-7-isopropyl-7H-pyrrolo[2,3-d]pyrimidine-5-carbonyl)-2-methyl-phenyl]-3-(3,5-difluoro-phenyl)-urea;

N-[5-(4-Amino-7-isopropyl-7H-pyrrolo[2,3-d]pyrimidine-5-carbonyl)-2-fluoro-phenyl]-3,5-dichloro-benzenesulfonamide;

N-[3-(4-Amino-7-isopropyl-7H-pyrrolo[2,3-d]pyrimidine-5-carbonyl)-2-methyl-phenyl]-3-chloro-4-fluoro-benzenesulfonamide;

N-[3-(4-Amino-7-isopropyl-7H-pyrrolo[2,3-d]pyrimidine-5-carbonyl)-2-methyl-phenyl]-2,4-dichloro-benzenesulfonamide;

N-[3-(4-Amino-7-isopropyl-7H-pyrrolo[2,3-d]pyrimidine-5-carbonyl)-2-methyl-phenyl]-3-chloro-4-methyl-benzenesulfonamide;

N-[5-(4-Amino-7-isopropyl-7H-pyrrolo[2,3-d]pyrimidine-5-carbonyl)-2-fluoro-phenyl]-2-chloro-benzenesulfonamide;

N-[5-(4-Amino-7-isopropyl-7H-pyrrolo[2,3-d]pyrimidine-5-carbonyl)-2-fluoro-phenyl]-3-chloro-4-fluoro-benzenesulfonamide;

1-[5-(4-Amino-7-isopropyl-7H-pyrrolo[2,3-d]pyrimidine-5-carbonyl)-2-fluoro-phenyl]-3-(3,5-difluoro-phenyl)-urea;

N-[5-(4-Amino-7-isopropyl-7H-pyrrolo[2,3-d]pyrimidine-5-carbonyl)-2-fluoro-phenyl]-2,4-dichloro-benzenesulfonamide;

N-[5-(4-Amino-7-isopropyl-7H-pyrrolo[2,3-d]pyrimidine-5-carbonyl)-2-chloro-phenyl]-2,4-dichloro-benzenesulfonamide;

N-[5-(4-Amino-7-isopropyl-7H-pyrrolo[2,3-d]pyrimidine-5-carbonyl)-2-methoxy-phenyl]-3-chloro-4-fluoro-benzenesulfonamide;

N-[5-(4-Amino-7-isopropyl-7H-pyrrolo[2,3-d]pyrimidine-5-carbonyl)-2-fluoro-phenyl]-3-chloro-4-methyl-benzenesulfonamide;

N-[5-(4-Amino-7-isopropyl-7H-pyrrolo[2,3-d]pyrimidine-5-carbonyl)-2-chloro-phenyl]-3,5-dichloro-benzenesulfonamide;

1-[5-(4-Amino-7-isopropyl-7H-pyrrolo[2,3-d]pyrimidine-5-carbonyl)-2-fluoro-phenyl]-3-(2,4-dichloro-phenyl)-urea;

1-[5-(4-Amino-7-isopropyl-7H-pyrrolo[2,3-d]pyrimidine-5-carbonyl)-2-chloro-phenyl]-3-(4-chloro-phenyl)-urea;

1-[5-(4-Amino-7-isopropyl-7H-pyrrolo[2,3-d]pyrimidine-5-carbonyl)-2-fluoro-phenyl]-3-(2-chloro-phenyl)-urea;

1-[5-(4-Amino-7-isopropyl-7H-pyrrolo[2,3-d]pyrimidine-5-carbonyl)-2-fluoro-phenyl]-3-(4-chloro-phenyl)-urea;

N-[5-(4-Amino-7-isopropyl-7H-pyrrolo[2,3-d]pyrimidine-5-carbonyl)-2-chloro-phenyl]-3-chloro-4-methyl-benzenesulfonamide;

N-[5-(4-Amino-7-isopropyl-7H-pyrrolo[2,3-d]pyrimidine-5-carbonyl)-2-chloro-phenyl]-3-chloro-4-fluoro-benzenesulfonamide;

N-[5-(4-Amino-7-isopropyl-7H-pyrrolo[2,3-d]pyrimidine-5-carbonyl)-2-chloro-phenyl]-3,5-difluoro-benzenesulfonamide;

N-[5-(4-Amino-7-isopropyl-7H-pyrrolo[2,3-d]pyrimidine-5-carbonyl)-2-fluoro-phenyl]-C-(3,5-dichloro-phenyl)-methanesulfonamide;

1-[5-(4-Amino-7-isopropyl-7H-pyrrolo[2,3-d]pyrimidine-5-carbonyl)-2-chloro-phenyl]-3-(3,5-dichloro-phenyl)-urea;

1-[5-(4-Amino-7-isopropyl-7H-pyrrolo[2,3-d]pyrimidine-5-carbonyl)-2-chloro-phenyl]-3-(3,5-difluoro-phenyl)-urea;

N-[3-(4-Amino-7-isopropyl-7H-pyrrolo[2,3-d]pyrimidine-5-carbonyl)-2-chloro-phenyl]-2,4-dichloro-benzenesulfonamide;

N-[3-(4-Amino-7-isopropyl-7H-pyrrolo[2,3-d]pyrimidine-5-carbonyl)-2-chloro-phenyl]-2-chloro-benzenesulfonamide;

N-[3-(4-Amino-7-isopropyl-7H-pyrrolo[2,3-d]pyrimidine-5-carbonyl)-phenyl]-3-(pyridin-2-yloxy)-benzenesulfonamide;

N-[3-(4-Amino-7-isopropyl-7H-pyrrolo[2,3-d]pyrimidine-5-carbonyl)-2-chloro-phenyl]-3,5-dichloro-benzenesulfonamide;

N-[3-(4-Amino-7-isopropyl-7H-pyrrolo[2,3-d]pyrimidine-5-carbonyl)-2-chloro-phenyl]-3-chloro-4-fluoro-benzenesulfonamide;

N-[3-(4-Amino-7-isopropyl-7H-pyrrolo[2,3-d]pyrimidine-5-carbonyl)-2-chloro-phenyl]-3-chloro-4-methyl-benzenesulfonamide;

N-[3-(4-Amino-7-isopropyl-7H-pyrrolo[2,3-d]pyrimidine-5-carbonyl)-2-chloro-phenyl]-3,5-difluoro-benzenesulfonamide;

1-[5-(4-Amino-7-isopropyl-7H-pyrrolo[2,3-d]pyrimidine-5-carbonyl)-2-methoxy-phenyl]-3-(2,4-dichloro-phenyl)-urea;

1-[5-(4-Amino-7-isopropyl-7H-pyrrolo[2,3-d]pyrimidine-5-carbonyl)-2-methoxy-phenyl]-3-(3,5-difluoro-phenyl)-urea;

1-[3-(4-Amino-7-isopropyl-7H-pyrrolo[2,3-d]pyrimidine-5-carbonyl)-4-chloro-phenyl]-3-(2-chloro-phenyl)-urea;

1-[3-(4-Amino-7-isopropyl-7H-pyrrolo[2,3-d]pyrimidine-5-carbonyl)-4-chloro-phenyl]-3-(4-chloro-2-methylphenyl)-urea;

1-[3-(4-Amino-7-isopropyl-7H-pyrrolo[2,3-d]pyrimidine-5-carbonyl)-4-chloro-phenyl]-3-(4-chloro-phenyl)-urea;

1-[3-(4-Amino-7-isopropyl-7H-pyrrolo[2,3-d]pyrimidine-5-carbonyl)-4-chloro-phenyl]-3-m-tolyl-urea;

1-[5-(4-Amino-7-isopropyl-7H-pyrrolo[2,3-d]pyrimidine-5-carbonyl)-2-methoxy-phenyl]-3-phenyl-urea;

1-[5-(4-Amino-7-isopropyl-7H-pyrrolo[2,3-d]pyrimidine-5-carbonyl)-2-methoxy-phenyl]-3-p-tolyl-urea;

1-[5-(4-Amino-7-isopropyl-7H-pyrrolo[2,3-d]pyrimidine-5-carbonyl)-2-methoxy-phenyl]-3-o-tolyl-urea;

1-[5-(4-Amino-7-isopropyl-7H-pyrrolo[2,3-d]pyrimidine-5-carbonyl)-2-methoxy-phenyl]-3-(2-fluoro-phenyl)-urea;

1-[5-(4-Amino-7-isopropyl-7H-pyrrolo[2,3-d]pyrimidine-5-carbonyl)-2-methoxy-phenyl]-3-(3-fluoro-phenyl)-urea;

1-[5-(4-Amino-7-isopropyl-7H-pyrrolo[2,3-d]pyrimidine-5-carbonyl)-2-methoxy-phenyl]-3-(4-fluoro-phenyl urea;

1-[5-(4-Amino-7-isopropyl-7H-pyrrolo[2,3-d]pyrimidine-5-carbonyl)-2-methoxy-phenyl]-3-(3-cyano-phenyl)-urea;

1-[5-(4-Amino-7-isopropyl-7H-pyrrolo[2,3-d]pyrimidine-5-carbonyl)-2-methoxy-phenyl]-3-(4-cyano-phenyl)-urea;

1-[5-(4-Amino-7-isopropyl-7H-pyrrolo[2,3-d]pyrimidine-5-carbonyl)-2-methoxy-phenyl]-3-(2-methoxy-phenyl)-urea;

1-[5-(4-Amino-7-isopropyl-7H-pyrrolo[2,3-d]pyrimidine-5-carbonyl)-2-methoxy-phenyl]-3-(3-methoxy-phenyl)-urea;

1-[5-(4-Amino-7-isopropyl-7H-pyrrolo[2,3-d]pyrimidine-5-carbonyl)-2-methoxy-phenyl]-3-(4-methoxy-phenyl)-urea;

1-[5-(4-Amino-7-isopropyl-7H-pyrrolo[2,3-d]pyrimidine-5-carbonyl)-2-methoxy-phenyl]-3-(3-fluoro-4-methylphenyl)-urea;

1-[5-(4-Amino-7-isopropyl-7H-pyrrolo[2,3-d]pyrimidine-5-carbonyl)-2-methoxy-phenyl]-3-(3-chloro-phenyl)-urea;

1-[5-(4-Amino-7-isopropyl-7H-pyrrolo[2,3-d]pyrimidine-5-carbonyl)-2-methoxy-phenyl]-3-(4-chloro-phenyl)-urea;

1-(4-Acetyl-phenyl)-3-[5-(4-amino-7-isopropyl-7H-pyrrolo[2,3-d]pyrimidine-5-carbonyl)-2-methoxy-phenyl]-urea;

1-[5-(4-Amino-7-isopropyl-7H-pyrrolo[2,3-d]pyrimidine-5-carbonyl)-2-methoxy-phenyl]-3-(4-dimethylaminophenyl)-urea;

1-[5-(4-Amino-7-isopropyl-7H-pyrrolo[2,3-d]pyrimidine-5-carbonyl)-2-methoxy-phenyl]-3-(3-trifluoromethylphenyl)-urea;

N-[5-(4-Amino-7-isopropyl-7H-pyrrolo[2,3-d]pyrimidine-5-carbonyl)-2-methoxy-phenyl]-2-chloro-4-fluorobenzenesulfonamide;

1-[5-(4-Amino-7-isopropyl-7H-pyrrolo[2,3-d]pyrimidine-5-carbonyl)-2-methyl-phenyl]-3-(3,5-dichloro-phenyl)-urea;

1-[5-(4-Amino-7-isopropyl-7H-pyrrolo[2,3-d]pyrimidine-5-carbonyl)-2-methyl-phenyl]-3-(3-chloro-phenyl)-urea; and pharmaceutically acceptable salt, prodrug, hydrate or solvate of the aforementioned compounds.

66. A compound according to claim 65, wherein said compound is selected from the group consisting of:

1-[3-(4-Amino-7-isopropyl-7H-pyrrolo[2,3-d]pyrimidine-5-carbonyl)-phenyl]-3-(2-chloro-phenyl)-urea;

1-[3-(4-Amino-7-isopropyl-7H-pyrrolo[2,3-d]pyrimidine-5-carbonyl)-phenyl]-3-(2-methoxy-5-methyl-phenyl)-urea;

1-[3-(4-Amino-7-isopropyl-7H-pyrrolo[2,3-d]pyrimidine-5-carbonyl)-phenyl]-3-(2-fluoro-5-methyl-phenyl)-urea;

1-[3-(4-Amino-7-isopropyl-7H-pyrrolo[2,3-d]pyrimidine-5-carbonyl)-phenyl]-3-m-tolyl-urea;

1-[3-(4-Amino-7-isopropyl-7H-pyrrolo[2,3-d]pyrimidine-5-carbonyl)-phenyl]-3-(3-ethyl-phenyl)-urea;

1-[3-(4-Amino-7-isopropyl-7H-pyrrolo[2,3-d]pyrimidine-5-carbonyl)-phenyl]-3-(2-fluoro-phenyl)-urea;

1-[3-(4-Amino-7-isopropyl-7H-pyrrolo[2,3-d]pyrimidine-5-carbonyl)-phenyl]-3-(2,4-difluoro-phenyl)-urea;

1-[3-(4-Amino-7-isopropyl-7H-pyrrolo[2,3-d]pyrimidine-5-carbonyl)-phenyl]-3-(3,4-difluoro-phenyl)-urea;

1-[3-(4-Amino-7-isopropyl-7H-pyrrolo[2,3-d]pyrimidine-5-carbonyl)-phenyl]-3-(3-fluoro-phenyl)-urea;

1-[3-(4-Amino-7-isopropyl-7H-pyrrolo[2,3-d]pyrimidine-5-carbonyl)-phenyl]-3-(5-fluoro-2-methyl-phenyl)-urea;

1-[3-(4-Amino-7-isopropyl-7H-pyrrolo[2,3-d]pyrimidine-5-carbonyl)-phenyl]-3-(4-fluoro-phenyl)-urea;

1-[3-(4-Amino-7-isopropyl-7H-pyrrolo[2,3-d]pyrimidine-5-carbonyl)-phenyl]-3-(3-fluoro-4-methyl-phenyl)-urea;

1-[3-(4-Amino-7-isopropyl-7H-pyrrolo[2,3-d]pyrimidine-5-carbonyl)-phenyl]-3-(3,5-difluoro-phenyl)-urea;

1-[3-(4-Amino-7-isopropyl-7H-pyrrolo[2,3-d]pyrimidine-5-carbonyl)-phenyl]-3-(2,5-difluoro-phenyl)-urea;

1-[3-(4-Amino-7-isopropyl-7H-pyrrolo[2,3-d]pyrimidine-5-carbonyl)-phenyl]-3-(3-chloro-phenyl)-urea;

1-[3-(4-Amino-7-isopropyl-7H-pyrrolo[2,3-d]pyrimidine-5-carbonyl)-phenyl]-3-(4-chloro-phenyl)-urea;

1-[3-(4-Amino-7-isopropyl-7H-pyrrolo[2,3-d]pyrimidine-5-carbonyl)-phenyl]-3-p-tolyl-urea;

1-[3-(4-Amino-7-isopropyl-7H-pyrrolo[2,3-d]pyrimidine-5-carbonyl)-phenyl]-3-(2-ethyl-phenyl)-urea;

1-[3-(4-Amino-7-isopropyl-7H-pyrrolo[2,3-d]pyrimidine-5-carbonyl)-phenyl]-3-(2-isopropyl-phenyl)-urea;

1-[3-(4-Amino-7-isopropyl-7H-pyrrolo[2,3-d]pyrimidine-5-carbonyl)-phenyl]-3-(4-isopropyl-phenyl)-urea;

1-[3-(4-Amino-7-isopropyl-7H-pyrrolo[2,3-d]pyrimidine-5-carbonyl)-phenyl]-3-(4-methoxy-phenyl)-urea;

1-[3-(4-Amino-7-isopropyl-7H-pyrrolo[2,3-d]pyrimidine-5-carbonyl)-phenyl]-3-(2-methoxy-phenyl)-urea;

1-[3-(4-Amino-7-isopropyl-7H-pyrrolo[2,3-d]pyrimidine-5-carbonyl)-phenyl]-3-(2-ethoxy-phenyl)-urea;

1-[3-(4-Amino-7-isopropyl-7H-pyrrolo[2,3-d]pyrimidine-5-carbonyl)-phenyl]-3-(4-methylsulfanyl-phenyl)-urea;

1-[3-(4-Amino-7-isopropyl-7H-pyrrolo[2,3-d]pyrimidine-5-carbonyl)-phenyl]-3-(3-methylsulfanyl-phenyl)-urea;

1-[3-(4-Amino-7-isopropyl-7H-pyrrolo[2,3-d]pyrimidine-5-carbonyl)-phenyl]-3-(3-cyano-phenyl)-urea;

1-[3-(4-Amino-7-isopropyl-7H-pyrrolo[2,3-d]pyrimidine-5-carbonyl)-phenyl]-3-(3,5-dimethyl-phenyl)-urea;
1-[3-(4-Amino-7-isopropyl-7H-pyrrolo[2,3-d]pyrimidine-5-carbonyl)-phenyl]-3-(3,4-dimethyl-phenyl)-urea;
1-[3-(4-Amino-7-isopropyl-7H-pyrrolo[2,3-d]pyrimidine-5-carbonyl)-phenyl]-3-(2,5-dimethyl-phenyl)-urea;
1-[3-(4-Amino-7-isopropyl-7H-pyrrolo[2,3-d]pyrimidine-5-carbonyl)-phenyl]-3-(2,3-dimethyl-phenyl)-urea;
1-[3-(4-Amino-7-isopropyl-7H-pyrrolo[2,3-d]pyrimidine-5-carbonyl)-phenyl]-3-(2,4-dimethyl-phenyl)-urea;
1-[3-(4-Amino-7-isopropyl-7H-pyrrolo[2,3-d]pyrimidine-5-carbonyl)-phenyl]-3-thiophen-2-yl-urea;
1-[3-(4-Amino-7-isopropyl-7H-pyrrolo[2,3-d]pyrimidine-5-carbonyl)-phenyl]-3-thiophen-3-yl-urea;
1-[3-(4-Amino-7-isopropyl-7H-pyrrolo[2,3-d]pyrimidine-5-carbonyl)-phenyl]-3-cyclohexyl-urea;
1-[3-(4-Amino-7-isopropyl-7H-pyrrolo[2,3-d]pyrimidine-5-carbonyl)-phenyl]-3-o-tolyl-urea;
1-[3-(4-Amino-7-isopropyl-7H-pyrrolo[2,3-d]pyrimidine-5-carbonyl)-phenyl]-3-(4-ethyl-phenyl)-urea;
1-(3-Acetyl-phenyl)-3-[3-(4-amino-7-isopropyl-7H-pyrrolo[2,3-d]pyrimidine-5-carbonyl)-phenyl]-urea;
1-(4-Acetyl-phenyl)-3-[3-(4-amino-7-isopropyl-7H-pyrrolo[2,3-d]pyrimidine-5-carbonyl)-phenyl]-urea;
1-[3-(4-Amino-7-isopropyl-7H-pyrrolo[2,3-d]pyrimidine-5-carbonyl)-phenyl]-3-(4-ethoxy-phenyl)-urea;
1-[3-(4-Amino-7-isopropyl-7H-pyrrolo[2,3-d]pyrimidine-5-carbonyl)-phenyl]-3-(4-methoxy-2-methyl-phenyl)-urea;
4-{3-[3-(4-Amino-7-isopropyl-7H-pyrrolo[2,3-d]pyrimidine-5-carbonyl)-phenyl]-ureido}-benzoic acid methyl ester;
1-[3-(4-Amino-7-isopropyl-7H-pyrrolo[2,3-d]pyrimidine-5-carbonyl)-phenyl]-3-(2-methylsulfanyl-phenyl)-urea;
1-[3-(4-Amino-7-isopropyl-7H-pyrrolo[2,3-d]pyrimidine-5-carbonyl)-phenyl]-3-(2-chloro-benzyl)-urea;
1-[3-(4-Amino-7-isopropyl-7H-pyrrolo[2,3-d]pyrimidine-5-carbonyl)-phenyl]-3-(2-chloro-5-methyl-phenyl)-urea;
1-[3-(4-Amino-7-isopropyl-7H-pyrrolo[2,3-d]pyrimidine-5-carbonyl)-phenyl]-3-(3-chloro-2-methyl-phenyl urea;
1-[3-(4-Amino-7-isopropyl-7H-pyrrolo[2,3-d]pyrimidine-5-carbonyl)-phenyl]-3-(5-chloro-2-methyl-phenyl)-urea;
1-[3-(4-Amino-7-isopropyl-7H-pyrrolidin-5-carbonyl)-phenyl]-3-(3-chloro-4-methyl-phenyl)-urea;
1-[3-(4-Amino-7-isopropyl-7H-pyrrolo[2,3-d]pyrimidine-5-carbonyl)-phenyl]-3-(4-chloro-2-methyl-phenyl)-urea;
1-[3-(4-Amino-7-isopropyl-7H-pyrrolo[2,3-d]pyrimidine-5-carbonyl)-phenyl]-3-(3-chloro-4-fluoro-phenyl)-urea;
1-[3-(4-Amino-7-isopropyl-7H-pyrrolo[2,3-d]pyrimidine-5-carbonyl)-phenyl]-3-(4-tert-butyl-phenyl)-urea;
1-[3-(4-Amino-7-isopropyl-7H-pyrrolo[2,3-d]pyrimidine-5-carbonyl)-phenyl]-3-isopropyl-urea;
1-[3-(4-Amino-7-isopropyl-7H-pyrrolo[2,3-d]pyrimidine-5-carbonyl)-phenyl]-3-phenyl-urea;
N-[3-(4-Amino-7-isopropyl-7H-pyrrolo[2,3-d]pyrimidine-5-carbonyl)-phenyl]-4-ethyl-benzenesulfonamide;
N-[3-(4-Amino-7-isopropyl-7H-pyrrolo[2,3-d]pyrimidine-5-carbonyl)-phenyl]-5-chloro-2-methoxy-benzenesulfonamide;
N-[3-(4-Amino-7-isopropyl-7H-pyrrolo[2,3-d]pyrimidine-5-carbonyl)-phenyl]-4-butoxy-benzenesulfonamide;
N-[3-(4-Amino-7-isopropyl-7H-pyrrolo[2,3-d]pyrimidine-5-carbonyl)-phenyl]-2,4-dichloro-5-methyl-benzenesulfonamide;
N-[5-(4-Amino-7-isopropyl-7H-pyrrolo[2,3-d]pyrimidine-5-carbonyl)-2-methoxy-phenyl]-3,5-dichloro-benzenesulfonamide;
1-[5-(4-Amino-7-isopropyl-7H-pyrrolo[2,3-d]pyrimidine-5-carbonyl)-2-methoxy-phenyl]-3-(2-fluoro-5-methyl-phenyl)-urea;
1-[5-(4-Amino-7-isopropyl-7H-pyrrolo[2,3-d]pyrimidine-5-carbonyl)-2-methoxy-phenyl]-3-(2-chloro-phenyl urea;
1-[5-(4-Amino-7-isopropyl-7H-pyrrolo[2,3-d]pyrimidine-5-carbonyl)-2-methoxy-phenyl]-3-(3,5-dichloro-phenyl)-urea;
1-[5-(4-Amino-7-isopropyl-7H-pyrrolo[2,3-d]pyrimidine-5-carbonyl)-2-methoxy-phenyl]-3-m-tolyl-urea;
1-[5-(4-Amino-7-isopropyl-7H-pyrrolo[2,3-d]pyrimidine-5-carbonyl)-2-methoxy-phenyl]-3-(3,5-difluoro-phenyl)-urea;
1-[5-(4-Amino-7-isopropyl-7H-pyrrolo[2,3-d]pyrimidine-5-carbonyl)-2-methoxy-phenyl]-3-(2,4-dichloro-phenyl)-urea;
N-[5-(4-Amino-7-isopropyl-7H-pyrrolo[2,3-d]pyrimidine-5-carbonyl)-2-methoxy-phenyl]-2,4-dichloro-benzenesulfonamide
1-[5-(4-Amino-7-isopropyl-7H-pyrrolo[2,3-d]pyrimidine-5-carbonyl)-2-methyl-phenyl]-3-(2,4-dichloro-phenyl)-urea;
1-[5-(4-Amino-7-isopropyl-7H-pyrrolo[2,3-d]pyrimidine-5-carbonyl)-2-methyl-phenyl]-3-(2-chloro-phenyl)-urea;
1-[5-(4-Amino-7-isopropyl-7H-pyrrolo[2,3-d]pyrimidine-5-carbonyl)-2-methyl-phenyl]-3-m-tolyl-urea;
1-[5-(4-Amino-7-isopropyl-7H-pyrrolo[2,3-d]pyrimidine-5-carbonyl)-2-methyl-phenyl]-3-(2-fluoro-5-methyl-phenyl)-urea;
1-[5-(4-Amino-7-isopropyl-7H-pyrrolo[2,3-d]pyrimidine-5-carbonyl)-2-methyl-phenyl]-3-cyclohexyl-urea;
1-[5-(4-Amino-7-isopropyl-7H-pyrrolo[2,3-d]pyrimidine-5-carbonyl)-2-methyl-phenyl]-3-(2,4-dichloro-benzyl)-urea;
1-[5-(4-Amino-7-isopropyl-7H-pyrrolo[2,3-d]pyrimidine-5-carbonyl)-2-methyl-phenyl]-3-(3,5-difluoro-phenyl)-urea;
1-[5-(4-Amino-7-isopropyl-7H-pyrrolo[2,3-d]pyrimidine-5-carbonyl)-2-methyl-phenyl]-3-(4-chloro-phenyl)-urea;
1-[3-(4-Amino-7-isopropyl-7H-pyrrolo[2,3-d]pyrimidine-5-carbonyl)-2-methyl-phenyl]-3-(2,4-dichloro-phenyl)-urea;
N-[5-(4-Amino-7-isopropyl-7H-pyrrolo[2,3-d]pyrimidine-5-carbonyl)-2-fluoro-phenyl]-3,5-dichloro-benzenesulfonamide;
N-[3-(4-Amino-7-isopropyl-7H-pyrrolo[2,3-d]pyrimidine-5-carbonyl)-2-methyl-phenyl]-3-chloro-4-fluoro-benzenesulfonamide;
N-[3-(4-Amino-7-isopropyl-7H-pyrrolo[2,3-d]pyrimidine-5-carbonyl)-2-methyl-phenyl]-2,4-dichloro-benzenesulfonamide;
N-[3-(4-Amino-7-isopropyl-7H-pyrrolo[2,3-d]pyrimidine-5-carbonyl)-2-methyl-phenyl]-3-chloro-4-methyl-benzenesulfonamide;
N-[5-(4-Amino-7-isopropyl-7H-pyrrolo[2,3-d]pyrimidine-5-carbonyl)-2-fluoro-phenyl]-3-chloro-4-fluoro-benzenesulfonamide;

1-[5-(4-Amino-7-isopropyl-7H-pyrrolo[2,3-d]pyrimidine-5-carbonyl)-2-fluoro-phenyl]-3-(3,5-difluoro-phenyl)-urea;

N-[5-(4-Amino-7-isopropyl-7H-pyrrolo[2,3-d]pyrimidine-5-carbonyl)-2-chloro-phenyl]-3,5-dichloro-benzenesulfonamide;

1-[5-(4-Amino-7-isopropyl-7H-pyrrolo[2,3-d]pyrimidine-5-carbonyl)-2-fluoro-phenyl]-3-(2,4-dichloro-phenyl)-urea;

1-[5-(4-Amino-7-isopropyl-7H-pyrrolo[2,3-d]pyrimidine-5-carbonyl)-2-chloro-phenyl]-3-(4-chloro-phenyl)-urea;

1-[5-(4-Amino-7-isopropyl-7H-pyrrolo[2,3-d]pyrimidine-5-carbonyl)-2-fluoro-phenyl]-3-(2-chloro-phenyl)-urea;

1-[5-(4-Amino-7-isopropyl-7H-pyrrolo[2,3-d]pyrimidine-5-carbonyl)-2-fluoro-phenyl]-3-(4-chloro-phenyl)-urea;

N-[5-(4-Amino-7-isopropyl-7H-pyrrolo[2,3-d]pyrimidine-5-carbonyl)-2-chloro-phenyl]-3-chloro-4-fluoro-benzenesulfonamide;

N-[5-(4-Amino-7-isopropyl-7H-pyrrolo[2,3-d]pyrimidine-5-carbonyl)-2-chloro-phenyl]-3,5-difluoro-benzenesulfonamide;

1-[5-(4-Amino-7-isopropyl-7H-pyrrolo[2,3-d]pyrimidine-5-carbonyl)-2-chloro-phenyl]-3-(3,5-dichloro-phenyl)-urea;

1-[5-(4-Amino-7-isopropyl-7H-pyrrolo[2,3-d]pyrimidine-5-carbonyl)-2-chloro-phenyl]-3-(3,5-difluoro-phenyl)-urea;

N-[3-(4-Amino-7-isopropyl-7H-pyrrolo[2,3-d]pyrimidine-5-carbonyl)-2-chloro-phenyl]-2,4-dichloro-benzenesulfonamide;

N-[3-(4-Amino-7-isopropyl-7H-pyrrolo[2,3-d]pyrimidine-5-carbonyl)-2-chloro-phenyl]-2-chloro-benzenesulfonamide;

1-[5-(4-Amino-7-isopropyl-7H-pyrrolo[2,3-d]pyrimidine-5-carbonyl)-2-methoxy-phenyl]-3-(2,4-dichloro-phenyl)-urea;

1-[5-(4-Amino-7-isopropyl-7H-pyrrolo[2,3-d]pyrimidine-5-carbonyl)-2-methoxy-phenyl]-3-(3,5-difluoro-phenyl)-urea;

1-[3-(4-Amino-7-isopropyl-7H-pyrrolo[2,3-d]pyrimidine-5-carbonyl)-4-chloro-phenyl]-3-(2-chloro-phenyl)-urea;

1-[3-(4-Amino-7-isopropyl-7H-pyrrolo[2,3-d]pyrimidine-5-carbonyl)-4-chloro-phenyl]-3-(4-chloro-2-methyl-phenyl)-urea;

1-[3-(4-Amino-7-isopropyl-7H-pyrrolo[2,3-d]pyrimidine-5-carbonyl)-4-chloro-phenyl]-3-(4-chloro-phenyl)-urea;

1-[3-(4-Amino-7-isopropyl-7H-pyrrolo[2,3-d]pyrimidine-5-carbonyl)-4-chloro-phenyl]-3-m-tolyl-urea;

1-[5-(4-Amino-7-isopropyl-7H-pyrrolo[2,3-d]pyrimidine-5-carbonyl)-2-methoxy-phenyl]-3-p-tolyl-urea;

1-[5-(4-Amino-7-isopropyl-7H-pyrrolo[2,3-d]pyrimidine-5-carbonyl)-2-methoxy-phenyl]-3-(3-fluoro-phenyl)-urea;

1-[5-(4-Amino-7-isopropyl-7H-pyrrolo[2,3-d]pyrimidine-5-carbonyl)-2-methoxy-phenyl]-3-(4-fluoro-phenyl)-urea;

1-[5-(4-Amino-7-isopropyl-7H-pyrrolo[2,3-d]pyrimidine-5-carbonyl)-2-methoxy-phenyl]-3-(2-methoxy-phenyl)-urea;

1-[5-(4-Amino-7-isopropyl-7H-pyrrolo[2,3-d]pyrimidine-5-carbonyl)-2-methoxy-phenyl]-3-(3-methoxy-phenyl)-urea;

1-[5-(4-Amino-7-isopropyl-7H-pyrrolo[2,3-d]pyrimidine-5-carbonyl)-2-methoxy-phenyl]-3-(4-methoxy-phenyl)-urea;

1-[5-(4-Amino-7-isopropyl-7H-pyrrolo[2,3-d]pyrimidine-5-carbonyl)-2-methoxy-phenyl]-3-(3-fluoro-4-methyl-phenyl)-urea;

1-[5-(4-Amino-7-isopropyl-7H-pyrrolo[2,3-d]pyrimidine-5-carbonyl)-2-methoxy-phenyl]-3-(3-chloro-phenyl)-urea;

1-[5-(4-Amino-7-isopropyl-7H-pyrrolo[2,3-d]pyrimidine-5-carbonyl)-2-methoxy-phenyl]-3-(4-chloro-phenyl)-urea;

1-(4-Acetyl-phenyl)-3-[5-(4-amino-7-isopropyl-7H-pyrrolo[2,3-d]pyrimidine-5-carbonyl)-2-methoxy-phenyl]-urea;

1-[5-(4-Amino-7-isopropyl-7H-pyrrolo[2,3-d]pyrimidine-5-carbonyl)-2-methoxy-phenyl]-3-(4-dimethylamino-phenyl)-urea;

1-[5-(4-Amino-7-isopropyl-7H-pyrrolo[2,3-d]pyrimidine-5-carbonyl)-2-methoxy-phenyl]-3-(3-trifluoromethyl-phenyl)-urea;

N-[5-(4-Amino-7-isopropyl-7H-pyrrolo[2,3-d]pyrimidine-5-carbonyl)-2-methoxy-phenyl]-2-chloro-4-fluoro-benzenesulfonamide;

1-[5-(4-Amino-7-isopropyl-7H-pyrrolo[2,3-d]pyrimidine-5-carbonyl)-2-methyl-phenyl]-3-(3,5-dichloro-phenyl)-urea;

1-[5-(4-Amino-7-isopropyl-7H-pyrrolo[2,3-d]pyrimidine-5-carbonyl)-2-methyl-phenyl]-3-(3-chloro-phenyl)-urea; and pharmaceutically acceptable salt, prodrug, hydrate or solvate of the aforementioned compounds.

Other specific embodiments of the compounds of formula 1 include those selected from the group consisting of:

N-[3-(4-Amino-7-isopropyl-7H-pyrrolo[2,3-d]pyrimidine-5-carbonyl)-phenyl]-2,4-dichloro-benzenesulfonamide;

1-[3-(4-Amino-7-isopropyl-7H-pyrrolo[2,3-d]pyrimidine-5-carbonyl)-phenyl]-3-(4-chloro-phenyl)-urea;

1-[3-(4-Amino-7-isopropyl-7H-pyrrolo[2,3-d]pyrimidine-5-carbonyl)-phenyl]-3-(4-chloro-2-methyl-phenyl)-urea;

1-[5-(4-Amino-7-isopropyl-7H-pyrrolo[2,3-d]pyrimidine-5-carbonyl)-2-methoxy-phenyl]-3-(3,5-dichloro-phenyl)-urea;

1-[5-(4-Amino-7-isopropyl-7H-pyrrolo[2,3-d]pyrimidine-5-carbonyl)-2-methoxy-phenyl]-3-(3,5-difluoro-phenyl)-urea;

1-[5-(4-Amino-7-isopropyl-7H-pyrrolo[2,3-d]pyrimidine-5-carbonyl)-2-methoxy-phenyl]-3-(2,4-dichloro-phenyl)-urea;

1-[5-(4-Amino-7-isopropyl-7H-pyrrolo[2,3-d]pyrimidine-5-carbonyl)-2-methyl-phenyl]-3-(3,5-difluoro-phenyl)-urea;

1-[3-(4-Amino-7-isopropyl-7H-pyrrolo[2,3-d]pyrimidine-5-carbonyl)-2-methyl-phenyl]-3-(2-chloro-phenyl)-urea;

1-[3-(4-Amino-7-isopropyl-7H-pyrrolo[2,3-d]pyrimidine-5-carbonyl)-2-methyl-phenyl]-3-(3,5-difluoro-phenyl)-urea;

N-[5-(4-Amino-7-isopropyl-7H-pyrrolo[2,3-d]pyrimidine-5-carbonyl)-2-fluoro-phenyl]-3-chloro-4-fluoro-benzenesulfonamide;

N-[5-(4-Amino-7-isopropyl-7H-pyrrolo[2,3-d]pyrimidine-5-carbonyl)-2-fluoro-phenyl]-2,4-dichloro-benzenesulfonamide;

N-[5-(4-Amino-7-isopropyl-7H-pyrrolo[2,3-d]pyrimidine-5-carbonyl)-2-chloro-phenyl]-3,5-dichloro-benzenesulfonamide;

1-[5-(4-Amino-7-isopropyl-7H-pyrrolo[2,3-d]pyrimidine-5-carbonyl)-2-fluoro-phenyl]-3-(2-chloro-phenyl)-urea;

N-[5-(4-Amino-7-isopropyl-7H-pyrrolo[2,3-d]pyrimidine-5-carbonyl)-2-chloro-phenyl]-3-chloro-4-fluoro-benzenesulfonamide;

N-[5-(4-Amino-7-isopropyl-7H-pyrrolo[2,3-d]pyrimidine-5-carbonyl)-2-chloro-phenyl]-3,5-difluoro-benzenesulfonamide;

N-[3-(4-Amino-7-isopropyl-7H-pyrrolo[2,3-d]pyrimidine-5-carbonyl)-2-chloro-phenyl]-3-chloro-4-fluoro-benzenesulfonamide;

N-[3-(4-Amino-7-isopropyl-7H-pyrrolo[2,3-d]pyrimidine-5-carbonyl)-2-chloro-phenyl]-3-chloro-4-methyl-benzenesulfonamide;

N-[3-(4-Amino-7-isopropyl-7H-pyrrolo[2,3-d]pyrimidine-5-carbonyl)-2-chloro-phenyl]-3,5-difluoro-benzenesulfonamide; and pharmaceutically acceptable salt, prodrug, hydrate or solvate of the aforementioned compounds.

Other specific embodiments of the compounds of formula 1 include those selected from the group consisting of:

1-[5-(4-Amino-7-isopropyl-7H-pyrrolo[2,3-d]pyrimidine-5-carbonyl 2-methoxy-phenyl]-3-(2,4-dichloro-phenyl)-urea;

1-[5-(4-Amino-7-isopropyl-7H-pyrrolo[2,3-d]pyrimidine-5-carbonyl)-2-methyl-phenyl]-3-(3,5-difluoro-phenyl)-urea;

1-[3-(4-Amino-7-isopropyl-7H-pyrrolo[2,3-d]pyrimidine-5-carbonyl)-2-methyl-phenyl]-3-(2-chloro-phenyl)-urea;

1-[3-(4-Amino-7-isopropyl-7H-pyrrolo[2,3-d]pyrimidine-5-carbonyl)-2-methyl-phenyl]-3-(3,5-difluoro-phenyl)-urea;

N-[5-(4-Amino-7-isopropyl-7H-pyrrolo[2,3-d]pyrimidine-5-carbonyl)-2-fluoro-phenyl]-3-chloro-4-fluoro-benzenesulfonamide;

N-[5-(4-Amino-7-isopropyl-7H-pyrrolo[2,3-d]pyrimidine-5-carbonyl)-2-fluoro-phenyl]-2,4-dichloro-benzenesulfonamide;

N-[5-(4-Amino-7-isopropyl-7H-pyrrolo[2,3-d]pyrimidine-5-carbonyl)-2-chloro-phenyl]-3,5-dichloro-benzenesulfonamide;

1-[5-(4-Amino-7-isopropyl-7H-pyrrolo[2,3-d]pyrimidine-5-carbonyl)-2-fluoro-phenyl]-3-(2-chloro-phenyl)-urea;

N-[5-(4-Amino-7-isopropyl-7H-pyrrolo[2,3-d]pyrimidine-5-carbonyl)-2-chloro-phenyl]-3-chloro-4-fluoro-benzenesulfonamide;

N-[5-(4-Amino-7-isopropyl-7H-pyrrolo[2,3-d]pyrimidine-5-carbonyl)-2-chloro-phenyl]-3,5-difluoro-benzenesulfonamide;

N-[3-(4-Amino-7-isopropyl-7H-pyrrolo[2,3-d]pyrimidine-5-carbonyl)-2-chloro-phenyl]-3-chloro-4-fluoro-benzenesulfonamide;

N-[3-(4-Amino-7-isopropyl-7H-pyrrolo[2,3-d]pyrimidine-5-carbonyl)-2-chloro-phenyl]-3-chloro-4-methyl-benzenesulfonamide;

N-[3-(4-Amino-7-isopropyl-7H-pyrrolo[2,3-d]pyrimidine-5-carbonyl)-2-chloro-phenyl]-3,5-difluoro-benzenesulfonamide; and pharmaceutically acceptable salt, prodrug, hydrate or solvate of the aforementioned compounds.

The present invention also relates to a process for preparing a compound of the formula 1A,

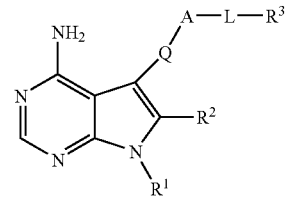

or a pharmaceutically acceptable salt, prodrug, solvate or hydrate thereof, wherein the substituents of 1A have the same definition as the compound of formula 1 above which comprises treating a compound of the formula 8 wherein Z is halo

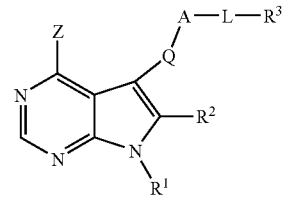

with a compound of the formula $H_3N$.

The present invention also relates to a process of preparing a compound of the formula 1B,

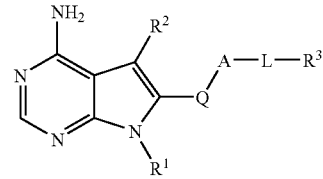

or a pharmaceutically acceptable salt, prodrug, solvate or hydrate thereof, or a pharmaceutically acceptable salt, prodrug, solvate or hydrate thereof, wherein the substituents of 1B therein have the same definition as the compound of formula 1 above which comprises treating a compound of the formula 9 wherein Z is halo

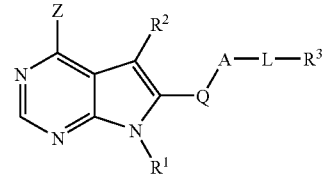

with a compound of the formula $H_3N$.

In one preferred embodiment of the processes of the present invention Z is Cl.

The invention also relates to a pharmaceutical composition for the treatment of a hyperproliferative disorder in a mammal which comprises a therapeutically effective amount of a compound of formula 1, or a pharmaceutically acceptable salt, prodrug or hydrate thereof, and a pharmaceutically acceptable carrier. In one embodiment, said pharmaceutical composition is for the treatment of cancer, wherein said cancer is selected from lung cancer, bone cancer, pancreatic cancer, gastric, skin cancer, cancer of the head or neck, cutaneous or intraocular melanoma, uterine cancer, ovarian cancer, gynecological, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, squamous cell, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain, pituitary adenoma, or a combination of one or more of the foregoing cancers.

In one preferred embodiment the cancer is selected from the group consisting of brain, squamous cell, bladder, gastric, pancreatic, breast, head, neck, oesophageal, prostate, colorectal, lung, renal, kidney, ovarian, gynecological and thyroid cancer.

In a more preferred embodiment the cancer is selected from the group consisting of prostate, breast, lung, colon and ovarian cancer.

In another more preferred embodiment the cancer is selected from the group consisting of prostate, breast, and lung cancer.

In a most preferred embodiment the breast cancer is metastatic breast cancer.

In a most preferred embodiment the lung cancer is non-small cell lung cancer.

In another embodiment, said pharmaceutical composition is for the treatment of a non-cancerous hyperproliferative disorder such as benign hyperplasia of the skin (e.g., psoriasis) or prostate (e.g., benign prostatic hypertropy (BPH)).

The invention also relates to a pharmaceutical composition for the treatment of pancreatitis or kidney disease (including proliferative glomerulonephritis and diabetes-induced renal disease) in a mammal which comprises a therapeutically effective amount of a compound of formula 1, or a pharmaceutically acceptable salt, prodrug or hydrate thereof, and a pharmaceutically acceptable carrier.

The invention also relates to a pharmaceutical composition for the prevention of blastocyte implantation in a mammal which comprises a therapeutically effective amount of a compound of formula 1, or a pharmaceutically acceptable salt, prodrug or hydrate thereof, and a pharmaceutically acceptable carrier.

The invention also relates to a pharmaceutical composition for treating a disease related to vasculogenesis or angiogenesis in a mammal which comprises a therapeutically effective amount of a compound of formula 1, or a pharmaceutically acceptable salt, prodrug or hydrate thereof, and a pharmaceutically acceptable carrier. In one embodiment, said pharmaceutical composition is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal which comprises administering to said mammal a therapeutically effective amount of the compound of formula 1, or a pharmaceutically acceptable salt, prodrug or hydrate thereof. In one embodiment, said method relates to the treatment of cancer such as brain, squamous cell, bladder, gastric, pancreatic, breast, head, neck, oesophageal, prostate, colorectal, lung, renal, kidney, ovarian, gynecological or thyroid cancer. In another embodiment, said method relates to the treatment of a non-cancerous hyperproliferative disorder such as benign hyperplasia of the skin (e.g., psoriasis) or prostate (e.g., benign prostatic hypertropy (BPH)).

The invention also relates to a method for the treatment of a hyperproliferative disorder in a mammal which comprises administering to said mammal a therapeutically effective amount of a compound of formula 1, or a pharmaceutically acceptable salt, prodrug or hydrate thereof, in combination with an anti-tumor agent selected from the group consisting of, but not limited to, mitotic inhibitors, alkylating agents, anti-metabolites, intercalating agents, growth factor inhibitors, cell cycle inhibitors, enzymes, topoisomerase inhibitors, biological response modifiers, anti-hormones, kinase inhibitors, matrix metalloprotease inhibitors, genetic therapeutics and anti-androgens.

The invention also relates to a method of treating pancreatitis or kidney disease in a mammal which comprises administering to said mammal a therapeutically effective amount of a compound of formula 1, or a pharmaceutically acceptable salt, prodrug or hydrate thereof.

The invention also relates to a method of preventing blastocyte implantation in a mammal which comprises administering to said mammal a therapeutically effective amount of a compound of formula 1, or a pharmaceutically acceptable salt, prodrug or hydrate thereof.

The invention also relates to a method of treating diseases related to vasculogenesis or angiogenesis in a mammal which comprises administering to said mammal an effective amount of a compound of formula 1, or a pharmaceutically acceptable salt, prodrug or hydrate thereof. In one embodiment, said method is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with a compounds of formula 1, and the pharmaceutically acceptable salts, prodrugs and hydrates of said compounds, according to the methods of this invention include, for example, patients that have been diagnosed as having psoriasis, BPH, lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphonas, cancer of the bladder, cancer of the kidney or ureter (e.g., renal cell carcinoma, carcinoma of the renal pelvis), or neoplasms of the central nervous system (e.g., primary CNS lymphona, spinal axis tumors, brain stem gliomas or pituitary adenomas).

This invention also relates to a pharmaceutical composition for inhibiting abnormal cell growth in a mammal which comprises an amount of a compound of formula 1, or a pharmaceutically acceptable salt or solvate or prodrug thereof, in combination with an amount of a chemotherapeutic, wherein the amounts of the compound, salt, solvate, or prodrug, and of the chemotherapeutic are together effective in inhibiting abnormal cell growth. Many chemotherapeutics are presently known in the art. In one embodiment, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, e.g. anti-androgens.

This invention further relates to a method for inhibiting abnormal cell growth in a mammal which method comprises administering to the mammal an amount of a compound of formula 1, or a pharmaceutically acceptable salt or solvate or prodrug thereof, in combination with radiation therapy, wherein the amount of the compound, salt, solvate or prodrug is in combination with the radiation therapy effective in inhibiting abnormal cell growth in the mammal. Techniques for administering radiation therapy are known in the art, and these techniques can be used in the combination therapy described herein. The administration of the compound of the invention in this combination therapy can be determined as described herein.

It is believed that the compounds of formula 1 can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of formula 1 or pharmaceutically acceptable salt, prodrug or solvate thereof, which amount is effective in sensitizing abnormal cells to treatment with radiation. The amount of the compound, salt, or solvate in this method can be determined according to the means for ascertaining effective amounts of such compounds described herein.

This invention also relates to a pharmaceutical composition for inhibiting abnormal cell growth in a mammal, including a human, comprising an amount of a compound of the formula 1 as defined above, or a pharmaceutically acceptable salt, prodrug or solvate thereof, that is effective in inhibiting farnesyl protein transferase, and a pharmaceutically acceptable carrier.

This invention further relates to a pharmaceutical composition for inhibiting abnormal cell growth in a mammal comprising an amount of a compound of formula 1, or a pharmaceutically acceptable salt or solvate or prodrug thereof, that is effective in inhibiting abnormal cell growth, and a pharmaceutically acceptable carrier.

This invention also relates to a method of and to a pharmaceutical composition for inhibiting abnormal cell growth in a mammal which comprises an amount of a compound of formula 1, a pharmaceutically acceptable salt or solvate thereof, a prodrug thereof, or an isotopically-labelled derivative thereof, and an amount of one or more substances selected from anti-angiogenesis agents, signal transduction inhibitors, and antiproliferative agents.

This invention also relates to a pharmaceutical composition for inhibiting abnormal cell growth in a mammal, including a human, comprising an amount of a compound of formula 1 as defined above, or a pharmaceutically acceptable salt or solvate thereof, that is effective in inhibiting farnesyl protein transferase, and a pharmaceutically acceptable carrier.

This invention also relates to a method of and to a pharmaceutical composition for inhibiting abnormal cell growth in a mammal which comprises an amount of a compound of formula 1, a pharmaceutically acceptable salt or solvate thereof, a prodrug thereof, or an isotopically-labelled derivative thereof, and an amount of one or more substances selected from anti-angiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of formula 1 and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP inhibitors are those that do not demonstrate arthralgia. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and the compounds recited in the following list:

3-[[4-(4-fluoro-phenoxy)-benzenesulfonyl]-(1-hydroxycarbamoyl-cyclopentyl)-amino]-propionic acid;

3-exo-3-[4-(4-fluoro-phenoxy)-benzenesulfonylamino]-8-oxa-bicyclo[3.2.1]octane-3-carboxylic acid hydroxyamide;

(2R,3R)1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonylamino]-tetrahydro-pyran-4-carboxylic acid hydroxyamide;

(R)3-[4-(4-chloro-phenoxy)-benzenesulfonylamino]-tetrahydro-pyran-3-carboxylic acid hydroxyamide;

(2R,3R)1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1]octane-3-carboxylic acid hydroxyamide; and (R)3-[4-(4-fluoro-phenoxy)-benzenesulfonylamino]-tetrahydro-furan-3-carboxylic acid hydroxyamide;

and pharmaceutically acceptable salts and solvates of said compounds.

A compound of formula 1 can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated of New York, N.Y., USA), ABX-EGF (Abgenix/Cell Genesys), EMD-7200 (Merck KgaA), EMD-5590 (Merck KgaA), MDX-447/H-477 (Medarex Inc. of Annandale, N.J., USA and Merck KgaA), and the compounds ZD-1834, ZD-1838 and ZD-1839 (AstraZeneca), PKI-166 (Novartis), PKI-166/CGP-75166 (Novartis), PTK 787 (Novartis), CP 701 (Cephalon), leflunomide (Pharmacia/Sugen), CI-1033 (Warner Lambert Parke Davis), CI-1033/PD 183,805 (Warner Lambert Parke Davis), CL-387,785 (Wyeth-Ayerst), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co. of Whitehouse Station, N.J., USA), VRCTC-310 (Ventech Research), EGF fusion toxin (Seragen Inc. of Hopkinton, Mass.), DAB-389 (Seragen/Lilgand), ZM-252808 (Imperical Cancer Res arch Fund), RG-50864 (INSERM), LFM-A12 (Parker Hughes Cancer Center), WHI-P97 (Parker Hughes Cancer Center), GW-282974 (Glaxo), KT-8391 (Kyowa Hakko) and EGFR Vaccine (York Medical/Centro de Immunologia Molecular (CIM)). These and other EGFR-inhibiting agents can be used in the present invention.

VEGF inhibitors, for example CP-547,632 and AG-13736 (Pfizer Inc.), SU-5416 and SU-6668 (Sugen Inc. of South San Francisco, Calif., USA), SH-268 (Schering), and NX-1838 (NeXstar) can also be combined with the compound of the present invention. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as CP-724,714 (Pfizer, Inc.), GW-2016 and GW-282974 (Glaxo Wellcome plc), and the monoclonal antibodies AR-209 (Aronex Pharmaceuticals Inc. of The Woodlands, Tex., USA) and 2B-1 (Chiron), can furthermore be combined with the compound of the invention, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with the compound of the present invention in accordance with the present invention.

The compound of the invention can also be used with other agents useful in treating abnormal cell growth or cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors, and the like. Specific CTLA4 antibodies that can be used in the present invention include those described in U.S. Provisional Application 60/113,647 (filed Dec. 23, 1998) which is incorporated by reference in its entirety, however other CTLA4 antibodies can be used in the present invention.

Other anti-angiogenesis agents, including, but not limited to, CI-1040, CI-1030 and CI-994 (all of the foregoing Pfizer, Inc.) other COX-II inhibitors, other MMP inhibitors, other anti-VEGF antibodies or inhibitors of other effectors of vascularization can also be used in the present invention.

The subject invention also includes isotopically-labelled compounds, which are identical to those recited in formula 1 but for the fact that one or more atoms are replaced by an atom having an atomic mass or mass number different from the atomic mass or mass number usually found in nature.

Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula 1 of this invention and prodrugs thereof can generally b prepared by carrying out the procedures disclosed in the Schemes and/or in the Examples below, by substituting a readily available isotopically labelled reagent for a non-isotopically labelled reagent.

The compounds of formula 1 and their pharmaceutically acceptable salts and solvates can each independently also furthermore be used in a palliative neo-adjuvant/adjuvant therapy in alleviating the symptoms associated with the diseases recited herein as well as the symptoms associated with abnormal cell growth. Such therapy can be a monotherapy or can be in a combination with chemotherapy and/or immunotherapy.

The terms "abnormal cell growth" and "hyperproliferative disorder" are used interchangeably in this application.

"Abnormal cell growth", as used herein, refers to cell growth that is independent of normal regulatory mechanisms (e.g., loss of contact inhibition), including the abnormal growth of normal cells and the growth of abnormal cells. This includes, but is not limited to, the abnormal growth of: (1) tumor cells (tumors), both benign and malignant, expressing an activated Ras oncogene; (2) tumor cells, both benign and malignant, in which the Ras protein is activated as a result of oncogenic mutation in another gene; (3) benign and malignant cells of other proliferative diseases in which aberrant Ras activation occurs. Examples of such benign proliferative diseases are psoriasis, benign prostatic hypertrophy, human papilloma virus (HPV), and restinosis. "Abnormal cell growth" also refers to and includes the abnormal growth of cells, both benign and malignant, resulting from activity of the enzyme farnesyl protein transferase.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "halo", as used herein, unless otherwise indicated, means fluoro, chloro, bromo or iodo. Preferred halo groups are fluoro, chloro and bromo.

The term "alkyl", as used herein, unless otherwise indicated, means saturated monovalent hydrocarbon radicals having straight, cyclic or branched moieties. Said "alkyl" group may include an optional carbon-carbon double or triple bond where said alkyl group comprises at least two carbon atoms. It is understood that for cyclic moieties at least three carbon atoms are required in said alkyl group.

The term "alkenyl", as used herein, unless otherwise indicated, means straight or branched chain alkyl moieties having at least one carbon-carbon double bond. Examples, without limitation, of alkenyl groups include 1-propenyl, 1- and 2-butenyl, etc.

The term "alkynyl", as used herein, unless otherwise indicated, means straight or branched chain alkyl moieties having at least one carbon-carbon triple bond. Examples, without limitation, of alkynyl groups include 1-propynyl, 1- and 2-butynyl, etc.

The term "alkoxy", as used herein, unless otherwise indicated, means O-alkyl groups wherein "alkyl" is as defined above.

The term "aryl" or "aromatic", as used herein, unless otherwise indicated, means an organic radical derived from an aromatic hydrocarbon by removal of one hydrogen, such as phenyl or naphthyl.

The term "cycloalkyl", as used herein, unless otherwise indicated, means an all-carbon monocyclic ring. Examples, without limitation, of cycloalkyl groups are cyclopropyl, cyclobutyl, cyclopentyl, and cyclohexyl.

The term "arylalkyl", as used herein, means an alkyl moiety, as defined above, that is substituted by an aryl ring.

The term "acyl", as used herein, refers to a species containing a carbon-oxygen double bond.

The terms "heteroaromatic" or "heteroaryl", as used herein, refer to aromatic moieties that contain oxygen, nitrogen, or sulfur atoms as part of the aromatic system.

The term "heteroalkyl", as used herein, refers to saturated monovalent hydrocarbon radicals containing nitrogen, oxygen or sulfur atoms and having straight, cyclic or branched moieties. Said "alkyl" group may include an optional carbon-carbon double or triple bond where said alkyl group comprises at least two carbon atoms.

The term "5 to 10 membered heterocyclic" or "5 to 13 membered heterocyclic", as used herein, unless otherwise indicated, means aromatic and non-aromatic heterocyclic groups containing one to four heteroatoms each selected from O, S and N, wherein each heterocyclic group has from 5 to 10 or 5 to 13 atoms in its ring system. The heterocyclic groups include benzo-fused ring systems and ring systems substituted with one or two oxo (=O) moieties such as pyrrolidin-2-one. An example of a 5 membered heterocyclic group is thiazolyl, an example of a 10 membered heterocyclic group is quinolinyl and an example of a 13 membered heterocyclic group is a carbazole group.

Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, benzo[1,3]dioxolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The phrase "pharmaceutically acceptable salt(s)", as used herein, unless otherwise indicated, includes salts of acidic or basic groups which may be present in the compounds of formula 1. The compounds of formula 1 that are basic in nature are capable of forming a wide variety of salts with various inorganic and organic acids. The acids that may be used to prepare pharmaceutically acceptable acid addition salts of such basic compounds of formula 1 are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the formula 1 that are acidic in nature are capable of forming bas salts with various pharmacologically acceptable cations. Examples of such salts include the alkali metal or alkaline earth metal salts and particularly, the sodium and potassium salts.

The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. The compounds of formula 1 may also exist as tautomers. This invention relates to the use of all such tautomers and mixtures thereof.

This invention also encompasses pharmaceutical compositions containing and methods of treating proliferative disorders or abnormal cell growth through administering prodrugs of compounds of the formula 1. Compounds of formula 1 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews*, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

DETAILED DESCRIPTION OF THE INVENTION

The compounds of the present invention (1) are readily prepared according to synthetic methods familiar to those skilled in the art. Scheme 1 illustrates a general synthetic sequence for preparing compounds of the present invention where Q is a carbonyl group (C=O) and $R^2$ is a hydrogen atom (H).

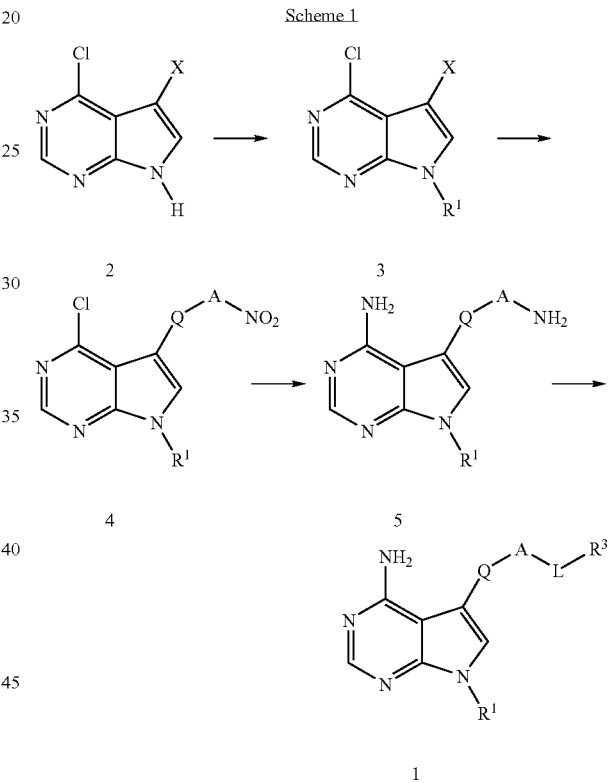

Compound 2 (X=H, Br or I) may be prepared according to literature procedures, for example, described by Townsend et al: J. Med. Chem. 1990, 33(7), 1984-1992 or by Ugarkar et al: J. Med. Chem. 2000, 43(15), 2883. The group $R^1$ in compound 3 may be H, alkyl, cycloalkyl, heteroalkyl, heterocyclic, aromatic or heteroaromatic moieties with or without additional substituents chosen from one or more of the following entities: hydroxyl, alkoxyl, amino, substituted amino, alkyl, cycloalkyl, or heterocyclic moieties. Compound 3 is usually obtained via a simple alkylation of 2, using for example, NaH/DMF in the presence of alkyl halide, or via a Mitsunobu reaction. Introduction of halogen atoms can be performed on either 2 or 3 using literature procedures, for example, described by Townsend et al: J. Med. Chem. 1990, 33(7), 1984-1992. Compound 3 (X=Br) may be converted to 4 (Q is C=O) by treatment of 3 with, for example, n-butyllithium in an aprotic solvent, such as tetrahydrofuran (THF), at a temperature of about −78° C. for a period of 0.5 to 1 h and followed by treatment with an acyl chloride (BCOCl) or Wenreib amide. The preferred acyl chlorides or Wenreib amides usually have the acyl group attached directly to an aromatic moiety (A=Ar). Furthermore, a nitro group or protected amino group may be attached directly to the aryl moiety at various positions, or indirectly attached through a C1 to C3 saturated or unsaturated carbon chain at various positions. The aryl moiety of the acyl chloride usually is an unsubstituted five or six membered aromatic ring, or substituted with halogen, alkoxyl, or small alkyl groups at various positions on the ring.

The chlorine atom of compound 4 may be replaced with an amino group by treatment of the compound with ammonia hydroxide at elevated temperature and pressure. The nitro group is then reduced to the amino group to furnish 5 using procedures familiar to those skilled in the art.

Compounds of the present invention may be obtained by treatment of 5 with acid chloride, sulfonyl chloride, isocyanate, or subjecting 5 under reductive alkylation condition with aldehyde or ketone, or coupling conditions with carboxylic acid. Protocols for all such chemical treatment/conversions are well established and are familiar to those practiced in the field. The reagents used in these procedures may have their reactive functional group attached directly to an aromatic moiety, or indirectly through a C1 to C3 saturated or unsaturated carbon chain, or may be attached to a non-aromatic moiety. In cases where an aromatic moiety is part of these reagents, the aromatic moiety may be a five or six membered ring, with one or more substituents of halogen, lower alkyls, lower alkoxyls, additionally substituted or unsubstituted aryls. This aromatic moiety may also be fused with other aromatic ring structures. In cases where these reagents are not readily commercially available, the reagents may be prepared using protocols well established in the field, or the compounds of the present invention may be specifically synthesized using alternative methods familiar to those practice in the field, for example by converting 5 to its phenyl carbamate, and subsequently converting the carbamate into ureas.

Alternatively, the acyl chlorides or the Wenreib amides used in step 1 may be functionalized with an iodo- or bromo-substituent at various positions of an aryl. In this case, compounds of the present invention may be obtained via Suzuki coupling using aryl and heteroaryl boronic acids, or Castro-Stevens coupling using substituted terminal alkynes. The boronic acids and the alkynes may be attached to a proper functional groups, for example amide, sulfonamide, urea or amine.

Compounds of the present invention where Q is a methylene group (Q=CH$_2$) may b prepared through reduction of the corresponding carbonyl compound (Q=CO) using protocols well known to those practice the art, for example the Wolff-Kishner conditions or its modified version, the Huang Minlon condition.

Compounds of the present invention where Q is a sulfur linker (Q=S) may be prepared through a modified thio-Ullman coupling of 2 with various aromatic thiols. The aromatic thiols employed may be functionalized with a nitro-group at various positions of the aromatic moiety and the nitro group is subsequently manipulated through a synthesis sequence similar to the one outlined in Scheme 1 to obtain compounds of the present invention; or the aromatic thiols may be functionalized with the proper moieties already in place so that the thio-Ullman coupling directly furnishes compounds of the present invention.

Compounds of the present invention where Q is a sulfoxide (Q=SO) or sulfone (Q=SO$_2$) may be prepared through an oxidation of the corresponding sulfer linker compounds (Q=S) using, for example "oxone".

Alternatively, compounds of the present invention may be prepared via scheme 2, where compound 2 may be lithiated with n-BuLi and quenched with a substituted benzaldehyde to furnish an alcohol 6. The alcohol may be then oxidized to 7 the corresponding ketone using methods familiar to those skilled in the art. The ketone 7 thus obtained may be converted to the bisamino compound 8 using protocols similar to those for the conversion of 4 to 5 outlined in scheme 1. The amino group on the phenyl ring of the bisamino compound 8 may be selectively functionalized using protocols similar to those employed in the conversion of 5 to 1, thus furnishing a set of analogs where R$^1$ is hydrogen. This set of analogs 8 may also be selectively alkylated on N7 using Mitsunobu conditions to furnish compounds 1 of the present invention.

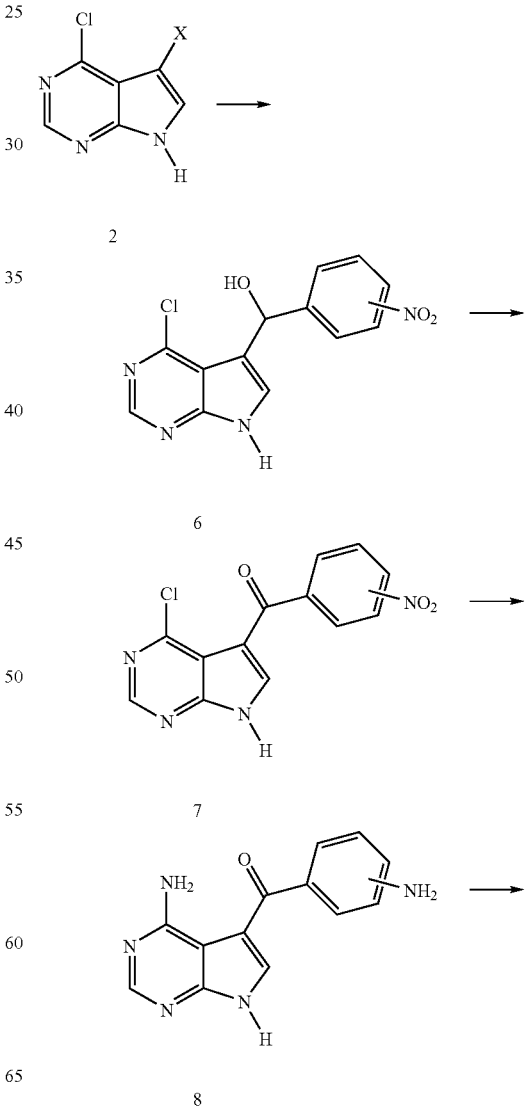

Scheme 2

-continued

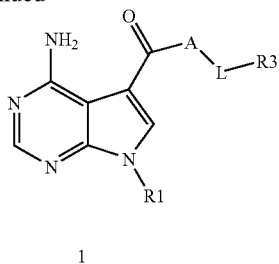

1

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The compounds of formula 1 that are basic in nature are capable of forming a wide variety of different salts with various inorganic and organic acids. Although such salts must be pharmaceutically acceptable for administration to animals, it is often desirable in practice to initially isolate the compound of formula 1 from the reaction mixture as a pharmaceutically unacceptable salt and then simply convert the later back to the free base compound by treatment with an alkaline reagent and subsequently convert the latter free base to a pharmaceutically acceptable acid addition salt. The acid addition salt of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formula 1 that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those, which form non-toxic, base salts with the acidic compounds of formula 1. Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of the present invention are inhibitors/antagonists of various enzymes/receptors. They are active against a variety of kinase targets which are involved in angiogenesis/vasculogenesis, oncogenic and protooncogenic signal transduction and cell cycle regulations. As such, the compounds of the present invention are useful in the prevention and treatment of a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions such as benign hyperplasia of the prostate (e.g., BPH). It is, in addition, expected that a compound of the present invention may possess activity against a range of leukemias and lymphoid malignancies.

The compounds of the present invention may also be useful in the treatment of additional disorders in which aberrant ligand/receptor expression, interaction, activation or signal events related to various protein kinases, are involved. Such disorders may include those of neuronal, glial, astrocytal, hypothalamic, and other glandular macrophagal, epithelia, stromal, and blastocoelic nature in which aberrant function, expression, activation or signaling of a protein kinase are involved. In addition, the compounds of the present invention may have therapeutic utility in inflammatory, angiogenic and immunologic disorders involving both identified and as yet unidentified kinases that are inhibited by the compounds of this invention.

The compounds of the present invention may also be useful in the treatment of additional disorders in which aberrant expression ligand/receptor interactions or activation or signaling events related to various protein tyrosine kinases, are involved. Such disorders may include those of neuronal, glial, astrocytal, hypothalamic, and other glandular, macrophagal, epithelial, stromal, and blastocoelic nature in which aberrant function, expression, activation or signaling of tyrosine kinases are involved. In addition, the compounds of the present invention may have therapeutic utility in inflammatory, angiogenic and immunologic disorders involving both identified and as yet unidentified tyrosine kinases that are inhibited by the compounds of the present invention.

The compounds of the present invention have been found to be selective inhibitors of the tyrosine kinases, Tie-2, TrkA and related family member TrkB. The potency of the compounds of the present invention at the tyrosine kinases may be determined using the following assays.

The in vitro activity of the compounds of formula 1 in inhibiting the Tie-2 receptor may be determined by the following procedure.

Inhibition of Tie-2 tyrosine kinase activity was measured in 96-well Maxisorp plates (Nunc) coated with poly-Glu-Tyr (PGT 4:1, Sigma) by the addition of 100 μL/well of a 25 μg/mL solution of PGT in PBS. Plates were incubated at 37° C. overnight, and transferred to 4° C. until use. Prior to compound testing, appropriate dilutions of compounds were made in 96-well polypropylene plates. The compounds were diluted to 60-fold the desired final concentrations in DMSO, and subsequently diluted to 4-fold the desired final concentrations in phosphorylation buffer-DTT (PB-DTT), a buffer composed of 50 mM HEPES, pH 7.4, 125 mM NaCl, 24 mM MgCl$_2$, and 2 mM of freshly added dithiothreitol (DTT; Sigma). The PGT-coated plates were removed from 4° C., and washed 5 times with TBST, a wash buffer composed of 1×Tris-buffered saline made from powder (Sigma) containing 0.1% polyoxyethylenesorbitan monolaurate (Tween-20, Sigma). Twenty-five μL of each compound dilution per well was added to the washed PGT-coated plate. Plates then received 50 μL/well of a solution of 200 mM ATP (Sigma), freshly diluted in PB-DTT from a frozen 50 mM stock solution. Control wells received 50 μL/well PB-DTT lacking ATP. Reactions were initiated by the addition of 25 μL of purified GST-Tie2 fusion protein in PB-DTT. GST-Tie2 was previously isolated from insect cells infected with GST-Tie2 baculoviruses, and used at concentrations determined to provide $OD_{450}$ signals of approximately 1.0 in the presence of ATP and the absence of chemical inhibitors. Reactions were allowed to proceed for 15 minutes at ambient temperatures with shaking, and terminated by washing 5 times with TBST. To detect phosphotyrosine, the wash buffer was removed, and each well received 75 μL of a horseradish peroxidase-conjugated monoclonal antibody to phosphotyrosine (HRP-PY20; Signal Transduction Labs), diluted 1:2000 in block buffer, a buffer composed of wash buffer and 5% bovine serum albumin (BSA: Sigma). Plates were incubated for 30 minutes with shaking at ambient temperature, and washed 5 times with wash buffer. The bound HRP-PY20 antibody was detected by the addition of 70 μL/well TMB microwell substrate (KPL), and color development was terminated by the addition of an equal volume of 0.9 M $H_2SO_4$. The background signal from wells lacking ATP was subtracted from all ATP-stimulated wells, and $IC_{50}$ values were calculated.

The cell assay utilized NIH/3T3 fibroblasts expressing a chimeric receptor composed of the extracellular domain of the human EGFR, and the intracellular domain of human Tie-2. To measure cellular activity, fifteen thousand cells were seeded into 96-well U-bottom plates (Falcon) in Dulbecco's Modified Essential Medium (DMEM) containing 2 mM L-glutamine, 0.1 U/mL penicillin, 0.1 μg/mL streptomycin and 10% fetal calf serum (FCS; all supplements from Gibco). Cells were allowed to attach for six hours at 37° C., 5% $CO_2$, at which time the medium was replaced with 190 μL/well starvation medium (fresh medium containing 0.1% FCS). The cell plates were returned to the incubator until the next day. Prior to compound testing, appropriate dilutions of compounds were made in 96-well polypropylene plates. The initial dilution series began with the addition of 15 μL of a 4 mM compound stock solution in DMSO to 45 μL DMSO; the resulting concentration of 1 mM was diluted in a serial 1:4 fashion in DMSO to give concentrations of 1000, 250, 62.5, 15.63, 3.91, 0.98, 0.25 and 0 μM. In a separate 96-well plate, 20 μL of each compound dilution was then added to 80 μL of starvation medium to give compound concentrations of 200, 50, 12.5, 3.13, 0.78, 0.20, 0.049 and 0 μM in a final DMSO concentration of 20%. To dose cells, 10 μL of the various compound dilutions were added to the plates containing cells, to give final compound concentrations of 10, 2.5, 0.63, 0.16, 0.039, 0.01, 0.002 and 0 μM in 1% DMSO. Cell plates were allowed to incubate with compounds for 60 minutes at 37° C., 5% $CO_2$. To activate the chimeric receptors, recombinant EGF (Sigma) was added to a final concentration of 200 ng/mL, and plates were incubated for an additional 10 minutes at 37° C., 5% $CO_2$. Medium was then removed, and the cells were fixed for 5 minutes on ice with 100 μL/well cold methanol containing 200 μM $NaVO_4$. The fixative was removed and plates were allowed to dry at ambient temperature. Phosphotyrosine levels were measured in a time-resolved immunoassay with DELFIA Eu-$N^1$-labeled Anti-Phosphotyrosine Antibody (PT66) from Perkin Elmer™. The antibody was diluted to a final concentration of 0.5 μg/mL in DELFIA Assay Buffer (Perkin Elmer™), and 100 μL/well was added for 60 minutes at ambient temperature with shaking. The antibody solution was removed, and plates were washed six times using 300 μL/well DELFIA Wash Buffer (Perkin Elmer™). After the final wash, 100 μL/well of DELFIA Enhancement Solution (Perkin Elmer™) was added to each well. The DELFIA Enhancement Solution (Perkin Elmer™) acts to dissociate the Europium ions, which form highly fluorescent chelates. After incubation at ambient temperatures for 5 minutes with shaking, the plates are read on a Victor 2 Multilab I HTS Counter (Perkin Elmer™). The background signal from mock-stimulated wells is subtracted from the EGF-stimulated wells, and $IC_{50}$ values are calculated.

The in vitro activity of the compounds of formula 1 in inhibiting the TrkA receptor may b determined by the following procedure.

The ability of the compounds of the present invention to inhibit tyrosine kinase activity of TrkA may be measured using a recombinant enzyme in an assay that measures the ability of compounds to inhibit the phosphorylation of the exogenous substrate, polyGluTyr (PGT, Sigma™, 4:1). The kinase domain of the human NGF/TrkA receptor is expressed in Sf9 insect cells as a glutathione S-transferase (GST)-fusion protein using the baculovirus expression system. The protein is purified from the lysates of these cells using glutathione agarose affinity columns. The enzyme assay is performed in 96-well plates that are coated with the PGT substrate (1.0 ug PGT per well). The final concentration of ATP in the plates is 40 uM. Test compounds are first diluted in dimethylsulfoxide (DMSO) and then serial-diluted in a 96-well plate. When added to the PGT plates, the final concentration of DMSO in the assay is 0.06%. The recombinant enzyme is diluted in phosphorylation buffer (50 mM HEPES, pH 7.4, 0.14M NaCl, 2.2 mM $MgCl_2$, 2.5 mM $MnCl_2$, 0.1 mM DTT, 0.2 mM $Na_3VO_4$). The reaction is initiated by the addition of the recombinant enzyme to the ATP and to the test compounds. After a 30 minute incubation at room temperature with shaking, the reaction is stopped with 0.5M EDTA, pH 8.0, and then aspirated. The plates are washed with wash buffer (1× imidazole wash buffer). The amount of phosphorylated PGT is quantitated by incubation with a HRP-conjugated (HRP is horseradish peroxidase) PY-54 antibody (Transduction Labs), developed with ABTS substrate, and the reaction is quantitated on a Wallac Victor$^2$ plate reader at 405 nm. Inhibition of the kinase enzymatic activity by the test compound is detected as a reduced absorbance, and the concentration of the compound that is required to inhibit the signal by 50% is reported as the $IC_{50}$ value for the test compound.

To measure the ability of the compounds to inhibit TrkA tyrosine kinase activity for the full length protein that exists in a cellular context, the porcine aortic endothelial (PAE) cells transfected with the human TrkA may be used. Cells are plated and allowed to attach to 96-well dishes in the same media (Ham's F12) with 10% FBS (fetal bovine serum). Test compounds, dissolved in DMSO, are serial-diluted in 96-well assay blocks with serum free media containing 0.1% fatty-acid free bovin serum albumin (BSA). The cells are then washed, re-fed with serum free media with and without test compounds, and allowed to incubate for 2 hr. At the end of the 2 hr. incubation, NGF (150 ng/ml final) is added to the media for a 10 minute incubation. The cells are washed and lysed in Tris-lysis buffer (50 mM Tris, pH 7.4, 150 mM NaCl, 1% NP-40, 10% glycerol, 2 mM $Na_3VO_4$, 0.5 mM EDTA, complete protease inhibitor cocktail tablets without EDTA). TBS is used as a diluter solution to mix the cell lysates. The extent of phosphorylation of TrkA is measured using an ELISA assay. The black, Maxisorb 96-well plates are custom-coated with goat anti-rabbit antibody (Pierce). The Trk(C-14)sc-11 antibody (Santa Cruz) at 0.4 µg/well is bound to the plates for 2 hr. in SuperBlock Blocking Buffer in TBS (Pierce). Any unbound antibody is washed off the plates prior to addition of the cell lysate. After a 2 hr. incubation of the lysates with the Trk(C-14)sc-11 antibody, the TrkA associated phosphotyrosine is quantitated by development with the HRP-conjugated PY54 antibody and SuperSignal ELISA Femto substrate (Pierce). The ability of the compounds to inhibit the NGF-stimulated autophosphorylation reaction by 50%, relative to NGF-stimulated controls, is reported as the $IC_{50}$ value for the test compound.

The in vitro activity of the compounds of formula 1 in inhibiting the TrkB receptor may be determined by the following procedure.

The ability of the compounds of the present invention to inhibit tyrosine kinase activity of TrkB may be measured using a recombinant enzyme in an assay that measures the ability of compounds to inhibit the phosphorylation of the exogenous substrate, polyGluTyr (PGT, Sigma™, 4:1). The kinase domain of the human BDNF/TrkB receptor is expressed in Sf9 insect cells as a glutathione S-transferase (GST)-fusion protein using the baculovirus expression system. The protein is purified from the lysates of these cells using glutathione agarose affinity columns. The enzyme assay is performed in 96-well plates that are coated with the PGT substrate (1.0 ug PGT per well). The ATP is diluted in phosphorylation buffer (50 mM HEPES, pH 7.4, 0.14M NaCl, 0.56 mM $MnCl_2$, 0.1 mM DTT, 0.2 mM $Na_3VO_4$). The final concentration of ATP in the plates is 300 uM. Test compounds are first diluted in dimethylsulfoxide (DMSO) and then serial-diluted in a 96-well plate. When added to the PGT plates, the final concentration of DMSO in the assay is 0.06%. The recombinant enzyme is diluted in phosphorylation buffer without $MnCl_2$. The reaction is initiated by the addition of the recombinant enzyme to the ATP and to the test compounds. After a 2.5 hr. incubation at 30° C. with shaking, the reaction is stopped with 0.5M EDTA, pH 8.0, and then aspirated. The plates are washed with wash buffer (1× imidazole wash buffer). The amount of phosphorylated PGT is quantitated by incubation with a HRP-conjugated antiphosphotyrosine antibody, developed with ABTS substrate, and the reaction is quantitated on a Wallac Victor² plat read r at 405 nm. Inhibition of the kinase enzymatic activity by the test compound is detected as a reduced absorbance, and the concentration of the compound that is required to inhibit the signal by 50% is reported as the $IC_{50}$ value for the test compound.

To measure the ability of the compounds to inhibit TrkB tyrosine kinase activity for the full-length protein that exists in a cellular context, the porcine aortic endothelial (PAE) cells transfected with the human TrkB may be used. Cells are plated and allowed to attach to 96-well dishes in the same media (Ham's F12) with 10% FBS (fetal bovine serum). Test compounds, dissolved in DMSO, are serial-diluted in 96-well assay blocks with serum free media containing 0.1% fatty-acid free bovine serum albumin (BSA). The cells are then washed, re-fed with serum free media with and without test compounds, and allowed to incubate for 2 hr. At the end of the 2 hr. incubation, BDNF (100 ng/ml final) is added to the media for a 10 minute incubation. The cells are washed and lysed in Tris-lysis buffer (50 mM Tris, pH 7.4, 150 mM NaCl, 1% NP-40, 10% glycerol, 2 mM $Na_3VO_4$, 0.5 mM EDTA, complete protease inhibitor cocktail tablets without EDTA). TBS is used as a diluter solution to mix the cell lysates. The extent of phosphorylation of TrkB is measured using an ELISA assay. The black, Maxisorb 96-well plates are custom-coated with goat anti-rabbit antibody (Pierce). The α-Trk(C-14)sc-11 antibody (Santa Cruz) at 0.4 µg/well is bound to the plates for 2 hr. in SuperBlock Blocking Buffer in TBS (Pierce). Any unbound antibody is washed off the plates prior to addition of the cell lysate. After a 2 hr. incubation of the lysates with the Trk(C-14)sc-11 antibody, the TrkB associated phosphotyrosine is quantitated by development with a HRP-conjugated antiphosphotyrosine antibody and SuperSignal ELISA Femto substrate (Pierce). The ability of the compounds to inhibit the BDNF-stimulated autophosphorylation reaction by 50%, relative to BDNF-stimulated controls, is reported as the $IC_{50}$ value for the test compound.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration and the judgment of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve on or more other anti-tumor substances, for example those selected from, for example, mitotic inhibitors, for example vinblastine; alkylating agents, for example cic-platin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-(N-(3,4-dihydro-2-methyl-4-oxoquinazolin-6-ylmethyl)-N-methylamino]-2-thenoyl)-L-glutamic acid; growth factor inhibitor, cell cycle inhibitors; intercalating antibiotics, for example adriamycin and bleomycin; enzymes, for example interferon; and anti-hormones, for, example anti-estrogens such as Nolvadex™ (tamoxifen) or, for example anti-androgens such as Casodex™ (4'-cyano-3-(4-fluorophenylsulphonyl)-2-hydroxy-2-methyl-3'-trifluoromethyl)propionanilide). Such conjoint treatment may be achieved by way of simultaneous, sequential or separate dosing of the individual components of the treatment.

The pharmaceutical composition may, for example, be in a form suitable for oral administration as a tablet, capsule, pill, powder, sustained release formulations, solution, and suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextros solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled n this art. For example, see Remington's Pharmaceutical Sciences, Mack Publishing Company, Easter, Pa., 15th Edition (1975).

The examples and preparations provided below further illustrate and exemplify th compounds of the present invention and methods of preparing such compounds. It is to b understood that the scope of the present invention is not limited in any way by the scope of th following examples and preparations.

Detailed analytical and preparative HPLC chromatography methods referred to in th preparations and examples below are outlined as follows.

Analytical HPLC method 1, 2 and 3: Gilson HPLC equipped with a diode array detector and a MetaChem Polaris 5 um C18-A 20×2.0 mm column; peak detection reported usually in total intensity chromatogram and 210 nm wavelength; solvent A: water with 2% acetonitrile and 0.01% formic acid, solvent B: acetonitrile with 0.05% formic acid; flow rate at 1 mL/min.

Method 1 gradient: 5% to 20% solvent B in 1 min., ramp up to 100% solvent B at 2.25 min., stay at 100% B until 2.5 min., and back to 5% B at 3.75 min.

Method 2 gradient: 5% to 20% solvent B in 1.25 min., ramp up to 50% at 2.5 min., and up to 100% B at 3.25 min., stay at 100% B until 4.25 min., and back to 5% B at 4.5 min.

Method 3 gradient: stay at 0% solvent B until 1.0 min., ramp up to 20% at 2.0 min., up to 100% B at 3.5 min., back to 0% B at 3.75 min.

Analytical HPLC method 4: Hewlett Packard-1050 equipped with a diode array detector and a 150×4 mm Hewlett Packard ODS Hypersil column; peak detection reported at 254 and 300 nm wavelength; solvent A: water with ammonium acetate/acetic acid buffer (0.2 M), solvent B: acetonitrile; flow rate at 3 mL/min.

Method 4 gradient: 0% to 100% B in 10 min., hold at 100% B for 1.5 min.

Preparative HPLC method: Shimadzu HPLC equipped with a diode array detector and a Waters Symmetry or Extera C8 column, 19×50 mm or 30×50 mm; peak detection reported usually at 210 nm wavelength; solvent A: water with 2% acetonitrile and 0.1% formic acid, solvent B: acetonitrile with 0.1% formic acid; flow rate between 18 to 40 mL/min.

General preparative HPLC gradient methods are usually a linear 0 to 5% B to 100% B over 10 to 25 min. Special gradient methods with a narrower gradient window, customized using methods familiar to those skilled in the art, are used for some compounds.

EXAMPLE 1

1A.
4-Chloro-7-cyclopentyl-7H-pyrrolo[2,3-d]pyrimidine

NaH (3.8 g, 95.3 mmol) was added to a solution of 4-Chloro-7H-pyrrolo[2,3-d]pyrimidine (10 g, 63.5 mmol) in DMF (50 mL) at 0° C. The resulting mixture was stirred at 0° C. for 30 min, then warmed to room temperature. At this time Cyclopentylbromide (18.9 g, 127 mmol) was added and the reaction was heated to 60° C. After 4 h the reaction was cooled to 0° C. and quenched with water. The aqueous layer was extracted with EtOAc (3×), the combined organic layers were washed with water (1×), dried over $Na_2SO_4$, and concentrated. Purification by flash column chromatography (Hexanes/Ethyl acetate 9:1) afforded the title compound as a clear oil (10.6 g, 75%). MS: 222.1/224.1 ($MH^+$); HPLC Rf: 5.77 min. (HPLC method 4).

Similar alkylation procedures were also employed using $Cs_2CO_3$ or $K_2CO_3$ as th base, or using the Mitsunobu condition.

1B. 5-Bromo-4-chloro-7-cyclopentyl-7H-pyrrolo[2,3-d]pyrimidine

N-Bromosuccinimide (15.4 g, 86.8 mmol) was added to a solution of 4-Chloro-7-cyclopentyl-7H-pyrrolo[2,3-d]pyrimidine (15.4 g, 69.5 mmol) in $CH_2Cl_2$ (100 mL). After 12 h the reaction was quenched with saturated aqueous $NaHCO_3$ (100 mL). The layers were separated and the aqueous layer was extracted with $CH_2Cl_2$ (2×100 mL). The combined organic layers were dried over $Na_2SO_4$ and concentrated. Purification by flash column chromatography (hexanes/ethyl acetate 9:1) afforded the title compound as a white solid (12.8 g, 61%). MS: 300.1/302.0/304.1 ($MH^+$); HPLC Rf: 6.68 min. (HPLC method 4).

1C. (4-Chloro-7-cyclopentyl-7H-pyrrolo[2,3-d]pyrimidin-5-yl)-(3-nitro-phenyl)-methanone n-BuLi (22 mL, 2.5 M in Hexane, 55.0 mmol) was added dropwise to a solution of 5-Bromo-4-chloro-7-cyclopentyl-7H-pyrrolo[2,3-d]pyrimidine (15.0 g, 50.0 mmol) in THF (200 mL) at −78° C. After 1 h the resulting solution was added via cannula to a solution of 3-Nitrobenzoyl Chloride in THF (100 mL) at −78° C. After 30 min the reaction was quenched with saturated aqueous $NH_4Cl$ and warmed to room temperature. The layers were separated and the aqueous layer was extracted with EtOAc (1×200 mL). The THF was concentrated off under reduced pressure and the resulting organic layer was diluted with EtOAc. The organic layer was washed with 1N NaOH (2×) and water (1×) then dried over $Na_2SO_4$ and concentrated. Recrystallization from EtOAc afforded the title compound as a white solid (12.1 g, 65%). MS: 371.2/373.1 (MH+); HPLC Rf: 6.59 min. (HPLC method 4).

1D. (4-Amino-7-cyclopentyl-7H-pyrrolo[2,3-d]pyrimidin-5-yl)-(3-nitro-phenyl)-methanone A solution of (4-Chloro-7-cyclopentyl-7H-pyrrolo[2,3-d]pyrimidin-5-yl)-(3-nitro-phenyl)-methanone (11.3 g, 30.5 mmol) and NH$_4$OH (200 mL) in 1,4-Dioxane (300 mL) was heated to 50° C. in a pressure reactor. After 2 h the reaction was concentrated under reduced pressure. The residue was dissolved in CH$_2$Cl$_2$ and washed with water. The organic layer was dried over MgSO$_4$ and concentrated to afford the title compound as a yellow solid (10.37 g, 97%). MS: 352.1 (MH+); HPLC Rf: 5.56 min. (HPLC method 4).

1E. (4-Amino-7-cyclopentyl-7H-pyrrolo[2,3-d]pyrimidin-5-yl)-(3-amino-phenyl)-methanone Fe (8.24 g, 147.55 mmol) was added to a solution of (4-Amino-7-cyclopentyl-7H-pyrrolo[2,3-d]pyrimidin-5-yl)-(3-nitro-phenyl)methanone (10.37 g, 29.51 mmol) and NH$_4$Cl (6.31 g, 118.0 mmol) in 1,4-Dioxane (200 mL), EtOH (150 mL), and water (100 mL). The resulting suspension was heated to reflux for 2 h, at this time the reaction was cooled to room temperature then filtered through celite eluting with EtOAc. The filtrate was dried over MgSO$_4$ and concentrated to afford the title compound as a yellow solid (9.48 g, 100%). MS: 322.3 (MH+); HPLC Rf: 4.55 min. (HPLC method 4).

EXAMPLE 2

(4-Amino-7-cyclopentyl-7H-pyrrolo[2,3-d]pyrimidin-5-yl)-(2-amino-phenyl)methanone The title compound was prepared from 2-Nitrobenzoyl chloride and 5-Bromo-4-chloro-7-cyclopentyl-7H-pyrrolo[2,3-d]pyrimidine by procedures analogous to those described for the preparation of (4-Amino-7-cyclopentyl-7H-pyrrolo[2,3-d]pyrimidin-5-yl)-(3-amino-phenyl)-methanone. MS: 322.3 (MH+); HPLC Rf: 5.52 min. (HPLC method 4).

EXAMPLE 3

(4-Amino-7-cyclopentyl-7H-pyrrolo[2,3-d]pyrimidin-5-yl)-(4-amino-phenyl)-methanone The title compound was prepared from 4-Nitrobenzoyl chloride and 5-Bromo-4-chloro-7-cyclopentyl-7H-pyrrolo[2,3-d]pyrimidine by procedures analogous to those described for the preparation of (4-Amino-7-cyclopentyl-7H-pyrrolo[2,3-d]pyrimidin-5-yl)-(3-amino-phenyl)-methanone. MS: 322.3 (MH+); HPLC Rf: 4.45 min. (HPLC method 4).

EXAMPLE 4

N-[3-(4-Amino-7-cyclopentyl-7H-pyrrolo[2,3-d]pyrimidine-5-carbonyl)-phenyl]-2-chloro-4-fluoro-benzenesulfonamide 2-Chloro-4-fluorobenzenesulphonyl chloride (85.7 mg, 0.37 mmol) was added to a solution of (4-Amino-7-cyclopentyl-7H-pyrrolo[2,3-d]pyrimidin-5-yl)-(3-amino-phenyl)-methanone (80 mg, 0.25 mmol) in pyridine (3 mL). The resulting solution was heated to 120° C. for 3 h. The reaction was quenched with water and concentrated. The residue was dissolved in EtOAc and washed with 1N NaOH (1×) and water (1×). The organic layer was dried over Na$_2$SO$_4$ and concentrated. Purification by flash column chromatography (CH$_2$Cl$_2$/MeOH 98:2) afforded the title compound as a white solid (32 mg, 25%). MS: 514.1/516.1 (MH+); HPLC Rf: 6.12 min. (HPLC method 4).

EXAMPLES 5-24

Example 5-24 listed in the following table were prepared using procedures analogous to those described in Example 4.

| Example | Compound Name | MH+ | HPLC Rf (min) | method |
|---|---|---|---|---|
| 5 | N-[3-(4-Amino-7-cyclopentyl-7H-pyrrolo[2,3-d]pyrimidine-5-carbonyl)-phenyl]-2-chloro-benzenesulfonamide | 496.0/498.0 | 5.93 | 4 |
| 6 | N-[3-(4-Amino-7-cyclopentyl-7H-pyrrolo[2,3-d]pyrimidine-5-carbonyl)-phenyl]-2,4-difluoro-benzenesulfonamide | 498.0 | 5.88 | 4 |
| 7 | N-[3-(4-Amino-7-cyclopentyl-7H-pyrrolo[2,3-d]pyrimidine-5-carbonyl)-phenyl]-2,6-difluoro-benzenesulfonamide | 498.0 | 5.68 | 4 |
| 8 | N-[3-(4-Amino-7-cyclopentyl-7H-pyrrolo[2,3-d]pyrimidine-5-carbonyl)-phenyl]-2,6-dichloro-benzenesulfonamide | 530.0 | 6.12 | 4 |
| 9 | N-[3-(4-Amino-7-cyclopentyl-7H-pyrrolo[2,3-d]pyrimidine-5-carbonyl)-phenyl]-2-chloro-4-fluoro-benzenesulfonamide | 514.1/516.1 | 6.12 | 4 |
| 10 | N-[3-(4-Amino-7-cyclopentyl-7H-pyrrolo[2,3-d]pyrimidine-5-carbonyl)-phenyl]-2,3-dichloro-benzenesulfonamide | 530.0/531.9 | 6.16 | 4 |
| 11 | N-[3-(4-Amino-7-cyclopentyl-7H-pyrrolo[2,3-d]pyrimidine-5-carbonyl)-phenyl]-2-chloro-6-methyl-benzenesulfonamide | 510.0/512.1 | 6.10 | 4 |

-continued

| Example | Compound Name | MH+ | HPLC Rf (min) | method |
|---|---|---|---|---|
| 12 | N-[3-(4-Amino-7-cyclopentyl-7H-pyrrolo[2,3-d]pyrimidine-5-carbonyl)-phenyl]-methanesulfonamide | 400.1 | 4.62 | 4 |
| 13 | N-[2-(4-Amino-7-cyclopentyl-7H-pyrrolo[2,3-d]pyrimidine-5-carbonyl)-phenyl]-2,3-dichloro-benzenesulfonamide | 530.0/532.1 | 6.18 | 4 |
| 14 | N-[2-(4-Amino-7-cyclopentyl-7H-pyrrolo[2,3-d]pyrimidine-5-carbonyl)-phenyl]-2-chloro-benzenesulfonamide | 496.1/498.1 | 6.04 | 4 |
| 15 | N-[4-(4-Amino-7-cyclopentyl-7H-pyrrolo[2,3-d]pyrimidine-5-carbonyl)-phenyl]-2,4-difluoro-benzenesulfonamide | 498.1 | 5.65 | 4 |
| 16 | N-[4-(4-Amino-7-cyclopentyl-7H-pyrrolo[2,3-d]pyrimidine-5-carbonyl)-phenyl]-2,6-difluoro-benzenesulfonamide | 498.1 | 5.32 | 4 |
| 17 | N-[4-(4-Amino-7-cyclopentyl-7H-pyrrolo[2,3-d]pyrimidine-5-carbonyl)-phenyl]-2-chloro-4-fluoro-benzenesulfonamide | 514.0/516.1 | 5.89 | 4 |
| 18 | N-[4-(4-Amino-7-cyclopentyl-7H-pyrrolo[2,3-d]pyrimidine-5-carbonyl)-phenyl]-2,3-dichloro-benzenesulfonamide | 529.9/531.8 | 5.95 | 4 |
| 19 | N-[4-(4-Amino-7-cyclopentyl-7H-pyrrolo[2,3-d]pyrimidine-5-carbonyl)-phenyl]-2-chloro-benzenesulfonamide | 496/498; 322.2 | 5.66 | 4 |
| 20 | N-[4-(4-Amino-7-cyclopentyl-7H-pyrrolo[2,3-d]pyrimidine-5-carbonyl)-phenyl]-methanesulfonamide | 400.2 | 4.57 | 4 |
| 21 | N-{3-[3-(4-Amino-7-cyclopentyl-7H-pyrrolo[2,3-d]pyrimidine-5-carbonyl)-phenyl]-prop-2-ynyl}-methanesulfonamide | 438.1 | 5.15 | 4 |
| 22 | N-{3-[3-(4-Amino-7-cyclopentyl-7H-pyrrolo[2,3-d]pyrimidine-5-carbonyl)-phenyl]-prop-2-ynyl}-benzenesulfonamide | 500.2 | 6.05 | 4 |
| 23 | N-{3-[3-(4-Amino-7-cyclopentyl)-7H-pyrrolo[2,3-d]pyrimidine-5-carbonyl)-phenyl]-prop-2-ynyl}-2,3-dichloro-benzenesulfonamide | 567.9/569.8 | 6.50 | 4 |
| 24 | 5-Bromo-6-chloro-pyridine-3-sulfonic acid [3-(4-amino-7-cyclopentyl-7H-pyrrolo[2,3-d]pyrimidine-5-carbonyl)-phenyl]-amide | 574.9/576.8 | 5.86 | 4 |

EXAMPLE 25

1-[3-(4-Amino-7-cyclopentyl-7H-pyrrolo[23-d]pyrimidine-5-carbonyl)-phenyl]-3-(2,6-difluoro-phenyl)-urea 2,6-Difluorophenyl isocyanate (36.1 mg, 0.233 mmol) was added to a solution of (4-Amino-7-cyclopentyl-7H-pyrrolo[2,3-d]pyrimidin-5-yl)-(3-amino-phenyl)-methanone (50 mg, 0.15 mol) in pyridine (3 mL). The resulting solution was heated to 90° C. for 3 h. The reaction was quenched with water and concentrated. The residue was dissolved in EtOAc and washed with water. The organic layer was dried over $Na_2SO_4$ and concentrated. Purification by flash column chromatography ($CH_2Cl_2$/MeOH 98:2) afforded the title compound as a yellow solid (21 mg, 28%). MS: 477.2/322.2 (MH+); HPLC Rf: 5.66 min. (HPLC method

EXAMPLES 26-38

Examples 26-38 listed in the following table were prepared using procedures analogous to those described in Example 25.

| Example | Compound Name | MH+ | HPLC Rf (min) | method |
|---|---|---|---|---|
| 26 | 1-[3-(4-Amino-7-cyclopentyl-7H-pyrrolo[2,3-d]pyrimidine-5-carbonyl)-phenyl]-3-(2,4-difluoro-phenyl)-urea | 477.1/322.2 | 6.41 | 4 |
| 27 | 1-[3-(4-Amino-7-cyclopentyl-7H-pyrrolo[2,3-d]pyrimidine-5-carbonyl)-phenyl]-3-(2-chloro-phenyl)-urea | 475.1/477.2 | 6.78 | 4 |
| 28 | 1-[3-(4-Amino-7-cyclopentyl-7H-pyrrolo[2,3-d]pyrimidine-5-carbonyl)-phenyl]-3-(2,6-difluoro-phenyl)-urea | 477.2/322.2 | 5.66 | 4 |

-continued

| Example | Compound Name | MH+ | HPLC Rf (min) | method |
|---|---|---|---|---|
| 29 | 1-[3-(4-Amino-7-cyclopentyl-7H-pyrrolo[2,3-d]pyrimidine-5-carbonyl)-phenyl]-3-ethyl-urea | 393.2/322.2 | 4.64 | 4 |
| 30 | 1-[3-(4-Amino-7-cyclopentyl-7H-pyrrolo[2,3-d]pyrimidine-5-carbonyl)-phenyl]-3-(2,6-dichloro-pyridin-4-yl)-urea | 510.0 | 6.42 | 4 |
| 31 | 1-[2-(4-Amino-7-cyclopentyl-7H-pyrrolo[2,3-d]pyrimidine-5-carbonyl)-phenyl]-3-(2-chloro-phenyl)-urea | 475.2/477.2; 322.2 | 6.12 | 4 |
| 32 | 1-[2-(4-Amino-7-cyclopentyl-7H-pyrrolo[2,3-d]pyrimidine-5-carbonyl)-phenyl]-3-(2,4-difluoro-phenyl)-urea | 477.1/322.1 | 6.13 | 4 |
| 33 | 1-[4-(4-Amino-7-cyclopentyl-7H-pyrrolo[2,3-d]pyrimidine-5-carbonyl)-phenyl]-3-(2-chloro-phenyl)-urea | 475.1/477.1 | 6.36 | 4 |
| 34 | 1-[4-(4-Amino-7-cyclopentyl-7H-pyrrolo[2,3-d]pyrimidine-5-carbonyl)-phenyl]-3-(2,6-difluoro-phenyl)-urea | 477.2/322.3 | 5.44 | 4 |
| 35 | 1-[4-(4-Amino-7-cyclopentyl-7H-pyrrolo[2,3-d]pyrimidine-5-carbonyl)-phenyl]-3-(2,4-difluoro-phenyl)-urea | 477.2/322.3 | 6.06 | 4 |
| 36 | 1-[4-(4-Amino-7-cyclopentyl-7H-pyrrolo[2,3-d]pyrimidine-5-carbonyl)-phenyl]-3-(2-chloro-6-methyl-phenyl)-urea | 489.1/491.2; 322.2 | 5.88 | 4 |
| 37 | 1-{3-[3-(4-Amino-7-cyclopentyl-7H-pyrrolo[2,3-d]pyrimidine-5-carbonyl)-phenyl]-prop-2-ynyl}-3-ethyl-urea | 431.2 | 4.81 | 4 |
| 38 | 1-{3-[3-(4-Amino-7-cyclopentyl-7H-pyrrolo[2,3-d]pyrimidine-5-carbonyl)-phenyl]-prop-2-ynyl}-3-(2-chloro-phenyl)-urea | 513.1/515.1 | 6.32 | 4 |

EXAMPLE 39

N-[3-(4-Amino-7-cyclopentyl-7H-pyrrolo[2,3-d]pyrimidine-5-carbonyl)-phenyl]-2,6-difluoro-benzamide 2,6-difluorobenzoyl chloride (82.1 mg, 0.47 mmol) was added to a solution of (4-Amino-7-cyclopentyl-7H-pyrrolo[2,3-d]pyrimidin-5-yl)-(3-amino-phenyl)-methanone (100 mg, 0.31 mol) in pyridine (3 mL). The resulting solution was heated to 120° C. for 1 h at this time the reaction was quenched with water and concentrated. The residue was dissolved in EtOAc and washed with 1N NaOH and water. The organic layer was dried over $Na_2SO_4$ and concentrated. Purification by flash column chromatography ($CH_2Cl_2$/MeOH 97:3) afforded the title compound as a white solid (105 mg, 73%). MS: 462.2 (MH+); HPLC Rf: 5.70 min. (HPLC method 4).

EXAMPLES 40-47

Examples 40-47 listed in the following table were prepared using procedures analogous to those described in Example 39.

| Example | Compound Name | MH+ | HPLC Rf (min) | method |
|---|---|---|---|---|
| 40 | N-[3-(4-Amino-7-cyclopentyl-7H-pyrrolo[2,3-d]pyrimidine-5-carbonyl)-phenyl]-2,4-difluoro-benzamide | 462.1 | 6.27 | 4 |
| 41 | N-[3-(4-Amino-7-cyclopentyl-7H-pyrrolo[2,3-d]pyrimidine-5-carbonyl)-phenyl]-2-chloro-benzamide | 460.1/462.1 | 6.08 | 4 |
| 42 | N-[3-(4-Amino-7-cyclopentyl-7H-pyrrolo[2,3-d]pyrimidine-5-carbonyl)-phenyl]-2,6-difluoro-benzamide | 462.2 | 5.70 | 4 |
| 43 | N-[2-(4-Amino-7-cyclopentyl-7H-pyrrolo[2,3-d]pyrimidine-5-carbonyl)-phenyl]-2-chloro-benzamide | 460.1/462.1 | 5.86 | 4 |
| 44 | N-[4-(4-Amino-7-cyclopentyl-7H-pyrrolo[2,3-d]pyrimidine-5-carbonyl)-phenyl]-2-chloro-benzamide | 460.1/462.1; 322.2 | 5.89 | 4 |
| 45 | N-[4-(4-Amino-7-cyclopentyl-7H-pyrrolo[2,3-d]pyrimidine-5-carbonyl)-phenyl]-2,6-difluoro-benzamide | 462.1/322.2 | 5.11 | 4 |

-continued

| Example | Compound Name | MH+ | HPLC Rf (min) | method |
|---|---|---|---|---|
| 46 | N-[4-(4-Amino-7-cyclopentyl-7H-pyrrolo[2,3-d]pyrimidine-5-carbonyl)-phenyl]-2,4-difluoro-benzamide | 461.9 | 6.02 | 4 |
| 47 | N-{3-[3-(4-Amino-7-cyclopentyl-7H-pyrrolo[2,3-d]pyrimidine-5-carbonyl)-phenyl]-prop-2-ynyl}-acetamide | 402.2 | 4.65 | 4 |

EXAMPLE 48

(4-Amino-7-cyclopentyl-7H-pyrrolo[2,3-d]pyrimidin-5-yl)-[3-(2,5-difluoro-benzylamino)-phenyl]-methanone 2,5-difluorobenzaldehyde (88.1 mg, 0.62 mmol) was added to a solution of (4-Amino-7-cyclopentyl-7H-pyrrolo[2,3-d]pyrimidin-5-yl)-(3-amino-phenyl)-methanone (100 mg, 0.31 mmol) and AcOH (18.6 mg, 0.31 mmol) in MeOH (10 mL). After 5 min NaCNBH$_3$ was added. After 3 h the reaction was quenched with 1N NaOH. The aqueous layer was extracted with EtOAc (2×). The combined organic layers were washed with water, dried over MgSO$_4$, and concentrated. Purification by flash column chromatography (CH$_2$Cl$_2$/MeOH 98:2) afforded the title compound as a white solid (80 mg, 58%). MS: 448.1 (MH+); HPLC Rf: 6.59 min. (HPLC method 4).

EXAMPLES 49-56

Examples 49-56 listed in the following table were prepared using procedures analogous to those described in Example 48.

EXAMPLE 57

N-[3-(4-Amino-7-cyclopentyl-7H-pyrrolo[2,3-d]pyrimidine-5-carbonyl)-phenyl]-2-chloro-sulfonamide To a mixture of 0.062 mmole of the substrate and 400 uL pyridine was added 0.093 to 0.186 mole of a sulfonyl chloride. The resulting mixture was shaken at 100° C. for 2 to 14 hours. Pyridine was removed in vaccu and the residue dissolved in 2 mL of DMSO and purified using reverse phase preparative HPLC to furnish the title compound as an off whit solid (18 mg, 59%). MS: 496.2 (MH+); HPLC Rf: 1.9 min. (HPLC method 2).

EXAMPLES 58-132

Examples 58-132 listed in the following table were prepared using procedures analogous to those described in Example 57.

| Example | Compound Name | MH+ | HPLC Rf (min) | method |
|---|---|---|---|---|
| 49 | (4-Amino-7-cyclopentyl-7H-pyrrolo[2,3-d]pyrimidin-5-yl)-[3-(2,6-difluoro-benzylamino)-phenyl]-methanone | 448.1 | 6.59 | 4 |
| 50 | (4-Amino-7-cyclopentyl-7H-pyrrolo[2,3-d]pyrimidin-5-yl)-[3-(2,5-difluoro-benzylamino)-phenyl]-methanone | 448.1 | 6.58 | 4 |
| 51 | (4-Amino-7-cyclopentyl-7H-pyrrolo[2,3-d]pyrimidin-5-yl)-[3-(2-chloro-benzylamino)-phenyl]-methanone | 446.1/448.1 | 6.94 | 4 |
| 52 | (4-Amino-7-cyclopentyl-7H-pyrrolo[2,3-d]pyrimidin-5-yl)-[2-(2-chloro-benzylamino)-phenyl]-methanone | 446.2/448.2 | 7.80 | 4 |
| 53 | (4-Amino-7-cyclopentyl-7H-pyrrolo[2,3-d]pyrimidin-5-yl)-[2-(2,5-difluoro-benzylamino)-phenyl]-methanone | 448.1 | 7.32 | 4 |
| 54 | (4-Amino-7-cyclopentyl-7H-pyrrolo[2,3-d]pyrimidin-5-yl)-[4-(2,5-difluoro-benzylamino)-phenyl]-methanone | 448.1 | 6.48 | 4 |
| 55 | (4-Amino-7-cyclopentyl-7H-pyrrolo[2,3-d]pyrimidin-5-yl)-[4-(2-chloro-benzylamino)-phenyl]-methanone | 446.1/448.1 | 6.86 | 4 |
| 56 | (4-Amino-7-cyclopentyl-7H-pyrrolo[2,3-d]pyrimidin-5-yl)-[4-(2,6-difluoro-benzylamino)-phenyl]-methanone | 448.1 | 6.48 | 4 |

|  |  |  | HPLC | |
|---|---|---|---|---|
| Example | Compound Name | MS | Rf (min) | method |
| 58 | N-[3-(4-Amino-7-cyclopentyl-7H-pyrrolo[2,3-d]pyrimidine-5-carbonyl)-phenyl]-C-methanesulfonyl-methanesulfonamide | 477.2 | 1.5 | 2 |
| 59 | N-[3-(4-Amino-7-cyclopentyl-7H-pyrrolo[2,3-d]pyrimidine-5-carbonyl)-phenyl]-2-trifluoromethyl-benzenesulfonamide | 529.2 | 2.0 | 2 |
| 60 | N-[3-(4-Amino-7-cyclopentyl-7H-pyrrolo[2,3-d]pyrimidine-5-carbonyl)-phenyl]-4-ethyl-benzenesulfonamide | 489.2 | 2.5 | 2 |
| 61 | N-[3-(4-Amino-7-cyclopentyl-7H-pyrrolo[2,3-d]pyrimidine-5-carbonyl)-phenyl]-5-chloro-2-methoxy-benzenesulfonamide | 525.2 | 2.5 | 2 |
| 62 | N-[3-(4-Amino-7-cyclopentyl-7H-pyrrolo[2,3-d]pyrimidine-5-carbonyl)-phenyl]-C-(3,5-dichloro-phenyl)-methanesulfonamide | 543.2 | 2.6 | 2 |
| 63 | N-[3-(4-Amino-7-cyclopentyl-7H-pyrrolo[2,3-d]pyrimidine-5-carbonyl)-phenyl]-C-(3,4-dichloro-phenyl)-methanesulfonamide | 543.2 | 2.5 | 2 |
| 64 | N-[3-(4-Amino-7-cyclopentyl-7H-pyrrolo[2,3-d]pyrimidine-5-carbonyl)-phenyl]-2-trifluoromethoxy-benzenesulfonamide | 545.2 | 2.5 | 2 |
| 65 | N-[3-(4-Amino-7-cyclopentyl-7H-pyrrolo[2,3-d]pyrimidine-5-carbonyl)-phenyl]-3-trifluoromethoxy-benzenesulfonamide | 545.3 | 2.6 | 2 |
| 66 | N-[3-(4-Amino-7-cyclopentyl-7H-pyrrolo[2,3-d]pyrimidine-5-carbonyl)-phenyl]-4-phenoxy-benzenesulfonamide | 553.4 | 2.7 | 2 |
| 67 | N-[3-(4-Amino-7-cyclopentyl-7H-pyrrolo[2,3-d]pyrimidine-5-carbonyl)-phenyl]-3-phenoxy-benzenesulfonamide | 553.3 | 2.6 | 2 |
| 68 | 5-Dimethylamino-naphthalene-1-sulfonic acid [3-(4-amino-7-cyclopentyl-7H-pyrrolo[2,3-d]pyrimidine-5-carbonyl)-phenyl]-amide | 554.4 | 2.6 | 2 |
| 69 | 5-Chloro-3-methyl-benzo[b]thiophene-2-sulfonic acid [3-(4-amino-7-cyclopentyl-7H-pyrrolo[2,3-d]pyrimidine-5-carbonyl)-phenyl]-amide | 565.2 | 2.8 | 2 |
| 70 | N-[3-(4-Amino-7-cyclopentyl-7H-pyrrolo[2,3-d]pyrimidine-5-carbonyl)-phenyl]-3-(pyridin-2-yloxy)-benzenesulfonamide | 554.4 | 2.4 | 2 |
| 71 | N-[3-(4-Amino-7-cyclopentyl-7H-pyrrolo[2,3-d]pyrimidine-5-carbonyl)-phenyl]-4-(pyridin-4-yloxy)-benzenesulfonamide | 554.4 | 2.0 | 2 |
| 72 | 4-Benzenesulfonyl-thiophene-2-sulfonic acid [3-(4-amino-7-cyclopentyl-7H-pyrrolo[2,3-d]pyrimidine-5-carbonyl)-phenyl]-amide | 607.3 | 2.5 | 2 |
| 73 | 5-Benzenesulfonyl-thiophene-2-sulfonic acid [3-(4-amino-7-cyclopentyl-7H-pyrrolo[2,3-d]pyrimidine-5-carbonyl)-phenyl]-amide | 607.3 | 2.5 | 2 |
| 74 | 2-Trifluoroacetyl-1,2,3,4-tetrahydro-isoquinoline-7-sulfonic acid [3-(4-amino-7-cyclopentyl-7H-pyrrolo[2,3-d]pyrimidine-5-carbonyl)-phenyl]-amide | 612.4 | 2.4 | 2 |
| 75 | N-[3-(4-Amino-7-cyclopentyl-7H-pyrrolo[2,3-d]pyrimidine-5-carbonyl)-phenyl]-4-(pyridin-3-yloxy)-benzenesulfonamide | 554.4 | 2.3 | 2 |
| 76 | N-[3-(4-Amino-7-cyclopentyl-7H-pyrrolo[2,3-d]pyrimidine-5-carbonyl)-phenyl]-2-cyano-benzenesulfonamide | 486.2 | 1.8 | 2 |
| 77 | N-[3-(4-Amino-7-cyclopentyl-7H-pyrrolo[2,3-d]pyrimidine-5-carbonyl)-phenyl]-2,5-dimethyl-benzenesulfonamide | 489.2 | 2.5 | 2 |
| 78 | N-[3-(4-Amino-7-cyclopentyl-7H-pyrrolo[2,3-d]pyrimidine-5-carbonyl)-phenyl]-4-methoxy-benzenesulfonamide | 491.1 | 2.3 | 2 |
| 79 | N-[3-(4-Amino-7-cyclopentyl-7H-pyrrolo[2,3-d]pyrimidine-5-carbonyl)-phenyl]-3,4-dimethoxy-benzenesulfonamide | 521.4 | 2.2 | 2 |
| 80 | N-[3-(4-Amino-7-cyclopentyl-7H-pyrrolo[2,3-d]pyrimidine-5-carbonyl)-phenyl]-4-methanesulfonyl-benzenesulfonamide | 539.3 | 2.1 | 2 |
| 81 | N-[3-(4-Amino-7-cyclopentyl-7H-pyrrolo[2,3-d]pyrimidine-5-carbonyl)-phenyl]-2-methoxy-4-methyl-benzenesulfonamide | 505.3 | 2.3 | 2 |

-continued

| Example | Compound Name | MS | HPLC Rf (min) | method |
|---|---|---|---|---|
| 82 | N-[3-(4-Amino-7-cyclopentyl-7H-pyrrolo[2,3-d]pyrimidine-5-carbonyl)-phenyl]-2-methanesulfonyl-benzenesulfonamide | 539.3 | 2.3 | 2 |
| 83 | N-[3-(4-Amino-7-cyclopentyl-7H-pyrrolo[2,3-d]pyrimidine-5-carbonyl)-phenyl]-5-fluoro-2-methyl-benzenesulfonamide | 493.4 | 2.4 | 2 |
| 84 | N-[3-(4-Amino-7-cyclopentyl-7H-pyrrolo[2,3-d]pyrimidine-5-carbonyl)-phenyl]-3-fluoro-4-methoxy-benzenesulfonamide | 509.3 | 2.4 | 2 |
| 85 | N-[3-(4-Amino-7-cyclopentyl-7H-pyrrolo[2,3-d]pyrimidine-5-carbonyl)-phenyl]-3-trifluoromethyl-benzenesulfonamide | 529.3 | 2.5 | 2 |
| 86 | N-[3-(4-Amino-7-cyclopentyl-7H-pyrrolo[2,3-d]pyrimidine-5-carbonyl)-phenyl]-C-(4-fluoro-phenyl)-methanesulfonamide | 493.4 | 2.3 | 2 |
| 87 | N-[3-(4-Amino-7-cyclopentyl-7H-pyrrolo[2,3-d]pyrimidine-5-carbonyl)-phenyl]-3-chloro-2-methyl-benzenesulfonamide | 509.2 | 2.6 | 2 |
| 88 | N-[3-(4-Amino-7-cyclopentyl-7H-pyrrolo]2,3-d]pyrimidine-5-carbonyl)-phenyl]-4-trifluoromethyl-benzenesulfonamide | 529.3 | 2.6 | 2 |
| 89 | 1,3,5-Trimethyl-1H-pyrazole-4-sulfonic acid [3-(4-amino-7-cyclopentyl-7H-pyrrolo[2,3-d]pyrimidine-5-carbonyl)-phenyl]-amide | 493.4 | 2.1 | 2 |
| 90 | N-[3-(4-Amino-7-cyclopentyl-7H-pyrrolo[2,3-d]pyrimidine-5-carbonyl)-phenyl]-3-chloro-4-methyl-benzenesulfonamide | 509.3 | 2.6 | 2 |
| 91 | N-[3-(4-Amino-7-cyclopentyl-7H-pyrrolo[2,3-d]pyrimidine-5-carbonyl)-phenyl]-3-chloro-benzenesulfonamide | 495.1 | 2.5 | 2 |
| 92 | Naphthalene-1-sulfonic acid [3-(4-amino-7-cyclopentyl-7H-pyrrolo[2,3-d]pyrimidine-5-carbonyl)-phenyl]-amide | 511.3 | 2.5 | 2 |
| 93 | 2-Oxo-2H-chromene-6-sulfonic acid [3-(4-amino-7-cyclopentyl-7H-pyrrolo[2,3-d]pyrimidine-5-carbonyl)-phenyl]-amide | 529.3 | 2.2 | 2 |
| 94 | N-[3-(4-Amino-7-cyclopentyl-7H-pyrrolo[2,3-d]pyrimidine-5-carbonyl)-phenyl]-3,5-difluoro-benzenesulfonamide | 497.1 | 2.5 | 2 |
| 95 | Naphthalene-2-sulfonic acid [3-(4-amino-7-cyclopentyl-7H-pyrrolo[2,3-d]pyrimidine-5-carbonyl)-phenyl]-amide | 511.3 | 2.5 | 2 |
| 96 | N-[3-(4-Amino-7-cyclopentyl-7H-pyrrolo[2,3-d]pyrimidine-5-carbonyl)-phenyl]-2,5-difluoro-benzenesulfonamide | 497.3 | 2.4 | 2 |
| 97 | Quinoline-8-sulfonic acid [3-(4-amino-7-cyclopentyl-7H-pyrrolo[2,3-d]pyrimidine-5-carbonyl)-phenyl]-amide | 512.3 | 2.3 | 2 |
| 98 | N-[3-(4-Amino-7-cyclopentyl-7H-pyrrolo[2,3-d]pyrimidine-5-carbonyl)-phenyl]-3,4-dichloro-benzenesulfonamide | 529.3 | 2.6 | 2 |
| 99 | N-[3-(4-Amino-7-cyclopentyl-7H-pyrrolo[2,3-d]pyrimidine-5-carbonyl)-phenyl]-3,4-difluoro-benzenesulfonamide | 497.3 | 2.4 | 2 |
| 100 | Isoquinoline-5-sulfonic acid [3-(4-amino-7-cyclopentyl-7H-pyrrolo[2,3-d]pyrimidine-5-carbonyl)-phenyl]-amide | 512.3 | 2.2 | 2 |
| 101 | N-[3-(4-Amino-7-cyclopentyl-7H-pyrrolo[2,3-d]pyrimidine-5-carbonyl)-phenyl]-3,5-dichloro-benzenesulfonamide | 529.3 | 2.7 | 2 |
| 102 | 5-Chloro-thiophene-2-sulfonic acid [3-(4-amino-7-cyclopentyl-7H-pyrrolo[2,3-d]pyrimidine-5-carbonyl)-phenyl]-amide | 501.3 | 2.5 | 2 |
| 103 | N-[3-(4-Amino-7-cyclopentyl-7H-pyrrolo[2,3-d]pyrimidine-5-carbonyl)-phenyl]-3-chloro-4-fluoro-benzenesulfonamide | 513.3 | 2.5 | 2 |
| 104 | N-[3-(4-Amino-7-cyclopentyl-7H-pyrrolo[2,3-d]pyrimidine-5-carbonyl)-phenyl]-2,4-dichloro-benzenesulfonamide | 529.3 | 2.6 | 2 |
| 105 | 4-Acetyl-N-[3-(4-amino-7-cyclopentyl-7H-pyrrolo[2,3-d]pyrimidine-5-carbonyl)-phenyl]-benzenesulfonamide | 503.3 | 2.3 | 2 |
| 106 | N-{4-[3-(4-Amino-7-cyclopentyl-7H-pyrrolo[2,3-d]pyrimidine-5-carbonyl)-phenylsulfamoyl]-phenyl}-acetamide | 518.3 | 2.1 | 2 |

-continued

| Example | Compound Name | MS | HPLC Rf (min) | method |
|---|---|---|---|---|
| 107 | Biphenyl-4-sulfonic acid [3-(4-amino-7-cyclopentyl-7H-pyrrolo[2,3-d]pyrimidine-5-carbonyl)-phenyl]-amide | 537.4 | 2.7 | 2 |
| 108 | N-[3-(4-Amino-7-cyclopentyl-7H-pyrrolo[2,3-d]pyrimidine-5-carbonyl)-phenyl]-4-propyl-benzenesulfonamide | 503.4 | 2.6 | 2 |
| 109 | N-[3-(4-Amino-7-cyclopentyl-7H-pyrrolo[2,3-d]pyrimidine-5-carbonyl)-phenyl]-2,5-dimethoxy-benzenesulfonamide | 521.3 | 2.3 | 2 |
| 110 | Biphenyl-3-sulfonic acid [3-(4-amino-7-cyclopentyl-7H-pyrrolo[2,3-d]pyrimidine-5-carbonyl)-phenyl]-amide | 537.4 | 2.7 | 2 |
| 111 | N-[3-(4-Amino-7-cyclopentyl-7H-pyrrolo[2,3-d]pyrimidine-5-carbonyl)-phenyl]-4-trifluoromethoxy-benzenesulfonamide | 545.1 | 2.6 | 2 |
| 112 | N-[3-(4-Amino-7-cyclopentyl-7H-pyrrolo[2,3-d]pyrimidine-5-carbonyl)-phenyl]-4-isopropyl-benzenesulfonamide | 503.3 | 2.6 | 2 |
| 113 | Ethanesulfonic acid [3-(4-amino-7-cyclopentyl-7H-pyrrolo[2,3-d]pyrimidine-5-carbonyl)-phenyl]-amide | 413.2 | 2.0 | 2 |
| 114 | 1,2-Dimethyl-1H-imidazole-4-sulfonic acid [3-(4-amino-7-cyclopentyl-7H-pyrrolo[2,3-d]pyrimidine-5-carbonyl)-phenyl]-amide | 479.3 | 1.9 | 2 |
| 115 | Propane-2-sulfonic acid [3-(4-amino-7-cyclopentyl-7H-pyrrolo[2,3-d]pyrimidine-5-carbonyl)-phenyl]-amide | 427.3 | 2.1 | 2 |
| 116 | 3,5-Dimethyl-isoxazole-4-sulfonic acid [3-(4-amino-7-cyclopentyl-7H-pyrrolo[2,3-d]pyrimidine-5-carbonyl)-phenyl]-amide | 480.3 | 2.3 | 2 |
| 117 | Propane-1-sulfonic acid [3-(4-amino-7-cyclopentyl-7H-pyrrolo[2,3-d]pyrimidine-5-carbonyl)-phenyl]-amide | 427.3 | 2.1 | 2 |
| 118 | N-[3-(4-Amino-7-cyclopentyl-7H-pyrrolo[2,3-d]pyrimidine-5-carbonyl)-phenyl]-4-cyano-benzenesulfonamide | 486.3 | 2.3 | 2 |
| 119 | N-[3-(4-Amino-7-cyclopentyl-7H-pyrrolo[2,3-d]pyrimidine-5-carbonyl)-phenyl]-benzenesulfonamide | 461.2 | 2.3 | 2 |
| 120 | N-[3-(4-Amino-7-cyclopentyl-7H-pyrrolo[2,3-d]pyrimidine-5-carbonyl)-phenyl]-3-cyano-benzenesulfonamide | 486.3 | 2.3 | 2 |
| 121 | 1-Methyl-1H-imidazole-4-sulfonic acid [3-(4-amino-7-cyclopentyl-7H-pyrrolo[2,3-d]pyrimidine-5-carbonyl)-phenyl]-amide | 465.3 | 1.9 | 2 |
| 122 | 2-Phenyl-ethenesulfonic acid [3-(4-amino-7-cyclopentyl-7H-pyrrolo[2,3-d]pyrimidine-5-carbonyl)-phenyl]-amide | 487.4 | 2.4 | 2 |
| 123 | Thiophene-2-sulfonic acid [3-(4-amino-7-cyclopentyl-7H-pyrrolo[2,3-d]pyrimidine-5-carbonyl)-phenyl]-amide | 467.2 | 2.2 | 2 |
| 124 | N-[3-(4-Amino-7-cyclopentyl-7H-pyrrolo[2,3-d]pyrimidine-5-carbonyl)-phenyl]-4-vinyl-benzenesulfonamide | 487.3 | 2.5 | 2 |
| 125 | N-[3-(4-Amino-7-cyclopentyl-7H-pyrrolo[2,3-d]pyrimidine-5-carbonyl)-phenyl]-4-methyl-benzenesulfonamide | 475.3 | 2.3 | 2 |
| 126 | N-[3-(4-Amino-7-cyclopentyl-7H-pyrrolo[2,3-d]pyrimidine-5-carbonyl)-phenyl]-C-phenyl-methanesulfonamide | 475.4 | 2.3 | 2 |
| 127 | N-[3-(4-Amino-7-cyclopentyl-7H-pyrrolo[2,3-d]pyrimidine-5-carbonyl)-phenyl]-2-methyl-benzenesulfonamide | 475.3 | 2.4 | 2 |
| 128 | N-[3-(4-Amino-7-cyclopentyl-7H-pyrrolo[2,3-d]pyrimidine-5-carbonyl)-phenyl]-3-methyl-benzenesulfonamide | 475.2 | 2.4 | 2 |
| 129 | N-[3-(4-Amino-7-cyclopentyl-7H-pyrrolo[2,3-d]pyrimidine-5-carbonyl)-phenyl]-4-fluoro-benzenesulfonamide | 479.3 | 2.4 | 2 |
| 130 | N-[3-(4-Amino-7-cyclopentyl-7H-pyrrolo[2,3-d]pyrimidine-5-carbonyl)-phenyl]-2-fluoro-benzenesulfonamide | 479.2 | 2.3 | 2 |
| 131 | N-[3-(4-Amino-7-cyclopentyl-7H-pyrrolo[2,3-d]pyrimidine-5-carbonyl)-phenyl]-3-fluoro-benzenesulfonamide | 479.2 | 2.3 | 2 |

| | | | HPLC | |
|---|---|---|---|---|
| Example | Compound Name | MS | Rf (min) | method |
| 132 | N-[3-(4-Amino-7-cyclopentyl-7H-pyrrolo[2,3-d]pyrimidine-5-carbonyl)-phenyl]-4-chloro-benzenesulfonamide | 495.2 | 2.5 | 2 |

EXAMPLE 133

1-[3-(4-Amino-7-cyclopentyl-7H-Pyrrolo[2,3-d]pyrimidine-5-carbonyl)-phenyl]-3-(2,4-dichloro-benzyl)-urea To a mixture of 0.062 mmole of the substrate and 500 uL pyridine was added 0.075 mmole of an isocyanate. The resulting mixture was shaken at 80° C. for 2 to 3 hours. Pyridin was removed in vacu and the residue dissolved in 2 mL of DMSO and purified using reverse phase preparative HPLC to furnish the title compound as an off white solid (21 mg, 65%). MS: 498 (MH+); HPLC Rf: 2.4 min. (HPLC method 2).

EXAMPLES 134-226

Examples 134-226 listed in the following table were prepared using procedures analogous to those described in Example 133.

| | | | HPLC | |
|---|---|---|---|---|
| Example | Compound Name | MS | Rf (min) | method |
| 134 | 1-[3-(4-Amino-7-cyclopentyl-7H-pyrrolo[2,3-d]pyrimidine-5-carbonyl)-phenyl]-3-cyclopentyl-urea | 432.3 | 2.2 | 2 |
| 135 | 1-[3-(4-Amino-7-cyclopentyl-7H-pyrrolo[2,3-d]pyrimidine-5-carbonyl)-phenyl]-3-thiophen-2-yl-urea | 446.2 | 2.3 | 2 |
| 136 | 1-[3-(4-Amino-7-cyclopentyl-7H-pyrrolo[2,3-d]pyrimidine-5-carbonyl)-phenyl]-3-(4-cyano-phenyl)-urea | 465.3 | 2.4 | 2 |
| 137 | 1-[3-(4-Amino-7-cyclopentyl-7H-pyrrolo[2,3-d]pyrimidine-5-carbonyl)-phenyl]-3-(4-methoxy-phenyl)-urea | 470.3 | 1.8 | 2 |
| 138 | 1-[3-(4-Amino-7-cyclopentyl-7H-pyrrolo[2,3-d]pyrimidine-5-carbonyl)-phenyl]-3-(2-ethyl-6-methyl-phenyl)-urea | 482.3 | 2.0 | 2 |
| 139 | 1-[3-(4-Amino-7-cyclopentyl-7H-pyrrolo[2,3-d]pyrimidine-5-carbonyl)-phenyl]-3-(2-isopropyl-phenyl)-urea | 482.3 | 2.9 | 3 |
| 140 | 1-[3-(4-Amino-7-cyclopentyl-7H-pyrrolo[2,3-d]pyrimidine-5-carbonyl)-phenyl]-3-phenyl-urea | 440.2 | 2.9 | 3 |
| 141 | 1-[3-(4-Amino-7-cyclopentyl-7H-pyrrolo[2,3-d]pyrimidine-5-carbonyl)-phenyl]-3-thiophen-3-yl-urea | 446.2 | 2.7 | 3 |
| 142 | 1-[3-(4-Amino-7-cyclopentyl-7H-pyrrolo[2,3-d]pyrimidine-5-carbonyl)-phenyl]-3-p-tolyl-urea | 454.3 | 2.8 | 3 |
| 143 | 1-[3-(4-Amino-7-cyclopentyl-7H-pyrrolo[2,3-d]pyrimidine-5-carbonyl)-phenyl]-3-m-tolyl-urea | 454.3 | 2.8 | 3 |
| 144 | 1-[3-(4-Amino-7-cyclopentyl-7H-pyrrolo[2,3-d]pyrimidine-5-carbonyl)-phenyl]-3-benzyl-urea | 454.3 | 2.7 | 3 |
| 145 | 1-[3-(4-Amino-7-cyclopentyl-7H-pyrrolo[2,3-d]pyrimidine-5-carbonyl)-phenyl]-3-(2-fluoro-phenyl)-urea | 458.3 | 2.8 | 3 |
| 146 | 1-[3-(4-Amino-7-cyclopentyl-7H-pyrrolo[2,3-d]pyrimidine-5-carbonyl)-phenyl]-3-(3-fluoro-phenyl)-urea | 458.3 | 2.8 | 3 |
| 147 | 1-[3-(4-Amino-7-cyclopentyl-7H-pyrrolo[2,3-d]pyrimidine-5-carbonyl)-phenyl]-3-(4-fluoro-phenyl)-urea | 458.3 | 2.8 | 3 |
| 148 | 1-[3-(4-Amino-7-cyclopentyl-7H-pyrrolo[2,3-d]pyrimidine-5-carbonyl)-phenyl]-3-(3-cyano-phenyl)-urea | 465.3 | 2.8 | 3 |
| 149 | 1-[3-(4-Amino-7-cyclopentyl-7H-pyrrolo[2,3-d]pyrimidine-5-carbonyl)-phenyl]-3-(2-cyano-phenyl)-urea | 465.3 | 2.1 | 3 |

-continued

| Example | Compound Name | MS | HPLC Rf (min) | method |
|---|---|---|---|---|
| 150 | 1-[3-(4-Amino-7-cyclopentyl-7H-pyrrolo[2,3-d]pyrimidine-5-carbonyl)-phenyl]-3-benzoyl-urea | 468.4 | 2.8 | 3 |
| 151 | 1-[3-(4-Amino-7-cyclopentyl-7H-pyrrolo[2,3-d]pyrimidine-5-carbonyl)-phenyl]-3-(4-methyl-benzyl)-urea | 468.4 | 2.8 | 3 |
| 152 | 1-[3-(4-Amino-7-cyclopentyl-7H-pyrrolo[2,3-d]pyrimidine-5-carbonyl)-phenyl]-3-(3-methyl-benzyl)-urea | 468.4 | 2.8 | 3 |
| 153 | 1-[3-(4-Amino-7-cyclopentyl-7H-pyrrolo[2,3-d]pyrimidine-5-carbonyl)-phenyl]-3-(2-methyl-benzyl)-urea | 468.4 | 2.8 | 3 |
| 154 | 1-[3-(4-Amino-7-cyclopentyl-7H-pyrrolo[2,3-d]pyrimidine-5-carbonyl)-phenyl]-3-phenethyl-urea | 468.4 | 2.8 | 3 |
| 155 | 1-[3-(4-Amino-7-cyclopentyl-7H-pyrrolo[2,3-d]pyrimidine-5-carbonyl)-phenyl]-3-(3-chloro-2-methyl-phenyl)-urea | 468.4 | 2.9 | 3 |
| 156 | 1-[3-(4-Amino-7-cyclopentyl-7H-pyrrolo[2,3-d]pyrimidine-5-carbonyl)-phenyl]-3-(4-ethyl-phenyl)-urea | 468.4 | 2.9 | 3 |
| 157 | 1-[3-(4-Amino-7-cyclopentyl-7H-pyrrolo[2,3-d]pyrimidine-5-carbonyl)-phenyl]-3-(3,5-dimethyl-phenyl)-urea | 468.4 | 2.9 | 3 |
| 158 | 1-[3-(4-Amino-7-cyclopentyl-7H-pyrrolo[2,3-d]pyrimidine-5-carbonyl)-phenyl]-3-(3,4-dimethyl-phenyl)-urea | 468.4 | 2.9 | 3 |
| 159 | 1-[3-(4-Amino-7-cyclopentyl-7H-pyrrolo[2,3-d]pyrimidine-5-carbonyl)-phenyl]-3-(2,5-dimethyl-phenyl)-urea | 468.4 | 2.9 | 3 |
| 160 | 1-[3-(4-Amino-7-cyclopentyl-7H-pyrrolo[2,3-d]pyrimidine-5-carbonyl)-phenyl]-3-(2,3-dimethyl-phenyl)-urea | 468.4 | 2.8 | 3 |
| 161 | 1-[3-(4-Amino-7-cyclopentyl-7H-pyrrolo[2,3-d]pyrimidine-5-carbonyl)-phenyl]-3-(2-ethyl-phenyl)-urea | 468.4 | 2.8 | 3 |
| 162 | 1-[3-(4-Amino-7-cyclopentyl-7H-pyrrolo[2,3-d]pyrimidine-5-carbonyl)-phenyl]-3-(2,4-dimethyl-phenyl)-urea | 468.4 | 2.9 | 3 |
| 163 | 1-[3-(4-Amino-7-cyclopentyl-7H-pyrrolo[2,3-d]pyrimidine-5-carbonyl)-phenyl]-3-(3-ethyl-phenyl)-urea | 468.2 | 2.9 | 3 |
| 164 | 1-[3-(4-Amino-7-cyclopentyl-7H-pyrrolo[2,3-d]pyrimidine-5-carbonyl)-phenyl]-3-(2-methoxy-phenyl)-urea | 470.2 | 2.8 | 3 |
| 165 | 1-[3-(4-Amino-7-cyclopentyl-7H-pyrrolo[2,3-d]pyrimidine-5-carbonyl)-phenyl]-3-(3-methoxy-phenyl)-urea | 470.2 | 2.8 | 3 |
| 166 | 1-[3-(4-Amino-7-cyclopentyl-7H-pyrrolo[2,3-d]pyrimidine-5-carbonyl)-phenyl]-3-(4-fluoro-benzyl)-urea | 472.3 | 2.7 | 3 |
| 167 | 1-[3-(4-Amino-7-cyclopentyl-7H-pyrrolo[2,3-d]pyrimidine-5-carbonyl)-phenyl]-3-(2-fluoro-5-methyl-phenyl)-urea | 472.3 | 2.9 | 3 |
| 168 | 1-[3-(4-Amino-7-cyclopentyl-7H-pyrrolo[2,3-d]pyrimidine-5-carbonyl)-phenyl]-3-(2-fluoro-benzyl)-urea | 472.3 | 2.7 | 3 |
| 169 | 1-[3-(4-Amino-7-cyclopentyl-7H-pyrrolo[2,3-d]pyrimidine-5-carbonyl)-phenyl]-3-(3-fluoro-4-methyl-phenyl)-urea | 472.3 | 2.9 | 3 |
| 170 | 1-[3-(4-Amino-7-cyclopentyl-7H-pyrrolo[2,3-d]pyrimidine-5-carbonyl)-phenyl]-3-(5-fluoro-2-methyl-phenyl)-urea | 472.4 | 2.9 | 3 |
| 171 | 1-[3-(4-Amino-7-cyclopentyl-7H-pyrrolo[2,3-d]pyrimidine-5-carbonyl)-phenyl]-3-(2-thiophen-2-yl-ethyl)-urea | 474.3 | 2.7 | 3 |
| 172 | 1-[3-(4-Amino-7-cyclopentyl-7H-pyrrolo[2,3-d]pyrimidine-5-carbonyl)-phenyl]-3-(3-chloro-phenyl)-urea | 474.3 | 2.9 | 3 |
| 173 | 1-[3-(4-Amino-7-cyclopentyl-7H-pyrrolo[2,3-d]pyrimidine-5-carbonyl)-phenyl]-3-(4-chloro-phenyl)-urea | 474.3 | 2.9 | 3 |
| 174 | 1-[3-(4-Amino-7-cyclopentyl-7H-pyrrolo[2,3-d]pyrimidine-5-carbonyl)-phenyl]-3-(3,5-difluoro-phenyl)-urea | 476.3 | 2.9 | 3 |

-continued

| Example | Compound Name | MS | HPLC Rf (min) | method |
|---|---|---|---|---|
| 175 | 1-[3-(4-Amino-7-cyclopentyl-7H-pyrrolo[2,3-d]pyrimidine-5-carbonyl)-phenyl]-3-(3,4-difluoro-phenyl)-urea | 476.4 | 2.9 | 3 |
| 176 | 1-[3-(4-Amino-7-cyclopentyl-7H-pyrrolo[2,3-d]pyrimidine-5-carbonyl)-phenyl]-3-(2,5-difluoro-phenyl)-urea | 476.3 | 2.9 | 3 |
| 177 | 1-[3-(4-Amino-7-cyclopentyl-7H-pyrrolo[2,3-d]pyrimidine-5-carbonyl)-phenyl]-3-(2-phenyl-cyclopropyl)-urea | 480.4 | 2.8 | 3 |
| 178 | 1-[3-(4-Amino-7-cyclopentyl-7H-pyrrolo[2,3-d]pyrimidine-5-carbonyl)-phenyl]-3-(2,3-dihydro-benzofuran-5-yl)-urea | 482.4 | 2.7 | 3 |
| 179 | 1-(3-Acetyl-phenyl)-3-[3-(4-amino-7-cyclopentyl-7H-pyrrolo[2,3-d]pyrimidine-5-carbonyl)-phenyl]-urea | 482.2 | 2.9 | 3 |
| 180 | 1-[3-(4-Amino-7-cyclopentyl-7H-pyrrolo[2,3-d]pyrimidine-5-carbonyl)-phenyl]-3-(4-isopropyl-phenyl)-urea | 482.3 | 3.0 | 3 |
| 181 | 1-[3-(4-Amino-7-cyclopentyl-7H-pyrrolo[2,3-d]pyrimidine-5-carbonyl)-phenyl]-3-(4-dimethylamino-phenyl)-urea | 483.3 | 2.5 | 3 |
| 182 | 1-[3-(4-Amino-7-cyclopentyl-7H-pyrrolo[2,3-d]pyrimidine-5-carbonyl)-phenyl]-3-benzo[1,3]dioxol-5-yl-urea | 484.3 | 2.8 | 3 |
| 183 | 1-[3-(4-Amino-7-cyclopentyl-7H-pyrrolo[2,3-d]pyrimidine-5-carbonyl)-phenyl]-3-(4-methoxy-benzyl)-urea | 484.4 | 2.7 | 3 |
| 184 | 1-[3-(4-Amino-7-cyclopentyl-7H-pyrrolo[2,3-d]pyrimidine-5-carbonyl)-phenyl]-3-(4-ethoxy-phenyl)-urea | 484.4 | 2.8 | 3 |
| 185 | 1-[3-(4-Amino-7-cyclopentyl-7H-pyrrolo[2,3-d]pyrimidine-5-carbonyl)-phenyl]-3-(4-methoxy-2-methyl-phenyl)-urea | 484.4 | 2.7 | 3 |
| 186 | 1-[3-(4-Amino-7-cyclopentyl-7H-pyrrolo[2,3-d]pyrimidine-5-carbonyl)-phenyl]-3-(2-ethoxy-phenyl)-urea | 484.4 | 2.9 | 3 |
| 187 | 1-[3-(4-Amino-7-cyclopentyl-7H-pyrrolo[2,3-d]pyrimidine-5-carbonyl)-phenyl]-3-(2-methoxy-5-methyl-phenyl)-urea | 484.4 | 2.9 | 3 |
| 188 | 1-[3-(4-Amino-7-cyclopentyl-7H-pyrrolo[2,3-d]pyrimidine-5-carbonyl)-phenyl]-3-(4-methylsulfanyl-phenyl)-urea | 486.4 | 2.8 | 3 |
| 189 | 1-[3-(4-Amino-7-cyclopentyl-7H-pyrrolo[2,3-d]pyrimidine-5-carbonyl)-phenyl]-3-(2-methylsulfanyl-phenyl)-urea | 486.4 | 2.9 | 3 |
| 190 | 1-[3-(4-Amino-7-cyclopentyl-7H-pyrrolo[2,3-d]pyrimidine-5-carbonyl)-phenyl]-3-(2-chloro-benzyl)-urea | 488.4 | 2.8 | 3 |
| 191 | 1-[3-(4-Amino-7-cyclopentyl-7H-pyrrolo[2,3-d]pyrimidine-5-carbonyl)-phenyl]-3-(2-chloro-5-methyl-phenyl)-urea | 488.4 | 2.6 | 3 |
| 192 | 1-[3-(4-Amino-7-cyclopentyl-7H-pyrrolo[2,3-d]pyrimidine-5-carbonyl)-phenyl]-3-(2-chloro-6-methyl-phenyl)-urea | 489.1 | 2.0 | 2 |
| 193 | 1-[3-(4-Amino-7-cyclopentyl-7H-pyrrolo[2,3-d]pyrimidine-5-carbonyl)-phenyl]-3-(5-chloro-2-methyl-phenyl)-urea | 489.1 | 2.4 | 2 |
| 194 | 1-[3-(4-Amino-7-cyclopentyl-7H-pyrrolo[2,3-d]pyrimidine-5-carbonyl)-phenyl]-3-(3-chloro-4-methyl-phenyl)-urea | 489.3 | 2.8 | 2 |
| 195 | 1-[3-(4-Amino-7-cyclopentyl-7H-pyrrolo[2,3-d]pyrimidine-5-carbonyl)-phenyl]-3-naphthalen-2-yl-urea | 491.2 | 2.5 | 2 |
| 196 | 1-[3-(4-Amino-7-cyclopentyl-7H-pyrrolo[2,3-d]pyrimidine-5-carbonyl)-phenyl]-3-benzo[b]thiophen-3-yl-urea | 497.2 | 2.4 | 2 |
| 197 | 3-{3-[3-(4-Amino-7-cyclopentyl-7H-pyrrolo[2,3-d]pyrimidine-5-carbonyl)-phenyl]-ureido}-benzoic acid methyl ester | 499.3 | 2.1 | 2 |
| 198 | 4-{3-[3-(4-Amino-7-cyclopentyl-7H-pyrrolo[2,3-d]pyrimidine-5-carbonyl)-phenyl]-ureido}-benzoic acid methyl ester | 499.3 | 2.0 | 2 |
| 199 | 1-[3-(4-Amino-7-cyclopentyl-7H-pyrrolo[2,3-d]pyrimidine-5-carbonyl)-phenyl]-3-(2,5-dimethoxy-phenyl)-urea | 501.3 | 2.0 | 2 |

| Example | Compound Name | MS | HPLC Rf (min) | method |
|---|---|---|---|---|
| 200 | 1-[3-(4-Amino-7-cyclopentyl-7H-pyrrolo[2,3-d]pyrimidine-5-carbonyl)-phenyl]-3-(2,4-dimethoxy-phenyl)-urea | 501.3 | 2.1 | 2 |
| 201 | 1-[3-(4-Amino-7-cyclopentyl-7H-pyrrolo[2,3-d]pyrimidine-5-carbonyl)-phenyl]-3-(3,5-dimethoxy-phenyl)-urea | 501.3 | 2.1 | 2 |
| 202 | 1-[3-(4-Amino-7-cyclopentyl-7H-pyrrolo[2,3-d]pyrimidine-5-carbonyl)-phenyl]-3-(4-trifluoromethyl-phenyl)-urea | 509.2 | 2.7 | 2 |
| 203 | 1-[3-(4-Amino-7-cyclopentyl-7H-pyrrolo[2,3-d]pyrimidine-5-carbonyl)-phenyl]-3-(2-trifluoromethyl-phenyl)-urea | 509.3 | 2.1 | 2 |
| 204 | 1-[3-(4-Amino-7-cyclopentyl-7H-pyrrolo[2,3-d]pyrimidine-5-carbonyl)-phenyl]-3-(3-trifluoromethyl-phenyl)-urea | 509.3 | 2.6 | 2 |
| 205 | 1-[3-(4-Amino-7-cyclopentyl-7H-pyrrolo[2,3-d]pyrimidine-5-carbonyl)-phenyl]-3-(2,5-dichloro-phenyl)-urea | 509.2 | 2.7 | 2 |
| 206 | 1-[3-(4-Amino-7-cyclopentyl-7H-pyrrolo[2,3-d]pyrimidine-5-carbonyl)-phenyl]-3-(5-methyl-2-trifluoromethyl-furan-3-yl)-urea | 513.3 | 2.3 | 2 |
| 207 | 4-{3-[3-(4-Amino-7-cyclopentyl-7H-pyrrolo[2,3-d]pyrimidine-5-carbonyl)-phenyl]-ureido}-benzoic acid ethyl ester | 513.4 | 2.6 | 2 |
| 208 | 3-{3-[3-(4-Amino-7-cyclopentyl-7H-pyrrolo[2,3-d]pyrimidine-5-carbonyl)-phenyl]-ureido}-benzoic acid ethyl ester | 513.4 | 2.5 | 2 |
| 209 | 1-[3-(4-Amino-7-cyclopentyl-7H-pyrrolo[2,3-d]pyrimidine-5-carbonyl)-phenyl]-3-(4-bromo-phenyl)-urea | 521.2 | 2.7 | 2 |
| 210 | 1-[3-(4-Amino-7-cyclopentyl-7H-pyrrolo[2,3-d]pyrimidine-5-carbonyl)-phenyl]-3-(5-phenyl-thiophen-2-yl)-urea | 523.3 | 2.8 | 2 |
| 211 | 1-[3-(4-Amino-7-cyclopentyl-7H-pyrrolo[2,3-d]pyrimidine-5-carbonyl)-phenyl]-3-(3,4-dichloro-benzyl)-urea | 523.3 | 2.6 | 2 |
| 212 | 1-[3-(4-Amino-7-cyclopentyl-7H-pyrrolo[2,3-d]pyrimidine-5-carbonyl)-phenyl]-3-(2-trifluoromethoxy-phenyl)-urea | 525.4 | 2.7 | 2 |
| 213 | 1-[3-(4-Amino-7-cyclopentyl-7H-pyrrolo[2,3-d]pyrimidine-5-carbonyl)-phenyl]-3-(4-fluoro-3-trifluoromethyl-phenyl)-urea | 527.2 | 2.3 | 2 |
| 214 | 1-[3-(4-Amino-7-cyclopentyl-7H-pyrrolo[2,3-d]pyrimidine-5-carbonyl)-phenyl]-3-(4-fluoro-2-trifluoromethyl-phenyl)-urea | 527.2 | 2.3 | 2 |
| 215 | 1-[3-(4-Amino-7-cyclopentyl-7H-pyrrolo[2,3-d]pyrimidine-5-carbonyl)-phenyl]-3-(2-fluoro-6-trifluoromethyl-phenyl)-urea | 527.3 | 2.0 | 2 |
| 216 | 1-[3-(4-Amino-7-cyclopentyl-7H-pyrrolo[2,3-d]pyrimidine-5-carbonyl)-phenyl]-3-(3-fluoro-5-trifluoromethyl-phenyl)-urea | 527.3 | 2.5 | 2 |
| 217 | 1-[3-(4-Amino-7-cyclopentyl-7H-pyrrolo[2,3-d]pyrimidine-5-carbonyl)-phenyl]-3-(2-fluoro-3-trifluoromethyl-phenyl)-urea | 527.3 | 2.4 | 2 |
| 218 | 1-[3-(4-Amino-7-cyclopentyl-7H-pyrrolo[2,3-d]pyrimidine-5-carbonyl)-phenyl]-3-(2-benzyl-phenyl)-urea | 531.2 | 2.7 | 2 |
| 219 | 1-[3-(4-Amino-7-cyclopentyl-7H-pyrrolo[2,3-d]pyrimidine-5-carbonyl)-phenyl]-3-(4-benzyl-phenyl)-urea | 531.4 | 2.8 | 2 |
| 220 | 1-[3-(4-Amino-7-cyclopentyl-7H-pyrrolo[2,3-d]pyrimidine-5-carbonyl)-phenyl]-3-(2-phenoxy-phenyl)-urea | 533.2 | 2.5 | 2 |
| 221 | 1-[3-(4-Amino-7-cyclopentyl-7H-pyrrolo[2,3-d]pyrimidine-5-carbonyl)-phenyl]-3-(3-phenoxy-phenyl)-urea | 533.0 | 2.4 | 2 |
| 222 | 1-[3-(4-Amino-7-cyclopentyl-7H-pyrrolo[2,3-d]pyrimidine-5-carbonyl)-phenyl]-3-(5-chloro-2,4-dimethoxy-phenyl)-urea | 533.1 | 2.4 | 2 |
| 223 | 1-[3-(4-Amino-7-cyclopentyl-7H-pyrrolo[2,3-d]pyrimidine-5-carbonyl)-phenyl]-3-(4-trifluoromethylsulfanyl-phenyl)-urea | 541.2 | 2.5 | 2 |
| 224 | 1-[3-(4-Amino-7-cyclopentyl-7H-pyrrolo[2,3-d]pyrimidine-5-carbonyl)-phenyl]-3-cyclohexyl-urea | 447.2 | 1.7 | 2 |

-continued

| Example | Compound Name | MS | HPLC Rf (min) | method |
|---|---|---|---|---|
| 225 | 1-[3-(4-Amino-7-cyclopentyl-7H-pyrrolo[2,3-d]pyrimidine-5-carbonyl)-phenyl]-3-(3-fluoro-benzyl)-urea | 473.1 | 1.9 | 2 |
| 226 | 1-(4-Acetyl-phenyl)-3-[3-(4-amino-7-cyclopentyl-7H-pyrrolo[2,3-d]pyrimidine-5-carbonyl)-phenyl]-urea | 483.1 | 1.9 | 2 |

EXAMPLE 227

[3-(4-Amino-7-cyclopentyl-7H-pyrrolo[2,3-d]pyrimidine-5-carbonyl)-phenyl]-carbamic acid phenyl ester NaH (0.21 g, 5.1 mmol) was added to a solution of (4-Amino-7-cyclopentyl-7H-pyrrolo[2,3-d]pyrimidin-5-yl)-(3-amino-phenyl)-methanone (1.5 g, 4.7 mmol) in THF. (35 mL). After stirring for 1 h at room temperature, phenyl chloroformate (0.82 g, 5.4 mmol) was added. The resulting reaction mixture was stirred for an additional 3.5 h, quenched with water (15 mL), and extracted with ethyl acetate (3×25 mL). The combined organic extracts were washed with saturated sodium bicarbonate (20 mL) and brine (20 mL), dried (MgSO$_4$), filtered, and concentrated in vacuo. The crude reaction mixture was triturated (CH$_2$Cl$_2$) and filtered to afford the title compound as a white solid (1.78 g, 87%). MS: 442.3 (MH$^+$); HPLC R$_f$: 2.5 min. (HPLC method 2).

EXAMPLE 228

1-[3-(4-Amino-7-cyclopentyl-7H-pyrrolo[2,3-d]pyrimidine-5-carbonyl)-phenyl]-3-cyclopropyl-urea Cyclopropyl amine (130 mg, 2.3 mmol) was added to a solution of [3-(4-Amino-7-cyclopentyl-7H-pyrrolo[2,3-d]pyrimidine-5-carbonyl)-phenyl]-carbamic acid phenyl ester (50 mg, 0.11 mmol) in THF (3 mL). The reaction mixture was stirred at room temperature for 2 h and concentrated in vacuo. Purification by flash column chromatography (silica, 4:96→15:85 MeOH:CH$_2$Cl$_2$) provided the title compound as a pale yellow solid (44 mg, 95%). MS: 405.2 (MH$^+$); HPLC R$_f$: 4.73 min. (HPLC method 4); HPLC purity: 100%.

EXAMPLES 229-238

Examples 229-238 listed in the following table were prepared using procedures analogous to those described in Example 228.

| Example | Compound Name | MH+ | HPLC Rf(min) | method |
|---|---|---|---|---|
| 229 | 1-[3-(4-Amino-7-cyclopentyl-7H-pyrrolo[2,3-d]pyrimidine-5-carbonyl)-phenyl]-3-cyclobutyl-urea | 419.3 | 5.31 | 4 |
| 230 | 1-[3-(4-Amino-7-cyclopentyl-7H-pyrrolo[2,3-d]pyrimidine-5-carbonyl)-phenyl]-3-cyclopropylmethyl-urea | 419.3 | 5.28 | 4 |
| 231 | 1-[3-(4-Amino-7-cyclopentyl-7H-pyrrolo[2,3-d]pyrimidine-5-carbonyl)-phenyl]-3-(4-methyl-cyclohexyl)-urea | 460.9 | 1.8 | 2 |
| 232 | 1-[3-(4-Amino-7-cyclopentyl-7H-pyrrolo[2,3-d]pyrimidine-5-carbonyl)-phenyl]-3-piperidin-4-yl-urea | 448.1 | 3.91 | 4 |
| 233 | [3-(4-Amino-7-cyclopentyl-7H-pyrrolo[2,3-d]pyrimidine-5-carbonyl)-phenyl]-urea | 365.2 | 4.03 | 4 |
| 234 | 3-[3-(4-Amino-7-cyclopentyl-7H-pyrrolo[2,3-d]pyrimidine-5-carbonyl)-phenyl]-1-benzyl-1-methyl-urea | 469.6 | 6.15 | 4 |
| 235 | Piperidine-1-carboxylic acid [3-(4-amino-7-cyclopentyl-7H-pyrrolo[2,3-d]pyrimidine-5-carbonyl)-phenyl]-amide | 433.5 | 5.63 | 4 |
| 236 | 1-[3-(4-Amino-7-cyclopentyl-7H-pyrrolo[2,3-d]pyrimidine-5-carbonyl)-phenyl]-3-pyridin-4-ylmethyl-urea | 456.5 | 4.48 | 4 |
| 237 | 1-[3-(4-Amino-7-cyclopentyl-7H-pyrrolo[2,3-d]pyrimidine-5-carbonyl)-phenyl]-3-pyridin-4-yl-urea | 442.5 | 4.78 | 4 |
| 238 | Morpholine-4-carboxylic acid [3-(4-amino-7-cyclopentyl-7H-pyrrolo[2,3-d]pyrimidine-5-carbonyl)-phenyl]-amide | 435.5 | 4.60 | 4 |

EXAMPLE 239

239A. 3-Iodo-N-methoxy-N-methyl-benzamide

A solution of 3-Iodo-benzoic acid (5.0 g, 20.15 mmol), thionyl chloride (3.6 g, 30.2 mmol), and DMF (10 mL) in CH$_2$Cl$_2$ (100 mL) was heated to reflux for 3 h. The reaction was then concentrated under reduced pressure and the residue was dissolved in CH$_2$Cl$_2$ (100 mL). O,N-Dimethylhydroxylamine hydrochloide (2.16 g, 22.2 mmol) was added and the solution was cooled to 0° C. N,N-diisopropylethylamine (2.6 g, 20.2 mmol) was added drop wise. The reaction was warmed to room temperature. After 4 h the reaction was quenched with water, the layers were separated and the aqueous layer was extracted with CH$_2$Cl$_2$ (1×). The combined organic layers were dried over Na$_2$SO$_4$. Purification by flash column chromatography (hexanes/ethyl acetate 6:4) afforded the title compound as a white solid (3.69 g, 63%). MS: 291.8 (MH+); HPLC Rf: 4.87 min. (HPLC method 4).

239B. (4-Chloro-7-cyclopentyl-7H-pyrrolo[2,3-d]pyrimidin-5-yl)-(3-iodo-phenyl)-methanone n-BuLi (3.65 mL, 2.5 M in hexanes, 9.14 mmol) was added dropwise to a solution of 5-Bromo-4-chloro-7-cyclopentyl-7H-pyrrolo[2,3-d]pyrimidine (2.5 g, 8.31 mmol) in THF (50 mL) at −78° C. After 30 min a solution of 3-Iodo-N-methoxy-N-methyl-benzamide (2.29 g, 7.8 mmol) in THF (10 mL) was added. After 30 min the reaction was quenched with water and allowed to warm to room temperature. The layers were separated and the aqueous layer was extracted with EtOAc (2×). The combined organic layers were washed with water and dried over Na$_2$SO$_4$. Recrystallization from MeOH afforded the title compound as a white solid (1.74 g, 49%). MS: 451.9/453.9 (MH+); HPLC Rf: 7.44 min. (HPLC method 4).

239C. Prop-2-ynyl-carbamic acid tert-butyl ester

Propargyl amine (9.6 g, 174.4 mmol) was added dropwise to a solution of di-tert-butyl dicarbonate (46.1 g, 211.0 mmol) in THF (70 mL). After 12 h the reaction was concentrated, the residue was dissolved in diethyl ether and washed with water (1×) and brine (1×). The organic layer was dried over Na$_2$SO$_4$ then concentrated to afford the title compound as a yellow oil (26 g, 97%).

239D. {3-[3-(4-Chloro-7-cyclopentyl-7H-pyrrolo[2,3-d]pyrimidine-5-carbonyl)-phenyl]-prop-2-ynyl}-carbamic acid tert-butyl ester A solution of (4-Chloro-7-cyclopentyl-7H-pyrrolo[2,3-d]pyrimidin-5-yl)-(3-iodo-phenyl)-methanone (500 mg, 1.1 mmol), Prop-2-ynyl-carbamic acid tert-butyl ester (341 mg, 2.2 mmol), Copper Iodide (21 mg, 0.11 mmol), PdCl$_2$(PPh$_3$)$_2$ (77 mg, 0.11 mmol), and diisopropylamine (111 mg, 1.1 mmol) in THF (25 mL) was stirred at room temperature under N$_2$. After 24 h the reaction was quenched with saturated aqueous NH$_4$Cl and the aqueous layer was extracted with EtOAc (3×). The combined organic layers were dried over Na$_2$SO$_4$ and concentrated. Purification by flash column chromatography (hexanes/ethyl acetate 7:3) afforded the title compound as a yellow solid (452 mg, 86%). %). MS: 479.2/481.2 (MH+); HPLC Rf: 7.26 min. (HPLC method 4).

239E. {3-[3-(4-Amino-7-cyclopentyl-7H-pyrrolo[2,3-d]pyrimidine-5-carbonyl)-phenyl]-prop-2-ynyl}-carbamic acid tert-butyl ester The title compound was prepared from {3-[3-(4-Chloro-7-cyclopentyl-7H-pyrrolo[2,3-d]pyrimidine-5-carbonyl)-phenyl]-prop-2-ynyl}-carbamic acid tert-butyl ester (452 mg, 0.94 mmol) by a procedure analogous to that described for (4-Amino-7-cyclopentyl-7H-pyrrolo[2,3-d]pyrimidin-5-yl)-(3-nitro-phenyl)methanone. MS: 460.3/360.3 (MH+); HPLC Rf: 6.45 min. (HPLC method 4).

239F. (4-Amino-7-cyclopentyl-7H-pyrrolo[2,3-d]pyrimidin-5-yl)-[3-(3-amino-prop-1-ynyl)-phenyl]-methanone HCl (g) was introduced into a solution of {3-[3-(4-Amino-7-cyclopentyl-7H-pyrrolo[2,3-d]pyrimidine-5-carbonyl)-phenyl]-prop-2-ynyl}-carbamic acid tert-butyl ester (421 mg, 0.92 mmol) in MeOH (50 mL). After 5 min the reaction was concentrated to afford the title compound as a brown solid (376 mg, 100%). MS: 360.2 (MH+); HPLC Rf: 4.05 min. (HPLC method 4).

EXAMPLE 240

240A. (4-Chloro-7-cyclopentyl-7H-pyrrolo[2,3-d]pyrimidin-5-yl)-(4'-dimethylamino-biphenyl-3-yl)methanone A solution of (4-Chloro-7-cyclopentyl-7H-pyrrolo[2,3-d]pyrimidin-5-yl)-(3-iodo-phenyl)-methanone (100 mg, 0.22 mmol), 4-(dimethylamino)Phenyl boronic acid (42.9 mg, 0.26 mmol), PdCl$_2$(PPh$_3$)$_2$ (7.7 mg, 0.011 mmol), and K$_2$CO$_3$ (45.6 mg, 0.33 mmol) in 1,4-dioxane (3 mL) and water (0.5 mL) was heated to 90° C. After 24 h the reaction was diluted with EtOAc and filtered through celite. The filtrate was washed with water, dried over Na$_2$SO$_4$, and concentrated. Purification by flash column chromatography (hexanes/ethyl acetate 8:2) afforded the title compound as a white solid (46 mg, 47%). MS: 445.1/447.1 (MH+); HPLC Rf: 8.05 min. (HPLC method 4).

240B. (4-Amino-7-cyclopentyl-7H-pyrrolo[2,3-d]pyrimidin-5-yl)-(4'-dimethylamino-biphenyl-3-yl)-methanone A solution of (4-Chloro-7-cyclopentyl-7H-pyrrolo[2,3-d]pyrimidin-5-yl)-(4'-dimethylamino-biphenyl-3-yl)-methanone ((40 mg, 0.089 mmol) and NH$_4$OH (2 mL) in 1,4-dioxane (2 mL) was heated to 50° C. in a sealed tube. After 12 h the reaction was concentrated under reduced pressure and purified by flash column chromatography (CH$_2$Cl$_2$/MeOH 95:5) to afford the title compound as a yellow solid (28 mg, 74%). MS: 426.0 (MH+); HPLC Rf: 7.38 min. (HPLC method 4).

EXAMPLES 241-246

Examples 241-246 listed in the following table were prepared using procedures analogous to those described in Example 240.

layer was washed with water, brine, dried over sodium sulfate and concentrated. Purification through flash column afforded the product as a light yellow solid (108 mg, 85%). MS: 426.1 (MH+); HPLC Rf: 6.332 min.; HPLC purity: 96%.

| | | | HPLC | |
|---|---|---|---|---|
| Example | Compound Name | MH+ | Rf (min) | method |
| 241 | (4-Amino-7-cyclopentyl-7H-pyrrolo[2,3-d]pyrimidin-5-yl)-(3-furan-2-yl-phenyl)-methanone | 373.2 | 6.52 | 4 |
| 242 | (4-Amino-7-cyclopentyl-7H-pyrrolo[2,3-d]pyrimidin-5-yl)-(3-benzofuran-2-yl-phenyl)-methanone | 423.2 | 7.60 | 4 |
| 243 | (4-Amino-7-cyclopentyl-7H-pyrrolo[2,3-d]pyrimidin-5-yl)-biphenyl-3-yl-methanone | 383.2 | 6.95 | 4 |
| 244 | (4-Amino-7-cyclopentyl-7H-pyrrolo[2,3-d]pyrimidin-5-yl)-(4'-fluoro-biphenyl-3-yl)-methanone | 401.2 | 7.04 | 4 |
| 245 | (4-Amino-7-cyclopentyl-7H-pyrrolo[2,3-d]pyrimidin-5-yl)-(2'-chloro-biphenyl-3-yl)-methanone | 417.1/419.2 | 7.36 | 4 |
| 246 | (4-Amino-7-cyclopentyl-7H-pyrrolo[2,3-d]pyrimidin-5-yl)-(3-iodo-phenyl)-methanone | 433.1 | 6.62 | 4 |

EXAMPLE 247

247A. 7-Cyclopentyl-5-iodo-7H-pyrrolo[2,3-d]pyrimidin-4-ylamine

To a pressure tube with dioxane (5 mL) was added 4-Chloro-7-cyclopentyl-5-iodo-7H-pyrrolo[2,3-d]pyrimidine, then ammonia hydroxide (5 mL). The pressure tube was sealed and heated at 120 C overnight. All solvents were removed via reduced pressure, and the residue were purified through flash column (methylene chloride/methanol:97/3). The product was obtained as a white solid (300 mg, 92%). MS: 329.1 (MH+); HPLC Rf: 5.018 min.; HPLC

247B. (3-Mercapto-phenyl)-carbamic acid tert-butyl ester

To a round-bottom flask with acetone (8 mL) was added 3-Amino-benzenethiol (501 mg, 4 mmole) and di-tert-butyl dicarbonate (1.75 gram, 8 mmole) and 3 mL of saturated sodium bicarbonate. The resulting solution was stirred at room temperature overnight, and then extracted with EtOAc (150 mL) and 1 N HCl (100 mL). The organic layer was washed with water, brine, dried over sodium sulfate and concentrated. Purification through flash column (EtOAc/Hexanes:1/3) afforded the product as a clean colorless oil (730 mg, 81%). MS: 226.1 (MH+); HPLC Rf: 6.152 min.; HPLC purity: 99%.

247C. [3-(4-Amino-7-cyclopentyl-7H-pyrrolo[2,3-d]pyrimidin-5-ylsulfanyl)-phenyl]-carbamic acid tert-butyl ester To a round bottom flask with DMF (5 mL), was added 7-Cyclopentyl-5-iodo-7H-pyrrolo[2,3-d]pyrimidin-4-ylamine, CuI, N-methylmorphline and (3-Mercapto-phenyl)-carbamic acid tert-butyl ester. The reaction was heated at 110° C. overnight. After cooling to room temperature, the reaction mixture was extracted with EtOAc (80 mL) and saturated sodium bicarbonate solution (60 ml). The organic

247D. 5-(3-Amino-phenylsulfanyl)-7-cyclopentyl-7H-pyrrolo[2,3-d]pyrimidin-4-ylamine To a solution of [3-(4-Amino-7-cyclopentyl-7H-pyrrolo[2,3-d]pyrimidin-5-ylsulfanyl)-phenyl]-carbamic acid tert-butyl ester (108 mg, 0.25 mmole) in a mixture of MeOH and Methylene Chloride (4 mL/2 mL) was bubbled through HCl gas for 20 minutes. The resulting solution was stirred for 20 minutes at room temperature. Then the reaction mixture was extracted with EtOAc (50 mL) and saturated sodium bicarbonate solution (50 mL). The organic layer was washed with brine, dried over sodium sulfate and concentrated. The title compound was obtained as a yellow solid (79 mg, 96%). MS: 326.2 (MH+); HPLC Rf: 5.332 min.; HPLC purity: 90%.

247E. 1-[3-(4-Amino-7-cyclopentyl-7H-pyrrolo[2,3-d]pyrimidin-5-ylsulfanyl)-phenyl]-3-(2,6-difluoro-phenyl)-urea To a round-bottom flask with pyridine (3 mL) was added 5-(3-Amino-phenylsulfanyl)-7-cyclopentyl-7H-pyrrolo[2,3-d]pyrimidin-4-ylamine (16.3 mg, 0.05 mmole) and 1,3-Difluoro-2-isocyanato-benzene (15.5 mg, 0.1 mmole). The reaction mixture was stirred at room temperature overnight and extracted with EtOAc (40 mL) and water (40 mL). The organic layer was washed with brine, dried over anhydrous sodium sulfate, and concentrated. Purification through flash column (methylene chloride/methanol: 96/4) gave the title compound as a light yellow solid (9.8 mg, 41%). MS: 481.1 (MH+); HPLC Rf: 7.559 min.; HPLC purity: 96%.

EXAMPLES 248-252

Examples 248-252 listed in the following table were prepared using procedures analogous to those described in Example 247.

|         |                                                                                                                    |       | HPLC    |        |
|---------|--------------------------------------------------------------------------------------------------------------------|-------|---------|--------|
| Example | Compound Name                                                                                                      | MH+   | Rf (min)| method |
| 248     | 1-[3-(4-Amino-7-cyclopentyl-7H-pyrrolo[2,3-d]pyrimidin-5-ylsulfanyl)-phenyl]-3-(2,6-difluoro-phenyl)-urea           | 481.1 | 7.559   | 4      |
| 249     | 1-[3-(4-Amino-7-cyclopentyl-7H-pyrrolo[2,3-d]pyrimidin-5-ylsulfanyl)-phenyl]-3-(2,4-difluoro-phenyl)-urea           | 481.1 | 7.613   | 4      |
| 250     | N-[4-(4-Amino-7-cyclopentyl-7H-pyrrolo[2,3-d]pyrimidin-5-ylsulfanyl)-phenyl]-2,6-difluoro-benzenesulfonamide        | 502.1 | 6.231   | 4      |
| 251     | 1-[4-(4-Amino-7-cyclopentyl-7H-pyrrolo[2,3-d]pyrimidin-5-ylsulfanyl)-phenyt]-3-(2,6-difluoro-phenyl)-urea           | 481.2 | 7.581   | 4      |
| 252     | 1-[4-(4-Amino-7-cyclopentyl-7H-pyrrolo[2,3-d]pyrimidin-5-ylsulfanyl)-phenyl]-3-(2,4-difluoro-phenyl)-urea           | 481.1 | 7.572   | 4      |

EXAMPLES 253-256

Examples 253-256 listed in the following table were prepared using procedures analogous those described in Example 4 and Example 247E as the starting material.

|         |                                                                                                                    |       | HPLC    |        |
|---------|--------------------------------------------------------------------------------------------------------------------|-------|---------|--------|
| Example | Compound Name                                                                                                      | MH+   | Rf (min)| method |
| 253     | N-[2-(4-Amino-7-cyclopentyl-7H-pyrrolo[2,3-d]pyrimidin-5-ylsulfanyl)-phenyl]-2,6-difluoro-benzenesulfonamide        | 502.1 | 5.972   | 4      |
| 254     | N-[2-(4-Amino-7-cyclopentyl-7H-pyrrolo[2,3-d]pyrimidin-5-ylsulfanyl)-phenyl]-2,4-difluoro-benzenesulfonamide        | 502.1 | 5.992   | 4      |
| 255     | N-[4-(4-Amino-7-cyclopentyl-7H-pyrrolo[2,3-d]pyrimidin-5-ylsulfanyl)-phenyl]-2,6-difluoro-benzenesulfonamide        | 502.1 | 6.231   | 4      |
| 256     | N-[4-(4-Amino-7-cyclopentyl-7H-pyrrolo[2,3-d]pyrimidin-5-ylsulfanyl)-phenyl]-2,4-difluoro-benzenesulfonamide        | 502.1 | 6.237   | 4      |

EXAMPLE 257

257A. 4-Chloro-7-cyclopropylmethyl-7H-pyrrolo[2,3-d]pyrimidine (Bromomethyl)cyclopropane (7.6 mL, 78 mmol) was added to a solution of 4-Chloro-7H-pyrrolo[2,3-d]pyrimidine (10.0 g, 65 mmol) and cesium carbonate (25.4 g, 78 mmol) in DMF (100 mL). The reaction mixture was stirred at room temperature 12 h, filtered, and concentrated in vacuo. Purification by flash column chromatography (silica, 1:9→2:8 EtOAc:hexanes) provided the title compound as a white solid (12.9 g, 95%). MS: 208.5 (MH+); HPLC $R_f$: 5.21 min. (HPLC method 4); HPLC purity: 100%.

257B. (4-Amino-7-cyclopropylmethyl-7H-pyrrolo[2,3-d]pyrimidin-5-yl)-(3-amino-phenyl)-methanone The title compound was prepared from 4-Chloro-7-cyclopropylmethyl-7H-pyrrolo[2,3-d]pyrimidine by procedures analogous to those described for the preparation of (4-Amino-7-cyclopentyl-7H-pyrrolo[2,3-d]pyrimidin-5-yl)-(3-amino-phenyl)-methanone. MS: 308.4 (MH+); HPLC $R_f$: 4.17 min. (HPLC method 4); HPLC purity: 100%.

EXAMPLES 258-260

Examples 258-260 listed in the following table were prepared using procedures analogous to those described in Example 4 with Example 257B as the starting material.

|         |                                                                                                                    |       | HPLC    |        |
|---------|--------------------------------------------------------------------------------------------------------------------|-------|---------|--------|
| Example | Compound Name                                                                                                      | MH+   | Rf (min)| method |
| 258     | Thiophene-2-sulfonic acid [3-(4-amino-7-cyclopropylmethyl-7H-pyrrolo[2,3-d]pyrimidine-5-carbonyl)-phenyl]-amide     | 454.5 | 5.18    | 4      |

| Example | Compound Name | MH+ | HPLC Rf (min) | method |
|---|---|---|---|---|
| 259 | N-[3-(4-Amino-7-cyclopropylmethyl-7H-pyrrolo[2,3-d]pyrimidine-5-carbonyl)-phenyl]-2,4-dichloro-benzenesulfonamide | 517.4 | 6.01 | 4 |
| 260 | N-[3-(4-Amino-7-cyclopropylmethyl-7H-pyrrolo[2,3-d]pyrimidine-5-carbonyl)-phenyl]-2-chloro-benzenesulfonamide | 483 | 5.54 | 4 |

EXAMPLES 261-268

Examples 261-268 listed in the following table were prepared using procedures analogous to those described in Example 25 with Example 257B as the starting material.

| Example | Compound Name | MH+ | HPLC Rf (min) | method |
|---|---|---|---|---|
| 261 | 1-[3-(4-Amino-7-cyclopropylmethyl-7H-pyrrolo[2,3-d]pyrimidine-5-carbonyl)-phenyl]-3-(2-chloro-phenyl)-urea | 462 | 6.08 | 4 |
| 262 | 1-[3-(4-Amino-7-cyclopropylmethyl-7H-pyrrolo[2,3-d]pyrimidine-5-carbonyl)-phenyl]-3-m-tolyl-urea | 441.5 | 5.85 | 4 |
| 263 | 1-[3-(4-Amino-7-cyclopropylmethyl-7H-pyrrolo[2,3-d]pyrimidine-5-carbonyl)-phenyl]-3-cyclohexyl-urea | 433.5 | 5.58 | 4 |
| 264 | 1-[3-(4-Amino-7-cyclopropylmethyl-7H-pyrrolo[2,3-d]pyrimidine-5-carbonyl)-phenyl]-3-(3-methyl-benzyl)-urea | 455.5 | 5.67 | 4 |
| 265 | 1-[3-(4-Amino-7-cyclopropylmethyl-7H-pyrrolo[2,3-d]pyrimidine-5-carbonyl)-phenyl]-3-(2-fluoro-5-methyl-phenyl)-urea | 459.5 | 6.14 | 4 |
| 266 | 1-[3-(4-Amino-7-cyclopropylmethyl-7H-pyrrolo[2,3-d]pyrimidine-5-carbonyl)-phenyl]-3-(5-fluoro-2-methyl-phenyl)-urea | 459.5 | 6.02 | 4 |
| 267 | 1-[3-(4-Amino-7-cyclopropylmethyl-7H-pyrrolo[2,3-d]pyrimidine-5-carbonyl)-phenyl]-3-(2,4-dichloro-phenyl)-urea | 496.4 | 6.74 | 4 |
| 268 | 1-[3-(4-Amino-7-cyclopropylmethyl-7H-pyrrolo[2,3-d]pyrimidine-5-carbonyl)-phenyl]-3-(3,5-difluoro-phenyl)-urea | 463.5 | 6.19 | 4 |

EXAMPLE 269

N-[3-(4-Amino-7-cyclopropylmethyl-7H-Pyrrolo[2,3-d]pyrimidine-5-carbonyl)-phenyl]-2-chloro-benzamide The title compound was prepared from (4-Amino-7-cyclopropylmethyl-7H-pyrrolo[2,3-d]pyrimidin-5-yl)-(3-amino-phenyl)-methanone by procedures analogous to those described for the preparation of N-[3-(4-Amino-7-cyclopentyl-7H-pyrrolo[2,3-d]pyrimidine-5-carbonyl)-phenyl]-2,6-difluoro-benzamide. MS: 447 (MH+); HPLC R$_f$: 5.56 min. (HPLC method 4); HPLC purity: 100%.

EXAMPLE 270

270A.
4-Chloro-7-methyl-7H-pyrrolo[2,3-d]pyrimidine

Iodomethane (12.2 mL, 195 mmol) was added to a solution of 4-Chloro-7H-pyrrolo[2,3-d]pyrimidine (15.0 g, 97.7 mmol) and cesium carbonate (47.7 g, 146.5 mmol) in DMF (200 mL). The reaction mixture was stirred at room temperature 1 h, quenched with H$_2$O (500 mL), and extracted with EtOAc (3×200 mL). The combined organic extracts were dried (Na$_2$SO$_4$), filtered, and concentrated in vacuo. Purification by flash column chromatography (silica, 2:8→3:7 EtOAc:hexanes) provided the title compound as an off-white solid (15.4 g, 94%). MS: 168.5 (MH+); HPLC R$_f$: 3.45 min. (HPLC method 4); HPLC purity: 96%.

270B. (4-Amino-7-methyl-7H-pyrrolo[2,3-d]pyrimidin-5-yl)-(3-amino-phenyl)-methanone The title compound was prepared from 4-Chloro-7-methyl-7H-pyrrolo[2,3-d]pyrimidin by procedures analogous to those described for the preparation of (4-Amino-7-cyclopentyl-7H-pyrrolo[2,3-d]pyrimidin-5-yl)-(3-amino-phenyl)-methanone. MS: 268.1 (MH+); HPLC R$_f$: 3.17 min. (HPLC method 4); HPLC purity: 92%.

EXAMPLES 271-272

Examples 271-272 listed in the following table were prepared using procedures analogous to those described in Example 4 with Example 270B as the starting material.

| Example | Compound Name | MH+ | HPLC Rf (min) | method |
|---|---|---|---|---|
| 271 | N-[3-(4-Amino-7-methyl-7H-pyrrolo[2,3-d]pyrimidine-5-carbonyl)-phenyl]-3,5-dichloro-benzenesulfonamide | 477.3 | 5.63 | 4 |
| 272 | N-[3-(4-Amino-7-methyl-7H-pyrrolo[2,3-d]pyrimidine-5-carbonyl)-phenyl]-3,5-difluoro-benzenesulfonamide | 444.4 | 5.04 | 4 |

EXAMPLES 273-274

Examples 273-274 listed in the following table were prepared using procedures analogous to those described in Example 25 with Example 270B as the starting material.

| Example | Compound Name | MH+ | HPLC Rf (min) | method |
|---|---|---|---|---|
| 273 | 1-[3-(4-Amino-7-methyl-7H-pyrrolo[2,3-d]pyrimidine-5-carbonyl)-phenyl]-3-(3,5-difluoro-phenyl)-urea | 423.4 | 5.37 | 4 |
| 274 | 1-[3-(4-Amino-7-methyl-7H-pyrrolo[2,3-d]pyrimidine-5-carbonyl)-phenyl]-3-(3,5-dichloro-phenyl)-urea | 456.3 | 6.12 | 4 |

EXAMPLE 275

275A. N-Methoxy-2,N-dimethyl-3-nitro-benzamide

Carbonyl diimidazole (9.8 g, 60.7 mmol) was added to a solution of 2-methyl-3-nitrobenzoic acid (10 g, 55 mmol) in $CH_2Cl_2$ (200 mL) at 0° C. and stirred for 30 min. The reaction mixture was warmed to room temperature, stirred for 2 h, and cooled to 0 C. N,O-dimethylhydroxylamine hydrochloride was added to the reaction mixture at 0 C, stirred for 30 min., and heated to 45 C for 1 h. The reaction mixture was cooled to room temperature, stirred for 12 h, and quenched with aqueous $K_2CO_3$ (10%, 200 mL). The reaction mixture was extracted with $CH_2Cl_2$ (3×200 mL) and the combined extracts were dried ($MgSO_4$), filtered, and concentrated in vacuo. Purification by flash column chromatography (silica, 6:4 hexanes:EtOAc) provided the title compound a white solid (2.6 g, 21%). MS: 225 (MH+); HPLC $R_f$: 3.96 min. (HPLC method 4); HPLC purity: 98%.

275B. (4-Chloro-7-isopropyl-7H-pyrrolo[2,3-d]pyrimidin-5-yl)-(2-methyl-3-nitro-phenyl)-methanone n-Butyllithium (2.5 M in hexanes, 14.3 mmol) was added dropwise to a suspension of 5-Bromo-4-chloro-7-isopropyl-7H-pyrrolo[2,3-d]pyrimidine (3.7 g, 13.6 mmol) and ethyl ether (75 mL), cooled to −78 C, and stirred for 1 h. N-Methoxy-2,N-dimethyl-3-nitro-benzamide (4.0 g, 17.7 mmol) was added to the reaction mixture, stirred for 2 h, quenched with aqueous $NH_4Cl$ (100 mL), and extracted with EtOAc (3×100 mL). The combined organic extracts were dried ($Na_2SO_4$), filtered, and concentrated in vacuo. Purification by flash column chromatography (silica, 3:7 EtOAc:hexanes) provided the title compound as an yellow solid (1.84 g, 38%). MS: 357.5 (MH−); HPLC $R_f$: 2.0 min. (HPLC method 2); HPLC purity: 100%.

275C. (4-Amino-7-isopropyl-7H-pyrrolo[2,3-d]pyrimidin-5-yl)-(3-amino-2-methyl-phenyl)methanone The title compound was prepared from (4-Chloro-7-isopropyl-7H-pyrrolo[2,3-d]pyrimidin-5-yl)-(2-methyl-3-nitro-phenyl)-methanone by procedures analogous to those described for the preparation of (4-Amino-7-cyclopentyl-7H-pyrrolo[2,3-d]pyrimidin-5-yl)-(3-amino-phenyl)methanone. MS: 310.1 (MH+); HPLC $R_f$: 1.3 min. (HPLC method 2); HPLC purity: 100%.

EXAMPLES 276-281

Examples 276-281 listed in the following table were prepared using procedures analogous to those described in Example 4 with Example 275C as the starting material.

| Example | Compound Name | MH+ | HPLC Rf (min) | method |
|---|---|---|---|---|
| 276 | N-[3-(4-Amino-7-isopropyl-7H-pyrrolo[2,3-d]pyrimidine-5-carbonyl)-2-methyl-phenyl]-2-chloro-benzenesulfonamide | 485 | 1.9 | 2 |
| 277 | N-[3-(4-Amino-7-isopropyl-7H-pyrrolo[2,3-d]pyrimidine-5-carbonyl)-2-methyl-phenyl]-3,5-dichloro-benzenesulfonamide | 519.4 | 2.0 | 2 |
| 278 | N-[3-(4-Amino-7-isopropyl-7H-pyrrolo[2,3-d]pyrimidine-5-carbonyl)-2-methyl-phenyl]-3,5-difluoro-benzenesulfonamide | 486.5 | 1.8 | 2 |
| 279 | N-[3-(4-Amino-7-isopropyl-7H-pyrrolo[2,3-d]pyrimidine-5-carbonyl)-2-methyl-phenyl]-3-chloro-4-fluoro-benzenesulfonamide | 503 | 2.1 | 2 |

| Example | Compound Name | MH+ | HPLC Rf (min) | method |
|---|---|---|---|---|
| 280 | N-[3-(4-Amino-7-isopropyl-7H-pyrrolo[2,3-d]pyrimidine-5-carbonyl)-2-methyl-phenyl]-2,4-dichloro-benzenesulfonamide | 519.4 | 2.2 | 2 |
| 281 | N-[3-(4-Amino-7-isopropyl-7H-pyrrolo[2,3-d]pyrimidine-5-carbonyl)-2-methyl-phenyl]-3-chloro-4-methyl-benzenesulfonamide | 499 | 2.1 | 2 |

EXAMPLES 282-286

Examples 282-286 listed in the following table were prepared using procedures analogous to those described in Example 25 with Example 275C as the starting material.

2-Chloro-N-methoxy-N-methyl-3-nitro-benzamide by procedures analogous to those described for the preparation of (4-Amino-7-isopropyl-7H-pyrrolo[2,3-d]pyrimidin-5-yl)-(3-amino-2-methyl-phenyl)-methanone. MS: 330.3 (MH+); HPLC R$_f$: 1.6 min. (HPLC HPLC purity: 99%.

| Example | Compound Name | MH+ | HPLC Rf (min) | method |
|---|---|---|---|---|
| 282 | 1-[3-(4-Amino-7-isopropyl-7H-pyrrolo[2,3-d]pyrimidine-5-carbonyl)-2-methyl-phenyl]-3-(3,5-dichloro-phenyl)-urea | 498 | 2.1 | 2 |
| 283 | 1-[3-(4-Amino-7-isopropyl-7H-pyrrolo[2,3-d]pyrimidine-5-carbonyl)-2-methyl-phenyl]-3-(2-chloro-phenyl)-urea | 464 | 2.0 | 2 |
| 284 | 1-[3-(4-Amino-7-isopropyl-7H-pyrrolo[2,3-d]pyrimidine-5-carbonyl)-2-methyl-phenyl]-3-isopropyl-urea | 395.5 | 1.3 | 2 |
| 285 | 1-[3-(4-Amino-7-isopropyl-7H-pyrrolo[2,3-d]pyrimidine-5-carbonyl)-2-methyl-phenyl]-3-(2,4-dichloro-phenyl)-urea | 498.4 | 2.2 | 2 |
| 286 | 1-[3-(4-Amino-7-isopropyl-7H-pyrrolo[2,3-d]pyrimidine-5-carbonyl)-2-methyl-phenyl]-3-(3,5-difluoro-phenyl)-urea | 465.5 | 2.1 | 2 |

EXAMPLE 287

(3-Amino-2-chloro-phenyl)-(4-amino-7-isopropyl-7H-pyrrolo[2,3-d]pyrimidin-5-yl)-methanone The title compound was prepared from 5-Bromo-4-chloro-7-isopropyl-7H-pyrrolo[2,3-d]pyrimidine and

EXAMPLES 288-293

Examples 288-293 listed in the following table were prepared using procedures analogous to those described in Example 4 with Example 287 as the starting material.

| Example | Compound Name | MH+ | HPLC Rf (min) | method |
|---|---|---|---|---|
| 288 | N-[3-(4-Amino-7-isopropyl-7H-pyrrolo[2,3-d]pyrimidine-5-carbonyl)-2-chloro-phenyl]-2,4-dichloro-benzenesulfonamide | 540 | 2.2 | 2 |
| 289 | N-[3-(4-Amino-7-isopropyl-7H-pyrrolo[2,3-d]pyrimidine-5-carbonyl)-2-chloro-phenyl]-2-chloro-benzenesulfonamide | 505.4 | 2.0 | 2 |
| 290 | N-[3-(4-Amino-7-isopropyl-7H-pyrrolo[2,3-d]pyrimidine-5-carbonyl)-2-chloro-phenyl]-3,5-dichloro-benzenesulfonamide | 539.8 | 2.1 | 2 |
| 291 | N-[3-(4-Amino-7-isopropyl-7H-pyrrolo[2,3-d]pyrimidine-5-carbonyl)-2-chloro-phenyl]-3-chloro-4-fluoro-benzenesulfonamide | 523.4 | 2.0 | 2 |
| 292 | N-[3-(4-Amino-7-isopropyl-7H-pyrrolo[2,3-d]pyrimidine-5-carbonyl)-2-chloro-phenyl]-3-chloro-4-methyl-benzenesulfonamide | 519.4 | 2.0 | 2 |

| | | | HPLC | |
|---|---|---|---|---|
| Example | Compound Name | MH+ | Rf (min) | method |
| 293 | N-[3-(4-Amino-7-isopropyl-7H-pyrrolo[2,3-d]pyrimidine-5-carbonyl)-2-chloro-phenyl]-3,5-difluoro-benzenesulfonamide | 507 | 2.0 | 2 |

EXAMPLES 294-299

Examples 294-299 listed in the following table were prepared using procedures analogous to those described in Example 25 with Example 287 as the starting material.

| | | | HPLC | |
|---|---|---|---|---|
| Example | Compound Name | MH+ | Rf (min) | method |
| 294 | 1-[3-(4-Amino-7-isopropyl-7H-pyrrolo[2,3-d]pyrimidine-5-carbonyl)-2-chloro-phenyl]-3-(3,5-dichloro-phenyl)-urea | 519 | 2.7 | 2 |
| 295 | 1-[3-(4-Amino-7-isopropyl-7H-pyrrolo[2,3-d]pyrimidine-5-carbonyl)-2-chloro-phenyl]-3-m-tolyl-urea | 464 | 2.2 | 2 |
| 296 | 1-[3-(4-Amino-7-isopropyl-7H-pyrrolo[2,3-d]pyrimidine-5-carbonyl)-2-chloro-phenyl]-3-(2,4-dichloro-phenyl)-urea | 519 | 2.7 | 2 |
| 297 | 1-[3-(4-Amino-7-isopropyl-7H-pyrrolo[2,3-d]pyrimidine-5-carbonyl)-2-chloro-phenyl]-3-(2-chloro-phenyl)-urea | 484.4 | 2.2 | 2 |
| 298 | 1-[3-(4-Amino-7-isopropyl-7H-pyrrolo[2,3-d]pyrimidine-5-carbonyl)-2-chloro-phenyl]-3-isopropyl-urea | 416 | 1.5 | 2 |
| 299 | 1-[3-(4-Amino-7-isopropyl-7H-pyrrolo[2,3-d]pyrimidine-5-carbonyl)-2-chloro-phenyl]-3-(3,5-difluoro-phenyl)-urea | 486 | 2.3 | 2 |

EXAMPLE 300

300A. 4-(4-Chloro-pyrrolo[2,3-d]pyrimidin-7-yl)-piperidine-1-carboxylic acid tert-butyl ester Diethyl azodicarboxylate (14.4 g, 82.7 mmol) was added dropwise over a period of 1 h (exothermic) to a solution of 4-chloro-7H-pyrrolo[2,3-d]pyrimidine (6.4 g, 41.4 mmol), 4-hydroxy-piperidine-1-carboxylic acid tert-butyl ester (25.0 g, 124 mmol), and triphenyl phosphine 21.7 g, 82.7 mmol) in THF (500 mL). The reaction mixture was stirred at room temperature 3 h and concentrated in vacuo. The crude reaction mixture was washed with EtOAc, filtered, and concentrated in vacuo. Purification by flash column chromatography (silica, 5:95→15:85 EtOAc:hexanes) provided the title compound as a white solid (6.5 g, 93%). MS: 338 (MH+); HPLC R$_f$: 6.21 min. (HPLC method 4); HPLC purity: 91%.

300B. 4-[4-Amino-5-(3-amino-benzoyl)-pyrrolo[2,3-d]pyrimidin-7-yl]-piperidine-1-carboxylic acid tert-butyl ester The title compound was prepared from 4-(4-Chloro-pyrrolo[2,3-d]pyrimidin-7-yl)-piperidine-1-carboxylic acid tert-butyl ester by procedures analogous to those described for the preparation of (4-Amino-7-cyclopentyl-7H-pyrrolo[2,3-d]pyrimidin-5-yl)-(3-amino-phenyl)-methanone. MS: 437.5 (MH+); HPLC R$_f$: 5.18 min. (HPLC method 4); HPLC purity: 100%.

300C. 4-(4-Amino-5-{3-[3-(3,5-dichloro-phenyl)-ureido]-benzoyl}-pyrrolo[2,3-d]pyrimidin-7-yl)-piperidine-1-carboxylic acid tert-butyl ester 3,5-Dichlorophenyl isocyanate (0.26 g, 1.37 mmol) was added to a solution of 4-[4-amino-5-(3-amino-benzoyl)-pyrrolo[2,3-d]pyrimidin-7-yl]-piperidine-1-carboxylic acid tert-butyl ester (0.5 g, 1.15 mmol) in pyridine (13 mL). The reaction mixture was stirred at 75 C for 4.5 h and room temperature for 12 h in a sealed tube, quenched with H$_2$O (13 mL), and extracted with EtOAc (4×15 mL). The combined organic extracts were washed with CuSO$_4$ (3×15 mL), H$_2$O (20 mL), and brine (30 mL) and dried (MgSO$_4$), filtered, and concentrated in vacuo. The crude reaction mixture was triturated in CH$_2$Cl$_2$ and filtered to obtain the titled compound as a white solid (0.45 g, 63%). MS: 625.5 (MH+); HPLC R$_f$: 7.48 min. (HPLC method 4); HPLC purity: 100%.

300D. 1-[3-(4-Amino-7-piperidin-4-yl-7H-pyrrolo[23-d]pyrimidine-5-carbonyl)-phenyl]-3-(3,5-dichloro-phenyl)-urea A solution of TFA/CH$_2$Cl$_2$ (0.49 mL/3.5 mL) was added to a solution of 4-(4-amino-5-{3-[3-(3,5-dichloro-phenyl)-ureido]-benzoyl}-pyrrolo[2,3-d]pyrimidin-7-yl)-piperidine-1-carboxylic acid tert-butyl ester (0.2 g, 0.32 mmol) in CH$_2$Cl$_2$ (1 mL) at 0 C. The reaction mixture was warmed to room temperature, stirred for 12 h, and concentrated in vacuo. The crude reaction mixture was quenched with H₂O (5 mL) and Na₂CO₃ (5 mL) and extracted with CH₂Cl₂ (4×5 mL). The combined organic extracts were dried (MgSO₄), filtered, and concentrated in vacuo to provide the title compound as a yellow solid (0.16 g, 93%). MS: 525.5 (MH$^+$); HPLC R$_f$: 5.35 min. (HPLC method 4); HPLC purity: 84%.

300E. 1-{3-[4-Amino-7-(1-ethyl-piperidin-4-yl)-7H-pyrrolo[2,3-d]pyrimidine-5-carbonyl]-phenyl}-3-(3, 5-dichloro-phenyl)-urea A solution of 1-[3-(4-Amino-7-piperidin-4-yl-7H-pyrrolo [2,3-d]pyrimidine-5-carbonyl)-phenyl]-3-(3,5-dichloro-phenyl)-urea (100 mg, 0.19 mmol) and acetaldehyde (8.4 mg, 0.19 mmol) in DMF/THF (20%, 10 mL) was stirred for 30 minutes at room temperature. Sodium triacetoxyborohydride (61 mg, 0.29 mmol) was added to the reaction mixture, stirred for 3.5 hours, and concentrated in vacuo. Purification by reverse phase preparative HPLC (HPLC method 2) provided the title compound as a white solid (11 mg, 10%). MS: 553.5 (MH$^+$); HPLC R$_f$: 1.7 min. (HPLC method 2); HPLC purity: 100%.

EXAMPLES 301-309

Examples 301-309 listed in the following table were prepared using procedures analogous to those described in Example 300C-E with Example 300B as the starting material.

EXAMPLE 310

1-{3-[4-Amino-7-(1-benzoyl-piperidin-4-yl)-7H-pyrrolo[2,3-d]pyrimidine-5-carbonyl]-phenyl}-3-(3, 5-dichloro-phenyl)-urea A solution of 1-[3-(4-Amino-7-piperidin-4-yl-7H-pyrrolo [2,3-d]pyrimidine-5-carbonyl)-phenyl]-3-(3,5-dichloro-phenyl)-urea (100 mg, 0.19 mmol), HATU (73 mg, 0.19 mmol), and benzoic acid (24 mg, 0.19 mmol) in DMF (5 mL) was stirred for 12 hours at room temperature The reaction mixture concentrated in vacuo. Purification by reverse phase preparative HPLC (HPLC method 2) provided the title compound as a white solid (17 mg, 14%). MS: 629.5 (MH$^+$); HPLC R$_f$: 2.5 min. (HPLC method 2); HPLC purity: 100%.

EXAMPLES 311-315

Examples 311-315 listed in the following table were prepared using procedures analogous to those described in Example 300C-D & 310 with Example 300B as the starting material.

| Example | Compound Name | MH+ | HPLC Rf (min) | HPLC method |
|---|---|---|---|---|
| 301 | 1-{3-[4-Amino-7-(1-benzyl-piperidin-4-yl)-7H-pyrrolo[2,3-d]pyrimidine-5-carbonyl]-phenyl}-3-(3,5-dichloro-phenyl)-urea | 615.5 | 2.6 | 2 |
| 302 | 4-(4-Amino-5-{3-[3-(2-fluoro-5-methyl-phenyl)-ureido]-benzoyl}-pyrrolo[2,3-d]pyrimidin-7-yl)-piperidine-1-carboxylic acid tert-butyl ester | 588.6 | 2.5 | 2 |
| 303 | 1-[3-(4-Amino-7-piperidin-4-yl-7H-pyrrolo[2,3-d]pyrimidine-5-carbonyl)-phenyl]-3-(2-fluoro-5-methyl-phenyl)-urea | 488.5 | 1.3 | 2 |
| 304 | 1-{3-[4-Amino-7-(1-isobutyl-piperidin-4-yl)-7H-pyrrolo[2,3-d]pyrimidine-5-carbonyl]-phenyl}-3-(3,5-dichloro-phenyl)-urea | 581.5 | 1.7 | 2 |
| 305 | 1-{3-[4-Amino-7-(1-isobutyl-piperidin-4-yl)-7H-pyrrolo[2,3-d]pyrimidine-5-carbonyl]-phenyl}-3-(2-fluoro-5-methyl-phenyl)-urea | 544.6 | 1.5 | 2 |
| 306 | 1-{3-[4-Amino-7-(1-cyclobutyl-piperidin-4-yl)-7H-pyrrolo[2,3-d]pyrimidine-5-carbonyl]-phenyl}-3-(2-fluoro-5-methyl-phenyl)-urea | 542.6 | 1.4 | 2 |
| 307 | 1-{3-[4-Amino-7-(1-ethyl-piperidin-4-yl)-7H-pyrrolo[2,3-d]pyrimidine-5-carbonyl]-phenyl}-3-(2-fluoro-5-methyl-phenyl)-urea | 516.6 | 0.9 | 2 |
| 308 | 1-{3-[4-Amino-7-(1-cyclobutyl-piperidin-4-yl)-7H-pyrrolo[2,3-d]pyrimidine-5-carbonyl]-phenyl}-3-(3,5-dichloro-phenyl)-urea | 579.5 | 1.6 | 2 |
| 309 | 1-{3-[4-Amino-7-(1-benzyl-piperidin-4-yl)-7H-pyrrolo[2,3-d]pyrimidine-5-carbonyl]-phenyl}-3-(2-fluoro-5-methyl-phenyl)-urea | 578.7 | 1.7 | 2 |

| Example | Compound Name | MH+ | HPLC Rf (min) | method |
|---|---|---|---|---|
| 311 | 1-{3-[7-(1-Acetyl-piperidin-4-yl)-4-amino-7H-pyrrolo[2,3-d]pyrimidine-5-carbonyl]-phenyl}-3-(3,5-dichloro-phenyl)-urea | 567.5 | 2.1 | 2 |
| 312 | 1-{3-[4-Amino-7-(1-isobutyryl-piperidin-4-yl)-7H-pyrrolo[2,3-d]pyrimidine-5-carbonyl]-phenyl}-3-(2-fluoro-5-methyl-phenyl)-urea | 558.2 | 2.0 | 2 |
| 313 | 1-{3-[4-Amino-7-(1-benzoyl-piperidin-4-yl)-7H-pyrrolo[2,3-d]pyrimidine-5-carbonyl]-phenyl}-3-(2-fluoro-5-methyl-phenyl)-urea | 592.2 | 2.2 | 2 |
| 314 | 1-(3-{4-Amino-7-[1-(pyridine-4-carbonyl)-piperidin-4-yl]-7H-pyrrolo[2,3-d]pyrimidine-5-carbonyl}-phenyl)-3-(2-fluoro-5-methyl-phenyl)-urea | 593.2 | 1.8 | 2 |
| 315 | 1-{3-[7-(1-Acetyl-piperidin-4-yl)-4-amino-7H-pyrrolo[2,3-d]pyrimidine-5-carbonyl]-phenyl}-3-(2-fluoro-5-methyl-phenyl)-urea | 530.2 | 1.8 | 2 |

EXAMPLE 316

4-(4-Amino-5-{3-[3-(3,5-dichloro-phenyl)-ureido]-benzoyl}-Pyrrolo[2,3-d]pyrimidin-7-yl)-carboxylic acid tert-butyl-amide A solution of 1-[3-(4-Amino-7-piperidin-4-yl-7H-pyrrolo[2,3-d]pyrimidine-5-carbonyl)-phenyl]-3-(3,5-dichloro-phenyl)-urea (50 mg, 0.091 mmol) and t-butyl isocyanate (9 mg, 0.091 mmol) in pyridine (2 mL) was stirred in a sealed tube for 4 hours at 40 C. The reaction mixture concentrated in vacuo. Purification by reverse phase preparative HPLC (HPLC method 2) provided the title compound as a white solid (18 mg, 31%). MS: 624.5 (MH+); HPLC R$_f$: 2.6 min. (HPLC method 2); HPLC purity: 100%.

EXAMPLE 317

4-(4-Amino-5-{3-[3-(2-fluoro-5-methyl-phenyl)-ureido]-benzoyl}-pyrrolo[2,3-d]pyrimidin-7-yl)-peridine-1-carboxylic acid tert-butyl-amide 4-(4-Amino-5-{3[3-(2-fluoro-5-methyl-phenyl)-ureido]-benzoyl}-pyrrolo[2,3-d]pyrimidin-7-yl)-piperidine-1-carboxylic acid tert-butyl-amide was prepared using procedures analogous to those described in Example 300C-D & 316 with Example 300B as the starting material.

EXAMPLE 318

1-{3-[4-Amino-7-(1-methanesulfonyl-piperidin-4-yl)-7H-pyrrolo[2,3-d]pyrimidine-5-carbonyl]-phenyl}-3-(3,5-dichloro-phenyl)-urea A solution of 1-[3-(4-Amino-7-piperidin-4-yl-7H-pyrrolo[2,3-d]pyrimidine-5-carbonyl)-phenyl]-3-(3,5-dichloro-phenyl)-urea (100 mg, 0.19 mmol) and methanesulfonyl-chloride (22 mg, 0.19 mmol) in DMF/CH$_2$Cl$_2$ (2/3, 5 mL) was stirred in a sealed tube for 1.5 hours at room temperature. The reaction mixture concentrated in vacuo. Purification by reverse phase preparative HPLC (HPLC method 2) provided the title compound as a white solid (21.8 mg, 19%). MS: 603.5 (MH+); HPLC R$_f$: 2.3 min. (HPLC method 2); HPLC purity: 100%.

EXAMPLE 319

1-{3-[4-Amino-7-(1-methanesulfonyl-piperidin-4-yl)-7H-pyrrolo[2,3-d]pyrimidine-5-carbonyl]-phenyl}-3-(2-fluoro-5-methyl-phenyl)-urea 1-{3-[4-Amino-7-(1-methanesulfonyl-piperidin-4-yl)-7H-pyrrolo[2,3-d]pyrimidine-5-carbonyl]-phenyl}-3-(2-fluoro-5-methyl-phenyl)-urea was prepared using procedures analogous to those described in Example 300C-D & 318 with Example 300B as the starting material.

| Example | Compound Name | MH+ | HPLC Rf (min) | method |
|---|---|---|---|---|
| 317 | 4-(4-Amino-5-{3-[3-(2-fluoro-5-methyl-phenyl)-ureido]-benzoyl}-pyrrolo[2,3-d]pyrimidin-7-yl)-piperidine-1-carboxylic acid tert-butyl-amide | 588.7 | 2.2 | 2 |

| Example | Compound Name | MH+ | HPLC Rf (min) | method |
|---|---|---|---|---|
| 319 | 1-{3-[4-Amino-7-(1-methanesulfonyl-piperidin-4-yl)-7H-pyrrolo[2,3-d]pyrimidine-5-carbonyl]-phenyl}-3-(2-fluoro-5-methyl-phenyl)-urea | 566.1 | 2.1 | 2 |

EXAMPLE 320

320A. 4-{4-Amino-5-[3-(3,5-dichloro-benzenesulfonylamino)-benzoyl]-pyrrolo[2,3-d]pyrimidin-7-yl}-piperidine-1-carboxylic acid tert-butyl ester 3,5-Dichlorophenyl sulfonylchloride (2.8 g, 11.5 mmol) was added to a solution of 4-[4-amino-5-(3-amino-benzoyl)-pyrrolo[2,3-d]pyrimidin-7-yl]-piperidine-1-carboxylic acid tert-butyl ester (2.5 g, 5.7 mmol) in pyridine (55 mL). The reaction mixture was stirred at 40 C for 12 h in a sealed tube, quenched with $H_2O$ (45 mL), and extracted with EtOAc (3×50 mL). The combined organic extracts were washed with $CuSO_4$ (3×150 mL), $H_2O$ (200 mL), and brine (200 mL) and dried ($MgSO_4$), filtered, and concentrated in vacuo. The crude reaction mixture was filtered to obtain the titled compound as an off-white solid (1.5 g, 41%). MS: 646.5 ($MH^+$); HPLC $R_f$: 6.95 min. (HPLC method 4); HPLC purity: 100%.

320B. N-[3-(4-Amino-7-piperidin-4-yl-7H-pyrrolo[2,3-d]pyrimidine-5-carbonyl)-phenyl]-3,5-dichloro-benzenesulfonamide The title compound was prepared from 4-{4-Amino-5-[3-(3,5-dichloro-benzenesulfonylamino)-benzoyl]-pyrrolo[2,3-d]pyrimidin-7-yl}-piperidine-1-carboxylic acid tert-butyl ester by procedures analogous to those described for the preparation of 1-[3-(4-Amino-7-piperidin-4-yl-7H-pyrrolo[2,3-d]pyrimidine-5-carbonyl)-phenyl]-3-(3,5-dichloro-phenyl)-urea. MS: 546.5 ($MH^+$); HPLC $R_f$: 4.91 min. (HPLC method 4); HPLC purity: 100%.

EXAMPLES 321-324

Examples 321-324 listed in the following table were prepared using procedures analogous to those described in Example 300E with Example 320B as the starting material.

| Example | Compound Name | MH+ | HPLC Rf (min) | method |
|---|---|---|---|---|
| 321 | N-{3-[4-Amino-7-(1-benzyl-piperidin-4-yl)-7H-pyrrolo[2,3-d]pyrimidine-5-carbonyl]-phenyl}-3,5-dichloro-benzenesulfonamide | 536.5 | 6.20 | 4 |
| 322 | N-{3-[4-Amino-7-(1-cyclobutyl-piperidin-4-yl)-7H-pyrrolo[2,3-d]pyrimidine-5-carbonyl]-phenyl}-3,5-dichloro-benzenesulfonamide | 600 | xx | 2 |
| 323 | N-{3-[4-Amino-7-(1-ethyl-piperidin-4-yl)-7H-pyrrolo[2,3-d]pyrimidine-5-carbonyl]-phenyl}-3,5-dichloro-benzenesulfonamide | 574.5 | 1.6 | 2 |
| 324 | N-{3-[4-Amino-7-(1-isobutyl-piperidin-4-yl)-7H-pyrrolo[2,3-d]pyrimidine-5-carbonyl]-phenyl}-3,5-dichloro-benzenesulfonamide | 602.5 | 1.9 | 2 |

EXAMPLES 325-328

Examples 325-328 listed in the following table were prepared using procedures analogous to those described in Example 310 with Example 320B as the starting material.

| Example | Compound Name | MH+ | HPLC Rf (min) | method |
|---|---|---|---|---|
| 325 | N-{3-[7-(1-Acetyl-piperidin-4-yl)-4-amino-7H-pyrrolo[2,3-d]pyrimidine-5-carbonyl]-phenyl}-3,5-dichloro-benzenesulfonamide | 588.5 | 1.6 | 2 |
| 326 | N-(3-{4-Amino-7-[1-(pyridine-4-carbonyl)-piperidin-4-yl]-7H-pyrrolo[2,3-d]pyrimidine-5- | 651.5 | 1.9 | 2 |

| | | | HPLC | |
|---|---|---|---|---|
| Example | Compound Name | MH+ | Rf (min) | method |
| | carbonyl}-phenyl)-3,5-dichloro-benzenesulfonamide | | | |
| 327 | N-{3-[4-Amino-7-(1-benzoyl-piperidin-4-yl)-7H-pyrrolo[2,3-d]pyrimidine-5-carbonyl]-phenyl}-3,5-dichloro-benzenesulfonamide | 650.5 | 2.3 | 2 |
| 328 | N-{3-[4-Amino-7-(1-isobutyryl-piperidin-4-yl)-7H-pyrrolo[2,3-d]pyrimidine-5-carbonyl]-phenyl)-3,5-dichloro-benzenesulfonamide | 616.5 | 2.1 | 2 |

EXAMPLE 329

4-{4-Amino-5-[3-(3,5-dichloro-benzenesulfonylamino)-benzoyl]-pyrrolo[2,3-d]pyrimidin-7-yl}-piperidine-1-carboxylic acid tert-butyl-amide 4-{4-Amino-5-[3-(3,5-dichloro-benzenesulfonylamino)-benzoyl]-pyrrolo[2,3-d]pyrimidin-7-yl}-piperidine-1-carboxylic acid tert-butyl-amide was prepared using procedures analogous to those described in Example 316 with Example 320B as the starting material.

| | | | HPLC | |
|---|---|---|---|---|
| Example | Compound Name | MH+ | Rf (min) | method |
| 329 | 4-{4-Amino-5-[3-(3,5-dichloro-benzenesulfonylamino)-benzoyl]-pyrrolo[2,3-d]pyrimidin-7-yl}-piperidine-1-carboxylic acid tert-butyl-amide | 645.5 | 2.3 | 2 |

The following compounds were also prepared using the methods described in this application:

7-Cyclopentyl-5-(1H-indol-5-yl)-7H-pyrrolo[2,3-d]pyrimidin-4-ylamine;

5-[1-(2-Chloro-benzenesulfonyl)-1H-indol-5-yl]-7-cyclopentyl-7H-pyrrolo[2,3-d]pyrimidin-4-ylamine;

7-Cyclopentyl-5-[1-(2,6-difluoro-benzenesulfonyl)-1H-indol-5-yl]-7H-pyrrolo[2,3-d]pyrimidin-4-ylamine;

7-Cyclopentyl-5-[1-(2,4-difluoro-benzenesulfonyl)-1H-indol-5-yl]-7H-pyrrolo[2,3-d]pyrimidin-4-ylamine;

7-Cyclopentyl-5-[1-(2,3-dichloro-benzenesulfonyl)-1H-indol-5-yl]-7H-pyrrolo[2,3-d]pyrimidin-4-ylamine;

7-Cyclopentyl-5-[1-(3-methoxy-benzenesulfonyl)-1H-indol-5-yl]-7H-pyrrolo[2,3-d]pyrimidin-4-ylamine;

7-Cyclopentyl-5-[1-(2-fluoro-benzenesulfonyl)-1H-indol-5-yl]-7H-pyrrolo[2,3-d]pyrimidin-4-ylamine;

7-Cyclopentyl-5-[1-(toluene-2-sulfonyl)-1H-indol-5-yl]-7H-pyrrolo[2,3-d]pyrimidin-4-ylamine;

N-[3-(4-Amino-7-cyclopentyl-7H-pyrrolo[2,3-d]pyrimidin-5-ylmethyl)-phenyl]-2-methyl-benzenesulfonamide;

N-[3-(4-Amino-7-cyclopentyl-7H-pyrrolo[2,3-d]pyrimidin-5-ylmethyl)-phenyl]-2-fluoro-benzenesulfonamide;

N-[3-(4-Amino-7-cyclopentyl-7H-pyrrolo[2,3-d]pyrimidin-5-ylmethyl)-phenyl]-3-methoxy-benzenesulfonamide;

N-[3-(4-Amino-7-cyclopentyl-7H-pyrrolo[2,3-d]pyrimidin-5-ylmethyl)-phenyl]-2,3-dichloro-benzenesulfonamide;

N-[3-(4-Amino-7-cyclopentyl-7H-pyrrolo[2,3-d]pyrimidin-5-ylmethyl)-phenyl]-2,4-difluoro-benzenesulfonamide;

N-[3-(4-Amino-7-cyclopentyl-7H-pyrrolo[2,3-d]pyrimidin-5-ylmethyl)-phenyl]-2,6-difluoro-benzenesulfonamide;

N-[3-(4-Amino-7-cyclopentyl-7H-pyrrolo[2,3-d]pyrimidin-5-ylmethyl)-phenyl]-2-chloro-benzenesulfonamide;

5-(3-Amino-benzyl)-7-cyclopentyl-7H-pyrrolo[2,3-d]pyrimidin-4-ylamine;

N-[5-(4-Amino-7-isopropyl-7H-pyrrolo[2,3-d]pyrimidine-5-carbonyl)-2-methoxy-phenyl]-3,5-dichloro-benzenesulfonamide;

N-[5-(4-Amino-7-isopropyl-7H-pyrrolo[2,3-d]pyrimidine-5-carbonyl)-2-methoxy-phenyl]-C-(3,5-dichloro-phenyl)-methanesulfonamide;

N-[5-(4-Amino-7-isopropyl-7H-pyrrolo[2,3-d]pyrimidine-5-carbonyl)-2-methoxy-phenyl]-3,5-difluoro-benzenesulfonamide;

1-[5-(4-Amino-7-isopropyl-7H-pyrrolo[2,3-d]pyrimidine-5-carbonyl)-2-methoxy-phenyl]-3-(2-chloro-phenyl)-urea;

1-[5-(4-Amino-7-isopropyl-7H-pyrrolo[2,3-d]pyrimidine-5-carbonyl)-2-methoxy-phenyl]-3-(2-fluoro-5-methyl-phenyl)-urea;

1-[5-(4-Amino-7-isopropyl-7H-pyrrolo[2,3-d]pyrimidine-5-carbonyl)-2-methoxy-phenyl]-3-m-tolyl-urea;

1-[5-(4-Amino-7-isopropyl-7H-pyrrolo[2,3-d]pyrimidine-5-carbonyl)-2-methoxy-phenyl]-3-(3,5-dichloro-phenyl)-urea;

1-[5-(4-Amino-7-isopropyl-7H-pyrrolo[2,3-d]pyrimidine-5-carbonyl)-2-methoxy-phenyl]-3-(3,5-difluoro-phenyl)-urea;

1-[5-(4-Amino-7-isopropyl-7H-pyrrolo[2,3-d]pyrimidine-5-carbonyl)-2-methoxy-phenyl]-3-(2,4-dichloro-phenyl)-urea;

1-[5-(4-Amino-7-isopropyl-7H-pyrrolo[2,3-d]pyrimidine-5-carbonyl)-2-methoxy-phenyl]-3-cyclohexyl-urea;

N-[5-(4-Amino-7-isopropyl-7H-pyrrolo[2,3-d]pyrimidine-5-carbonyl)-2-methoxy-phenyl]-3-chloro-4-methyl-benzenesulfonamide;

2-{2-[2-(3,5-Difluoro-phenyl)-acetylamino]-butyrylamino}-4-trifluoromethyl-oxazole-5-carboxylic acid ethyl ester;

N-[5-(4-Amino-7-isopropyl-7H-pyrrolo[2,3-d]pyrimidine-5-carbonyl)-2-methoxy-phenyl]-2,4-dichloro-benzenesulfonamide;

N-[5-(4-Amino-7-isopropyl-7H-pyrrolo[2,3-d]pyrimidine-5-carbonyl)-2-methyl-phenyl]-2,4-dichloro-benzenesulfonamide;

1-[3-(4-Amino-7H-pyrrolo[2,3-d]pyrimidine-5-carbonyl)-phenyl]-3-(2,4-dichloro-phenyl)-urea;

1-[3-(4-Amino-7H-pyrrolo[2,3-d]pyrimidine-5-carbonyl)-phenyl]-3-(3,5-dichloro-phenyl)-urea;

1-[3-(4-Amino-7H-pyrrolo[2,3-d]pyrimidine-5-carbonyl)-phenyl]-3-(3,5-difluoro-phenyl)-urea;

1-[3-(4-Amino-7H-pyrrolo[2,3-d]pyrimidine-5-carbonyl)-phenyl]-3-(3,4-dichloro-benzyl)-urea;

N-[3-(4-Amino-7H-pyrrolo[2,3-d]pyrimidine-5-carbonyl)-phenyl]-3-chloro-4-fluoro-benzenesulfonamide;

N-[3-(4-Amino-7H-pyrrolo[2,3-d]pyrimidine-5-carbonyl)-phenyl]-2-chloro-benzenesulfonamide;

1-{3-[4-Amino-7-(2-hydroxy-ethyl)-7H-pyrrolo[2,3-d]pyrimidine-5-carbonyl]-phenyl}-3-(3,5-difluoro-phenyl)-urea;

N-{3-[4-Amino-7-(2-hydroxy-ethyl)-7H-pyrrolo[2,3-d]pyrimidine-5-carbonyl]-phenyl}-3,5-dichloro-benzenesulfonamide;

N-{3-[4-Amino-7-(2-hydroxy-ethyl)-7H-pyrrolo[2,3-d]pyrimidine-5-carbonyl]-phenyl}-3-chloro-4-methyl-benzenesulfonamide;

N-{3-[4-Amino-7-(2-hydroxy-ethyl)-7H-pyrrolo[2,3-d]pyrimidine-5-carbonyl]-phenyl}-3-chloro-4-fluoro-benzenesulfonamide;

N-{3-[4-Amino-7-(2-hydroxy-ethyl)-7H-pyrrolo[2,3-d]pyrimidine-5-carbonyl]-phenyl}-2,4-dichloro-benzenesulfonamide;

N-{3-[4-Amino-7-(2-hydroxy-ethyl)-7H-pyrrolo[2,3-d]pyrimidine-5-carbonyl]-phenyl}-3,5-difluoro-benzenesulfonamide;

1-{3-[4-Amino-7-(2-hydroxy-ethyl)-7H-pyrrolo[2,3-d]pyrimidine-5-carbonyl]-phenyl}-3-(3,5-dichloro-phenyl)-urea;

Thiophene-2-sulfonic acid{3-[4-amino-7-(2-hydroxy-ethyl)-7H-pyrrolo[2,3-d]pyrimidine-5-carbonyl]-phenyl}-amide;

1-{3-[4-Amino-7-(2-morpholin-4-yl-ethyl)-7H-pyrrolo[2,3-d]pyrimidine-5-carbonyl]-phenyl}3-(2-chloro-phenyl)-urea;

1-{3-[4-Amino-7-(2-morpholin-4-yl-ethyl)-7H-pyrrolo[2,3-d]pyrimidine-5-carbonyl]-phenyl}3-(2-methoxy-5-methyl-phenyl)-urea;

N-{3-[4-Amino-7-(2-morpholin-4-yl-ethyl)-7H-pyrrolo[2,3-d]pyrimidine-5-carbonyl]-phenyl}3,5-dichloro-benzenesulfonamide;

N-{3-[4-Amino-7-(2-morpholin-4-yl-ethyl)-7H-pyrrolo[2,3-d]pyrimidine-5-carbonyl]-phenyl}2,4-dichloro-benzenesulfonamide;

1-{3-[4-Amino-7-(2-morpholin-4-yl-ethyl)-7H-pyrrolo[2,3-d]pyrimidine-5-carbonyl]-phenyl}-3-(2-fluoro-4-methyl-phenyl urea;

1-{3-[4-Amino-7-(2-morpholin-4-yl-ethyl)-7H-pyrrolo[2,3-d]pyrimidine-5-carbonyl]-phenyl}3-m-tolyl-urea;

1-{3-[4-Amino-7-(2-morpholin-4-yl-ethyl)-7H-pyrrolo[2,3-d]pyrimidine-5-carbonyl]-phenyl}3-(3-ethyl-phenyl)-urea;

N-{3-[4-Amino-7-(2-morpholin-4-yl-ethyl)-7H-pyrrolo[2,3-d]pyrimidine-5-carbonyl]-phenyl}3-chloro-4-methyl-benzenesulfonamide;

N-{3-[4-Amino-7-(2-morpholin-4-yl-ethyl)-7H-pyrrolo[2,3-d]pyrimidine-5-carbonyl]-phenyl}3-chloro-4-fluoro-benzenesulfonamide;

1-(3-{4-Amino-7-[4-(4-methyl-piperazin-1-yl)-cyclohexyl]-7H-pyrrolo[2,3-d]pyrimidine-5-carbonyl}-phenyl)-3-(2,4-dichloro-phenyl)-urea;

1-(3-{4-Amino-7-[4-(4-methyl-piperazin-1-yl)-cyclohexyl]-7H-pyrrolo[2,3-d]pyrimidine-5-carbonyl}-phenyl)-3-(2,4-dichloro-phenyl)-urea;

N-[3-(4-Amino-7H-pyrrolo[2,3-d]pyrimidine-5-carbonyl)-phenyl]-2,6-difluoro-benzenesulfonamide;

1-[3-(4-Amino-7H-pyrrolo[2,3-d]pyrimidine-5-carbonyl)-phenyl]-3-(2,4-dichloro-benzyl)-urea;

N-[3-(4-Amino-7H-pyrrolo[2,3-d]pyrimidine-5-carbonyl)-phenyl]-2,4-dichloro-benzenesulfonamide;

N-[3-(4-Amino-7H-pyrrolo[2,3-d]pyrimidine-5-carbonyl)-phenyl]-2,4-difluoro-benzenesulfonamide;

N-[3-(4-Amino-7H-pyrrolo[2,3-d]pyrimidine-5-carbonyl)-phenyl]-C-(3,5-dichloro-phenyl)-methanesulfonamide;

1-[3-(4-Amino-7H-pyrrolo[2,3-d]pyrimidine-5-carbonyl)-phenyl]-3-(2-chloro-phenyl)-urea;

1-[3-(4-Amino-7H-pyrrolo[2,3-d]pyrimidine-5-carbonyl)-phenyl]-3-(2-fluoro-5-methyl-phenyl)-urea;

N-[3-(4-Amino-7H-pyrrolo[2,3-d]pyrimidine-5-carbonyl)-phenyl]-3,5-dichloro-benzenesulfonamide;

1-[3-(4-Amino-7H-pyrrolo[2,3-d]pyrimidine-5-carbonyl)-phenyl]-3-cyclohexyl-urea;

1-[3-(4-Amino-7H-pyrrolo[2,3-d]pyrimidine-5-carbonyl)-phenyl]-3-m-tolyl-urea;

1-[3-(4-Amino-7H-pyrrolo[2,3-d]pyrimidine-5-carbonyl)-phenyl]-3-(2-methoxy-5-methyl-phenyl)-urea;

1-[3-(4-Amino-7-benzyl-7H-pyrrolo[2,3-d]pyrimidine-5-carbonyl)-phenyl]-3-(2-fluoro-5-methyl-phenyl)-urea;

1-[3-(4-Amino-7-benzyl-7H-pyrrolo[2,3-d]pyrimidine-5-carbonyl)-phenyl]-3-(2-methoxy-5-methyl-phenyl)-urea;

N-[3-(4-Amino-7-benzyl-7H-pyrrolo[2,3-d]pyrimidine-5-carbonyl)-phenyl]-2,3-dichloro-benzenesulfonamide;

N-[3-(4-Amino-7-benzyl-7H-pyrrolo[2,3-d]pyrimidine-5-carbonyl)-phenyl]-2,6-difluoro-benzenesulfonamide;

1-[3-(4-Amino-7-isopropyl-7H-pyrrolo[2,3-d]pyrimidine-5-carbonyl)-phenyl]-3-(2-chloro-phenyl)-urea;

1-[3-(4-Amino-7-isopropyl-7H-pyrrolo[2,3-d]pyrimidine-5-carbonyl)-phenyl]-3-(2-methoxy-5-methyl-phenyl)-urea;

1-[3-(4-Amino-7-isopropyl-7H-pyrrolo[2,3-d]pyrimidine-5-carbonyl)-phenyl]-3-(2-fluoro-5-methyl-phenyl)-urea;

1-[3-(4-Amino-7-isopropyl-7H-pyrrolo[2,3-d]pyrimidine-5-carbonyl)-phenyl]-3-m-tolyl-urea;

1-[3-(4-Amino-7-isopropyl-7H-pyrrolo[2,3-d]pyrimidine-5-carbonyl)-phenyl]-3-(3-methyl-benzyl)-urea;

1-[3-(4-Amino-7-isopropyl-7H-pyrrolo[2,3-d]pyrimidine-5-carbonyl)-phenyl]-3-(3-ethyl-phenyl)-urea;

N-[3-(4-Amino-7-isopropyl-7H-pyrrolo[2,3-d]pyrimidine-5-carbonyl)-phenyl]-3-chloro-4-methyl-benzenesulfonamide;

N-[3-(4-Amino-7-isopropyl-7H-pyrrolo[2,3-d]pyrimidine-5-carbonyl)-phenyl]-3-chloro-4-fluoro-benzenesulfonamide;

N-[3-(4-Amino-7-isopropyl-7H-pyrrolo[2,3-d]pyrimidine-5-carbonyl)-phenyl]-3,5-dichloro-benzenesulfonamide;

N-[3-(4-Amino-7-isopropyl-7H-pyrrolo[2,3-d]pyrimidine-5-carbonyl)-phenyl]-2,4-dichloro-benzenesulfonamide;

1-[3-(4-Amino-7-isopropyl-7H-pyrrolo[2,3-d]pyrimidine-5-carbonyl)-phenyl]-3-(2,4-difluoro-phenyl)-urea;

1-[3-(4-Amino-7-isopropyl-7H-pyrrolo[2,3-d]pyrimidine-5-carbonyl)-phenyl]-3-(2,6-difluoro-phenyl)-urea;

1-[3-(4-Amino-7-isopropyl-7H-pyrrolo[2,3-d]pyrimidine-5-carbonyl)-phenyl]-3-(3,4-difluoro-phenyl)-urea;

1-[3-(4-Amino-7-isopropyl-7H-pyrrolo[2,3-d]pyrimidine-5-carbonyl)-phenyl]-3-(3-fluoro-phenyl)-urea;

1-[3-(4-Amino-7-isopropyl-7H-pyrrolo[2,3-d]pyrimidine-5-carbonyl)-phenyl]-3-(5-fluoro-2-methyl-phenyl)-urea;

1-[3-(4-Amino-7-isopropyl-7H-pyrrolo[2,3-d]pyrimidine-5-carbonyl)-phenyl]-3-(4-fluoro-phenyl)-urea;

1-[3-(4-Amino-7-isopropyl-7H-pyrrolo[2,3-d]pyrimidine-5-carbonyl)-phenyl]-3-(3-fluoro-4-methyl-phenyl)-urea;

1-[3-(4-Amino-7-isopropyl-7H-pyrrolo[2,3-d]pyrimidine-5-carbonyl)-phenyl]-3-(3,5-difluoro-phenyl)-urea;

1-[3-(4-Amino-7-isopropyl-7H-pyrrolo[2,3-d]pyrimidine-5-carbonyl)-phenyl]-3-(2,5-difluoro-phenyl)-urea;

N-[3-(4-Amino-7-isopropyl-7H-pyrrolo[2,3-d]pyrimidine-5-carbonyl)-phenyl]-3,5-difluoro-benzenesulfonamide;

1-[3-(4-Amino-7-sec-butyl-7H-pyrrolo[2,3-d]pyrimidine-5-carbonyl)-phenyl]-3-(2-chloro-phenyl)-urea;

1-[3-(4-Amino-7-sec-butyl-7H-pyrrolo[2,3-d]pyrimidine-5-carbonyl)-phenyl]-3-(2-methoxy-5-methyl-phenyl)-urea;

1-[3-(4-Amino-7-sec-butyl-7H-pyrrolo[2,3-d]pyrimidine-5-carbonyl)-phenyl]-3-(2-fluoro-5-methyl-phenyl)-urea;

1-[3-(4-Amino-7-sec-butyl-7H-pyrrolo[2,3-d]pyrimidine-5-carbonyl)-phenyl]-3-m-tolyl-urea;

1-[3-(4-Amino-7-sec-butyl-7H-pyrrolo[2,3-d]pyrimidine-5-carbonyl)-phenyl]-3-(3-ethyl-phenyl)-urea;

N-[3-(4-Amino-7-sec-butyl-7H-pyrrolo[2,3-d]pyrimidine-5-carbonyl)-phenyl]-3,5-dichloro-benzenesulfonamide;

N-[3-(4-Amino-7-sec-butyl-7H-pyrrolo[2,3-d]pyrimidine-5-carbonyl)-phenyl]-3-chloro-4-methyl-benzenesulfonamide;

N-[3-(4-Amino-7-sec-butyl-7H-pyrrolo[2,3-d]pyrimidine-5-carbonyl)-phenyl]-3-chloro-4-fluoro-benzenesulfonamide;

N-[3-(4-Amino-7-sec-butyl-7H-pyrrolo[2,3-d]pyrimidine-5-carbonyl)-phenyl]-2,4-dichloro-benzenesulfonamide;

N-[3-(4-Amino-7-cyclobutyl-7H-pyrrolo[2,3-d]pyrimidine-5-carbonyl)-phenyl]-3-chloro-4-methyl-benzenesulfonamide;

N-[3-(4-Amino-7-cyclobutyl-7H-pyrrolo[2,3-d]pyrimidine-5-carbonyl)-phenyl]-3,5-dichloro-benzenesulfonamide;

N-[3-(4-Amino-7-cyclobutyl-7H-pyrrolo[2,3-d]pyrimidine-5-carbonyl)-phenyl]-3-chloro-4-fluoro-benzenesulfonamide;

N-[3-(4-Amino-7-cyclobutyl-7H-pyrrolo[2,3-d]pyrimidine-5-carbonyl)-phenyl]-2,4-dichloro-benzenesulfonamide;

1-[3-(4-Amino-7-cyclobutyl-7H-pyrrolo[2,3-d]pyrimidine-5-carbonyl)-phenyl]-3-(2-methoxy-5-methyl-phenyl)-urea;

1-[3-(4-Amino-7-cyclobutyl-7H-pyrrolo[2,3-d]pyrimidine-5-carbonyl)-phenyl]-3-(2-fluoro-5-methyl-phenyl)-urea;

1-[3-(4-Amino-7-cyclobutyl-7H-pyrrolo[2,3-d]pyrimidine-5-carbonyl)-phenyl]-3-m-tolyl-urea;

1-[3-(4-Amino-7-cyclobutyl-7H-pyrrolo[2,3-d]pyrimidine-5-carbonyl)-phenyl]-3-(3-ethyl-phenyl)-urea;

1-[3-(4-Amino-7-cyclobutyl-7H-pyrrolo[2,3-d]pyrimidine-5-carbonyl)-phenyl]-3-(2-chloro-phenyl)-urea;

N-[3-(4-Amino-7-isopropyl-7H-pyrrolo[2,3-d]pyrimidine-5-carbonyl)-phenyl]-benzenesulfonamide;

N-[3-(4-Amino-7-isopropyl-7H-pyrrolo[2,3-d]pyrimidine-5-carbonyl)-phenyl]-2-cyano-benzenesulfonamide;

N-[3-(4-Amino-7-isopropyl-7H-pyrrolo[2,3-d]pyrimidine-5-carbonyl)-phenyl]-2,6-difluoro-benzenesulfonamide;

N-[3-(4-Amino-7-isopropyl-7H-pyrrolo[2,3-d]pyrimidine-5-carbonyl)-phenyl]-2,6-dichloro-benzenesulfonamide;

1-[3-(4-Amino-7-isopropyl-7H-pyrrolo[2,3-d]pyrimidine-5-carbonyl)-phenyl]-3-(3-chloro phenyl)-urea;

1-[3-(4-Amino-7-isopropyl-7H-pyrrolo[2,3-d]pyrimidine-5-carbonyl)-phenyl]-3-(4-chloro-phenyl)-urea;

1-[3-(4-Amino-7-isopropyl-7H-pyrrolo[2,3-d]pyrimidine-5-carbonyl)-phenyl]-3-p-tolyl-urea;

1-[3-(4-Amino-7-isopropyl-7H-pyrrolo[2,3-d]pyrimidine-5-carbonyl)-phenyl]-3-(2-ethyl-phenyl)-urea;

1-[3-(4-Amino-7-isopropyl-7H-pyrrolo[2,3-d]pyrimidine-5-carbonyl)-phenyl]-3-(2-isopropyl-phenyl)-urea;

1-[3-(4-Amino-7-isopropyl-7H-pyrrolo[2,3-d]pyrimidine-5-carbonyl)-phenyl]-3-(4-isopropyl-phenyl)-urea;

1-[3-(4-Amino-7-isopropyl-7H-pyrrolo[2,3-d]pyrimidine-5-carbonyl)-phenyl]-3-(4-methoxy-phenyl)-urea;

1-[3-(4-Amino-7-isopropyl-7H-pyrrolo[2,3-d]pyrimidine-5-carbonyl)-phenyl]-3-(2-methoxy-phenyl)-urea;

1-[3-(4-Amino-7-isopropyl-7H-pyrrolo[2,3-d]pyrimidine-5-carbonyl)-phenyl]-3-(2-ethoxy-phenyl)-urea;

1-[3-(4-Amino-7-isopropyl-7H-pyrrolo[2,3-d]pyrimidine-5-carbonyl)-phenyl]-3-(4-methylsulfanyl-phenyl)-urea;

1-[3-(4-Amino-7-isopropyl-7H-pyrrolo[2,3-d]pyrimidine-5-carbonyl)-phenyl]-3-(3-methylsulfanyl-phenyl)-urea;

1-[3-(4-Amino-7-isopropyl-7H-pyrrolo[2,3-d]pyrimidine-5-carbonyl)-phenyl]-3-(3-cyano-phenyl)-urea;

1-[3-(4-Amino-7-isopropyl-7H-pyrrolo[2,3-d]pyrimidine-5-carbonyl)-phenyl]-3-(3,5-dimethyl-phenyl)-urea;

1-[3-(4-Amino-7-isopropyl-7H-pyrrolo[2,3-d]pyrimidine-5-carbonyl)-phenyl]-3-(3,4-dimethyl-phenyl)-urea;

1-[3-(4-Amino-7-isopropyl-7H-pyrrolo[2,3-d]pyrimidine-5-carbonyl)-phenyl]-3-(2,5-dimethyl-phenyl)-urea;

1-[3-(4-Amino-7-isopropyl-7H-pyrrolo[2,3-d]pyrimidine-5-carbonyl)-phenyl]-3-(2,3-dimethyl-phenyl)-urea;

1-[3-(4-Amino-7-isopropyl-7H-pyrrolo[2,3-d]pyrimidine-5-carbonyl)-phenyl]-3-(2,4-dimethyl-phenyl)-urea;

1-[3-(4-Amino-7-isopropyl-7H-pyrrolo[2,3-d]pyrimidine-5-carbonyl)-phenyl]-3-propyl-urea;

1-[3-(4-Amino-7-isopropyl-7H-pyrrolo[2,3-d]pyrimidine-5-carbonyl)-phenyl]-3-butyl-urea;

1-[3-(4-Amino-7-isopropyl-7H-pyrrolo[2,3-d]pyrimidine-5-carbonyl)-phenyl]-3-thiophen-2-yl-urea;

1-[3-(4-Amino-7-isopropyl-7H-pyrrolo[2,3-d]pyrimidine-5-carbonyl)-phenyl]-3-thiophen-3-yl-urea;

1-[3-(4-Amino-7-isopropyl-7H-pyrrolo[2,3-d]pyrimidine-5-carbonyl)-phenyl]-3-cyclohexyl-urea;

1-[3-(4-Amino-7-isopropyl-7H-pyrrolo[2,3-d]pyrimidine-5-carbonyl)-phenyl]-3-o-tolyl-urea;

1-[3-(4-Amino-7-isopropyl-7H-pyrrolo[2,3-d]pyrimidine-5-carbonyl)-phenyl]-3-benzyl-urea;

1-[3-(4-Amino-7-isopropyl-7H-pyrrolo[2,3-d]pyrimidine-5-carbonyl)-phenyl]-3-(2-cyano-phenyl)-urea;

1-[3-(4-Amino-7-isopropyl-7H-pyrrolo[2,3-d]pyrimidine-5-carbonyl)-phenyl]-3-benzoyl-urea;

1-[3-(4-Amino-7-isopropyl-7H-pyrrolo[2,3-d]pyrimidine-5-carbonyl)-phenyl]-3-(4-methyl-benzyl)-urea;

1-[3-(4-Amino-7-isopropyl-7H-pyrrolo[2,3-d]pyrimidine-5-carbonyl)-phenyl]-3-(2-methyl-benzyl)-urea;

1-[3-(4-Amino-7-isopropyl-7H-pyrrolo[2,3-d]pyrimidine-5-carbonyl)-phenyl]-3-(2,6-dimethyl-phenyl)-urea;

1-[3-(4-Amino-7-isopropyl-7H-pyrrolo[2,3-d]pyrimidine-5-carbonyl)-phenyl]-3-(4-ethyl-phenyl)-urea;

1-[3-(4-Amino-7-isopropyl-7H-pyrrolo[2,3-d]pyrimidine-5-carbonyl)-phenyl]-3-(4-fluoro-benzyl)-urea;

1-[3-(4-Amino-7-isopropyl-7H-pyrrolo[2,3-d]pyrimidine-5-carbonyl)-phenyl]-3-(2-fluoro-benzyl)-urea;

1-[3-(4-Amino-7-isopropyl-7H-pyrrolo[2,3-d]pyrimidine-5-carbonyl)-phenyl]-3-(3-fluoro-benzyl)-urea;

1-(3-Acetyl-phenyl)-3-[3-(4-amino-7-isopropyl-7H-pyrrolo[2,3-d]pyrimidine-5-carbonyl)-phenyl]-urea;

1-(4-Acetyl-phenyl)-3-[3-(4-amino-7-isopropyl-7H-pyrrolo[2,3-d]pyrimidine-5-carbonyl)-phenyl]-urea;

1-[3-(4-Amino-7-isopropyl-7H-pyrrolo[2,3-d]pyrimidine-5-carbonyl)-phenyl]-3-(4-dimethylamino-phenyl)-urea;

1-[3-(4-Amino-7-isopropyl-7H-pyrrolo[2,3-d]pyrimidine-5-carbonyl)-phenyl]-3-(4-methoxy-benzyl)-urea;

1-[3-(4-Amino-7-isopropyl-7H-pyrrolo[2,3-d]pyrimidine-5-carbonyl)-phenyl]-3-(4-ethoxy-phenyl)-urea;

1-[3-(4-Amino-7-isopropyl-7H-pyrrolo[2,3-d]pyrimidine-5-carbonyl)-phenyl]-3-(4-methoxy-2-methyl-phenyl)-urea;

4-{3-[3-(4-Amino-7-isopropyl-7H-pyrrolo[2,3-d]pyrimidine-5-carbonyl)-phenyl]-ureido}-benzoic acid methyl ester;

1-[3-(4-Amino-7-isopropyl-7H-pyrrolo[2,3-d]pyrimidine-5-carbonyl)-phenyl]-3-(2-methylsulfanyl-phenyl)-urea;

1-[3-(4-Amino-7-isopropyl-7H-pyrrolo[2,3-d]pyrimidine-5-carbonyl)-phenyl]-3-(2-chloro-benzyl)-urea;

1-[3-(4-Amino-7-isopropyl-7H-pyrrolo[2,3-d]pyrimidine-5-carbonyl)-phenyl]-3-(2-chloro-5-methyl-phenyl urea;

1-[3-(4-Amino-7-isopropyl-7H-pyrrolo[2,3-d]pyrimidine-5-carbonyl)-phenyl]-3-(3-chloro-2-methyl-phenyl)-urea;

1-[3-(4-Amino-7-isopropyl-7H-pyrrolo[2,3-d]pyrimidine-5-carbonyl)-phenyl]-3-(2-chloro-6-methyl-phenyl)-urea;

1-[3-(4-Amino-7-isopropyl-7H-pyrrolo[2,3-d]pyrimidine-5-carbonyl)-phenyl]-3-(5-chloro-2-methyl-phenyl)-urea;

1-[3-(4-Amino-7-isopropyl-7H-pyrrolo[2,3-d]pyrimidine-5-carbonyl)-phenyl]-3-(3-chloro-4-methyl-phenyl)-urea;

1-[3-(4-Amino-7-isopropyl-7H-pyrrolo[2,3-d]pyrimidine-5-carbonyl)-phenyl]-3-(4-chloro-2-methyl-phenyl)-urea;

1-[3-(4-Amino-7-isopropyl-7H-pyrrolo[2,3-d]pyrimidine-5-carbonyl)-phenyl]-3-(3-chloro-4-fluoro-phenyl)-urea;

1-[3-(4-Amino-7-isopropyl-7H-pyrrolo[2,3-d]pyrimidine-5-carbonyl)-phenyl]-3-(4-tert-butyl-phenyl)-urea;

1-[3-(4-Amino-7-isopropyl-7H-pyrrolo[2,3-d]pyrimidine-5-carbonyl)-phenyl]-3-isopropyl-urea;

1-[3-(4-Amino-7-isopropyl-7H-pyrrolo[2,3-d]pyrimidine-5-carbonyl)-phenyl]-3-phenyl-urea;

1-[3-(4-Amino-7-isopropyl-7H-pyrrolo[2,3-d]pyrimidine-5-carbonyl)-phenyl]-3-(3-methoxy-phenyl)-urea;

N-[3-(4-Amino-7-isopropyl-7H-pyrrolo[2,3-d]pyrimidine-5-carbonyl)-phenyl]-C-phenyl-methanesulfonamide;

N-[3-(4-Amino-7-isopropyl-7H-pyrrolo[2,3-d]pyrimidine-5-carbonyl)-phenyl]-2-trifluoromethyl-benzenesulfonamide;

N-[3-(4-Amino-7-isopropyl-7H-pyrrolo[2,3-d]pyrimidine-5-carbonyl)-phenyl]-3,4-dichloro-benzenesulfonamide;

N-[3-(4-Amino-7-isopropyl-7H-pyrrolo[2,3-d]pyrimidine-5-carbonyl)-phenyl]-2,3-dichloro-benzenesulfonamide;

Ethanesulfonic acid[3-(4-amino-7-isopropyl-7H-pyrrolo[2,3-d]pyrimidine-5-carbonyl)-phenyl]-amide;

1-Methyl-1H-imidazole-4-sulfonic acid[3-(4-amino-7-isopropyl-7H-pyrrolo[2,3-d]pyrimidine-5-carbonyl)-phenyl]-amide;

N-[3-(4-Amino-7-isopropyl-7H-pyrrolo[2,3-d]pyrimidine-5-carbonyl)-phenyl]-2,4-difluoro-benzenesulfonamide;

N-[3-(4-Amino-7-isopropyl-7H-pyrrolo[2,3-d]pyrimidine-5-carbonyl)-phenyl]-2-methyl-benzenesulfonamide;

N-[3-(4-Amino-7-isopropyl-7H-pyrrolo[2,3-d]pyrimidine-5-carbonyl)-phenyl]-3-methyl-benzenesulfonamide;

N-[3-(4-Amino-7-isopropyl-7H-pyrrolo[2,3-d]pyrimidine-5-carbonyl)-phenyl]-4-methyl-benzenesulfonamide;

N-[3-(4-Amino-7-isopropyl-7H-pyrrolo[2,3-d]pyrimidine-5-carbonyl)-phenyl]-4-fluoro-benzenesulfonamide;

3,5-Dimethyl-isoxazole-4-sulfonic acid[3-(4-amino-7-isopropyl-7H-pyrrolo[2,3-d]pyrimidine-5-carbonyl)-phenyl]-amide;

N-[3-(4-Amino-7-isopropyl-7H-pyrrolo[2,3-d]pyrimidine-5-carbonyl)-phenyl]-4-cyano-benzenesulfonamide;

N-[3-(4-Amino-7-isopropyl-7H-pyrrolo[2,3-d]pyrimidine-5-carbonyl)-phenyl]-3-cyano-benzenesulfonamide;

2-phenyl-ethenesulfonic acid[3-(4-amino-7-isopropyl-7H-pyrrolo[2,3-d]pyrimidine-5-carbonyl)-phenyl]-amide N-[3-(4-Amino-7-isopropyl-7H-pyrrolo[2,3-d]pyrimidine-5-carbonyl)-phenyl]-2,5-dimethyl-benzenesulfonamide;

N-[3-(4-Amino-7-isopropyl-7H-pyrrolo[2,3-d]pyrimidine-5-carbonyl)-phenyl]-4-ethyl-benzenesulfonamide;

N-[3-(4-Amino-7-isopropyl-7H-pyrrolo[2,3-d]pyrimidine-5-carbonyl)-phenyl]-4-chloro-benzenesulfonamide;

N-[3-(4-Amino-7-isopropyl-7H-pyrrolo[2,3-d]pyrimidine-5-carbonyl)-phenyl]-2-chloro-benzenesulfonamide;

N-[3-(4-Amino-7-isopropyl-7H-pyrrolo[2,3-d]pyrimidine-5-carbonyl)-phenyl]-3-chloro-benzenesulfonamide;

N-[3-(4-Amino-7-isopropyl-7H-pyrrolo[2,3-d]pyrimidine-5-carbonyl)-phenyl]-2,5-difluoro-benzenesulfonamide;

4-Acetyl-N-[3-(4-amino-7-isopropyl-7H-pyrrolo[2,3-d]pyrimidine-5-carbonyl)-phenyl]-benzenesulfonamide;

N-[3-(4-Amino-7-isopropyl-7H-pyrrolo[2,3-d]pyrimidine-5-carbonyl)-phenyl]4-isopropyl-benzenesulfonamide;

N-[3-(4-Amino-7-isopropyl-7H-pyrrolo[2,3-d]pyrimidine-5-carbonyl)-phenyl]-3-chloro-2-methyl-benzenesulfonamide;

Naphthalene-2-sulfonic acid[3-(4-amino-7-isopropyl-7H-pyrrolo[2,3-d]pyrimidine-5-carbonyl)-phenyl]-amide;

Quinoline-8-sulfonic acid[3-(4-amino-7-isopropyl-7H-pyrrolo[2,3-d]pyrimidine-5-carbonyl)-phenyl]-amide;

N-[3-(4-Amino-7-isopropyl-7H-pyrrolo[2,3-d]pyrimidine-5-carbonyl)-phenyl]-4-tert-butyl-benzenesulfonamide;

N-[3-(4-Amino-7-isopropyl-7H-pyrrolo[2,3-d]pyrimidine-5-carbonyl)-phenyl]-2,5-dimethoxy-benzenesulfonamide;

N-[3-(4-Amino-7-isopropyl-7H-pyrrolo[2,3-d]pyrimidine-5-carbonyl)-phenyl]-3,4-dimethoxy-benzenesulfonamide;

N-[3-(4-Amino-7-isopropyl-7H-pyrrolo[2,3-d]pyrimidine-5-carbonyl)-phenyl]-4-chloro-2,5-dimethyl-benzenesulfonamide;

N-[3-(4-Amino-7-isopropyl-7H-pyrrolo[2,3-d]pyrimidine-5-carbonyl)-phenyl]-5-chloro-2-methoxy-benzenesulfonamide;

N-[3-(4-Amino-7-isopropyl-7H-pyrrolo[2,3-d]pyrimidine-5-carbonyl)-phenyl]-3-trifluoromethyl-benzenesulfonamide;

N-[3-(4-Amino-7-isopropyl-7H-pyrrolo[2,3-d]pyrimidine-5-carbonyl)-phenyl]-4-butoxy-benzenesulfonamide;

5-Isoxazol-3-yl-thiophene-2-sulfonic acid[3-(4-amino-7-isopropyl-7H-pyrrolo[2,3-d]pyrimidine-5-carbonyl)-phenyl]-amide;

N-[3-(4-Amino-7-isopropyl-7H-pyrrolo[2,3-d]pyrimidine-5-carbonyl)-phenyl]-C-(7,7-dimethyl-2-oxo-bicyclo[2.2.1]hept-1-yl)-methanesulfonamide;

Biphenyl-4-sulfonic acid[3-(4-amino-7-isopropyl-7H-pyrrolo[2,3-d]pyrimidine-5-carbonyl)-phenyl]-amide;

N-[3-(4-Amino-7-isopropyl-7H-pyrrolo[2,3-d]pyrimidine-5-carbonyl)-phenyl]-4-methanesulfonyl-benzenesulfonamide;

N-[3-(4-Amino-7-isopropyl-7H-pyrrolo[2,3-d]pyrimidine-5-carbonyl)-phenyl]-2-methanesulfonyl-benzenesulfonamide;

2-Naphthalen-1-yl-ethanesulfonic acid[3-(4-amino-7-isopropyl-7H-pyrrolo[2,3-d]pyrimidine-5-carbonyl)-phenyl]-amide;

N-[3-(4-Amino-7-isopropyl-7H-pyrrolo[2,3-d]pyrimidine-5-carbonyl)-phenyl]-2,4-dichloro-5-methyl-benzenesulfonamide;

N-[3-(4-Amino-7-isopropyl-7H-pyrrolo[2,3-d]pyrimidine-5-carbonyl)-phenyl]-3,5-dichloro-2-hydroxy-benzenesulfonamide;

N-[3-(4-Amino-7-isopropyl-7H-pyrrolo[2,3-d]pyrimidine-5-carbonyl)-phenyl]-3-fluoro-benzenesulfonamide;

N-[3-(4-Amino-7-isopropyl-7H-pyrrolo[2,3-d]pyrimidine-5-carbonyl)-phenyl]-2-fluoro-benzenesulfonamide;

N-[3-(4-Amino-7-isopropyl-7H-pyrrolo[2,3-d]pyrimidine-5-carbonyl)-phenyl]-3,4-difluoro-benzenesulfonamide;

N-[3-(4-Amino-7-isopropyl-7H-pyrrolo[2,3-d]pyrimidine-5-carbonyl)-phenyl]-2,5-dichloro-benzenesulfonamide;

N-[3-(4-Amino-7-isopropyl-7H-pyrrolo[2,3-d]pyrimidine-5-carbonyl)-phenyl]-4-methoxy-benzenesulfonamide;

N-[3-(4-Amino-7-methyl-7H-pyrrolo[2,3-d]pyrimidine-5-carbonyl)-phenyl]-3,5-dichloro-benzenesulfonamide;

1-[3-(4-Amino-7-methyl-7H-pyrrolo[2,3-d]pyrimidine-5-carbonyl)-phenyl]-3-isopropyl-urea;

1-[3-(4-Amino-7-methyl-7H-pyrrolo[2,3-d]pyrimidine-5-carbonyl)-phenyl]-3-propyl-urea;

1-[3-(4-Amino-7-methyl-7H-pyrrolo[2,3-d]pyrimidine-5-carbonyl)-phenyl]-3-phenyl-urea;

1-[3-(4-Amino-7-methyl-7H-pyrrolo[2,3-d]pyrimidine-5-carbonyl)-phenyl]-3-thiophen-2-yl-urea;

1-[3-(4-Amino-7-methyl-7H-pyrrolo[2,3-d]pyrimidine-5-carbonyl)-phenyl]-3-cyclohexyl-urea;

1-[3-(4-Amino-7-methyl-7H-pyrrolo[2,3-d]pyrimidine-5-carbonyl)-phenyl]-3-p-tolyl-urea;

1-[3-(4-Amino-7-methyl-7H-pyrrolo[2,3-d]pyrimidine-5-carbonyl)-phenyl]-3-o-tolyl-urea;

1-[3-(4-Amino-7-methyl-7H-pyrrolo[2,3-d]pyrimidine-5-carbonyl)-phenyl]-3-m-tol)-4-urea;

1-[3-(4-Amino-7-methyl-7H-pyrrolo[2,3-d]pyrimidine-5-carbonyl)-phenyl]-3-benzyl-urea;

1-[3-(4-Amino-7-methyl-7H-pyrrolo[2,3-d]pyrimidine-5-carbonyl)-phenyl]-3-(2-fluoro-phenyl)-urea;

1-[3-(4-Amino-7-methyl-7H-pyrrolo[2,3-d]pyrimidine-5-carbonyl)-phenyl]-3-(3-fluoro-phenyl)-urea;

1-[3-(4-Amino-7-methyl-7H-pyrrolo[2,3-d]pyrimidine-5-carbonyl)-phenyl]-3-(4-fluoro-phenyl)-urea;

1-[3-(4-Amino-7-methyl-7H-pyrrolo[2,3-d]pyrimidine-5-carbonyl)-phenyl]-3-(3-fluoro-phenyl)-urea;

1-[3-(4-Amino-7-methyl-7H-pyrrolo[2,3-d]pyrimidine-5-carbonyl)-phenyl]-3-(3-methyl-benzyl)-urea;

1-[3-(4-Amino-7-methyl-7H-pyrrolo[2,3-d]pyrimidine-5-carbonyl)-phenyl]-3-(2-methoxy-phenyl)-urea;

1-[3-(4-Amino-7-methyl-7H-pyrrolo[2,3-d]pyrimidine-5-carbonyl)-phenyl]-3-(3-methoxy-phenyl)-urea;

1-[3-(4-Amino-7-methyl-7H-pyrrolo[2,3-d]pyrimidine-5-carbonyl)-phenyl]-3-(4-methoxy-phenyl)-urea;

1-[3-(4-Amino-7-methyl-7H-pyrrolo[2,3-d]pyrimidine-5-carbonyl)-phenyl]-3-(2-fluoro-5-methyl-phenyl)-urea;

1-[3-(4-Amino-7-methyl-7H-pyrrolo[2,3-d]pyrimidine-5-carbonyl)-phenyl]-3-(5-fluoro-2-methyl-phenyl)-urea;

1-[3-(4-Amino-7-methyl-7H-pyrrolo[2,3-d]pyrimidine-5-carbonyl)-phenyl]-3-(3-chloro-phenyl)-urea;

1-[3-(4-Amino-7-methyl-7H-pyrrolo[2,3-d]pyrimidine-5-carbonyl)-phenyl]-3-(4-chloro-phenyl)-urea;

1-(4-Acetyl-phenyl)-3-[3-(4-amino-7-methyl-7H-pyrrolo[2,3-d]pyrimidine-5-carbonyl)-phenyl]-urea;

1-[3-(4-Amino-7-methyl-7H-pyrrolo[2,3-d]pyrimidine-5-carbonyl)-phenyl]-3-(2-trifluoromethyl-phenyl)-urea;

1-[3-(4-Amino-7-methyl-7H-pyrrolo[2,3-d]pyrimidine-5-carbonyl)-phenyl]-3-(2,4-dichloro-phenyl)-urea;

1-[3-(4-Amino-7-methyl-7H-pyrrolo[2,3-d]pyrimidine-5-carbonyl)-phenyl]-3-(2,6-dichloro-phenyl)-urea;

N-[3-(4-Amino-7-methyl-7H-pyrrolo[2,3-d]pyrimidine-5-carbonyl)-phenyl]-methanesulfonamide;

Propane-2-sulfonic acid[3-(4-amino-7-methyl-7H-pyrrolo[2,3-d]pyrimidine-5-carbonyl)-phenyl]-amide;

N-[3-(4-Amino-7-methyl-7H-pyrrolo[2,3-d]pyrimidine-5-carbonyl)-phenyl]-benzenesulfonamide;

1-Methyl-1H-imidazole-4-sulfonic acid[3-(4-amino-7-methyl-7H-pyrrolo[2,3-d]pyrimidine-5-carbonyl)-phenyl]-amide;

Thiophene-2-sulfonic acid[3-(4-amino-7-methyl-7H-pyrrolo[2,3-d]pyrimidine-5-carbonyl)-phenyl]-amide;

N-[3-(4-Amino-7-methyl-7H-pyrrolo[2,3-d]pyrimidine-5-carbonyl)-phenyl]-4-methyl-benzenesulfonamide;

N-[3-(4-Amino-7-methyl-7H-pyrrolo[2,3-d]pyrimidine-5-carbonyl)-phenyl]-C-phenyl-methanesulfonamide;

N-[3-(4-Amino-7-methyl-7H-pyrrolo[2,3-d]pyrimidine-5-carbonyl)-phenyl]-2-methyl-benzenesulfonamide;

N-[3-(4-Amino-7-methyl-7H-pyrrolo[2,3-d]pyrimidine-5-carbonyl)-phenyl]-3-methyl-benzenesulfonamide;

N-[3-(4-Amino-7-methyl-7H-pyrrolo[2,3-d]pyrimidine-5-carbonyl)-phenyl]-4-fluoro-benzenesulfonamide;

N-[3-(4-Amino-7-methyl-7H-pyrrolo[2,3-d]pyrimidine-5-carbonyl)-phenyl]-2-fluoro-benzenesulfonamide;

N-[3-(4-Amino-7-methyl-7H-pyrrolo[2,3-d]pyrimidine-5-carbonyl)-phenyl]-3-fluoro-benzenesulfonamide;

1,2-Dimethyl-1H-imidazole-4-sulfonic acid[3-(4-amino-7-methyl-7H-pyrrolo[2,3-d]pyrimidine-5-carbonyl)-phenyl]-amide;

N-[3-(4-Amino-7-methyl-7H-pyrrolo[2,3-d]pyrimidine-5-carbonyl)-phenyl]-4-cyano-benzenesulfonamide;
N-[3-(4-Amino-7-methyl-7H-pyrrolo[2,3-d]pyrimidine-5-carbonyl)-phenyl]-2-cyano-benzenesulfonamide;
N-[3-(4-Amino-7-methyl-7H-pyrrolo[2,3-d]pyrimidine-5-carbonyl)-phenyl]-3-cyano-benzenesulfonamide;
N-[3-(4-Amino-7-methyl-7H-pyrrolo[2,3-d]pyrimidine-5-carbonyl)-phenyl]-2,5-dimethyl-benzenesulfonamide;
N-[3-(4-Amino-7-methyl-7H-pyrrolo[2,3-d]pyrimidine-5-carbonyl)-phenyl]-4-ethyl-benzenesulfonamide;
N-[3-(4-Amino-7-methyl-7H-pyrrolo[2,3-d]pyrimidine-5-carbonyl)-phenyl]-4-methoxy-benzenesulfonamide;
N-[3-(4-Amino-7-methyl-7H-pyrrolo[2,3-d]pyrimidine-5-carbonyl)-phenyl]-3-methoxy-benzenesulfonamide;
N-[3-(4-Amino-7-methyl-7H-pyrrolo[2,3-d]pyrimidine-5-carbonyl)-phenyl]-5-fluoro-2-methyl-benzenesulfonamide;
N-[3-(4-Amino-7-methyl-7H-pyrrolo[2,3-d]pyrimidine-5-carbonyl)-phenyl]-C-(4-fluoro-phenyl)-methanesulfonamide;
N-[3-(4-Amino-7-methyl-7H-pyrrolo[2,3-d]pyrimidine-5-carbonyl)-phenyl]-4-chloro-benzenesulfonamide;
N-[3-(4-Amino-7-methyl-7H-pyrrolo[2,3-d]pyrimidine-5-carbonyl)-phenyl]-2-chloro-benzenesulfonamide;
N-[3-(4-Amino-7-methyl-7H-pyrrolo[2,3-d]pyrimidine-5-carbonyl)-phenyl]-3-chloro-4-methyl-benzenesulfonamide;
N-[3-(4-Amino-7-methyl-7H-pyrrolo[2,3-d]pyrimidine-5-carbonyl)-phenyl]-3-chloro-4-fluoro-benzenesulfonamide;
N-[3-(4-Amino-7-methyl-7H-pyrrolo[2,3-d]pyrimidine-5-carbonyl)-phenyl]-2-chloro-4-fluoro-benzenesulfonamide;
N-[3-(4-Amino-7-methyl-7H-pyrrolo[2,3-d]pyrimidine-5-carbonyl)-phenyl]-C-(3,4-dichloro-phenyl)-methanesulfonamide.
N-[3-(4-Amino-7-isopropyl-7H-pyrrolo[2,3-d]pyrimidine-5-carbonyl)-2-chloro-phenyl]-2,4-dichloro-benzenesulfonamide;
1-[3-(4-Amino-7H-pyrrolo[2,3-d]pyrimidine-5-carbonyl)-phenyl]-3-(2-fluoro-phenyl)-urea;
1-[3-(4-Amino-7H-pyrrolo[2,3-d]pyrimidine-5-carbonyl)-phenyl]-3-(3-chloro-phenyl)-urea;
1-[3-(4-Amino-7H-pyrrolo[2,3-d]pyrimidine-5-carbonyl)-phenyl]-3-p-tolyl-urea;
1-[3-(4-Amino-7H-pyrrolo[2,3-d]pyrimidine-5-carbonyl)-phenyl]-3-(3-methoxy-phenyl)-urea;
1-[3-(4-Amino-7H-pyrrolo[2,3-d]pyrimidine-5-carbonyl)-phenyl]-3-(3,4-difluoro-phenyl)-urea;
1-[3-(4-Amino-7H-pyrrolo[2,3-d]pyrimidine-5-carbonyl)-phenyl]-3-(2,3-dimethyl-phenyl)-urea;
1-[3-(4-Amino-7H-pyrrolo[2,3-d]pyrimidine-5-carbonyl)-phenyl]-3-(2,5-dimethyl-phenyl)-urea;
1-[3-(4-Amino-7H-pyrrolo[2,3-d]pyrimidine-5-carbonyl)-phenyl]-3-(3-fluoro-4-methyl-phenyl)-urea;
1-[3-(4-Amino-7H-pyrrolo[2,3-d]pyrimidine-5-carbonyl)-phenyl]-3-(3-chloro-4-fluoro-phenyl)-urea;
1-[3-(4-Amino-7H-pyrrolo[2,3-d]pyrimidine-5-carbonyl)-phenyl]-3-(2,5-dichloro-phenyl)-urea;
1-[3-(4-Amino-7H-pyrrolo[2,3-d]pyrimidine-5-carbonyl)-phenyl]-3-(2,6-dichloro-phenyl)-urea;
1-[3-(4-Amino-7H-pyrrolo[2,3-d]pyrimidine-5-carbonyl)-phenyl]-3-(3,4-dichloro-phenyl)-urea;
1-[3-(4-Amino-7H-pyrrolo[2,3-d]pyrimidine-5-carbonyl)-phenyl]-3-(3-fluoro-phenyl)-urea;
1-[3-(4-Amino-7H-pyrrolo[2,3-d]pyrimidine-5-carbonyl)-phenyl]-3-(4-fluoro-phenyl)-urea;
1-[3-(4-Amino-7H-pyrrolo[2,3-d]pyrimidine-5-carbonyl)-phenyl]-3-(4-chloro-phenyl)-urea;
1-[3-(4-Amino-7H-pyrrolo[2,3-d]pyrimidine-5-carbonyl)-phenyl]-3-(2,5-difluoro-phenyl)-urea;
1-[3-(4-Amino-7H-pyrrolo[2,3-d]pyrimidine-5-carbonyl)-phenyl]-3-(2,5-difluoro-phenyl)-urea;
1-[3-(4-Amino-7H-pyrrolo[2,3-d]pyrimidine-5-carbonyl)-phenyl]-3-(2,4-dimethyl-phenyl)-urea;
1-[3-(4-Amino-7H-pyrrolo[2,3-d]pyrimidine-5-carbonyl)-phenyl]-3-(3,4-dimethyl-phenyl)-urea;
1-[3-(4-Amino-7H-pyrrolo[2,3-d]pyrimidine-5-carbonyl)-phenyl]-3-(3,5-dimethyl-phenyl)-urea;
1-[3-(4-Amino-7H-pyrrolo[2,3-d]pyrimidine-5-carbonyl)-phenyl]-3-(4-chloro-2-methyl-phenyl)-urea;
N-[3-(4-Amino-7H-pyrrolo[2,3-d]pyrimidine-5-carbonyl)-phenyl]-2-fluoro-benzenesulfonamide;
1-[3-(4-Amino-7H-pyrrolo[2,3-d]pyrimidine-5-carbonyl)-phenyl]-3-thiophen-2-yl-urea;
N-[3-(4-Amino-7H-pyrrolo[2,3-d]pyrimidine-5-carbonyl)-phenyl]-4-fluoro-benzenesulfonamide;
N-[3-(4-Amino-7H-pyrrolo[2,3-d]pyrimidine-5-carbonyl)-phenyl]-3-chloro-benzenesulfonamide;
N-[3-(4-Amino-7H-pyrrolo[2,3-d]pyrimidine-5-carbonyl)-phenyl]-4-chloro-benzenesulfonamide;
N-[3-(4-Amino-7H-pyrrolo[2,3-d]pyrimidine-5-carbonyl)-phenyl]-2,5-difluoro-benzenesulfonamide;
N-[3-(4-Amino-7H-pyrrolo[2,3-d]pyrimidine-5-carbonyl)-phenyl]-3,4-difluoro-benzenesulfonamide;
N-[3-(4-Amino-7H-pyrrolo[2,3-d]pyrimidine-5-carbonyl)-phenyl]-2,5-dimethyl-benzenesulfonamide;
N-[3-(4-Amino-7H-pyrrolo[2,3-d]pyrimidine-5-carbonyl)-phenyl]-2-methoxy-5-methyl-benzenesulfonamide;
1-[3-(4-Amino-7H-pyrrolo[2,3-d]pyrimidine-5-carbonyl)-phenyl]-3-O-tolyl-urea;
1-[3-(4-Amino-7H-pyrrolo[2,3-d]pyrimidine-5-carbonyl)-phenyl]-3-(4-methoxy-phenyl)-urea;
1-[3-(4-Amino-7H-pyrrolo[2,3-d]pyrimidine-5-carbonyl)-phenyl]-3-(2,6-difluoro-phenyl)-urea;
1-[3-(4-Amino-7H-pyrrolo[2,3-d]pyrimidine-5-carbonyl)-phenyl]-3-(5-fluoro-2-methyl-phenyl)-urea;
1-[3-(4-Amino-7H-pyrrolo[2,3-d]pyrimidine-5-carbonyl)-phenyl]-3-(2,3-dichloro-phenyl)-urea;
N-[5-(4-Amino-7-isopropyl-7H-pyrrolo[2,3-d]pyrimidine-5-carbonyl)-2-methoxy-phenyl]-4-(pyridin-2-yloxy)-benzenesulfonamide;
N-[5-(4-Amino-7-isopropyl-7H-pyrrolo[2,3-d]pyrimidine-5-carbonyl)-2-methoxy-phenyl]-3-(pyridin-2-yloxy)-benzenesulfonamide;
N-[5-(4-Amino-7-isopropyl-7H-pyrrolo[2,3-d]pyrimidine-5-carbonyl)-2-methoxy-phenyl]-4-(pyridin-4-yloxy)-benzenesulfonamide;
N-[5-(4-Amino-7-isopropyl-7H-pyrrolo[2,3-d]pyrimidine-5-carbonyl)-2-methoxy-phenyl]-4-(pyridin-3-yloxy)-benzenesulfonamide;
1-[5-(4-Amino-7-isopropyl-7H-pyrrolo[2,3-d]pyrimidine-5-carbonyl)-2-methoxy-phenyl]-3-isopropyl-urea;
1-[5-(4-Amino-7-isopropyl-7H-pyrrolo[2,3-d]pyrimidine-5-carbonyl)-2-methoxy-phenyl]-3-propyl-urea;
1-[5-(4-Amino-7-isopropyl-7H-pyrrolo[2,3-d]pyrimidine-5-carbonyl)-2-methoxy-phenyl]-3-phenyl-urea;
1-[5-(4-Amino-7-isopropyl-7H-pyrrolo[2,3-d]pyrimidine-5-carbonyl)-2-methoxy-phenyl]-3-thiophen-2-yl-urea;
1-[5-(4-Amino-7-isopropyl-7H-pyrrolo[2,3-d]pyrimidine-5-carbonyl)-2-methoxy-phenyl]-3-p-tolyl-urea;
1-[5-(4-Amino-7-isopropyl-7H-pyrrolo[2,3-d]pyrimidine-5-carbonyl)-2-methoxy-phenyl]-3-o-tolyl-urea;

1-[5-(4-Amino-7-isopropyl-7H-pyrrolo[2,3-d]pyrimidine-5-carbonyl)-2-methoxy-phenyl]-3-benzyl-urea;

1-[5-(4-Amino-7-isopropyl-7H-pyrrolo[2,3-d]pyrimidine-5-carbonyl)-2-methoxy-phenyl]-3-(2-fluoro-phenyl)-urea;

1-[5-(4-Amino-7-isopropyl-7H-pyrrolo[2,3-d]pyrimidine-5-carbonyl)-2-methoxy-phenyl]-3-(3-fluoro-phenyl)-urea;

1-[5-(4-Amino-7-isopropyl-7H-pyrrolo[2,3-d]pyrimidine-5-carbonyl)-2-methoxy-phenyl]-3-(4-fluoro-phenyl)-urea;

1-[5-(4-Amino-7-isopropyl-7H-pyrrolo[2,3-d]pyrimidine-5-carbonyl)-2-methoxy-phenyl]-3-(3-cyano-phenyl)-urea;

1-[5-(4-Amino-7-isopropyl-7H-pyrrolo[2,3-d]pyrimidine-5-carbonyl)-2-methoxy-phenyl]-3-(4-cyano-phenyl)-urea;

1-[5-(4-Amino-7-isopropyl-7H-pyrrolo[2,3-d]pyrimidine-5-carbonyl)-2-methoxy-phenyl]-3-(3-methyl-benzyl)-urea;

1-[5-(4-Amino-7-isopropyl-7H-pyrrolo[2,3-d]pyrimidine-5-carbonyl)-2-methoxy-phenyl]-3-(2-methoxy-phenyl)-urea;

1-[5-(4-Amino-7-isopropyl-7H-pyrrolo[2,3-d]pyrimidine-5-carbonyl)-2-methoxy-phenyl]-3-(3-methoxy-phenyl)-urea;

1-[5-(4-Amino-7-isopropyl-7H-pyrrolo[2,3-d]pyrimidine-5-carbonyl)-2-methoxy-phenyl]-3-(4-methoxy-phenyl)-urea;

1-[5-(4-Amino-7-isopropyl-7H-pyrrolo[2,3-d]pyrimidine-5-carbonyl)-2-methoxy-phenyl]-3-(3-fluoro-4-methyl-phenyl)-urea;

1-[5-(4-Amino-7-isopropyl-7H-pyrrolo[2,3-d]pyrimidine-5-carbonyl)-2-methoxy-phenyl]-3-(3-chloro-phenyl)-urea;

1-[5-(4-Amino-7-isopropyl-7H-pyrrolo[2,3-d]pyrimidine-5-carbonyl)-2-methoxy-phenyl]-3-(4-chloro-phenyl)-urea;

1-(4-Acetyl-phenyl)-3-[5-(4-amino-7-isopropyl-7H-pyrrolo[2,3-d]pyrimidine-5-carbonyl)-2-methoxy-phenyl]-urea;

1-[5-(4-Amino-7-isopropyl-7H-pyrrolo[2,3-d]pyrimidine-5-carbonyl)-2-methoxy-phenyl]-3-(4-dimethylamino-phenyl)-urea;

1-[5-(4-Amino-7-isopropyl-7H-pyrrolo[2,3-d]pyrimidine-5-carbonyl)-2-methoxy-phenyl]-3-(2-trifluoromethyl-phenyl)-urea;

1-[5-(4-Amino-7-isopropyl-7H-pyrrolo[2,3-d]pyrimidine-5-carbonyl)-2-methoxy-phenyl]-3-(3-trifluoromethyl-phenyl)-urea;

N-[5-(4-Amino-7-isopropyl-7H-pyrrolo[2,3-d]pyrimidine-5-carbonyl)-2-methoxy-phenyl]-methanesulfonamide;

Propane-2-sulfonic acid[5-(4-amino-7-isopropyl-7H-pyrrolo[2,3-d]pyrimidine-5-carbonyl)-2-methoxy-phenyl]-amide;

N-[5-(4-Amino-7-isopropyl-7H-pyrrolo[2,3-d]pyrimidine-5-carbonyl)-2-methoxy-phenyl]-benzenesulfonamide;

1-Methyl-1H-imidazole-4-sulfonic acid[5-(4-amino-7-isopropyl-7H-pyrrolo[2,3-d]pyrimidine-5-carbonyl)-2-methoxy-phenyl]-amide;

N-[5-(4-Amino-7-isopropyl-7H-pyrrolo[2,3-d]pyrimidine-5-carbonyl)-2-methoxy-phenyl]-4-methyl-benzenesulfonamide;

N-[5-(4-Amino-7-isopropyl-7H-pyrrolo[2,3-d]pyrimidine-5-carbonyl)-2-methoxy-phenyl]-C-phenyl-methanesulfonamide;

N-[5-(4-Amino-7-isopropyl-7H-pyrrolo[2,3-d]pyrimidine-5-carbonyl)-2-methoxy-phenyl]-2-methyl-benzenesulfonamide;

N-[5-(4-Amino-7-isopropyl-7H-pyrrolo[2,3-d]pyrimidine-5-carbonyl)-2-methoxy-phenyl]-3-methyl-benzenesulfonamide;

N-[5-(4-Amino-7-isopropyl-7H-pyrrolo[2,3-d]pyrimidine-5-carbonyl)-2-methoxy-phenyl]-4-fluoro-benzenesulfonamide;

N-[5-(4-Amino-7-isopropyl-7H-pyrrolo[2,3-d]pyrimidine-5-carbonyl)-2-methoxy-phenyl]-2-fluoro-benzenesulfonamide;

N-[5-(4-Amino-7-isopropyl-7H-pyrrolo[2,3-d]pyrimidine-5-carbonyl)-2-methoxy-phenyl]-3-fluoro-benzenesulfonamide;

1,2-Dimethyl-1H-imidazole-4-sulfonic acid[5-(4-amino-7-isopropyl-7H-pyrrolo[2,3-d]pyrimidine-5-carbonyl)-2-methoxy-phenyl]-amide;

N-[5-(4-Amino-7-isopropyl-7H-pyrrolo[2,3-d]pyrimidine-5-carbonyl)-2-methoxy-phenyl]-4-cyano-benzenesulfonamide;

N-[5-(4-Amino-7-isopropyl-7H-pyrrolo[2,3-d]pyrimidine-5-carbonyl)-2-methoxy-phenyl]-2-cyano-benzenesulfonamide;

N-[5-(4-Amino-7-isopropyl-7H-pyrrolo[2,3-d]pyrimidine-5-carbonyl)-2-methoxy-phenyl]-3-cyano-benzenesulfonamide;

N-[5-(4-Amino-7-isopropyl-7H-pyrrolo[2,3-d]pyrimidine-5-carbonyl)-2-methoxy-phenyl]-2,5-dimethyl-benzenesulfonamide;

N-[5-(4-Amino-7-isopropyl-7H-pyrrolo[2,3-d]pyrimidine-5-carbonyl)-2-methoxy-phenyl]-4-ethyl-benzenesulfonamide;

N-[5-(4-Amino-7-isopropyl-7H-pyrrolo[2,3-d]pyrimidine-5-carbonyl)-2-methoxy-phenyl]-4-methoxy-benzenesulfonamide;

N-[5-(4-Amino-7-isopropyl-7H-pyrrolo[2,3-d]pyrimidine-5-carbonyl)-2-methoxy-phenyl]-3-methoxy-benzenesulfonamide;

N-[5-(4-Amino-7-isopropyl-7H-pyrrolo[2,3-d]pyrimidine-5-carbonyl)-2-methoxy-phenyl]-5-fluoro-2-methyl-benzenesulfonamide;

N-[5-(4-Amino-7-isopropyl-7H-pyrrolo[2,3-d]pyrimidine-5-carbonyl)-2-methoxy-phenyl]-C-(4-fluoro-phenyl)-methanesulfonamide;

N-[5-(4-Amino-7-isopropyl-7H-pyrrolo[2,3-d]pyrimidine-5-carbonyl)-2-methoxy-phenyl]-4-chloro-benzenesulfonamide;

N-[5-(4-Amino-7-isopropyl-7H-pyrrolo[2,3-d]pyrimidine-5-carbonyl)-2-methoxy-phenyl]-2-chloro-4-fluoro-benzenesulfonamide;

N-[5-(4-Amino-7-isopropyl-7H-pyrrolo[2,3-d]pyrimidine-5-carbonyl)-2-methoxy-phenyl]-C-(3,4-dichloro-phenyl)-ethanesulfonamide;

Thiophene-2-sulfonic acid[3-(4-amino-7H-pyrrolo[2,3-d]pyrimidine-5-carbonyl)-phenyl]-amide;

N-[3-(4-Amino-7H-pyrrolo[2,3-d]pyrimidine-5-carbonyl)-phenyl]-2-methyl-benzenesulfonamide;

N-[3-(4-Amino-7H-pyrrolo[2,3-d]pyrimidine-5-carbonyl)-phenyl]-3-methyl-benzenesulfonamide;

N-[3-(4-Amino-7H-pyrrolo[2,3-d]pyrimidine-5-carbonyl)-phenyl]-4-methyl-benzenesulfonamide;

N-[3-(4-Amino-7H-pyrrolo[2,3-d]pyrimidine-5-carbonyl)-phenyl]-2,3-dichloro-benzenesulfonamide;

N-[3-(4-Amino-7H-pyrrolo[2,3-d]pyrimidine-5-carbonyl)-phenyl]-2,5-dichloro-benzenesulfonamide;

N-[3-(4-Amino-7H-pyrrolo[2,3-d]pyrimidine-5-carbonyl)-phenyl]-3,4-dichloro-benzenesulfonamide;

N-[3-(4-Amino-7H-pyrrolo[2,3-d]pyrimidine-5-carbonyl)-phenyl]-5-fluoro-2-methyl-benzenesulfonamide;

N-[3-(4-Amino-7H-pyrrolo[2,3-d]pyrimidine-5-carbonyl)-phenyl]-2,6-dichloro-benzenesulfonamide;

N-[3-(4-Amino-7H-pyrrolo[2,3-d]pyrimidine-5-carbonyl)-phenyl]-4-(pyridin-3-yloxy)-benzenesulfonamide;

N-[3-(4-Amino-7H-pyrrolo[2,3-d]pyrimidine-5-carbonyl)-phenyl]-4-phenoxy-benzenesulfonamide;

N-[3-(4-Amino-7H-pyrrolo[2,3-d]pyrimidine-5-carbonyl)-phenyl]-4-(pyridin-2-yloxy)-benzenesulfonamide;

1-[3-(4-Amino-7H-pyrrolo[2,3-d]pyrimidine-5-carbonyl)-phenyl]-3-(2-methoxy-phenyl)-urea;

N-[3-(4-Amino-7H-pyrrolo[2,3-d]pyrimidine-5-carbonyl)-phenyl]-3-methoxy-benzenesulfonamide;

N-[3-(4-Amino-7H-pyrrolo[2,3-d]pyrimidine-5-carbonyl)-phenyl]-3-(pyridin-2-yloxy)-benzenesulfonamide;

N-[3-(4-Amino-7H-pyrrolo[2,3-d]pyrimidine-5-carbonyl)-phenyl]-3-phenoxy-benzenesulfonamide;

N-[3-(4-Amino-7H-pyrrolo[2,3-d]pyrimidine-5-carbonyl)-phenyl]-4-(pyridin-4-yloxy)-benzenesulfonamide;

N-[3-(4-Amino-7H-pyrrolo[2,3-d]pyrimidine-5-carbonyl)-phenyl]-benzenesulfonamide;

N-[3-(4-Amino-7H-pyrrolo[2,3-d]pyrimidine-5-carbonyl)-phenyl]-3-fluoro-benzenesulfonamide;

N-[3-(4-Amino-7H-pyrrolo[2,3-d]pyrimidine-5-carbonyl)-phenyl]-4-methoxy-benzenesulfonamide;

N-{3-[4-Amino-7-(4-methoxy-benzenesulfonyl)-7H-pyrrolo[2,3-d]pyrimidine-5-carbonyl]-phenyl}-4-methoxy-benzenesulfonamide;

N-{3-[4-Amino-7-(2,4-difluoro-benzenesulfonyl)-7H-pyrrolo[2,3-d]pyrimidine-5-carbonyl]-phenyl}-2,4-difluoro-benzenesulfonamide;

N-{3-[4-Amino-7-(4-fluoro-benzenesulfonyl)-7H-pyrrolo[2,3-d]pyrimidine-5-carbonyl]-phenyl}-4-fluoro-benzenesulfonamide;

N-[3-(4-Amino-7-isopropyl-7H-pyrrolo[2,3-d]pyrimidine-5-carbonyl)-2-chloro-phenyl]-benzenesulfonamide;

Thiophene-2-sulfonic acid[3-(4-amino-7-isopropyl-7H-pyrrolo[2,3-d]pyrimidine-5-carbonyl)-2-chloro-phenyl]-amide;

N-[3-(4-Amino-7-isopropyl-7H-pyrrolo[2,3-d]pyrimidine-5-carbonyl)-2-chloro-phenyl]-4-methyl-benzenesulfonamide;

N-[3-(4-Amino-7-isopropyl-7H-pyrrolo[2,3-d]pyrimidine-5-carbonyl)-2-chloro-phenyl]-C-phenyl-methanesulfonamide;

N-[3-(4-Amino-7-isopropyl-7H-pyrrolo[2,3-d]pyrimidine-5-carbonyl)-2-chloro-phenyl]-2-methyl-benzenesulfonamide;

N-[3-(4-Amino-7-isopropyl-7H-pyrrolo[2,3-d]pyrimidine-5-carbonyl)-2-chloro-phenyl]-3-methyl-benzenesulfonamide;

N-[3-(4-Amino-7-isopropyl-7H-pyrrolo[2,3-d]pyrimidine-5-carbonyl)-2-chloro-phenyl]-4-fluoro-benzenesulfonamide;

N-[3-(4-Amino-7-isopropyl-7H-pyrrolo[2,3-d]pyrimidine-5-carbonyl)-2-chloro-phenyl]-2-fluoro-benzenesulfonamide;

N-[3-(4-Amino-7-isopropyl-7H-pyrrolo[2,3-d]pyrimidine-5-carbonyl)-2-chloro-phenyl]-3-fluoro-benzenesulfonamide;

3,5-Dimethyl-isoxazole-4-sulfonic acid[3-(4-amino-7-isopropyl-7H-pyrrolo[2,3-d]pyrimidine-5-carbonyl)-2-chloro-phenyl]-amide;

N-[3-(4-Amino-7-isopropyl-7H-pyrrolo[2,3-d]pyrimidine-5-carbonyl)-2-chloro-phenyl]-4-cyano-benzenesulfonamide;

N-[3-(4-Amino-7-isopropyl-7H-pyrrolo[2,3-d]pyrimidine-5-carbonyl)-2-chloro-phenyl]-2,5-dimethyl-benzenesulfonamide;

N-[3-(4-Amino-7-isopropyl-7H-pyrrolo[2,3-d]pyrimidine-5-carbonyl)-2-chloro-phenyl]-4-ethyl-benzenesulfonamide;

N-[3-(4-Amino-7-isopropyl-7H-pyrrolo[2,3-d]pyrimidine-5-carbonyl)-2-chloro-phenyl]-4-methoxy-benzenesulfonamide;

N-[3-(4-Amino-7-isopropyl-7H-pyrrolo[2,3-d]pyrimidine-5-carbonyl)-2-chloro-phenyl]-3-methoxy-benzenesulfonamide;

N-[3-(4-Amino-7-isopropyl-7H-pyrrolo[2,3-d]pyrimidine-5-carbonyl)-2-chloro-phenyl]-5-fluoro-2-methyl-benzenesulfonamide;

N-[3-(4-Amino-7-isopropyl-7H-pyrrolo[2,3-d]pyrimidine-5-carbonyl)-2-chloro-phenyl]-C-(4-fluoro-phenyl)-methanesulfonamide;

N-[3-(4-Amino-7-isopropyl-7H-pyrrolo[2,3-d]pyrimidine-5-carbonyl)-2-chloro-phenyl]-4-chloro-benzenesulfonamide;

N-[3-(4-Amino-7-isopropyl-7H-pyrrolo[2,3-d]pyrimidine-5-carbonyl)-2-chloro-phenyl]-2-chloro-4-fluoro-benzenesulfonamide;

N-[3-(4-Amino-7-isopropyl-7H-pyrrolo[2,3-d]pyrimidine-5-carbonyl)-2-chloro-phenyl]-C-(3,4-dichloro-phenyl)-methanesulfonamide;

N-[3-(4-Amino-7-isopropyl-7H-pyrrolo[2,3-d]pyrimidine-5-carbonyl)-2-chloro-phenyl]-3-(pyridin-2-yloxy)-benzenesulfonamide;

N-[3-(4-Amino-7-isopropyl-7H-pyrrolo[2,3-d]pyrimidine-5-carbonyl)-2-chloro-phenyl]-4-(pyridin-4-yloxy)-benzenesulfonamide;

N-[3-(4-Amino-7-isopropyl-7H-pyrrolo[2,3-d]pyrimidine-5-carbonyl)-2-chloro-phenyl]-4-(pyridin-3-yloxy)-benzenesulfonamide;

1-[3-(4-Amino-7-isopropyl-7H-pyrrolo[2,3-d]pyrimidine-5-carbonyl)-2-chloro-phenyl]-3-propyl-urea;

1-[3-(4-Amino-7-isopropyl-7H-pyrrolo[2,3-d]pyrimidine-5-carbonyl)-2-chloro-phenyl]-3-phenyl-urea;

1-[3-(4-Amino-7-isopropyl-7H-pyrrolo[2,3-d]pyrimidine-5-carbonyl)-2-chloro-phenyl]-3-p-tolyl-urea;

1-[3-(4-Amino-7-isopropyl-7H-pyrrolo[2,3-d]pyrimidine-5-carbonyl)-2-chloro-phenyl]-3-o-tolyl-urea;

1-[3-(4-Amino-7-isopropyl-7H-pyrrolo[2,3-d]pyrimidine-5-carbonyl)-2-chloro-phenyl]-3-benzyl-urea;

1-[3-(4-Amino-7-isopropyl-7H-pyrrolo[2,3-d]pyrimidine-5-carbonyl)-2-chloro-phenyl]-3-(2-fluoro-phenyl)-urea;

1-[3-(4-Amino-7-isopropyl-7H-pyrrolo[2,3-d]pyrimidine-5-carbonyl)-2-chloro-phenyl]-3-(3-fluoro-phenyl)-urea;

1-[3-(4-Amino-7-isopropyl-7H-pyrrolo[2,3-d]pyrimidine-5-carbonyl)-2-chloro-phenyl]-3-(4-fluoro-phenyl)-urea;

1-[3-(4-Amino-7-isopropyl-7H-pyrrolo[2,3-d]pyrimidine-5-carbonyl)-2-chloro-phenyl]-3-(3-cyano-phenyl)-urea;

1-[3-(4-Amino-7-isopropyl-7H-pyrrolo[2,3-d]pyrimidine-5-carbonyl)-2-chloro-phenyl]-3-(2-cyano-phenyl)-urea;

1-[3-(4-Amino-7-isopropyl-7H-pyrrolo[2,3-d]pyrimidine-5-carbonyl)-2-chloro-phenyl]-3-(4-cyano-phenyl)-urea;

1-[3-(4-Amino-7-isopropyl-7H-pyrrolo[2,3-d]pyrimidine-5-carbonyl)-2-chloro-phenyl]-3-(3-methyl-benzyl)-urea;

1-[3-(4-Amino-7-isopropyl-7H-pyrrolo[2,3-d]pyrimidine-5-carbonyl)-2-chloro-phenyl]-3-(2-methoxy-phenyl)-urea;

1-[3-(4-Amino-7-isopropyl-7H-pyrrolo[2,3-d]pyrimidine-5-carbonyl)-2-chloro-phenyl]-3-(3-methoxy-phenyl)-urea;

1-[3-(4-Amino-7-isopropyl-7H-pyrrolo[2,3-d]pyrimidine-5-carbonyl)-2-chloro-phenyl]-3-(4-methoxy-phenyl)-urea;

1-[3-(4-Amino-7-isopropyl-7H-pyrrolo[2,3-d]pyrimidine-5-carbonyl)-2-chloro-phenyl]-3-(2-fluoro-5-methyl-phenyl)-urea;

1-[3-(4-Amino-7-isopropyl-7H-pyrrolo[2,3-d]pyrimidine-5-carbonyl)-2-chloro-phenyl]-3-(3-fluoro-4-methyl-phenyl)-urea;

1-[3-(4-Amino-7-isopropyl-7H-pyrrolo[2,3-d]pyrimidine-5-carbonyl)-2-chloro-phenyl]-3-(3-chloro-phenyl)-urea;

1-[3-(4-Amino-7-isopropyl-7H-pyrrolo[2,3-d]pyrimidine-5-carbonyl)-2-chloro-phenyl]-3-(4-chloro-phenyl)-urea;

1-[3-(4-Amino-7-isopropyl-7H-pyrrolo[2,3-d]pyrimidine-5-carbonyl)-2-chloro-phenyl]-3-(3,4-difluoro-phenyl)-urea;

1-[3-(4-Amino-7-isopropyl-7H-pyrrolo[2,3-d]pyrimidine-5-carbonyl)-2-chloro-phenyl]-3-(2,5-difluoro-phenyl)-urea;

1-[3-(4-Amino-7-isopropyl-7H-pyrrolo[2,3-d]pyrimidine-5-carbonyl)-2-chloro-phenyl]-3-(2,6-difluoro-phenyl)-urea;

1-[3-(4-Amino-7-isopropyl-7H-pyrrolo[2,3-d]pyrimidine-5-carbonyl)-2-chloro-phenyl]-3-(2,4-difluoro-phenyl)-urea;

1-(4-Acetyl-phenyl)-3-[3-(4-amino-7-isopropyl-7H-pyrrolo[2,3-d]pyrimidine-5-carbonyl)-2-chloro-phenyl]-urea;

1-[3-(4-Amino-7-isopropyl-7H-pyrrolo[2,3-d]pyrimidine-5-carbonyl)-2-chloro-phenyl]-3-(4-dimethylamino-phenyl)-urea;

1-[3-(4-Amino-7-isopropyl-7H-pyrrolo[2,3-d]pyrimidine-5-carbonyl)-2-chloro-phenyl]-3-(4-chloro-2-methyl-phenyl)-urea;

1-[3-(4-Amino-7-isopropyl-7H-pyrrolo[2,3-d]pyrimidine-5-carbonyl)-2-chloro-phenyl]-3-(3-trifluoromethyl-phenyl)-urea;

1-[3-(4-Amino-7-isopropyl-7H-pyrrolo[2,3-d]pyrimidine-5-carbonyl)-2-chloro-phenyl]-3-(3-chloro-4-methyl-phenyl)-urea;

1-[3-(4-Amino-7-isopropyl-7H-pyrrolo[2,3-d]pyrimidine-5-carbonyl)-4-methyl-phenyl]-3-isopropyl-urea;

1-[3-(4-Amino-7-isopropyl-7H-pyrrolo[2,3-d]pyrimidine-5-carbonyl)-4-methyl-phenyl]-3-phenyl-urea;

1-[3-(4-Amino-7-isopropyl-7H-pyrrolo[2,3-d]pyrimidine-5-carbonyl)-4-methyl-phenyl]-3-thiophen-2-yl-urea;

1-[3-(4-Amino-7-isopropyl-7H-pyrrolo[2,3-d]pyrimidine-5-carbonyl)-4-methyl-phenyl]-3-(3-ethyl-phenyl)-urea;

1-[3-(4-Amino-7-isopropyl-7H-pyrrolo[2,3-d]pyrimidine-5-carbonyl)-4-methyl-phenyl]-3-(3-cyano-phenyl)-urea;

1-[3-(4-Amino-7-isopropyl-7H-pyrrolo[2,3-d]pyrimidine-5-carbonyl)-4-methyl-phenyl]-3-(2-methoxy-phenyl)-urea;

1-[3-(4-Amino-7-isopropyl-7H-pyrrolo[2,3-d]pyrimidine-5-carbonyl)-4-methyl-phenyl]-3-o-tolyl-urea;

1-[3-(4-Amino-7-isopropyl-7H-pyrrolo[2,3-d]pyrimidine-5-carbonyl)-4-methyl-phenyl]-3-m-tolyl-urea;

1-[3-(4-Amino-7-isopropyl-7H-pyrrolo[2,3-d]pyrimidine-5-carbonyl)-4-methyl-phenyl]-3-p-tolyl-urea;

1-[3-(4-Amino-7-isopropyl-7H-pyrrolo[2,3-d]pyrimidine-5-carbonyl)-4-methyl-phenyl]-3-(2-fluoro-phenyl)-urea;

1-[3-(4-Amino-7-isopropyl-7H-pyrrolo[2,3-d]pyrimidine-5-carbonyl)-4-methyl-phenyl]-3-(3-fluoro-phenyl)-urea;

1-[3-(4-Amino-7-isopropyl-7H-pyrrolo[2,3-d]pyrimidine-5-carbonyl)-4-methyl-phenyl]-3-(2-cyano-phenyl)-urea;

1-[3-(4-Amino-7-isopropyl-7H-pyrrolo[2,3-d]pyrimidine-5-carbonyl)-4-methyl-phenyl]-3-(2-ethyl-phenyl)-urea;

1-[3-(4-Amino-7-isopropyl-7H-pyrrolo[2,3-d]pyrimidine-5-carbonyl)-4-methyl-phenyl]-3-(2,5-dimethyl-phenyl)-urea;

1-[3-(4-Amino-7-isopropyl-7H-pyrrolo[2,3-d]pyrimidine-5-carbonyl)-4-methyl-phenyl]-3-(3,4-dimethyl-phenyl)-urea;

1-[3-(4-Amino-7-isopropyl-7H-pyrrolo[2,3-d]pyrimidine-5-carbonyl)-4-methyl-phenyl]-3-(3,5-dimethyl-phenyl)-urea;

1-[3-(4-Amino-7-isopropyl-7H-pyrrolo[2,3-d]pyrimidine-5-carbonyl)-4-methyl-phenyl]-3-(2,3-dimethyl-phenyl)-urea;

1-[3-(4-Amino-7-isopropyl-7H-pyrrolo[2,3-d]pyrimidine-5-carbonyl)-4-methyl-phenyl]-3-(2,4-dimethyl-phenyl)-urea;

1-[3-(4-Amino-7-isopropyl-7H-pyrrolo[2,3-d]pyrimidine-5-carbonyl)-4-methyl-phenyl]-3-(3-methoxy-phenyl)-urea;

1-[3-(4-Amino-7-isopropyl-7H-pyrrolo[2,3-d]pyrimidine-5-carbonyl)-4-methyl-phenyl]-3-(4-methoxy-phenyl)-urea;

1-[3-(4-Amino-7-isopropyl-7H-pyrrolo[2,3-d]pyrimidine-5-carbonyl)-4-methyl-phenyl]-3-(3-fluoro-4-methyl-phenyl)-urea;

1-[3-(4-Amino-7-isopropyl-7H-pyrrolo[2,3-d]pyrimidine-5-carbonyl)-4-methyl-phenyl]-3-(5-fluoro-2-methyl-phenyl)-urea;

1-[3-(4-Amino-7-isopropyl-7H-pyrrolo[2,3-d]pyrimidine-5-carbonyl)-4-methyl-phenyl]-3-(2-fluoro-5-methyl-phenyl)-urea;

1-[3-(4-Amino-7-isopropyl-7H-pyrrolo[2,3-d]pyrimidine-5-carbonyl)-4-methyl-phenyl]-3-(2-chloro-phenyl)-urea;

1-[3-(4-Amino-7-isopropyl-7H-pyrrolo[2,3-d]pyrimidine-5-carbonyl)-4-methyl-phenyl]-3-(3-chloro-phenyl)-urea;

1-[3-(4-Amino-7-isopropyl-7H-pyrrolo[2,3-d]pyrimidine-5-carbonyl)-4-methyl-phenyl]-3-(4-chloro-phenyl)-urea;

1-[3-(4-Amino-7-isopropyl-7H-pyrrolo[2,3-d]pyrimidine-5-carbonyl)-4-methyl-phenyl]-3-(2,4-difluoro-phenyl)-urea;

1-[3-(4-Amino-7-isopropyl-7H-pyrrolo[2,3-d]pyrimidine-5-carbonyl)-4-methyl-phenyl]-3-(2,6-difluoro-phenyl)-urea;

1-[3-(4-Amino-7-isopropyl-7H-pyrrolo[2,3-d]pyrimidine-5-carbonyl)-4-methyl-phenyl]-3-(2,5-difluoro-phenyl)-urea;

1-[3-(4-Amino-7-isopropyl-7H-pyrrolo[2,3-d]pyrimidine-5-carbonyl)-4-methyl-phenyl]-3-(3,4-difluorophenyl)-urea;

1-[3-(4-Amino-7-isopropyl-7H-pyrrolo[2,3-d]pyrimidine-5-carbonyl)-4-methyl-phenyl]-3-(3,5-difluoro-phenyl)-urea;

1-(3-Acetyl-phenyl)-3-[3-(4-amino-7-isopropyl-7H-pyrrolo[2,3-d]pyrimidine-5-carbonyl)-4-methyl-phenyl]-urea;

1-(4-Acetyl-phenyl)-3-[3-(4-amino-7-isopropyl-7H-pyrrolo[2,3-d]pyrimidine-5-carbonyl)-4-methyl-phenyl]-urea;

1-[3-(4-Amino-7-isopropyl-7H-pyrrolo[2,3-d]pyrimidine-5-carbonyl)-4-methyl-phenyl]-3-(4-methoxy-2-methyl-phenyl)-urea;

1-[3-(4-Amino-7-isopropyl-7H-pyrrolo[2,3-d]pyrimidine-5-carbonyl)-4-methyl-phenyl]-3-(2-methoxy-5-methyl-phenyl)-urea;

1-[3-(4-Amino-7-isopropyl-7H-pyrrolo[2,3-d]pyrimidine-5-carbonyl)-4-methyl-phenyl]-3-(3-methylsulfanyl-phenyl)-urea;

1-[3-(4-Amino-7-isopropyl-7H-pyrrolo[2,3-d]pyrimidine-5-carbonyl)-4-methyl-phenyl]-3-(4-methylsulfanyl-phenyl)-urea;

1-[3-(4-Amino-7-isopropyl-7H-pyrrolo[2,3-d]pyrimidine-5-carbonyl)-4-methyl-phenyl]-3-(2-methylsulfanyl-phenyl)-urea;

1-[3-(4-Amino-7-isopropyl-7H-pyrrolo[2,3-d]pyrimidine-5-carbonyl)-4-methyl-phenyl]-3-(2-chloro-6-methyl-phenyl)-urea;

1-[3-(4-Amino-7-isopropyl-7H-pyrrolo[2,3-d]pyrimidine-5-carbonyl)-4-methyl-phenyl]-3-(3-chloro-2-methyl-phenyl)-urea;

1-[3-(4-Amino-7-isopropyl-7H-pyrrolo[2,3-d]pyrimidine-5-carbonyl)-4-methyl-phenyl]-3-(2-chloro-5-methyl-phenyl)-urea;

1-[3-(4-Amino-7-isopropyl-7H-pyrrolo[2,3-d]pyrimidine-5-carbonyl)-4-methyl-phenyl]-3-(3-chloro-4-methyl-phenyl)-urea;

1-[3-(4-Amino-7-isopropyl-7H-pyrrolo[2,3-d]pyrimidine-5-carbonyl)-4-methyl-phenyl]-3-(5-chloro-2-methyl-phenyl)-urea;

1-[3-(4-Amino-7-isopropyl-7H-pyrrolo[2,3-d]pyrimidine-5-carbonyl)-4-methyl-phenyl]-3-(4-chloro-2-methyl-phenyl)-urea;

1-[3-(4-Amino-7-isopropyl-7H-pyrrolo[2:3-d]pyrimidine-5-carbonyl)-4-methyl-phenyl]-3-(3-chloro-4-fluoro-phenyl)-urea;

1-[3-(4-Amino-7-isopropyl-7H-pyrrolo[2,3-d]pyrimidine-5-carbonyl)-4-methyl-phenyl]-3-(4-tert-butyl-phenyl)-urea;

1-[3-(4-Amino-7-isopropyl-7H-pyrrolo[2,3-d]pyrimidine-5-carbonyl)-4-methyl-phenyl]-3-cyclohexyl-urea;

1-[3-(4-Amino-7-isopropyl-7H-pyrrolo[2,3-d]pyrimidine-5-carbonyl)-4-methyl-phenyl]-3-benzyl-urea; and 1-[3-(4-Amino-7-isopropyl-7H-pyrrolo[2,3-d]pyrimidine-5-carbonyl)-4-methyl-phenyl]-3-(4-fluoro-phenyl)-urea.

What is claimed is:

1. A compound of the formula 1 or a pharmaceutically acceptable salt, prodrug, solvate or hydrate thereof, wherein:

Q is CO;

A is $C_6$-$C_{10}$ aryl, 5 to 13 membered heteroaromatic ring, $C_3$-$C_8$ alkyl, and 3 to 8 membered heteroalkyl ring and each of the foregoing A groups is optionally substituted with 1 to 5 $R^5$ groups;

L is —$(CH_2)_p$— wherein p is an integer from 0 to 5; —O—; —S—; —S(O)—; —S(O)$_2$; —N(R)—; N(C(O)OR)—; —N(C(O)R)—; —N(SO$_2$R); —CH$_2$O—; —CH$_2$S—; —CH$_2$N(R)—; —C(NR)—; —CH$_2$N(C(O)R))—; —CH$_2$N(C(O)OR)—; —CH$_2$N(SO$_2$R)—; —CH(NHR)—; —CH(NHC(O)R)—; —CH(NHSO$_2$R)—; —CH(NHC(O)OR)—; —CH(OC(O)R)—; —CH(OC(O)NHR)—; —CH=CH—; —C(=NOR)—; —C(O)—; —CH(OR)—; —C(O)N(R)—; —N(R)C(O)—; —N(R)S(O)—; —N(R)S(O)$_2$—; OC(O)N(R)—; —N(R)C(O)N(R)—; —NRC(O)O—; —S(O)N(R)—; —S(O)$_2$N(R)—; —N(C(O)R)S(O)—; —N(C(O)R)S(O)$_2$—; —N(R)S(O)N(R)—; —N(R)S(O)$_2$N(R)—; —C(O)N(R)C(O)—; —S(O)N(R)C(O)—; —S(O)$_2$N(R)C(O)—; —OS(O)N(R)—; —OS(O)$_2$N(R)—; —N(R)S(O)O—; —N(R)S(O)$_2$O—; —N(R)S(O)C(O)—; —N(R)S(O)$_2$C(O)—; —SON(C(O)R)—; —SO$_2$N(C(O)R)—; —N(R)SON(R)—; —N(R)SO$_2$N(R)—; —C(O)O—; —N(R)P(OR$^X$)O—; —N(R)P(OR$^X$)—; —N(R)P(O)(OR$^X$)O—; —N(R)P(O)(OR$^X$)—; —N(C(O)R)P(OR$^X$)O—; —N(C(O)R)P(OR$^X$)—; —N(C(O)R)P(O)(OR$^X$)O—; —N(C(O)R)P(OR$^X$)—; —CH(R)S(O)—; —CH(R)S(O)$_2$; —CH(R)N(C(O)OR)—; —CH(R)N(C(O)R)—; —CH(R)N(SO$_2$R)—; —CH(R)O—; —CH(R)S—; —CH(R)N(R)—; —CH(R)N(C(O)R))—; —CH(R)N(C(O)OR)—; —CH(R)N(SO$_2$R)—; —CH(R)C(=NOR)—; —CH(R)C(O)—; —CH(R)CH(OR)—; —CH(R)C(O)N(R)—; —CH(R)N(R)C(O)—; —CH(R)N(R)S(O)—; CH(R)N(R)S(O)$_2$; —CH(R)OC(O)N(R)—; —CH(R)N(R)C(O)N(R)—; —CH(R)N(R)C(O)O—; —CH(R)S(O)N(R)—; —CH(R)S(O)$_2$N(R)—; —CH(R)N(C(O)R)S(O)—; —CH(R)N(C(O)R)S(O)$_2$—; —CH(R)N(R)S(O)N(R)—; —CH(R)N(R)S(O)$_2$N(R)—; —CH(R)C(O)N(R)C(O)—; —CH(R)S(O)N(R)C(O)—; CH(R)S(O)$_2$N(R)C(O)—; —CH(R)OS(O)N(R)—; —CH(R)OS(O)$_2$N(R)—; CH(R)N(R)S(O)O—; —CH(R)N(R)S(O)$_2$O—; —CH(R)N(R)S(O)C(O)—; —CH(R)N(R)S(O)$_2$C(O)—; —CH(R)SON(C(O)R)—; —CH(R)S(O)$_2$N(C(O)R)—; —CH(R)N(R)SON(R)—; —CH(R)N(R)S(O)$_2$N(R)—; —CH(R)C(O)O—; —CH(R)N(R)P(OR')O—; —CH(R)N(R)P(OR$^X$)—; —CH(R)N(R)P(O)(OR$^X$)O—; —CH(R)N(R)P(O)(OR$^X$)—; —CH(R)N(C(O)R)P(OR$^X$)O—; —CH(R)N(C(O)R)P(OR$^X$)—; —CH(R)N(C(O)R)P(O)(OR$^X$)O— or —CH(R)N(C(O)R)P(OR$^X$)—, wherein each R and $R^X$ is independently selected from H, $C_1$-$C_6$ acyl, $C_1$-$C_6$ alkyl, $C_6$-aromatic group and 5 or 6 membered heteroaromatic group, wherein each of the foregoing R and $R^X$ groups are independently optionally substituted with 1-3 halo atoms, $C_1$-$C_6$ alkyl and $C_1$-$C_6$ alkoxy;

$R^1$ is H, $C_1$-$C_6$ alkyl, $C_3$-$C_8$ cycloalkyl, substituted bicloalkyl, 5 to 8 membered cycloalkenyl, 6 to 10 membered aromatic group, 5 to 13 membered heteroaromatic group, 3 to 8 membered heterocycloalkyl group, and heterobicycloalkyl group, and each of the foregoing $R^1$ groups is optionally substituted with 1 to 5 $R^{10}$ groups;

$R^2$ is H, halo, $C_1$-$C_6$ alkyl, $C_3$-$C_8$ cycloalkyl, 6 to 10 membered aromatic group, 5 to 13 membered heteroaromatic group, 3 to 8 membered heterocycloalkyl, —(CH$_2$)$_{1-3}$NR$^6$R$^7$, NR$^6$R$^7$ and —(CH$_2$)$_{1-3}$C(O)NR$^6$R$^7$, C(O)NR$^6$R$^7$ and each of the foregoing $R^2$ groups is optionally substituted with 1 to 5 $R^5$ groups;

$R^3$ is H, $C_1$-$C_6$ alkyl, $C_3$-$C_8$ cycloalkyl, —(CH$_2$)$_t$C$_6$-C$_{10}$ aromatic group, —(CH$_2$)$_t$(5 to 13 membered heteroaromatic group), and 3 to 8 membered heterocycloalkyl, and each of the foregoing $R^3$ groups is optionally substituted with 1 to 5 $R^5$ groups;

each $R^5$ is independently selected from the group consisting of halo, cyano, trifluoromethoxy, trifluoromethyl, —C(O)R$^8$, —NR$^6$C(O)R$^7$, —C(O)NR$^6$R$^7$, —NR$^6$R$^7$, —OR$^9$, —SO$_2$NR$^6$R$^7$, —SO$_2$R$^6$, —NR$^6$SO$_2$R$^7$, $C_1$-$C_6$ alkyl, $C_2$-$C_6$ alkenyl, $C_2$-$C_6$ alkynyl, —(CH$_2$)$_j$O(CH$_2$)$_q$NR$^6$R$^7$, —(CH$_2$)$_j$O(CH$_2$)$_q$OR$^9$, —(CH$_2$)$_t$OR$^9$, —S(O)$_j$(C$_1$-C$_6$ alkyl), —(CH$_2$)$_t$(C$_6$-C$_{10}$ aryl), —(CH$_2$)$_t$(5 to 10 membered heterocyclic), —(CH$_2$)$_j$O(CH$_2$)$_q$(5 to 10 membered heterocyclic), —C(O)(CH$_2$)$_t$(5 to 10 membered heterocyclic), —(CH$_2$)$_j$NR$^7$(CH$_2$)$_q$NR$^6$R$^7$, —(CH$_2$)$_j$NR$^7$CH$_2$C(O)NR$^6$R$^7$, —(CH$_2$)$_j$NR$^7$(CH$_2$)$_q$NR$^9$C(O)R$^8$, —(CH$_2$)$_j$NR$^7$(CH$_2$)$_t$O(CH$_2$)$_q$OR$^9$, —(CH$_2$)$_j$NR$^7$(CH$_2$)$_q$S(O)$_j$(C$_1$-C$_6$ alkyl), —(CH$_2$)$_j$NR$^7$(CH$_2$)$_t$R$^6$, —SO$_2$(CH$_2$)$_t$(C$_6$-C$_{10}$ aryl), and —SO$_2$(CH$_2$)$_t$(5 to 10 membered heterocyclic), wherein j is an integer from 0 to 2, t is an integer from 0 to 6, q is an integer from 2 to 6, the —(CH$_2$)$_q$— and —(CH$_2$)$_t$— moieties of the foregoing $R^5$ groups optionally include a carbon-carbon double or triple bond where t is an integer from 2 to 6, and the alkyl, aryl and heterocyclic moieties of the foregoing $R^5$ groups are optionally substituted by 1 to 3 substituents independently selected from halo, cyano, trifluoromethyl, —C(O)R$^8$, —NR$^6$C(O)R$^7$, —C(O)NR$^6$R$^7$, —(CH$_2$)$_t$NR$^6$R$^7$, —SO$_2$R$^6$, —SO$_2$NR$^6$R$^7$, $C_1$-$C_6$ alkyl, —(CH$_2$)$_t$(5 to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6;

each $R^6$ and $R^7$ is independently selected from H, $C_1$-$C_6$ alkyl, —(CH$_2$)$_t$(C$_6$-C$_{10}$ aryl), —(CH$_2$)$_t$(5 to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6, and the alkyl, aryl and heterocyclic moieties of the foregoing $R^6$ and $R^7$ groups are optionally substituted by 1 to 3 substituents independently selected from halo, cyano, trifluoromethyl, —C(O)R$^8$, —NR$^9$C(O)R$^{10}$, —C(O)NR$^9$R$^{10}$, —NR$^9$R$^{10}$, $C_1$-$C_6$ alkyl, —(CH$_2$)$_t$(C$_6$-C$_{10}$ aryl), —(CH$_2$)$_t$(5 to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6, with the proviso that where $R^6$ and $R^7$ are both attached to the same nitrogen, then $R^6$ and $R^7$ are not both bonded to the nitrogen directly through an oxygen;

each $R^8$ is independently selected from H, $C_1$-$C_{10}$ alkyl, —(CH$_2$)$_t$(C$_6$-C$_{10}$ aryl), and —(CH$_2$)$_t$(5 to 10 membered heterocyclic), wherein t is an integer from 0 to 6;

each $R^9$ and $R^{10}$ is independently selected from H and $C_1$-$C_6$ alkyl; and $R^{11}$ and $R^{12}$ are independently selected from the group consisting of H, $C_1$-$C_6$ alkyl, $C_3$-$C_6$ cycloalkyl, $C_1$-$C_6$ alkoxy or $R^{11}$ and $R^{12}$ taken together form a 3 to 7 membered alkyl or heteroalkyl ring.

2. A compound according to claim 1, wherein A is $C_6$-$C_{10}$ aryl or 5 to 13 membered heteroaromatic ring and each of the foregoing A groups is optionally substituted with 1 to 5 $R^5$ groups.

3. A compound according to claim 2, wherein A is $C_6$-$C_{10}$ aryl, wherein said aryl ring is optionally substituted with 1 to 5 $R^5$ groups.

4. A compound according to claim 2, wherein A is 5 to 13 membered heteroaromatic ring, wherein said ring is optionally substituted with 1 to 5 $R^5$ groups.

5. A compound according to claims 3 or 4, wherein each $R^5$ is independently selected from the group consisting of halo, cyano, trifluoromethoxy, trifluoromethyl, —C(O)R$^8$, —NR$^6$C(O)R$^7$, —C(O)NR$^6$R$^7$, —NR$^6$R$^7$, —OR$^9$, SO$_2$NR$^6$R$^7$, —SO$_2$R$^6$, —NR$^6$SO$_2$R$^7$, $C_1$-$C_6$ alkyl, —(CH$_2$)$_t$OR$^9$, —(CH$_2$)$_j$NR$^7$(CH$_2$)$_q$NR$^6$R$^7$, —(CH$_2$)$_j$NR$^7$CH$_2$C(O)NR$^6$R$^7$, —(CH$_2$)$_j$NR$^7$(CH$_2$)$_q$NR$^9$C(O)R$^8$, —(CH$_2$)$_j$NR$^7$(CH$_2$)$_t$O(CH$_2$)$_q$OR$^9$, —(CH$_2$)$_j$NR$^7$(CH$_2$)$_t$R$^6$, wherein j is an integer from 0 to 2, t is an integer from 0 to 6, q is an integer from 2 to 6, the —(CH$_2$)$_q$— and —(CH$_2$)$_t$— moieties of the foregoing $R^5$ groups optionally include a carbon-carbon double or triple bond where t is an integer from 2 to 6, and the alkyl, aryl and heterocyclic moieties of the foregoing $R^5$ groups are optionally substituted by 1 to 3 substituents independently selected from halo, cyano, trifluoromethyl, —C(O)R$^8$, —NR$^6$C(O)R$^7$, —C(O)NR$^6$R$^7$, —(CH$_2$)$_t$NR$^6$R$^7$, —SO$_2$R$^6$, —SO$_2$NR$^6$R$^7$, $C_1$-$C_6$ alkyl, —(CH$_2$)$_t$(5 to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6.

6. A compound according to claim 5, wherein each $R^5$ is independently selected from the group consisting of halo, cyano, trifluoromethoxy, trifluoromethyl, —C(O)R$^8$, —NR$^6$C(O)R$^7$, —C(O)NR$^6$R$^7$, —NR$^6$R$^7$, SO$_2$NR$^6$R$^7$, —SO$_2$R$^6$, —NR$^6$SO$_2$R$^7$, $C_1$-$C_6$ alkyl, —(CH$_2$ OR$^9$, and the alkyl moieties of the foregoing $R^5$ groups are optionally substituted by 1 to 3 substituents independently selected from halo, cyano, trifluoromethyl, —C(O)Re, —NR$^6$C(O)R$^7$, —C(O)NR$^6$R$^7$, —(CH$_2$)$_t$NR$^6$R$^7$, —SO$_2$R$^6$, —SO$_2$NR$^6$R$^7$, $C_1$-$C_6$ alkyl, —(CH$_2$)$_t$(5 to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6; and each $R^6$ and $R^7$ is independently selected from H, $C_1$-$C_6$ alkyl, and the alkyl, moieties of the foregoing $R^6$ and $R^7$ groups are optionally substituted by 1 to 3 substituents independently selected from halo, cyano, trifluoromethyl, —C(O)R$^8$, —NR$^9$C(O)R$^{10}$, —C(O)NR$^9$R$^{10}$, —NR$^9$R$^{10}$, $C_1$-$C_6$ alkyl.

7. A compound according to claim 6, wherein each $R^5$ is independently selected from the group consisting of halo, trifluoromethoxy, trifluoromethyl, $C_1$-$C_6$ alkyl and —(CH$_2$)$_t$OR$^9$ and the alkyl moieties of the foregoing $R^5$ groups are optionally substituted by 1 to 3 substituents independently selected from halo, cyano, trifluoromethyl, —C(O)R$^8$, —NR$^6$C(O)R$^7$, —C(O)NR$^6$R$^7$, —(CH$_2$)$_t$NR$^6$R$^7$, —SO$_2$R$^6$, —SO$_2$NR$^6$R$^7$, $C_1$-$C_6$ alkyl, —(CH$_2$)$_t$(5 to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6.

8. A compound according to claim 1, wherein L is —(CH$_2$)$_p$— wherein p is an integer from 0 to 5; —O—; —S—; —S(O)—; —S(O)$_2$; —N(R)—; N(C(O)OR)—; —N(C(O)R)—; —N(SO$_2$R); —N(R)C(O)—; —N(R)S(O)—; —N(R)S(O)$_2$—; OC(O)N(R)—; —N(R)C(O)N(R)—; —NRC(O)O—; —S(O)N(R)—; —S(O)$_2$N(R)—; —N(C(O)R)S(O)—; N(C(O)R)S(O)$_2$—; —N(R)S(O)N (R)—; —N(R)S(O)$_2$N(R)—; —C(O)N(R)C(O)—; —S(O)N(R)C(O)—; —S(O)$_2$N(R)C(O)—; —OS(O)N(R)—; —OS(O)$_2$N(R)—; —N(R)S(O)O—; —N(R)S(O)$_2$O—; —N(R)S(O)C(O)—; N(R)S(O)$_2$C(O)—; —SON(C(O)R)—; —SO$_2$N(C(O)R)—; —N(R)SON(R)—; —N(R)SO$_2$N(R)—; —C(O)O—, and wherein each R is independently selected from H, C$_1$-C$_6$ acyl, C$_1$-C$_6$ alkyl, C$_6$-aromatic group and 5 or 6 membered heteroaromatic group, and wherein each of the foregoing R groups is independently optionally substituted with 1-3 halo atoms, C$_1$-C$_6$ alkyl and C$_1$-C$_6$ alkoxy.

9. A compound according to claim 8, wherein L is —O—; —S—; —S(O)$_2$; —N(R)—; —N(C(O)R)—; —N(SO$_2$R); —N(R)C(O)—; —N(R)S(O)$_2$—; —N(R)C(O)N(R)—; —S(O)$_2$N(R)—; —N(C(O)R)S(O)$_2$; —N(R)S(O)$_2$N(R)—; —C(O)N(R)C(O)—; —S(O)$_2$N(R)C(O)—; —OS(O)$_2$NR—; —N(R)S(O)$_2$O—; N(R)S(O)$_2$C(O)—; —SO$_2$N(C(O)R)—; —N(R)SO$_2$N(R)—; —C(O)O—, and wherein each R is independently selected from H, C$_1$-C$_6$ acyl, C$_1$-C$_6$ alkyl, C$_6$-aromatic group and 5 or 6 membered heteroaromatic group, and wherein each of the foregoing R groups is independently optionally substituted with 1-3 halo atoms, C$_1$-C$_6$ alkyl and C$_1$-C$_6$ alkoxy.

10. A compound according to claim 9, wherein L is —N(SO$_2$R)— or —N(R)C(O)N(R)— and wherein each R is independently selected from H, C$_1$-C$_6$ acyl, C$_1$-C$_6$ alkyl, C$_6$-aromatic group and 5 or 6 membered heteroaromatic group, and wherein each of the foregoing R groups is independently optionally substituted with 1-3 halo atoms, C$_1$-C$_6$ alkyl and C$_1$-C$_6$ alkoxy.

11. A compound according to claim 10, wherein L is —N(R)C(O)N(R)— and wherein each R is independently selected from the group consisting of H or C$_1$-C$_6$ alkyl.

12. A compound according to claim 10, wherein L is —N(SO$_2$R)— and wherein each R is independently selected from the group consisting of H or C$_1$-C$_6$ alkyl.

13. A compound according to claim 1, wherein substituent Q is attached to the pyrrolopyrimidine ring at the 5-position.

14. A compound according to claim 1, wherein R$^1$ is selected from the group consisting of H, C$_1$-C$_6$ alkyl, C$_3$-C$_8$ cycloalkyl, and 3 to 8 membered heterocycloalkyl group and each of the foregoing R$^1$ groups is optionally substituted with 1 to 5 R$^5$ groups.

15. A compound according to claim 14, wherein R$^1$ is selected from the group consisting of H, C$_1$-C$_6$ alkyl, and C$_3$-C$_8$ cycloalkyl and each of the foregoing R$^1$ groups is optionally substituted with 1 to 5 R$^5$ groups.

16. A compound according to claim 15, wherein R$^1$ is selected from the group consisting of C$_1$-C$_6$ alkyl and C$_3$-C$_8$ cycloalkyl and each of the foregoing R$^1$ groups is optionally substituted with 1 to 5 R$^5$ groups.

17. A compound according to claim 16, wherein R$^1$ is C$_3$-C$_8$ cycloalkyl and said C$_3$-C$_8$ cycloalkyl group is optionally substituted with 1 to 5 R$^5$ groups.

18. A compound according to claims 14 wherein each R$^5$ is independently selected from the group consisting of halo, cyano, trifluoromethoxy, trifluoromethyl, —C(O)R$^8$, —NR$^6$C(O)R$^7$, —C(O)NR$^6$R$^7$, —NR$^6$R$^7$, —OR$^9$, SO$_2$NR$^6$R$^7$, —SO$_2$R$^6$, —NR$^6$SO$_2$R$^7$, C$_1$-C$_6$ alkyl, —(CH$_2$)$_t$OR$^9$, —(CH$_2$)$_j$NR$^7$(CH$_2$)$_q$NR$^6$R$^7$, —(CH$_2$)$_j$NR$^7$CH$_2$C(O)NR$^6$R$^7$, —(CH$_2$)$_j$NR$^7$(CH$_2$)$_q$NR$^9$C(O)R$^8$, —(CH$_2$)$_j$NR$^7$(CH$_2$)$_q$O(CH$_2$)$_q$OR$^9$, —(CH$_2$)$_j$NR$^7$(CH$_2$)$_t$R$^6$, wherein j is an integer from 0 to 2, t is an integer from 0 to 6, q is an integer from 2 to 6, the —(CH$_2$)$_q$— and —(CH$_2$)$_t$— moieties of the foregoing R$^5$ groups optionally include a carbon-carbon double or triple bond where t is an integer from 2 to 6, and the alkyl, aryl and heterocyclic moieties of the foregoing R$^5$ groups are optionally substituted by 1 to 3 substituents independently selected from halo, cyano, trifluoromethyl, —C(O)R$^8$, —NR$^6$C(O)R$^7$, —C(O)NR$^6$R$^7$, —(CH$_2$)$_t$NR$^6$R$^7$, —SO$_2$R$^6$, —SO$_2$NR$^6$R$^7$, C$_1$-C$_6$ alkyl, —(CH$_2$)$_t$(5 to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6.

19. A compound according to claim 18, wherein each R$^5$ is independently selected from the group consisting of halo, cyano, trifluoromethoxy, trifluoromethyl, —C(O)R$^8$, —NR$^6$C(O)R$^7$, —C(O)NR$^6$R$^7$, —NR$^6$R$^7$, SO$_2$NR$^6$R$^7$, —SO$_2$R$^6$, —NR$^6$SO$_2$R$^7$, C$_1$-C$_6$ alkyl, —(CH$_2$)$_t$OR$^9$, and the alkyl moieties of the foregoing R$^5$ groups are optionally substituted by 1 to 3 substituents independently selected from halo, cyano, trifluoromethyl, —C(O)R$^8$, —NR$^6$C(O)R$^7$, —C(O)NR$^6$R$^7$, —(CH$_2$)$_t$NR$^6$R$^7$, —SO$_2$R$^6$, —SO$_2$NR$^6$R$^7$, C$_1$-C$_6$ alkyl, —(CH$_2$)$_t$(5 to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6; and each R$^6$ and R$^7$ is independently selected from H, C$_1$-C$_6$ alkyl, and the alkyl, moieties of the foregoing R$^6$ and R$^7$ groups are optionally substituted by 1 to 3 substituents independently selected from halo, cyano, trifluoromethyl, —C(O)R$^8$, —NR$^9$C(O)R$^{10}$, —C(O)NR$^9$R$^{10}$, —NR$^9$R$^{10}$, C$_1$-C$_6$ alkyl.

20. A compound according to claim 19, wherein each R$^5$ is independently selected from the group consisting of halo, trifluoromethoxy, trifluoromethyl, C$_1$-C$_6$ alkyl and —(CH$_2$)$_t$OR$^9$ and the alkyl moieties of the foregoing R$^5$ groups are optionally substituted by 1 to 3 substituents independently selected from halo, cyano, trifluoromethyl, —C(O)R$^8$, —NR$^6$C(O)R$^7$, —C(O)NR$^6$R$^7$, —(CH$_2$)$_t$NR$^6$R$^7$, —SO$_2$R$^6$, —SO$_2$NR$^6$R$^7$, C$_1$-C$_6$ alkyl, —(CH$_2$)$_t$(5 to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6.

21. A compound according to claim 1, wherein R$^2$ is H, halo, C$_1$-C$_6$ alkyl, C$_3$-C$_8$ cycloalkyl, —(CH$_2$)$_{0-3}$NR$^6$R$^7$, and —(CH$_2$)$_{0-3}$C(O)NR$^6$R$^7$ and each of the foregoing R$^2$ groups is optionally substituted with 1 to 5 R$^5$ groups.

22. A compound according to claim 21, wherein R$^2$ is H, halo, and C$_1$-C$_6$ alkyl and each of the foregoing R$^2$ groups is optionally substituted with 1 to 5 R$^5$ groups.

23. A compound according to claim 1, wherein said R$^2$ substituent is attached to the pyrrolopyrimidine ring at the 6-position.

24. A compound according to claims 21 wherein each R$^5$ is independently selected from the group consisting of halo, cyano, trifluoromethoxy, trifluoromethyl, —C(O)R$^8$, —NR$^6$C(O)R$^7$, —C(O)NR$^6$R$^7$, —NR$^6$R$^7$, —OR$^9$, SO$_2$NR$^6$R$^7$, —SO$_2$R$^6$, —NR$^6$SO$_2$R$^7$, C$_1$-C$_8$ alky, —(CH$_2$)$_t$OR$^9$, —(CH$_2$)$_j$NR$^7$(CH$_2$)$_q$NR$^6$R$^7$, —(CH$_2$)$_j$NR$^7$CH$_2$C(O)NR$^6$R$^7$, —(CH$_2$)$_j$NR$^7$(CH$_2$)$_q$NR$^9$C(O)R$^8$, —(CH$_2$)$_j$NR$^7$(CH$_2$)$_q$O(CH$_2$)$_q$OR$^9$, —(CH$_2$)$_j$NR$^7$(CH$_2$)$_t$R$^6$, wherein j is an integer from 0 to 2, t is an integer from 0 to 6, q is an integer from 2 to 6, the —(CH$_2$)$_q$— and —(CH$_2$)$_t$— moieties of the foregoing R$^5$ groups optionally include a carbon-carbon double or triple bond where t is an integer from 2 to 6, and the alkyl, aryl and heterocyclic moieties of the foregoing R$^5$ groups are optionally substituted by 1 to 3 substituents independently selected from halo, cyano, trifluoromethyl, —C(O)R$^8$, —NR$^6$C(O)R$^7$, —C(O)NR$^6$R$^7$, —(CH$_2$)$_t$NR$^6$R$^7$, —SO$_2$R$^6$, —SO$_2$NR$^6$R$^7$, C$_1$-C$_6$ alkyl, —(CH$_2$)$_t$(5 to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6.

25. A compound according to claim 24, wherein each $R^5$ is independently selected from the group consisting of halo, cyano, trifluoromethoxy, trifluoromethyl, —C(O)$R^8$, —N$R^6$C(O)$R^7$, —C(O)N$R^6R^7$, —N$R^6R^7$, SO$_2$N$R^6R^7$, —SO$_2R^6$, —N$R^6$SO$_2R^7$, $C_1$-$C_6$ alkyl, —(CH$_2$)$_t$O$R^9$, and the alkyl moieties of the foregoing $R^5$ groups are optionally substituted by 1 to 3 substituents independently selected from halo, cyano, trifluoromethyl, —C(O)$R^8$, —N$R^6$C(O)$R^7$, —C(O)N$R^6R^7$, —(CH$_2$)$_t$N$R^6R^7$, —SO$_2R^6$, —SO$_2$N$R^6R^7$, $C_1$-$C_6$ alkyl, —(CH$_2$)$_t$(5 to 10 membered heterocyclic), —(CH$_2$)$_t$O(CH$_2$)$_q$O$R^9$, and —(CH$_2$)$_t$O$R^9$, wherein t is an integer from 0 to 6 and q is an integer from 2 to 6; and each $R^6$ and $R^7$ is independently selected from H, $C_1$-$C_6$ alkyl, and the alkyl, moieties of the foregoing $R^6$ and $R^7$ groups are optionally substituted by 1 to 3 substituents independently selected from halo, cyano, trifluoromethyl, —C(O)$R^8$, —N$R^9$C(O)$R^{10}$, —C(O)N$R^9R^{10}$, —N$R^9R^{10}$, $C_1$-$C_6$ alkyl.

26. A compound according to claim 25, wherein each $R^5$ is independently selected from the group consisting of halo, trifluoromethoxy, trifluoromethyl, $C_1$-$C_6$ alkyl and —(CH$_2$)$_t$O$R^9$ and the alkyl moieties of the foregoing $R^5$ groups are optionally substituted by 1 to 3 substituents independently selected from halo, cyano, trifluoromethyl, —C(O)$R^8$, —N$R^6$C(O)$R^7$, —C(O)N$R^6R^7$, —(CH$_2$)$_t$N$R^6R^7$, —SO$_2R^6$, —SO$_2$N$R^6R^7$, $C_1$-$C_6$ alkyl, —(CH$_2$)$_t$(5 to 10 membered heterocyclic), —(CH$_2$)$_t$O(CH$_2$)$_q$O$R^9$, and —(CH$_2$)$_t$O$R^9$, wherein t is an integer from 0 to 6 and q is an integer from 2 to 6.

27. A compound according to claim 1, wherein $R^3$ is $C_3$-$C_8$ cycloalkyl, —(CH$_2$)$_t$$C_6$-$C_{10}$ aryl, —(CH$_2$)$_t$(5 to 13 membered heteroaromatic group), and 3 to 8 membered heterocycloalkyl, and each of the foregoing $R^3$ groups is optionally substituted with 1 to 5 $R^5$ groups.

28. A compound according to claim 27, wherein $R^3$ is $C_3$-$C_8$ cycloalkyl, —(CH$_2$)$_t$$C_6$-$C_{10}$ aryl, and —(CH$_2$)$_t$(5 to 13 membered heteroaromatic group) and each of the foregoing $R^3$ groups is optionally substituted with 1 to 5 $R^5$ groups.

29. A compound according to claim 28, wherein $R^3$ is —(CH$_2$)$_t$$C_6$-$C_{10}$ aryl, and —(CH$_2$)$_t$(5 to 13 membered heteroaromatic group) and each of the foregoing $R^3$ groups is optionally substituted with 1 to 5 $R^5$ groups.

30. A compound according to claims 27 wherein each $R^5$ is independently selected from the group consisting of halo, cyano, trifluoromethoxy, trifluoromethyl, —C(O)$R^8$, —N$R^6$C(O)$R^7$, —C(O)N$R^6R^7$, —N$R^6R^7$, —O$R^9$, SO$_2$N$R^6R^7$, —SO$_2R^6$, N$R^6$SO$_2R^6$, $C_1$-$C_6$ alkyl, —(CH$_2$)$_t$O$R^9$, —(CH$_2$)$_j$N$R^7$(CH$_2$)$_q$N$R^6R^7$, —(CH$_2$)$_j$N$R^7$CH$_2$C(O)N$R^6R^7$, —(CH$_2$)$_j$N$R^7$(CH$_2$)$_q$N$R^9$C(O)$R^8$, —(CH$_2$)$_j$N$R^7$(CH$_2$)$_t$O(CH$_2$)$_q$O$R^9$, —(CH$_2$)$_j$N$R^7$(CH$_2$)$_t$$R^6$, wherein j is an integer from 0 to 2, t is an integer from 0 to 6, q is an integer from 2 to 6, the —(CH$_2$)$_q$— and —(CH$_2$)$_t$— moieties of the foregoing $R^5$ groups optionally include a carbon-carbon double or triple bond where t is an integer from 2 to 6, and the alkyl, aryl and heterocyclic moieties of the foregoing $R^5$ groups are optionally substituted by 1 to 3 substituents independently selected from halo, cyano, trifluoromethyl, —C(O)$R^8$, —N$R^6$C(O)$R^7$, —C(O)N$R^6R^7$, —(CH$_2$)$_t$N$R^6R^7$, —SO$_2R^6$, —SO$_2$N$R^6R^7$, $C_1$-$C_6$ alkyl, —(CH$_2$)$_t$(5 to 10 membered heterocyclic), —(CH$_2$)$_t$O(CH$_2$)$_q$O$R^9$, and —(CH$_2$)$_t$O$R^9$, wherein t is an integer from 0 to 6 and q is an integer from 2 to 6.

31. A compound according to claim 30, wherein each $R^5$ is independently selected from the group consisting of halo, cyano, trifluoromethoxy, trifluoromethyl, —C(O)$R^8$, —N$R^6$C(O)$R^7$, —C(O)N$R^6R^7$, —N$R^6R^7$, SO$_2$N$R^6R^7$, —SO$_2R^6$, —N$R^6$SO$_2R^7$, $C_1$-$C_6$ alkyl, —(CH$_2$)$_t$O$R^9$, and the alkyl moieties of the foregoing $R^5$ groups are optionally substituted by 1 to 3 substituents independently selected from halo, cyano, trifluoromethyl, —C(O)$R^8$, —N$R^6$C(O)$R^7$, —C(O)N$R^6R^7$, —(CH$_2$)$_t$N$R^6R^7$, —SO$_2R^6$, —SO$_2$N$R^6R^7$, $C_1$-$C_6$ alkyl —(CH$_2$)$_t$(5 to 10 membered heterocyclic), —(CH$_2$)$_t$O(CH$_2$)$_q$O$R^9$, and —(CH$_2$)$_t$O$R^9$, wherein t is an integer from 0 to 6 and q is an integer from 2 to 6; and each $R^6$ and $R^7$ is independently selected from H, $C_1$-$C_6$ alkyl, and the alkyl, moieties of the foregoing $R^6$ and $R^7$ groups are optionally substituted by 1 to 3 substituents independently selected from halo, cyano, trifluoromethyl, —C(O)$R^8$, —N$R^9$C(O)$R^{10}$, —C(O)N$R^9R^{10}$, —N$R^9R^{10}$, $C_1$-$C_6$ alkyl.

32. A compound according to claim 31, wherein each $R^5$ is independently selected from the group consisting of halo, trifluoromethoxy, trifluoromethyl, $C_1$-$C_6$ alkyl and —(CH$_2$)$_t$O$R^9$ and the alkyl moieties of the foregoing $R^5$ groups are optionally substituted by 1 to 3 substituents independently selected from halo, cyano, trifluoromethyl, —C(O)$R^8$, —N$R^6$C(O)$R^7$, —C(O)N$R^6R^7$, —(CH$_2$)$_t$N$R^6R^7$, —SO$_2R^6$, —SO$_2$N$R^6R^7$, $C_1$-$C_6$ alkyl, —(CH$_2$)$_t$(5 to 10 membered heterocyclic), —(CH$_2$)$_t$O(CH$_2$)$_q$O$R^9$, and —(CH$_2$)$_t$O$R^9$, wherein t is an integer from 0 to 6 and q is an integer from 2 to 6.

33. A compound according to claim 8, wherein $R^1$ is selected from the group consisting of H, $C_1$-$C_6$ alkyl, $C_3$-$C_8$ cycloalkyl, and 3 to 8 membered heterocycloalkyl group and each of the foregoing $R^1$ groups is optionally substituted with 1 to 5 $R^5$ groups.

34. A compound according to claim 33, wherein $R^2$ is H, halo, $C_1$-$C_6$ alkyl, $C_3$-$C_8$ cycloalkyl, —(CH$_2$)$_{0-3}$N$R^6R^7$, and —(CH$_2$)$_{0-3}$C(O)N$R^6R^7$ and each of the foregoing $R^2$ groups is optionally substituted with 1 to 5 $R^5$ groups.

35. A compound according to claim 34, wherein $R^3$ is $C_3$-$C_8$ cycloalkyl, —(CH$_2$)$_t$$C_6$-$C_{10}$ aryl, —(CH$_2$)$_t$(5 to 13 membered heteroaromatic group), and 3 to 8 membered heterocycloalkyl, and each of the foregoing $R^3$ groups is optionally substituted with 1 to 5 $R^5$ groups.

36. A compound according to claims 1, wherein each $R^5$ is independently selected from the group consisting of halo, cyano, trifluoromethoxy, trifluoromethyl, —C(O)$R^8$, —N$R^6$C(O)$R^7$, —C(O)N$R^6R^7$, —N$R^6R^7$, —O$R^9$, SO$_2$N$R^6R^7$, —SO$_2R^6$, —N$R^6$SO$_2R^7$, $C_1$-$C_6$ alkyl, —(CH$_2$)$_t$O$R^9$, —(CH$_2$)$_j$N$R^7$(CH$_2$)$_q$N$R^6R^7$, —(CH$_2$)$_j$N$R^7$CH$_2$C(O)N$R^6R^7$, —(CH$_2$)$_j$N$R^7$(CH$_2$)$_q$N$R^9$C(O)$R^8$, —(CH$_2$)$_j$N$R^7$(CH$_2$)$_t$O(CH$_2$)$_q$O$R^9$, —(CH$_2$)$_j$N$R^7$(CH$_2$)$_t$$R^6$, wherein j is an integer from 0 to 2, t is an integer from 0 to 6, q is an integer from 2 to 6, the —(CH$_2$)$_q$— and —(CH$_2$)$_t$— moieties of the foregoing $R^5$ groups optionally include a carbon-carbon double or triple bond where t is an integer from 2 to 6, and the alkyl, aryl and heterocyclic moieties of the foregoing $R^5$ groups are optionally substituted by 1 to 3 substituents independently selected from halo, cyano, trifluoromethyl, —C(O)$R^8$, —N$R^6$C(O)$R^7$, —C(O)N$R^6R^7$, —(CH$_2$)$_t$N$R^6R^7$, —SO$_2R^6$, —SO$_2$N$R^6R^7$, $C_1$-$C_6$ alkyl, —(CH$_2$)$_t$(5 to 10 membered heterocyclic), —(CH$_2$)$_t$O(CH$_2$)$_q$O$R^9$, and —(CH$_2$)$_t$O$R^9$, wherein t is an integer from 0 to 6 and q is an integer from 2 to 6.

37. A compound according to claim 2, wherein

L is —(CH$_2$)$_p$— wherein p is an integer from 0 to 5; —O—; —S—; —S(O)—; —S(O)—; —N(R)—; N(C(O)OR)—; —N(C(O)R)—; —N(SO$_2$R); —N(R)C(O)—; —N(R)S(O)—; —N(R)S(O)$_2$; OC(O)N(R)—; —N(R)C(O)N(R)—; —NRC(O)O—; —S(O)N(R)—;

—S(O)N(R)—; —N(C(O)R)S(O)—; N(C(O)R)S(O)$_2$; —N(R)S(O)N(R)—; —N(R)S(O)$_2$N(R)—; —C(O)N(R)C(O)—; —S(O)N(R)C(O)—; —S(O)$_2$N(R)C(O)—; —OS(O)N(R)—; —OS(O)N(R)—; —N(R)S(O)O—; —N(R)S(O)$_2$O—; —N(R)S(O)C(O)—; N(R)S(O)C(O)—; —SON(C(O)R)—; —SO$_2$N(C(O)R)—; —N(R)SON(R)—; —N(R)SO$_2$N(R)—; —C(O)O—, and wherein each R is independently selected from H, $C_1$-$C_6$ acyl, $C_1$-$C_6$ alkyl, $C_6$-aromatic group and 5 or 6 membered heteroaromatic group, and wherein each of the foregoing R groups is independently optionally substituted with 1-3 halo atoms, $C_1$-$C_6$ alkyl and $C_1$-$C_6$ alkoxy.

38. A compound according to claim 37, wherein A is $C_6$-$C_{10}$ aryl, wherein said aryl ring is optionally substituted with 1 to 5 $R^5$ groups.

39. A compound according to claim 38, wherein A is $C_6$-$C_8$ aryl, wherein said aryl ring is optionally substituted with 1 to 5 $R^5$ groups.

40. A compound according to claim 39, wherein A is $C_6$-aryl, wherein said aryl ring is optionally substituted with 1 to 5 $R^5$ groups.

41. A compound according to claim 37, wherein A is 5 to 13 membered heteroaromatic ring, wherein said ring is optionally substituted with 1 to 5 $R^5$ groups.

42. A compound according to claim 37, wherein $R^1$ is selected from the group consisting of H, $C_1$-$C_6$ alkyl, $C_3$-$C_8$ cycloalkyl, and 3 to 8 membered heterocycloalkyl group and each of the foregoing $R^1$ groups is optionally substituted with 1 to 5 $R^5$ groups.

43. A compound according to claim 37 or 42, wherein $R^2$ is H, halo, $C_1$-$C_6$ alkyl, $C_3$-$C_8$ cycloalkyl, —(CH$_2$)$_{0-3}$NR$^6$R$^7$, and —(CH$_2$)$_{0-3}$C(O)NR$^6$R$^7$ and each of the foregoing $R^2$ groups is optionally substituted with 1 to 5 $R^5$ groups.

44. A compound according to claim 37, wherein $R^3$ is $C_3$-$C_8$ cycloalkyl, —(CH$_2$)$_t$C$_6$-C$_{10}$ aryl, —(CH$_2$)$_t$(5 to 13 membered heteroaromatic group), and 3 to 8 membered heterocycloalkyl, and each of the foregoing $R^3$ groups is optionally substituted with 1 to 5 $R^5$ groups.

45. A compound according to claim 43, wherein $R^3$ is $C_3$-$C_8$ cycloalkyl, —(CH$_2$)$_t$C$_6$-C$_{10}$ aryl, —(CH$_2$)$_t$(5 to 13 membered heteroaromatic group), and 3 to 8 membered heterocycloalkyl, and each of the foregoing $R^3$ groups is optionally substituted with 1 to 5 $R^5$ groups.

46. A compound according to claims 37, wherein each $R^5$ is independently selected from the group consisting of halo, cyano, trifluoromethoxy, trifluoromethyl, —C(O)R$^8$, —NR$^6$C(O)R$^7$, —C(O)NR$^6$R$^7$, —NR$^6$R$^7$, —OR$^9$, SO$_2$NR$^6$R$^7$, —SO$_2$R$^6$, —NR$^6$SO$_2$R$^7$, $C_1$-$C_6$ alkyl, —(CH$_2$)$_t$OR$^9$, —(CH$_2$)$_j$NR$^7$(CH$_2$)$_q$NR$^6$R$^7$, —(CH$_2$)$_j$NR$^7$CH$_2$C(O)NR$^6$R$^7$, —(CH$_2$)$_j$NR$^7$(CH$_2$)$_q$NR$^9$C(O)R$^8$, —(CH$_2$)$_j$NR$^7$(CH$_2$)$_t$O(CH$_2$)$_q$OR$^9$, —(CH$_2$)$_j$NR$^7$(CH$_2$)$_t$R$^8$, wherein j is an integer from 0 to 2, t is an integer from 0 to 6, q is an integer from 2 to 6, the —(CH$_2$)$_q$— and —(CH$_2$)$_t$— moieties of the foregoing $R^5$ groups optionally include a carbon-carbon double or triple bond where t is an integer from 2 to 6, and the alkyl, aryl and heterocyclic moieties of the foregoing $R^5$ groups are optionally substituted by 1 to 3 substituents independently selected from halo, cyano, trifluoromethyl, —C(O)R$^8$, —NR$^6$C(O)R$^7$, —C(O)NR$^6$R$^7$, —(CH$_2$)$_t$NR$^6$R$^7$, —SO$_2$R$^6$, —SO$_2$NR$^6$R$^7$, $C_1$-$C_6$ alkyl, —(CH$_2$)$_t$(5 to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6.

47. A compound according to claims 45, wherein each $R^5$ is independently selected from the group consisting of halo, cyano, trifluoromethoxy, trifluoromethyl, —C(O)R$^8$, —NR$^6$C(O)R$^7$, —C(O)NR$^6$R$^7$, —NR$^6$R$^7$, —OR$^9$, SO$_2$NR$^6$R$^7$, —SO$_2$R$^6$, —NR$^6$SO$_2$R$^7$, $C_1$-$C_6$ alkyl, —(CH$_2$)$_t$OR$^9$, —(CH$_2$)$_j$NR$^7$(CH$_2$)$_q$NR$^6$R$^7$, —(CH$_2$)$_j$NR$^7$CH$_2$C(O)NR$^6$R$^7$, (CH$_2$)$_j$NR$^7$(CH$_2$)$_q$NR$^9$C(O)R$^8$, —(CH$_2$)$_j$NR$^7$(CH$_2$)$_t$O(CH$_2$)$_q$OR$^9$, —(CH$_2$)$_j$NR$^7$(CH$_2$)$_t$R$^6$, wherein j is an integer from 0 to 2, t is an integer from 0 to 6, q is an integer from 2 to 6, the —(CH$_2$)$_q$— and —(CH$_2$)$_t$— moieties of the foregoing $R^5$ groups optionally include a carbon-carbon double or triple bond where t is an integer from 2 to 6, and the alkyl, aryl and heterocyclic moieties of the foregoing $R^5$ groups are optionally substituted by 1 to 3 substituents independently selected from halo, cyano, trifluoromethyl, —C(O)R$^8$, —NR$^6$C(O)R$^7$, —C(O)NR$^6$R$^7$, —(CH$_2$)$_t$NR$^6$R$^7$, —SO$_2$R$^6$, —SO$_2$NR$^6$R$^7$, $C_1$-$C_6$ alkyl, —(CH$_2$)$_t$(5 to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6.

48. A compound according to claim 1, wherein
A is $C_6$-$C_{10}$ aryl or 5 to 13 membered heteroaromatic ring and each of the foregoing A groups is optionally substituted with 1 to 5 $R^5$ groups;
L is —N(SO$_2$R)— or —N(R)C(O)N(R)— and wherein each R is independently selected from H, $C_1$-$C_6$ acyl, $C_1$-$C_6$ alkyl, $C_6$-aromatic group and 5 or 6 membered heteroaromatic group, and wherein each of the foregoing R groups is independently optionally substituted with 1-3 halo atoms, $C_1$-$C_6$ alkyl and $C_1$-$C_6$ alkoxy;
$R^1$ is selected from the group consisting of $C_1$-$C_6$ alkyl and $C_3$-$C_8$ cycloalkyl and each of the foregoing $R^1$ groups is optionally substituted with 1 to 5 $R^5$ groups;
$R^2$ is H, halo, and $C_1$-$C_6$ alkyl and each of the foregoing $R^2$ groups is optionally substituted with 1 to 5 $R^5$ groups; and
$R^3$ is $C_3$-$C_8$ cycloalkyl, —(CH$_2$)$_t$C$_6$-C$_{10}$ aryl, and —(CH$_2$)$_t$(5 to 13 membered heteroaromatic group) and each of the foregoing $R^3$ groups is optionally substituted with 1 to 5 $R^5$ groups.

49. A compound according to claim 48, wherein L is —N(R)C(O)N(R)— and wherein each R is independently selected from the group consisting of H or $C_1$-$C_6$ alkyl.

50. A compound according to claims 47 or 49, wherein substituent Q is attached to the pyrrolopyrimidine ring at the 5-position.

51. A compound according to claim 1, wherein said compound is selected from the group consisting of:
1-[3-(4-Amino-7-isopropyl-7H-pyrrolo[2,3-d]pyrimidine-5-carbonyl)-phenyl]-3-(2-chloro-phenyl)-urea;
1-[3-(4-Amino-7-isopropyl-7H-pyrrolo[2,3-d]pyrimidine-5-carbonyl)-phenyl]-3-(2-methoxy-5-methyl-phenyl)-urea;
1-[3-(4-Amino-7-isopropyl-7H-pyrrolo[2,3-d]pyrimidine-5-carbonyl)-phenyl]-3-(2-fluoro-5-methyl-phenyl)-urea;
1-[3-(4-Amino-7-isopropyl-7H-pyrrolo[2,3-d]pyrimidine-5-carbonyl)-phenyl]-3-m-tolyl-urea;
1-[3-(4-Amino-7-isopropyl-7H-pyrrolo[2,3-d]pyrimidine-5-carbonyl)-phenyl]-3-(3-ethyl-phenyl)-urea;
N-[3-(4-Amino-7-isopropyl-7H-pyrrolo[2,3-d]pyrimidine-5-carbonyl)-phenyl]-3-chloro-4-methyl-benzenesulfonamide;
N-[3-(4-Amino-7-isopropyl-7H-pyrrolo[2,3-d]pyrimidine-5-carbonyl)-phenyl]-3,5-dichloro-benzenesulfonamide;
N-[3-(4-Amino-7-isopropyl-7H-pyrrolo[2,3-d]pyrimidine-5-carbonyl)-phenyl]-2,4-dichloro-benzenesulfonamide;

1-[3-(4-Amino-7-isopropyl-7H-pyrrolo[2,3-d]pyrimidine-5-carbonyl)-phenyl]-3-(2-fluoro-phenyl)-urea;
1-[3-(4-Amino-7-isopropyl-7H-pyrrolo[2,3-d]pyrimidine-5-carbonyl)-phenyl]-3-(2,4-difluoro-phenyl)-urea;
1-[3-(4-Amino-7-isopropyl-7H-pyrrolo[2,3-d]pyrimidine-5-carbonyl)-phenyl]-3-(2,6-difluoro-phenyl)-urea;
1-[3-(4-Amino-7-isopropyl-7H-pyrrolo[2,3-d]pyrimidine-5-carbonyl)-phenyl]-3-(3,4-difluoro-phenyl)-urea;
1-[3-(4-Amino-7-isopropyl-7H-pyrrolo[2,3-d]pyrimidine-5-carbonyl)-phenyl]-3-(3-fluoro-phenyl)-urea;
1-[3-(4-Amino-7-isopropyl-7H-pyrrolo[2,3-d]pyrimidine-5-carbonyl)-phenyl]-3-(5-fluoro-2-methyl-phenyl)-urea;
1-[3-(4-Amino-7-isopropyl-7H-pyrrolo[2,3-d]pyrimidine-5-carbonyl)-phenyl]-3-(4-fluoro-phenyl)-urea;
1-[3-(4-Amino-7-isopropyl-7H-pyrrolo[2,3-d]pyrimidine-5-carbonyl)-phenyl]-3-(3-fluoro-4-methyl-phenyl)-urea;
1-[3-(4-Amino-7-isopropyl-7H-pyrrolo[2,3-d]pyrimidine-5-carbonyl)-phenyl]-3-(3,5-difluoro-phenyl)-urea;
1-[3-(4-Amino-7-isopropyl-7H-pyrrolo[2,3-d]pyrimidine-5-carbonyl)-phenyl]-3-(2,5-difluoro-phenyl)-urea;
1-[3-(4-Amino-7-isopropyl-7H-pyrrolo[2,3-d]pyrimidine-5-carbonyl)-phenyl]-3-(3-chloro-phenyl)-urea;
1-[3-(4-Amino-7-isopropyl-7H-pyrrolo[2,3-d]pyrimidine-5-carbonyl)-phenyl]-3-(4-chloro-phenyl)-urea;
1-[3-(4-Amino-7-isopropyl-7H-pyrrolo[2,3-d]pyrimidine-5-carbonyl)-phenyl]-3-p-tolyl-urea;
1-[3-(4-Amino-7-isopropyl-7H-pyrrolo[2,3-d]pyrimidine-5-carbonyl)-phenyl]-3-(2-ethyl-phenyl)-urea;
1-[3-(4-Amino-7-isopropyl-7H-pyrrolo[2,3-d]pyrimidine-5-carbonyl)-phenyl]-3-(2-isopropyl-phenyl)-urea;
1-[3-(4-Amino-7-isopropyl-7H-pyrrolo[2,3-d]pyrimidine-5-carbonyl)-phenyl]-3-(4-isopropyl-phenyl)-urea;
1-[3-(4-Amino-7-isopropyl-7H-pyrrolo[2,3-d]pyrimidine-5-carbonyl)-phenyl]-3-(4-methoxy-phenyl)-urea;
1-[3-(4-Amino-7-isopropyl-7H-pyrrolo[2,3-d]pyrimidine-5-carbonyl)-phenyl]-3-(2-methoxy-phenyl)-urea;
1-[3-(4-Amino-7-isopropyl-7H-pyrrolo[2,3-d]pyrimidine-5-carbonyl)-phenyl]-3-(2-ethoxy-phenyl)-urea;
1-[3-(4-Amino-7-isopropyl-7H-pyrrolo[2,3-d]pyrimidine-5-carbonyl)-phenyl]-3-(4-methylsulfanyl-phenyl)-urea;
1-[3-(4-Amino-7-isopropyl-7H-pyrrolo[2,3-d]pyrimidine-5-carbonyl)-phenyl]-3-(3-methylsulfanyl-phenyl)-urea;
1-[3-(4-Amino-7-isopropyl-7H-pyrrolo[2,3-d]pyrimidine-5-carbonyl)-phenyl]-3-(3-cyano-phenyl)-urea;
1-[3-(4-Amino-7-isopropyl-7H-pyrrolo[2,3-d]pyrimidine-5-carbonyl)-phenyl]-3-(3,5-dimethyl-phenyl)-urea;
1-[3-(4-Amino-7-isopropyl-7H-pyrrolo[2,3-d]pyrimidine-5-carbonyl)-phenyl]-3-(3,4-dimethyl-phenyl)-urea;
1-[3-(4-Amino-7-isopropyl-7H-pyrrolo[2,3-d]pyrimidine-5-carbonyl)-phenyl]-3-(2,5-dimethyl-phenyl)-urea;
1-[3-(4-Amino-7-isopropyl-7H-pyrrolo[2,3-d]pyrimidine-5-carbonyl)-phenyl]-3-(2,3-dimethyl-phenyl)-urea;
1-[3-(4-Amino-7-isopropyl-7H-pyrrolo[2,3-d]pyrimidine-5-carbonyl)-phenyl]-3-(2,4-dimethyl-phenyl)-urea;
1-[3-(4-Amino-7-isopropyl-7H-pyrrolo[2,3-d]pyrimidine-5-carbonyl)-phenyl]-3-thiophen-2-yl-urea;
1-[3-(4-Amino-7-isopropyl-7H-pyrrolo[2,3-d]pyrimidine-5-carbonyl)-phenyl]-3-thiophen-3-yl-urea;
1-[3-(4-Amino-7-isopropyl-7H-pyrrolo[2,3-d]pyrimidine-5-carbonyl)-phenyl]-3-cyclohexyl-urea;
1-[3-(4-Amino-7-isopropyl-7H-pyrrolo[2,3-d]pyrimidine-5-carbonyl)-phenyl]-3-o-tolyl-urea;
1-[3-(4-Amino-7-isopropyl-7H-pyrrolo[2,3-d]pyrimidine-5-carbonyl)-phenyl]-3-(4-ethyl-phenyl)-urea;
1-(3-Acetyl-phenyl)-3-[3-(4-amino-7-isopropyl-7H-pyrrolo[2,3-d]pyrimidine-5-carbonyl)-phenyl]-urea;
1-(4-Acetyl-phenyl)-3-[3-(4-amino-7-isopropyl-7H-pyrrolo[2,3-d]pyrimidine-5-carbonyl)-phenyl]-urea;
1-[3-(4-Amino-7-isopropyl-7H-pyrrolo[2,3-d]pyrimidine-5-carbonyl)-phenyl]-3-(4-dimethylamino-phenyl)-urea;
1-[3-(4-Amino-7-isopropyl-7H-pyrrolo[2,3-d]pyrimidine-5-carbonyl)-phenyl]-3-(4-ethoxy-phenyl)-urea;
1-[3-(4-Amino-7-isopropyl-7H-pyrrolo[2,3-d]pyrimidine-5-carbonyl)-phenyl]-3-(4-methoxy-2-methyl-phenyl)-urea;
4-{3-[3-(4-Amino-7-isopropyl-7H-pyrrolo[2,3-d]pyrimidine-5-carbonyl)-phenyl]-ureido}-benzoic acid methyl ester
1-[3-(4-Amino-7-isopropyl-7H-pyrrolo[2,3-d]pyrimidine-5-carbonyl)-phenyl]-3-(2-methylsulfanyl-phenyl)-urea;
1-[3-(4-Amino-7-isopropyl-7H-pyrrolo[2,3-d]pyrimidine-5-carbonyl)-phenyl]-3-(2-chloro-benzyl)-urea;
1-[3-(4-Amino-7-isopropyl-7H-pyrrolo[2,3-d]pyrimidine-5-carbonyl)-phenyl]-3-(2-chloro-5-methyl-phenyl)-urea;
1-[3-(4-Amino-7-isopropyl-7H-pyrrolo[2,3-d]pyrimidine-5-carbonyl)-phenyl]-3-(3-chloro-2-methyl-phenyl)-urea;
1-[3-(4-Amino-7-isopropyl-7H-pyrrolo[2,3-d]pyrimidine-5-carbonyl)-phenyl]-3-(2-chloro-6-methyl-phenyl)-urea;
1-[3-(4-Amino-7-isopropyl-7H-pyrrolo[2,3-d]pyrimidine-5-carbonyl)-phenyl]-3-(5-chloro-2-methyl-phenyl)-urea;
1-[3-(4-Amino-7-isopropyl-7H-pyrrolo[2,3-d]pyrimidine-5-carbonyl)-phenyl]-3-(3-chloro-4-methyl-phenyl)-urea;
1-[3-(4-Amino-7-isopropyl-7H-pyrrolo[2,3-d]pyrimidine-5-carbonyl)-phenyl]-3-(4-chloro-2-methyl-phenyl)-urea;
1-[3-(4-Amino-7-isopropyl-7H-pyrrolo[2,3-d]pyrimidine-5-carbonyl)-phenyl]-3-(3-chloro-4-fluoro-phenyl)-urea;
1-[3-(4-Amino-7-isopropyl-7H-pyrrolo[2,3-d]pyrimidine-5-carbonyl)-phenyl]-3-(4-tert-butyl-phenyl)-urea;
1-[3-(4-Amino-7-isopropyl-7H-pyrrolo[2,3-d]pyrimidine-5-carbonyl)-phenyl]-3-isopropyl-urea;
1-[3-(4-Amino-7-isopropyl-7H-pyrrolo[2,3-d]pyrimidine-5-carbonyl)-phenyl]-3-phenyl-urea;
N-[3-(4-Amino-7-isopropyl-7H-pyrrolo[2,3-d]pyrimidine-5-carbonyl)-phenyl]-2-methyl-benzenesulfonamide;
N-[3-(4-Amino-7-isopropyl-7H-pyrrolo[2,3-d]pyrimidine-5-carbonyl)-phenyl]-4-methyl-benzenesulfonamide;

N-[3-(4-Amino-7-isopropyl-7H-pyrrolo[2,3-d]pyrimidine-5-carbonyl)-phenyl]-4-fluoro-benzenesulfonamide;
2-phenyl-ethenesulfonic acid[3-(4-amino-7-isopropyl-7H-pyrrolo[2,3-d]pyrimidine-5-carbonyl)-phenyl]-amide;
N-[3-(4-Amino-7-isopropyl-7H-pyrrolo[2,3-d]pyrimidine-5-carbonyl)-phenyl]-4-ethyl-benzenesulfonamide;
N-[3-(4-Amino-7-isopropyl-7H-pyrrolo[2,3-d]pyrimidine-5-carbonyl)-phenyl]-3-chloro-2-methyl-benzenesulfonamide;
Naphthalene-2-sulfonic acid[3-(4-amino-7-isopropyl-7H-pyrrolo[2,3-d]pyrimidine-5-carbonyl)-phenyl]-amide;
N-[3-(4-Amino-7-isopropyl-7H-pyrrolo[2,3-d]pyrimidine-5-carbonyl)-phenyl]-4-tert-butyl-benzenesulfonamide;
N-[3-(4-Amino-7-isopropyl-7H-pyrrolo[2,3-d]pyrimidine-5-carbonyl)-phenyl]-5-chloro-2-methoxy-benzenesulfonamide;
N-[3-(4-Amino-7-isopropyl-7H-pyrrolo[2,3-d]pyrimidine-5-carbonyl)-phenyl]-4-butoxy-benzenesulfonamide;
N-[3-(4-Amino-7-isopropyl-7H-pyrrolo[2,3-d]pyrimidine-5-carbonyl)-phenyl]-2,4-dichloro-5-methyl-benzenesulfonamide;
N-[3-(4-Amino-7-isopropyl-7H-pyrrolo[2,3-d]pyrimidine-5-carbonyl)-phenyl]-3-fluoro-benzenesulfonamide;
N-[3-(4-Amino-7-isopropyl-7H-pyrrolo[2,3-d]pyrimidine-5-carbonyl)-phenyl]-2-fluoro-benzenesulfonamide;
N-[3-(4-Amino-7-isopropyl-7H-pyrrolo[2,3-d]pyrimidine-5-carbonyl)-phenyl]-3,4-difluoro-benzenesulfonamide;
N-[5-(4-Amino-7-isopropyl-7H-pyrrolo[2,3-d]pyrimidine-5-carbonyl)-2-methoxy-phenyl]-3,5-dichloro-benzenesulfonamide;
1-[5-(4-Amino-7-isopropyl-7H-pyrrolo[2,3-d]pyrimidine-5-carbonyl)-2-methoxy-phenyl]-3-(2-fluoro-5-methyl-phenyl)-urea;
1-[5-(4-Amino-7-isopropyl-7H-pyrrolo[2,3-d]pyrimidine-5-carbonyl)-2-methoxy-phenyl]-3-(2-chloro-phenyl)-urea;
1-[5-(4-Amino-7-isopropyl-7H-pyrrolo[2,3-d]pyrimidine-5-carbonyl)-2-methoxy-phenyl]-3-(3,5-dichlorophenyl)-urea;
1-[5-(4-Amino-7-isopropyl-7H-pyrrolo[2,3-d]pyrimidine-5-carbonyl)-2-methoxy-phenyl]-3-m-tolyl-urea;
1-[5-(4-Amino-7-isopropyl-7H-pyrrolo[2,3-d]pyrimidine-5-carbonyl)-2-methoxy-phenyl]-3-(3,5-difluorophenyl)-urea;
1-[5-(4-Amino-7-isopropyl-7H-pyrrolo[2,3-d]pyrimidine-5-carbonyl)-2-methoxy-phenyl]-3-(2,4-dichlorophenyl)-urea;
1-[5-(4-Amino-7-isopropyl-7H-pyrrolo[2,3-d]pyrimidine-5-carbonyl)-2-methoxy-phenyl]-2-chloro-benzenesulfonamide;
1-[5-(4-Amino-7-isopropyl-7H-pyrrolo[2,3-d]pyrimidine-5-carbonyl)-2-methoxy-phenyl]-2,4-dichlorobenzenesulfonamide;
1-[5-(4-Amino-7-isopropyl-7H-pyrrolo[2,3-d]pyrimidine-5-carbonyl)-2-methyl-phenyl]-3-(2,4-dichlorophenyl)-urea;
N-[5-(4-Amino-7-isopropyl-7H-pyrrolo[2,3-d]pyrimidine-5-carbonyl)-2-methyl-phenyl]-3-chloro-4-fluorobenzenesulfonamide;
1-[5-(4-Amino-7-isopropyl-7H-pyrrolo[2,3-d]pyrimidine-5-carbonyl)-2-methyl-phenyl]-3-(2-chloro-phenyl)-urea;
1-[5-(4-Amino-7-isopropyl-7H-pyrrolo[2,3-d]pyrimidine-5-carbonyl)-2-methyl-phenyl]-3-m-tolyl-urea;
1-[5-(4-Amino-7-isopropyl-7H-pyrrolo[2,3-d]pyrimidine-5-carbonyl)-2-methyl-phenyl]-3-(2-fluoro-5-methyl-phenyl)-urea;
1-[5-(4-Amino-7-isopropyl-7H-pyrrolo[2,3-d]pyrimidine-5-carbonyl)-2-methyl-phenyl]-3-cyclohexyl-urea;
1-[5-(4-Amino-7-isopropyl-7H-pyrrolo[2,3-d]pyrimidine-5-carbonyl)-2-methyl-phenyl]-3-(2,4-dichlorobenzyl)-urea;
1-[5-(4-Amino-7-isopropyl-7H-pyrrolo[2,3-d]pyrimidine-5-carbonyl)-2-methyl-phenyl]-3-(3,5-difluorophenyl)-urea;
1-[5-(4-Amino-7-isopropyl-7H-pyrrolo[2,3-d]pyrimidine-5-carbonyl)-2-methyl-phenyl]-3-(4-chloro-phenyl)-urea;
1-[3-(4-Amino-7-isopropyl-7H-pyrrolo[2,3-d]pyrimidine-5-carbonyl)-2-methyl-phenyl]-3-(2-chloro-phenyl)-urea;
N-[3-(4-Amino-7-isopropyl-7H-pyrrolo[2,3-d]pyrimidine-5-carbonyl)-2-methyl-phenyl]-3,5-dichloro-benzenesulfonamide;
1-[3-(4-Amino-7-isopropyl-7H-pyrrolo[2,3-d]pyrimidine-5-carbonyl)-2-methyl-phenyl]-3-(2,4-dichlorophenyl urea;
1-[3-(4-Amino-7-isopropyl-7H-pyrrolo[2,3-d]pyrimidine-5-carbonyl)-2-methyl-phenyl]-3-(3,5-difluorophenyl)-urea;
N-[5-(4-Amino-7-isopropyl-7H-pyrrolo[2,3-d]pyrimidine-5-carbonyl)-2-fluoro-phenyl]-3,5-dichloro-benzenesulfonamide;
N-[3-(4-Amino-7-isopropyl-7H-pyrrolo[2,3-d]pyrimidine-5-carbonyl)-2-methyl-phenyl]-3-chloro-4-fluoro-benzenesulfonamide;
N-[3-(4-Amino-7-isopropyl-7H-pyrrolo[2,3-d]pyrimidine-5-carbonyl)-2-methyl-phenyl]-2,4-dichloro-benzenesulfonamide;
N-[3-(4-Amino-7-isopropyl-7H-pyrrolo[2,3-d]pyrimidine-5-carbonyl)-2-methyl-phenyl]-3-chloro-4-methyl-benzenesulfonamide;
N-[5-(4-Amino-7-isopropyl-7H-pyrrolo[2,3-d]pyrimidine-5-carbonyl)-2-fluoro-phenyl]-2-chloro-benzenesulfonamide;
N-[5-(4-Amino-7-isopropyl-7H-pyrrolo[2,3-d]pyrimidine-5-carbonyl)-2-fluoro-phenyl]-3-chloro-4-fluoro-benzenesulfonamide;
1-[5-(4-Amino-7-isopropyl-7H-pyrrolo[2,3-d]pyrimidine-5-carbonyl)-2-fluoro-phenyl]-3-(3,5-difluorophenyl)-urea;
N-[5-(4-Amino-7-isopropyl-7H-pyrrolo[2,3-d]pyrimidine-5-carbonyl)-2-fluoro-phenyl]-2,4-dichloro-benzenesulfonamide;
N-[5-(4-Amino-7-isopropyl-7H-pyrrolo[2,3-d]pyrimidine-5-carbonyl)-2-chloro-phenyl]-2,4-dichloro-benzenesulfonamide;
N-[5-(4-Amino-7-isopropyl-7H-pyrrolo[2,3-d]pyrimidine-5-carbonyl)-2-methoxy-phenyl]-3-chloro-4-fluoro-benzenesulfonamide;
N-[5-(4-Amino-7-isopropyl-7H-pyrrolo[2,3-d]pyrimidine-5-carbonyl)-2-fluoro-phenyl]-3-chloro-4-methyl-benzenesulfonamide;
N-[5-(4-Amino-7-isopropyl-7H-pyrrolo[2,3-d]pyrimidine-5-carbonyl)-2-chloro-phenyl]-3,5-dichloro-benzenesulfonamide;

1-[5-(4-Amino-7-isopropyl-7H-pyrrolo[2,3-d]pyrimidine-5-carbonyl)-2-fluoro-phenyl]-3-(2,4-dichloro-phenyl)-urea;

1-[5-(4-Amino-7-isopropyl-7H-pyrrolo[2,3-d]pyrimidine-5-carbonyl)-2-chloro-phenyl]-3-(4-chloro-phenyl)-urea;

1-[5-(4-Amino-7-isopropyl-7H-pyrrolo[2,3-d]pyrimidine-5-carbonyl)-2-fluoro-phenyl]-3-(2-chlorophenyl)-urea;

1-[5-(4-Amino-7-isopropyl-7H-pyrrolo[2,3-d]pyrimidine-5-carbonyl)-2-fluoro-phenyl]-3-(4-chloro-phenyl)-urea;

N-[5-(4-Amino-7-isopropyl-7H-pyrrolo[2,3-d]pyrimidine-5-carbonyl)-2-chloro-phenyl]-3-chloro-4-methyl-benzenesulfonamide;

N-[5-(4-Amino-7-isopropyl-7H-pyrrolo[2,3-d]pyrimidine-5-carbonyl)-2-chloro-phenyl]-3-chloro-4-fluoro-benzenesulfonamide;

N-[5-(4-Amino-7-isopropyl-7H-pyrrolo[2,3-d]pyrimidine-5-carbonyl)-2-chloro-phenyl]-3,5-difluoro-benzenesulfonamide;

N-[5-(4-Amino-7-isopropyl-7H-pyrrolo[2,3-d]pyrimidine-5-carbonyl)-2-fluoro-phenyl]-C-(3,5-dichloro-phenyl)-methanesulfonamide;

1-[5-(4-Amino-7-isopropyl-7H-pyrrolo[2,3-d]pyrimidine-5-carbonyl)-2-chloro-phenyl]-3-(3,5-dichloro-phenyl)-urea;

1-[5-(4-Amino-7-isopropyl-7H-pyrrolo[2,3-d]pyrimidine-5-carbonyl)-2-chloro-phenyl]-3-(3,5-difluoro-phenyl)-urea;

N-[3-(4-Amino-7-isopropyl-7H-pyrrolo[2,3-d]pyrimidine-5-carbonyl)-2-chloro-phenyl]-2,4-dichloro-benzenesulfonamide;

N-[3-(4-Amino-7-isopropyl-7H-pyrrolo[2,3-d]pyrimidine-5-carbonyl)-2-chloro-phenyl]-2-chloro-benzenesulfonamide;

N-[3-(4-Amino-7-isopropyl-7H-pyrrolo[2,3-d]pyrimidine-5-carbonyl)-phenyl]-3-(pyridin-2-yloxy)-benzenesulfonamide;

N-[3-(4-Amino-7-isopropyl-7H-pyrrolo[2,3-d]pyrimidine-5-carbonyl)-2-chloro-phenyl]-3,5-dichloro-benzenesulfonamide;

N-[3-(4-Amino-7-isopropyl-7H-pyrrolo[2,3-d]pyrimidine-5-carbonyl)-2-chloro-phenyl]-3-chloro-4-fluoro-benzenesulfonamide;

N-[3-(4-Amino-7-isopropyl-7H-pyrrolo[2,3-d]pyrimidine-5-carbonyl)-2-chloro-phenyl]-3-chloro-4-methyl-benzenesulfonamide;

N-[3-(4-Amino-7-isopropyl-7H-pyrrolo[2,3-d]pyrimidine-5-carbonyl)-2-chloro-phenyl]-3,5-difluoro-benzenesulfonamide;

1-[5-(4-Amino-7-isopropyl-7H-pyrrolo[2,3-d]pyrimidine-5-carbonyl)-2-methoxy-phenyl]-3-(2,4-dichloro-phenyl)-urea;

1-[5-(4-Amino-7-isopropyl-7H-pyrrolo[2,3-d]pyrimidine-5-carbonyl)-2-methoxy-phenyl]-3-(3,5-difluoro-phenyl)-urea;

1-[3-(4-Amino-7-isopropyl-7H-pyrrolo[2,3-d]pyrimidine-5-carbonyl)-4-chloro-phenyl]-3-(2-chloro-phenyl)-urea;

1-[3-(4-Amino-7-isopropyl-7H-pyrrolo[2,3-d]pyrimidine-5-carbonyl)-4-chloro-phenyl]-3-(4-chloro-2-methyl-phenyl)-urea;

1-[3-(4-Amino-7-isopropyl-7H-pyrrolo[2,3-d]pyrimidine-5-carbonyl)-4-chloro-phenyl]-3-(4-chloro-phenyl)-urea;

1-[3-(4-Amino-7-isopropyl-7H-pyrrolo[2,3-d]pyrimidine-5-carbonyl)-4-chloro-phenyl]-3-m-tolyl-urea;

1-[5-(4-Amino-7-isopropyl-7H-pyrrolo[2,3-d]pyrimidine-5-carbonyl)-2-methoxy-phenyl]-3-phenyl-urea;

1-[5-(4-Amino-7-isopropyl-7H-pyrrolo[2,3-d]pyrimidine-5-carbonyl)-2-methoxy-phenyl]-3-p-tolyl-urea;

1-[5-(4-Amino-7-isopropyl-7H-pyrrolo[2,3-d]pyrimidine-5-carbonyl)-2-methoxy-phenyl]-3-o-tolyl-urea;

1-[5-(4-Amino-7-isopropyl-7H-pyrrolo[2,3-d]pyrimidine-5-carbonyl)-2-methoxy-phenyl]-3-(2-fluoro-phenyl)-urea;

1-[5-(4-Amino-7-isopropyl-7H-pyrrolo[2,3-d]pyrimidine-5-carbonyl)-2-methoxy-phenyl]-3-(3-fluoro-phenyl)-urea;

1-[5-(4-Amino-7-isopropyl-7H-pyrrolo[2,3-d]pyrimidine-5-carbonyl)-2-methoxy-phenyl]-3-(4-fluoro-phenyl)-urea;

1-[5-(4-Amino-7-isopropyl-7H-pyrrolo[2,3-d]pyrimidine-5-carbonyl)-2-methoxy-phenyl]-3-(3-cyano-phenyl)-urea;

1-[5-(4-Amino-7-isopropyl-7H-pyrrolo[2,3-d]pyrimidine-5-carbonyl)-2-methoxy-phenyl]-3-(4-cyano-phenyl)-urea;

1-[5-(4-Amino-7-isopropyl-7H-pyrrolo[2,3-d]pyrimidine-5-carbonyl)-2-methoxy-phenyl]-3-(2-methoxy-phenyl)-urea;

1-[5-(4-Amino-7-isopropyl-7H-pyrrolo[2,3-d]pyrimidine-5-carbonyl)-2-methoxy-phenyl]-3-(3-methoxy-phenyl)-urea;

1-[5-(4-Amino-7-isopropyl-7H-pyrrolo[2,3-d]pyrimidine-5-carbonyl)-2-methoxy-phenyl]-3-(4-methoxy-phenyl urea;

1-[5-(4-Amino-7-isopropyl-7H-pyrrolo[2,3-d]pyrimidine-5-carbonyl)-2-methoxy-phenyl]-3-(3-fluoro-4-methyl-phenyl)-urea;

1-[5-(4-Amino-7-isopropyl-7H-pyrrolo[2,3-d]pyrimidine-5-carbonyl)-2-methoxy-phenyl]-3-(3-chloro-phenyl)-urea;

1-[5-(4-Amino-7-isopropyl-7H-pyrrolo[2,3-d]pyrimidine-5-carbonyl)-2-methoxy-phenyl]-3-(4-chloro-phenyl)-urea;

1-(4-Acetyl-phenyl)-3-[5-(4-amino-7-isopropyl-7H-pyrrolo[2,3-d]pyrimidine-5-carbonyl)-2-methoxy-phenyl]-urea;

1-[5-(4-Amino-7-isopropyl-7H-pyrrolo[2,3-d]pyrimidine-5-carbonyl)-2-methoxy-phenyl]-3-(4-dimethylamino-phenyl)-urea;

1-[5-(4-Amino-7-isopropyl-7H-pyrrolo[2,3-d]pyrimidine-5-carbonyl)-2-methoxy-phenyl]-3-(3-trifluoromethyl-phenyl)-urea;

N-[5-(4-Amino-7-isopropyl-7H-pyrrolo[2,3-d]pyrimidine-5-carbonyl)-2-methoxy-phenyl]-2-chloro-4-fluoro-benzenesulfonamide;

1-[5-(4-Amino-7-isopropyl-7H-pyrrolo[2,3-d]pyrimidine-5-carbonyl)-2-methyl-phenyl]-3-(3,5-dichloro-phenyl)-urea;

1-[5-(4-Amino-7-isopropyl-7H-pyrrolo[2,3-d]pyrimidine-5-carbonyl)-2-methyl-phenyl]-3-(3-chloro-phenyl)-urea; and pharmaceutically acceptable salt, prodrug, hydrate or solvate of the aforementioned compounds.

52. A compound according to claim 51, wherein said compound is selected from the group consisting of:

1-[3-(4-Amino-7-isopropyl-7H-pyrrolo[2,3-d]pyrimidine-5-carbonyl)-phenyl]-3-(2-chloro-phenyl)-urea;

1-[3-(4-Amino-7-isopropyl-7H-pyrrolo[2,3-d]pyrimidine-5-carbonyl)-phenyl]-3-(2-methoxy-5-methyl-phenyl)-urea;
1-[3-(4-Amino-7-isopropyl-7H-pyrrolo[2,3-d]pyrimidine-5-carbonyl)-phenyl]-3-(2-fluoro-5-methyl-phenyl)-urea;
1-[3-(4-Amino-7-isopropyl-7H-pyrrolo[2,3-d]pyrimidine-5-carbonyl)-phenyl]-3-m-tolyl-urea;
1-[3-(4-Amino-7-isopropyl-7H-pyrrolo[2,3-d]pyrimidine-5-carbonyl)-phenyl]-3-(3-ethyl-phenyl)-urea;
1-[3-(4-Amino-7-isopropyl-7H-pyrrolo[2,3-d]pyrimidine-5-carbonyl)-phenyl]-3-(2-fluoro-phenyl)-urea;
1-[3-(4-Amino-7-isopropyl-7H-pyrrolo[2,3-d]pyrimidine-5-carbonyl)-phenyl]-3-(2,4-difluoro-phenyl)-urea;
1-[3-(4-Amino-7-isopropyl-7H-pyrrolo[2,3-d]pyrimidine-5-carbonyl)-phenyl]-3-(3,4-difluoro-phenyl)-urea;
1-[3-(4-Amino-7-isopropyl-7H-pyrrolo[2,3-d]pyrimidine-5-carbonyl)-phenyl]-3-(3-fluoro-phenyl)-urea;
1-[3-(4-Amino-7-isopropyl-7H-pyrrolo[2,3-d]pyrimidine-5-carbonyl)-phenyl]-3-(5-fluoro-2-methyl-phenyl)-urea;
1-[3-(4-Amino-7-isopropyl-7H-pyrrolo[2,3-d]pyrimidine-5-carbonyl)-phenyl]-3-(4-fluoro-phenyl)-urea;
1-[3-(4-Amino-7-isopropyl-7H-pyrrolo[2,3-d]pyrimidine-5-carbonyl)-phenyl]-3-(3-fluoro-4-methyl-phenyl)-urea;
1-[3-(4-Amino-7-isopropyl-7H-pyrrolo[2,3-d]pyrimidine-5-carbonyl)-phenyl]-3-(3,5-difluoro-phenyl)-urea;
1-[3-(4-Amino-7-isopropyl-7H-pyrrolo[2,3-d]pyrimidine-5-carbonyl)-phenyl]-3-(2,5-difluoro-phenyl)-urea;
1-[3-(4-Amino-7-isopropyl-7H-pyrrolo[2,3-d]pyrimidine-5-carbonyl)-phenyl]-3-(3-chloro-phenyl)-urea;
1-[3-(4-Amino-7-isopropyl-7H-pyrrolo[2,3-d]pyrimidine-5-carbonyl)-phenyl]-3-(4-chloro-phenyl)-urea;
1-[3-(4-Amino-7-isopropyl-7H-pyrrolo[2,3-d]pyrimidine-5-carbonyl)-phenyl]-3-p-tolyl-urea;
1-[3-(4-Amino-7-isopropyl-7H-pyrrolo[2,3-d]pyrimidine-5-carbonyl)-phenyl]-3-(2-ethyl-phenyl)-urea;
1-[3-(4-Amino-7-isopropyl-7H-pyrrolo[2,3-d]pyrimidine-5-carbonyl)-phenyl]-3-(2-isopropyl-phenyl)-urea;
1-[3-(4-Amino-7-isopropyl-7H-pyrrolo[2,3-d]pyrimidine-5-carbonyl)-phenyl]-3-(4-isopropyl-phenyl)-urea;
1-[3-(4-Amino-7-isopropyl-7H-pyrrolo[2,3-d]pyrimidine-5-carbonyl)-phenyl]-3-(4-methoxy-phenyl)-urea;
1-[3-(4-Amino-7-isopropyl-7H-pyrrolo[2,3-d]pyrimidine-5-carbonyl)-phenyl]-3-(2-methoxy-phenyl)-urea;
1-[3-(4-Amino-7-isopropyl-7H-pyrrolo[2,3-d]pyrimidine-5-carbonyl)-phenyl]-3-(2-ethoxy-phenyl)-urea;
1-[3-(4-Amino-7-isopropyl-7H-pyrrolo[2,3-d]pyrimidine-5-carbonyl)-phenyl]-3-(4-methylsulfanyl-phenyl)-urea;
1-[3-(4-Amino-7-isopropyl-7H-pyrrolo[2,3-d]pyrimidine-5-carbonyl)-phenyl]-3-(3-methylsulfanyl-phenyl)-urea;
1-[3-(4-Amino-7-isopropyl-7H-pyrrolo[2,3-d]pyrimidine-5-carbonyl)-phenyl]-3-(3-cyano-phenyl)-urea;
1-[3-(4-Amino-7-isopropyl-7H-pyrrolo[2,3-d]pyrimidine-5-carbonyl)-phenyl]-3-(3,5-dimethyl-phenyl)-urea;
1-[3-(4-Amino-7-isopropyl-7H-pyrrolo[2,3-d]pyrimidine-5-carbonyl)-phenyl]-3-(3,4-dimethyl-phenyl)-urea;
1-[3-(4-Amino-7-isopropyl-7H-pyrrolo[2,3-d]pyrimidine-5-carbonyl)-phenyl]-3-(2,5-dimethyl-phenyl)-urea;
1-[3-(4-Amino-7-isopropyl-7H-pyrrolo[2,3-d]pyrimidine-5-carbonyl)-phenyl]-3-(2,3-dimethyl-phenyl)-urea;
1-[3-(4-Amino-7-isopropyl-7H-pyrrolo[2,3-d]pyrimidine-5-carbonyl)-phenyl]-3-(2,4-dimethyl-phenyl)-urea;
1-[3-(4-Amino-7-isopropyl-7H-pyrrolo[2,3-d]pyrimidine-5-carbonyl)-phenyl]-3-thiophen-2-yl-urea;
1-[3-(4-Amino-7-isopropyl-7H-pyrrolo[2,3-d]pyrimidine-5-carbonyl)-phenyl]-3-thiophen-3-yl-urea;
1-[3-(4-Amino-7-isopropyl-7H-pyrrolo[2,3-d]pyrimidine-5-carbonyl)-phenyl]-3-cyclohexyl-urea;
1-[3-(4-Amino-7-isopropyl-7H-pyrrolo[2,3-d]pyrimidine-5-carbonyl)-phenyl]-3-o-tolyl-urea;
1-[3-(4-Amino-7-isopropyl-7H-pyrrolo[2,3-d]pyrimidine-5-carbonyl)-phenyl]-3-(4-ethyl-phenyl)-urea;
1-(3-Acetyl-phenyl)-3-[3-(4-amino-7-isopropyl-7H-pyrrolo[2,3-d]pyrimidine-5-carbonyl)-phenyl]-urea;
1-(4-Acetyl-phenyl)-3-[3-(4-amino-7-isopropyl-7H-pyrrolo[2,3-d]pyrimidine-5-carbonyl)-phenyl]-urea;
1-[3-(4-Amino-7-isopropyl-7H-pyrrolo[2,3-d]pyrimidine-5-carbonyl)-phenyl]-3-(4-ethoxy-phenyl)-urea;
1-[3-(4-Amino-7-isopropyl-7H-pyrrolo[2,3-d]pyrimidine-5-carbonyl)-phenyl]-3-(4-methoxy-2-methyl-phenyl)-urea;
4-{3-[3-(4-Amino-7-isopropyl-7H-pyrrolo[2,3-d]pyrimidine-5-carbonyl)-phenyl]-ureido}-benzoic acid methyl ester;
1-[3-(4-Amino-7-isopropyl-7H-pyrrolo[2,3-d]pyrimidine-5-carbonyl)-phenyl]-3-(2-methylsulfanyl-phenyl)-urea;
1-[3-(4-Amino-7-isopropyl-7H-pyrrolo[2,3-d]pyrimidine-5-carbonyl)-phenyl]-3-(2-chloro-benzyl)-urea;
1-[3-(4-Amino-7-isopropyl-7H-pyrrolo[2,3-d]pyrimidine-5-carbonyl)-phenyl]-3-(2-chloro-5-methyl-phenyl)-urea;
1-[3-(4-Amino-7-isopropyl-7H-pyrrolo[2,3-d]pyrimidine-5-carbonyl)-phenyl]-3-(3-chloro-2-methyl-phenyl)-urea;
1-[3-(4-Amino-7-isopropyl-7H-pyrrolo[2,3-d]pyrimidine-5-carbonyl)-phenyl]-3-(5-chloro-2-methyl-phenyl)-urea;
1-[3-(4-Amino-7-isopropyl-7H-pyrrolo[2,3-d]pyrimidine-5-carbonyl)-phenyl]-3-(3-chloro-4-methyl-phenyl)-urea;
1-[3-(4-Amino-7-isopropyl-7H-pyrrolo[2,3-d]pyrimidine-5-carbonyl)-phenyl]-3-(4-chloro-2-methyl-phenyl)-urea;
1-[3-(4-Amino-7-isopropyl-7H-pyrrolo[2,3-d]pyrimidine-5-carbonyl)-phenyl]-3-(3-chloro-4-fluoro-phenyl)-urea;
1-[3-(4-Amino-7-isopropyl-7H-pyrrolo[2,3-d]pyrimidine-5-carbonyl)-phenyl]-3-(4-tert-butyl-phenyl)-urea;
1-[3-(4-Amino-7-isopropyl-7H-pyrrolo[2,3-d]pyrimidine-5-carbonyl)-phenyl]-3-isopropyl-urea;
1-[3-(4-Amino-7-isopropyl-7H-pyrrolo[2,3-d]pyrimidine-5-carbonyl)-phenyl]-3-phenyl-urea;
N-[3-(4-Amino-7-isopropyl-7H-pyrrolo[2,3-d]pyrimidine-5-carbonyl)-phenyl]-4-ethyl-benzenesulfonamide;
N-[3-(4-Amino-7-isopropyl-7H-pyrrolo[2,3-d]pyrimidine-5-carbonyl)-phenyl]-5-chloro-2-methoxy-benzenesulfonamide;

N-[3-(4-Amino-7-isopropyl-7H-pyrrolo[2,3-d]pyrimidine-5-carbonyl)-phenyl]-4-butoxy-benzenesulfonamide;

N-[3-(4-Amino-7-isopropyl-7H-pyrrolo[2,3-d]pyrimidine-5-carbonyl)-phenyl]-2,4-dichloro-5-methyl-benzenesulfonamide;

N-[5-(4-Amino-7-isopropyl-7H-pyrrolo[2,3-d]pyrimidine-5-carbonyl)-2-methoxy-phenyl]-3,5-dichloro-benzenesulfonamide;

1-[5-(4-Amino-7-isopropyl-7H-pyrrolo[2,3-d]pyrimidine-5-carbonyl)-2-methoxy-phenyl]-3-(2-fluoro-5-methyl-phenyl)-urea;

1-[5-(4-Amino-7-isopropyl-7H-pyrrolo[2,3-d]pyrimidine-5-carbonyl)-2-methoxy-phenyl]-3-(2-chloro-phenyl)-urea;

1-[5-(4-Amino-7-isopropyl-7H-pyrrolo[2,3-d]pyrimidine-5-carbonyl)-2-methoxy-phenyl]-3-(3,5-dichloro-phenyl)-urea;

1-[5-(4-Amino-7-isopropyl-7H-pyrrolo[2,3-d]pyrimidine-5-carbonyl)-2-methoxy-phenyl]-3-m-tolyl-urea;

1-[5-(4-Amino-7-isopropyl-7H-pyrrolo[2,3-d]pyrimidine-5-carbonyl)-2-methoxy-phenyl]-3-(3,5-difluoro-phenyl)-urea;

1-[5-(4-Amino-7-isopropyl-7H-pyrrolo[2,3-d]pyrimidine-5-carbonyl)-2-methoxy-phenyl]-3-(2,4-dichloro-phenyl)-urea;

N-[5-(4-Amino-7-isopropyl-7H-pyrrolo[2,3-d]pyrimidine-5-carbonyl)-2-methoxy-phenyl]-2,4-dichloro-benzenesulfonamide 1-[5-(4-Amino-7-isopropyl-7H-pyrrolo[2,3-d]pyrimidine-5-carbonyl)-2-methyl-phenyl]-3-(2,4-dichloro-phenyl)-urea;

1-[5-(4-Amino-7-isopropyl-7H-pyrrolo[2,3-d]pyrimidine-5-carbonyl)-2-methyl-phenyl]-3-(2-chloro-phenyl)-urea;

1-[5-(4-Amino-7-isopropyl-7H-pyrrolo[2,3-d]pyrimidine-5-carbonyl)-2-methyl-phenyl]-3-m-tolyl-urea;

1-[5-(4-Amino-7-isopropyl-7H-pyrrolo[2,3-d]pyrimidine-5-carbonyl)-2-methyl-phenyl]-3-(2-fluoro-5-methyl-phenyl)-urea;

1-[5-(4-Amino-7-isopropyl-7H-pyrrolo[2,3-d]pyrimidine-5-carbonyl)-2-methyl-phenyl]-3-cyclohexyl-urea;

1-[5-(4-Amino-7-isopropyl-7H-pyrrolo[2,3-d]pyrimidine-5-carbonyl)-2-methyl-phenyl]-3-(2,4-dichloro-benzyl)-urea;

1-[5-(4-Amino-7-isopropyl-7H-pyrrolo[2,3-d]pyrimidine-5-carbonyl)-2-methyl-phenyl]-3-(3,5-difluoro-phenyl)-urea;

1-[5-(4-Amino-7-isopropyl-7H-pyrrolo[2,3-d]pyrimidine-5-carbonyl)-2-methyl-phenyl]-3-(4-chloro-phenyl)-urea;

1-[3-(4-Amino-7-isopropyl-7H-pyrrolo[2,3-d]pyrimidine-5-carbonyl)-2-methyl-phenyl]-3-(2,4-dichloro-phenyl)-urea;

N-[5-(4-Amino-7-isopropyl-7H-pyrrolo[2,3-d]pyrimidine-5-carbonyl)-2-fluoro-phenyl]-3,5-dichloro-benzenesulfonamide;

N-[3-(4-Amino-7-isopropyl-7H-pyrrolo[2,3-d]pyrimidine-5-carbonyl)-2-methyl-phenyl]-3-chloro-4-fluoro-benzenesulfonamide;

N-[3-(4-Amino-7-isopropyl-7H-pyrrolo[2,3-d]pyrimidine-5-carbonyl)-2-methyl-phenyl]-2,4-dichloro-benzenesulfonamide;

N-[3-(4-Amino-7-isopropyl-7H-pyrrolo[2,3-d]pyrimidine-5-carbonyl)-2-methyl-phenyl]-3-chloro-4-methyl-benzenesulfonamide;

N-[5-(4-Amino-7-isopropyl-7H-pyrrolo[2,3-d]pyrimidine-5-carbonyl)-2-fluoro-phenyl]-3-chloro-4-fluoro-benzenesulfonamide;

1-[5-(4-Amino-7-isopropyl-7H-pyrrolo[2,3-d]pyrimidine-5-carbonyl)-2-fluoro-phenyl]-3-(3,5-difluoro-phenyl)-urea;

N-[5-(4-Amino-7-isopropyl-7H-pyrrolo[2,3-d]pyrimidine-5-carbonyl)-2-chloro-phenyl]-3,5-dichloro-benzenesulfonamide;

1-[5-(4-Amino-7-isopropyl-7H-pyrrolo[2,3-d]pyrimidine-5-carbonyl)-2-fluoro-phenyl]-3-(2,4-dichloro-phenyl)-urea;

1-[5-(4-Amino-7-isopropyl-7H-pyrrolo[2,3-d]pyrimidine-5-carbonyl)-2-chloro-phenyl]-3-(4-chloro-phenyl)-urea;

1-[5-(4-Amino-7-isopropyl-7H-pyrrolo[2,3-d]pyrimidine-5-carbonyl)-2-fluoro-phenyl]-3-(2-chloro-phenyl)-urea;

1-[5-(4-Amino-7-isopropyl-7H-pyrrolo[2,3-d]pyrimidine-5-carbonyl)-2-fluoro-phenyl]-3-(4-chloro-phenyl)-urea;

N-[5-(4-Amino-7-isopropyl-7H-pyrrolo[2,3-d]pyrimidine-5-carbonyl)-2-chloro-phenyl]-3-chloro-4-fluoro-benzenesulfonamide;

N-[5-(4-Amino-7-isopropyl-7H-pyrrolo[2,3-d]pyrimidine-5-carbonyl)-2-chloro-phenyl]-3,5-difluoro-benzenesulfonamide;

1-[5-(4-Amino-7-isopropyl-7H-pyrrolo[2,3-d]pyrimidine-5-carbonyl)-2-chloro-phenyl]-3-(3,5-dichloro-phenyl)-urea;

1-[5-(4-Amino-7-isopropyl-7H-pyrrolo[2,3-d]pyrimidine-5-carbonyl)-2-chloro-phenyl]-3-(3,5-difluoro-phenyl)-urea;

N-[3-(4-Amino-7-isopropyl-7H-pyrrolo[2,3-d]pyrimidine-5-carbonyl)-2-chloro-phenyl]-2,4-dichloro-benzenesulfonamide;

N-[3-(4-Amino-7-isopropyl-7H-pyrrolo[2,3-d]pyrimidine-5-carbonyl)-2-chloro-phenyl]-2-chloro-benzenesulfonamide;

1-[5-(4-Amino-7-isopropyl-7H-pyrrolo[2,3-d]pyrimidine-5-carbonyl)-2-methoxy-phenyl]-3-(2,4-dichloro-phenyl)-urea;

1-[5-(4-Amino-7-isopropyl-7H-pyrrolo[2,3-d]pyrimidine-5-carbonyl)-2-methoxy-phenyl]-3-(3,5-difluoro-phenyl)-urea;

1-[3-(4-Amino-7-isopropyl-7H-pyrrolo[2,3-d]pyrimidine-5-carbonyl)-4-chloro-phenyl]-3-(2-chloro-phenyl)-urea;

1-[3-(4-Amino-7-isopropyl-7H-pyrrolo[2,3-d]pyrimidine-5-carbonyl)-4-chloro-phenyl]-3-(4-chloro-2-methyl-phenyl)-urea;

1-[3-(4-Amino-7-isopropyl-7H-pyrrolo[2,3-d]pyrimidine-5-carbonyl)-4-chloro-phenyl]-3-(4-chloro-phenyl)-urea;

1-[3-(4-Amino-7-isopropyl-7H-pyrrolo[2,3-d]pyrimidine-5-carbonyl)-4-chloro-phenyl]-3-m-tolyl-urea;

1-[5-(4-Amino-7-isopropyl-7H-pyrrolo[2,3-d]pyrimidine-5-carbonyl)-2-methoxy-phenyl]-3-p-tolyl-urea;

1-[5-(4-Amino-7-isopropyl-7H-pyrrolo[2,3-d]pyrimidine-5-carbonyl)-2-methoxy-phenyl]-3-(3-fluoro-phenyl)-urea;

1-[5-(4-Amino-7-isopropyl-7H-pyrrolo[2,3-d]pyrimidine-5-carbonyl)-2-methoxy-phenyl]-3-(4-fluoro-phenyl)-urea;

1-[5-(4-Amino-7-isopropyl-7H-pyrrolo[2,3-d]pyrimidine-5-carbonyl)-2-methoxy-phenyl]-3-(2-methoxy-phenyl urea;

1-[5-(4-Amino-7-isopropyl-7H-pyrrolo[2,3-d]pyrimidine-5-carbonyl)-2-methoxy-phenyl]-3-(3-methoxy-phenyl)-urea;
1-[5-(4-Amino-7-isopropyl-7H-pyrrolo[2,3-d]pyrimidine-5-carbonyl)-2-methoxy-phenyl]-3-(4-methoxy-phenyl)-urea;
1-[5-(4-Amino-7-isopropyl-7H-pyrrolo[2,3-d]pyrimidine-5-carbonyl)-2-methoxy-phenyl]-3-(3-fluoro-4-methyl-phenyl)-urea;
1-[5-(4-Amino-7-isopropyl-7H-pyrrolo[2,3-d]pyrimidine-5-carbonyl)-2-methoxy-phenyl]-3-(3-chloro-phenyl)-urea;
1-[5-(4-Amino-7-isopropyl-7H-pyrrolo[2,3-d]pyrimidine-5-carbonyl)-2-methoxy-phenyl]-3-(4-chloro-phenyl)-urea;
1-(4-Acetyl-phenyl)-3-[5-(4-amino-7-isopropyl-7H-pyrrolo[2,3-d]pyrimidine-5-carbonyl)-2-methoxy-phenyl]-urea;
1-[5-(4-Amino-7-isopropyl-7H-pyrrolo[2,3-d]pyrimidine-5-carbonyl)-2-methoxy-phenyl]-3-(4-dimethylamino-phenyl)-urea;
1-[5-(4-Amino-7-isopropyl-7H-pyrrolo[2,3-d]pyrimidine-5-carbonyl)-2-methoxy-phenyl]-3-(3-trifluoromethyl-phenyl)-urea;
N-[5-(4-Amino-7-isopropyl-7H-pyrrolo[2,3-d]pyrimidine-5-carbonyl)-2-methoxy-phenyl]-2-chloro-4-fluoro-benzenesulfonamide;
1-[5-(4-Amino-7-isopropyl-7H-pyrrolo[2,3-d]pyrimidine-5-carbonyl)-2-methyl-phenyl]-3-(3,5-dichloro-phenyl)-urea;
1-[5-(4-Amino-7-isopropyl-7H-pyrrolo[2,3-d]pyrimidine-5-carbonyl)-2-methyl-phenyl]-3-(3-chloro-phenyl)-urea; and pharmaceutically acceptable salt, prodrug, hydrate or solvate of the aforementioned compounds.

53. A compound according to claim 52, wherein said compound is selected from the group consisting of:
N-[3-(4-Amino-7-isopropyl-7H-pyrrolo[2,3-d]pyrimidine-5-carbonyl)-phenyl]-2,4-dichloro-benzenesulfonamide;
1-[3-(4-Amino-7-isopropyl-7H-pyrrolo[2,3-d]pyrimidine-5-carbonyl)-phenyl]-3-(4-chloro-phenyl)-urea;
1-[3-(4-Amino-7-isopropyl-7H-pyrrolo[2,3-d]pyrimidine-5-carbonyl)-phenyl]-3-(4-chloro-2-methyl-phenyl)-urea;
1-[5-(4-Amino-7-isopropyl-7H-pyrrolo[2,3-d]pyrimidine-5-carbonyl)-2-methoxy-phenyl]-3-(3,5-dichloro-phenyl)-urea;
1-[5-(4-Amino-7-isopropyl-7H-pyrrolo[2,3-d]pyrimidine-5-carbonyl)-2-methoxy-phenyl]-3-(3,5-difluoro-phenyl)-urea;
1-[5-(4-Amino-7-isopropyl-7H-pyrrolo[2,3-d]pyrimidine-5-carbonyl)-2-methoxy-phenyl]-3-(2,4-dichloro-phenyl)-urea;
1-[5-(4-Amino-7-isopropyl-7H-pyrrolo[2,3-d]pyrimidine-5-carbonyl)-2-methyl-phenyl]-3-(3,5-difluoro-phenyl)-urea;
1-[3-(4-Amino-7-isopropyl-7H-pyrrolo[2,3-d]pyrimidine-5-carbonyl)-2-methyl-phenyl]-3-(2-chloro-phenyl)-urea;
1-[3-(4-Amino-7-isopropyl-7H-pyrrolo[2,3-d]pyrimidine-5-carbonyl)-2-methyl-phenyl]-3-(3,5-difluoro-phenyl)-urea;
N-[5-(4-Amino-7-isopropyl-7H-pyrrolo[2,3-d]pyrimidine-5-carbonyl)-2-fluoro-phenyl]-3-chloro-4-fluoro-benzenesulfonamide;
N-[5-(4-Amino-7-isopropyl-7H-pyrrolo[2,3-d]pyrimidine-5-carbonyl)-2-fluoro-phenyl]-2,4-dichloro-benzenesulfonamide;
N-[5-(4-Amino-7-isopropyl-7H-pyrrolo[2,3-d]pyrimidine-5-carbonyl)-2-chloro-phenyl]-3,5-dichloro-benzenesulfonamide;
1-[5-(4-Amino-7-isopropyl-7H-pyrrolo[2,3-d]pyrimidine-5-carbonyl)-2-fluoro-phenyl]-3-(2-chloro-phenyl)-urea;
N-[5-(4-Amino-7-isopropyl-7H-pyrrolo[2,3-d]pyrimidine-5-carbonyl)-2-chloro-phenyl]-3-chloro-4-fluoro-benzenesulfonamide;
N-[5-(4-Amino-7-isopropyl-7H-pyrrolo[2,3-d]pyrimidine-5-carbonyl)-2-chloro-phenyl]-3,5-difluoro-benzenesulfonamide;
N-[3-(4-Amino-7-isopropyl-7H-pyrrolo[2,3-d]pyrimidine-5-carbonyl)-2-chloro-phenyl]-3-chloro-4-fluoro-benzenesulfonamide;
N-[3-(4-Amino-7-isopropyl-7H-pyrrolo[2,3-d]pyrimidine-5-carbonyl)-2-chloro-phenyl]-3-chloro-4-methyl-benzenesulfonamide;
N-[3-(4-Amino-7-isopropyl-7H-pyrrolo[2,3-d]pyrimidine-5-carbonyl)-2-chloro-phenyl]-3,5-difluoro-benzenesulfonamide; and pharmaceutically acceptable salt, prodrug, hydrate or solvate of the aforementioned compounds.

54. A compound according to claim 53, wherein said compound is selected from the group consisting of:
1-[5-(4-Amino-7-isopropyl-7H-pyrrolo[2,3-d]pyrimidine-5-carbonyl)-2-methoxy-phenyl]-3-(2,4-dichloro-phenyl)-urea;
1-[5-(4-Amino-7-isopropyl-7H-pyrrolo[2,3-d]pyrimidine-5-carbonyl)-2-methyl-phenyl]-3-(3,5-difluoro-phenyl)-urea;
1-[3-(4-Amino-7-isopropyl-7H-pyrrolo[2,3-d]pyrimidine-5-carbonyl)-2-methyl-phenyl]-3-(2-chloro-phenyl)-urea;
1-[3-(4-Amino-7-isopropyl-7H-pyrrolo[2,3-d]pyrimidine-5-carbonyl)-2-methyl-phenyl]-3-(3,5-difluoro-phenyl)-urea;
N-[5-(4-Amino-7-isopropyl-7H-pyrrolo[2,3-d]pyrimidine-5-carbonyl)-2-fluoro-phenyl]-3-chloro-4-fluoro-benzenesulfonamide;
N-[5-(4-Amino-7-isopropyl-7H-pyrrolo[2,3-d]pyrimidine-5-carbonyl)-2-fluoro-phenyl]-2,4-dichloro-benzenesulfonamide;
N-[5-(4-Amino-7-isopropyl-7H-pyrrolo[2,3-d]pyrimidine-5-carbonyl)-2-chloro-phenyl]-3,5-dichloro-benzenesulfonamide;
1-[5-(4-Amino-7-isopropyl-7H-pyrrolo[2,3-d]pyrimidine-5-carbonyl)-2-fluoro-phenyl]-3-(2-chloro-phenyl)-urea;
N-[5-(4-Amino-7-isopropyl-7H-pyrrolo[2,3-d]pyrimidine-5-carbonyl)-2-chloro-phenyl]-3-chloro-4-fluoro-benzenesulfonamide;
N-[5-(4-Amino-7-isopropyl-7H-pyrrolo[2,3-d]pyrimidine-5-carbonyl)-2-chloro-phenyl]-3,5-difluoro-benzenesulfonamide;
N-[3-(4-Amino-7-isopropyl-7H-pyrrolo[2,3-d]pyrimidine-5-carbonyl)-2-chloro-phenyl]-3-chloro-4-fluoro-benzenesulfonamide;
N-[3-(4-Amino-7-isopropyl-7H-pyrrolo[2,3-d]pyrimidine-5-carbonyl)-2-chloro-phenyl]-3-chloro-4-methyl-benzenesulfonamide;
N-[3-(4-Amino-7-isopropyl-7H-pyrrolo[2,3-d]pyrimidine-5-carbonyl)-2-chloro-phenyl]-3,5-difluoro-benzenesulfonamide; and pharmaceutically acceptable salt, prodrug, hydrate or solvate of the aforementioned compounds.

55. A process of preparing a compound of the formula 1A,

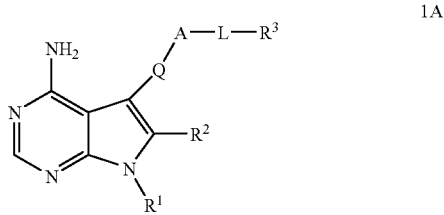

1A or a pharmaceutically acceptable salt, prodrug, solvate or hydrate thereof, wherein:

Q is CO;

A is $C_6$-$C_{10}$ aryl, 5 to 13 membered heteroaromatic ring, $C_3$-$C_8$ alkyl, and 3 to 8 membered heteroalkyl ring and each of the foregoing A groups is optionally substituted with 1 to 5 $R^5$ groups;

L is —$(CH_2)_p$— wherein p is an integer from 0 to 5; —O—; —S—; —S(O)—; —S(O)$_2$; —N(R)—; N(C(O)OR)—; —N(C(O)R)—; —N(SO$_2$R); —CH$_2$O—; —CH$_2$S—; —CH$_2$N(R)—; —C(NR)—; —CH$_2$N(C(O)R))—; —CH$_2$N(C(O)OR)—; —CH$_2$N(SO$_2$R)—; —CH(NHR)—; —CH(NHC(O)R)—; —CH(NHSO$_2$R)—; —CH(NHC(O)OR)—; —CH(OC(O)R)—; —CH(OC(O)NHR)—; —CH=CH—; —C(=NOR)—; —C(O)—; —CH(OR)—; —C(O)N(R)—; —N(R)C(O)—; —N(R)S(O)—; —N(R)S(O)$_2$—; OC(O)N(R)—; —N(R)C(O)N(R)—; —NRC(O)O—; —S(O)N(R)—; —S(O)$_2$N(R)—; —N(C(O)R)S(O)—; —N(C(O)R)S(O)$_2$—; —N(R)S(O)N(R)—; —N(R)S(O)$_2$N(R)—; —C(O)N(R)C(O)—; —S(O)N(R)C(O)—; —S(O)$_2$N(R)C(O)—; —OS(O)N(R)—; —OS(O)$_2$N(R)—; —N(R)S(O)O—; —N(R)S(O)$_2$O—; —N(R)S(O)C(O)—; —N(R)S(O)$_2$C(O)—; —SON(C(O)R)—; —SO$_2$N(C(O)R)—; —N(R)SON(R)—; —N(R)SO$_2$N(R)—; —C(O)O—; —N(R)P(OR$^X$)O—; —N(R)P(OR$^X$)—; —N(R)P(O)(OR$^X$)—; —N(C(O)R)P(OR$^X$)O—; —N(C(O)R)P(OR$^X$)—; —N(C(O)R)P(O)(OR$^X$)O—; —N(C(O)R)P(OR$^X$)—, —CH(R)S(O)—; —CH(R)S(O)$_2$; —CH(R)N(C(O)OR)—; —CH(R)N(C(O)R)—; —CH(R)N(SO$_2$R)—; —CH(R)O—; —CH(R)S—; —CH(R)N(R)—; —CH(R)N(C(O)R))—; —CH(R)N(C(O)OR)—; —CH(R)N(SO$_2$R)—; —CH(R)C(=NOR)—; —CH(R)C(O)—; —CH(R)CH(OR)—; —CH(R)C(O)N(R)—; —CH(R)N(R)C(O)—; —CH(R)N(R)S(O)—; CH(R)N(R)S(O)$_2$; —CH(R)OC(O)N(R)—; —CH(R)N(R)C(O)N(R)—; —CH(R)N(R)C(O)O—; —CH(R)S(O)N(R)—; —CH(R)S(O)$_2$N(R)—; —CH(R)N(C(O)R)S(O)—; —CH(R)N(C(O)R)S(O)$_2$—; —CH(R)N(R)S(O)N(R)—; —CH(R)N(R)S(O)$_2$N(R)—; —CH(R)C(O)N(R)C(O)—; —CH(R)S(O)N(R)C(O)—; CH(R)S(O)$_2$N(R)C(O)—; —CH(R)OS(O)N(R)—; —CH(R)OS(O)$_2$N(R)—; CH(R)N(R)S(O)O—; —CH(R)N(R)S(O)O—; —CH(R)N(R)S(O)C(O)—; —CH(R)N(R)S(O)$_2$C(O)—; —CH(R)SON(C(O)R)—; —CH(R)S(O)$_2$N(C(O)R)—; —CH(R)N(R)SON(R)—; —CH(R)N(R)S(O)$_2$N(R)—; —CH(R)C(O)O—; —CH(R)N(R)P(OR')O—; —CH(R)N(R)P(OR$^X$)—; —CH(R)N(R)P(O)(OR$^X$)O—; —CH(R)N(R)P(O)(OR$^X$)—; —CH(R)N(C(O)R)P(OR$^X$)O—; —CH(R)N(C(O)R)P(OR$^X$)—; —CH(R)N(C(O)R)P(O)(OR$^X$)O— or —CH(R)N(C(O)R)P(OR$^X$), wherein each R and R$^X$ is independently selected from H, $C_1$-$C_6$ acyl, $C_1$-$C_6$ alkyl, $C_6$-aromatic group and 5 or 6 membered heteroaromatic group, wherein each of the foregoing R and R$^X$ groups are independently optionally substituted with 1-3 halo atoms, $C_1$-$C_6$ alkyl and $C_1$-$C_6$ alkoxy;

$R^1$ is H, $C_1$-$C_6$ alkyl, $C_3$-$C_8$ cycloalkyl, substituted bicycloalkyl, 5 to 8 membered cycloalkenyl, 6 to 10 membered aromatic group, 5 to 13 membered heteroaromatic group, 3 to 8 membered heterocycloalkyl group, and heterobicycloalkyl group, and each of the foregoing $R^1$ groups is optionally substituted with 1 to 5 $R^{10}$ groups;

$R^2$ is H, halo, $C_1$-$C_6$ alkyl, $C_3$-$C_8$ cycloalkyl, 6 to 10 membered aromatic group, 5 to 13 membered heteroaromatic group, 3 to 8 membered heterocycloalkyl, —$(CH_2)_{0-3}$NR$^6$R$^7$, and —$(CH_2)_{0-3}$C(O)NR$^6$R$^7$, and each of the foregoing $R^2$ groups is optionally substituted with 1 to 5 $R^5$ groups;

$R^3$ is H, $C_1$-$C_6$ alkyl, $C_3$-$C_8$ cycloalkyl, —$(CH_2)_t$$C_6$-$C_{10}$ aromatic group, —$(CH_2)_t$(5 to 13 membered heteroaromatic group), and 3 to 8 membered heterocycloalkyl, and each of the foregoing $R^3$ groups is optionally substituted with 1 to 5 $R^5$ groups;

each $R^5$ is independently selected from the group consisting of halo, cyano, trifluoromethoxy, trifluoromethyl, —C(O)R$^8$, —NR$^6$C(O)R$^7$, —C(O)NR$^6$R$^7$, —NR$^6$R$^7$, —OR$^9$, —SO$_2$NR$^6$R$^7$, —SO$_2$R$^6$, —NR$^6$SO$_2$R$^7$, $C_1$-$C_6$ alkyl, $C_1$-$C_6$ alkenyl, $C_1$-$C_6$ alkynyl, —$(CH_2)_j$O$(CH_2)_q$NR$^6$R$^7$, —$(CH_2)_t$O$(CH_2)_q$OR$^9$, —$(CH_2)_t$OR$^9$, —S(O)$_j$($C_1$-$C_6$ alkyl), —$(CH_2)_t$($C_6$-$C_{10}$ aryl), —$(CH_2)_t$(5 to 10 membered heterocyclic), —$(CH_2)_t$O$(CH_2)_q$ (5 to 10 membered heterocyclic), —C(O)$(CH_2)_t$(5 to 10 membered heterocyclic), —$(CH_2)_j$NR$^7$$(CH_2)_q$NR$^6$R$^7$, —$(CH_2)_j$NR$^7$CH$_2$C(O)NR$^6$R$^7$, —$(CH_2)_j$NR$^7$$(CH_2)_q$NR$^9$C(O)R$^8$, —$(CH_2)_j$NR$^7$$(CH_2)_t$O$(CH_2)_q$OR$^9$, —$(CH_2)_j$NR$^7$$(CH_2)_q$S(O)$_j$($C_1$-$C_6$ alkyl), —$(CH_2)_j$NR$^7$$(CH_2)_t$R$^6$, —SO$_2$$(CH_2)_t$($C_6$-$C_{10}$ aryl), and —SO$_2$$(CH_2)_t$(5 to 10 membered heterocyclic), wherein j is an integer from 0 to 2, t is an integer from 0 to 6, q is an integer from 2 to 6, the —$(CH_2)_q$— and —$(CH_2)_t$— moieties of the foregoing $R^5$ groups optionally include a carbon-carbon double or triple bond where t is an integer from 2 to 6, and the alkyl, aryl and heterocyclic moieties of the foregoing $R^5$ groups are optionally substituted by 1 to 3 substituents independently selected from halo, cyano, trifluoromethyl, —C(O)R$^8$, —NR$^6$C(O)R$^7$, —C(O)NR$^6$R$^7$, —$(CH_2)_t$NR$^6$R$^7$, —SO$_2$R$^6$, —SO$_2$NR$^6$R$^7$, $C_1$-$C_6$ alkyl, —$(CH_2)_t$(5 to 10 membered heterocyclic), —$(CH_2)_t$O$(CH_2)_q$OR$^9$, and —$(CH_2)_t$OR$^9$, wherein t is an integer from 0 to 6 and q is an integer from 2 to 6;

each $R^6$ and $R^7$ is independently selected from H, $C_1$-$C_6$ alkyl, —$(CH_2)_t$($C_6$-$C_{10}$ aryl), —$(CH_2)_t$(5 to 10 membered heterocyclic), —$(CH_2)_t$O$(CH_2)_q$OR$^9$, and —$(CH_2)_t$OR$^9$, wherein t is an integer from 0 to 6 and q is an integer from 2 to 6, and the alkyl, aryl and heterocyclic moieties of the foregoing $R^6$ and $R^7$ groups are optionally substituted by 1 to 3 substituents independently selected from halo, cyano, trifluoromethyl, —C(O)R$^8$, —NR$^9$C(O)R$^{10}$, —C(O)NR$^9$R$^{10}$, —NR$^9$R$^{10}$, $C_1$-$C_6$ alkyl, —$(CH_2)_t$($C_6$-$C_{10}$ aryl), —$(CH_2)_t$(5 to 10 membered heterocyclic), —$(CH_2)_t$O$(CH_2)_q$OR$^9$, and —$(CH_2)_t$OR$^9$, wherein t is an integer from 0 to 6 and q is an integer from 2 to 6, with the proviso that where $R^6$ and $R^7$ are both attached to the same nitrogen, then $R^6$ and $R^7$ are not both bonded to the nitrogen directly through an oxygen;

each $R^8$ is independently selected from H, $C_1$-$C_{10}$ alkyl, —$(CH_2)_t(C_6$-$C_{10}$ aryl), and —$(CH_2)_t$(5 to 10 membered heterocyclic), wherein t is an integer from 0 to 6;

each $R^9$ and $R^{10}$ is independently selected from H and $C_1$-$C_6$ alkyl; and $R^{11}$ and $R^{12}$ are independently selected from the group consisting of H, $C_1$-$C_6$ alkyl, $C_3$-$C_6$ cycloalkyl, $C_1$-$C_6$ alkoxy or $R^{11}$ and $R^{12}$ taken together form a 3 to 7 membered alkyl or heteroalkyl ring, which comprises treating a compound of the formula 8 wherein Z is halo

8

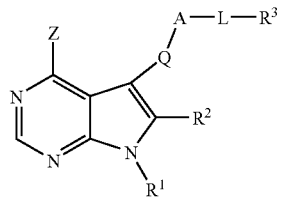

with a compound of the formula $H_3N$.

56. The process of claim 55, wherein Z is Cl.

57. A process of preparing a compound of the formula 1B,

1B

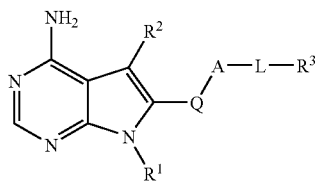

or a pharmaceutically acceptable salt, prodrug, solvate or hydrate thereof, wherein:

Q CO;

A is $C_6$-$C_{10}$ aryl, 5 to 13 membered heteroaromatic ring, $C_3$-$C_8$ alkyl, and 3 to 8 membered heteroalkyl ring and each of the foregoing A groups is optionally substituted with 1 to 5 $R^5$ groups;

L is —$(CH_2)_p$— wherein p is an integer from 0 to 5; —O—; —S—; —S(O)—; —S(O)$_2$; —N(R)—; N(C(O)OR)—; —N(C(O)R)—; —N(SO$_2$R); —CH$_2$O—; —CH$_2$S—; —CH$_2$N(R)—; —C(NR)—; —CH$_2$N(C(O)R))—; —CH$_2$N(C(O)OR)—; —CH$_2$N(SO$_2$R)—; —CH(NHR)—; —CH(NHC(O)R)—; —CH(NHSO$_2$R)—; —CH(NHC(O)OR)—; —CH(OC(O)R)—; —CH(OC(O)NHR)—; —CH=CH—; —C(=NOR)—; —C(O)—; —CH(OR)—; —C(O)N(R)—; —N(R)C(O)—; —N(R)S(O)—; —N(R)S(O)$_2$—; OC(O)N(R)—; —N(R)C(O)N(R)—; —NRC(O)O—; —S(O)N(R)—; —S(O)$_2$N(R)—; —N(C(O)R)S(O)—; —N(C(O)R)S(O)$_2$—; —N(R)S(O)N(R)—; —N(R)S(O)$_2$N(R)—; —C(O)N(R)C(O)—; —S(O)N(R)C(O)—; —S(O)$_2$N(R)C(O)—; —OS(O)N(R)—; —OS(O)$_2$N(R)—; —N(R)S(O)O—; —N(R)S(O)$_2$O—; —N(R)S(O)C(O)—; —N(R)S(O)$_2$C(O)—; —SON(C(O)R)—; —SO$_2$N(C(O)R)—; —N(R)SON(R)—; —N(R)SO$_2$N(R)—; —C(O)O—; —N(R)P(OR$^X$)O—; —N(R)P(OR$^X$)—; —N(R)P(O)(OR$^X$)O—; —N(R)P(O)(OR$^X$)—; —N(C(O)R)P(OR$^X$)O—; —N(C(O)R)P(OR$^X$)—; —N(C(O)R)P(O)(OR$^X$)O—; —N(C(O)R)P(OR$^X$)—, —CH(R)S(O)—; —CH(R)S(O)$_2$; —CH(R)N(C(O)OR)—; —CH(R)N(C(O)R)—; —CH(R)N(SO$_2$R)—; —CH(R)O—; —CH(R)S—; —CH(R)N(R)—; —CH(R)N(C(O)R))—; —CH(R)N(C(O)OR)—; —CH(R)N(SO$_2$R)—; —CH(R)C(=NOR)—; —CH(R)C(O)—; —CH(R)CH(OR)—; —CH(R)C(O)N(R)—; —CH(R)N(R)C(O)—; —CH(R)N(R)S(O)—; CH(R)N(R)S(O)$_2$; —CH(R)OC(O)N(R)—; —CH(R)N(R)C(O)N(R)—; —CH(R)N(R)C(O)O—; —CH(R)S(O)N(R)—; —CH(R)S(O)$_2$N(R)—; —CH(R)N(C(O)R)S(O)—; —CH(R)N(C(O)R)S(O)$_2$—; —CH(R)N(R)S(O)N(R)—; —CH(R)N(R)S(O)$_2$N(R)—; —CH(R)C(O)N(R)C(O)—; —CH(R)S(O)N(R)C(O)—; CH(R)S(O)$_2$N(R)C(O)—; —CH(R)OS(O)N(R)—; —CH(R)OS(O)$_2$N(R)—; CH(R)N(R)S(O)O—; —CH(R)N(R)S(O)$_2$O—; —CH(R)N(R)S(O)C(O)—; —CH(R)N(R)S(O)$_2$C(O)—; —CH(R)SON(C(O)R)—; —CH(R)S(O)$_2$N(C(O)R)—; —CH(R)N(R)SON(R)—; —CH(R)N(R)S(O)$_2$N(R)—; —CH(R)C(O)O—; —CH(R)N(R)P(OR')O—; —CH(R)N(R)P(OR$^X$)—; —CH(R)N(R)P(O)(OR$^X$)O—; —CH(R)N(R)P(O)(OR$^X$)—; —CH(R)N(C(O)R)P(OR$^X$)O—; —CH(R)N(C(O)R)P(OR$^X$)—; —CH(R)N(C(O)R)P(O)(OR$^X$)O— or —CH(R)N(C(O)R)P(OR$^X$)—, wherein each R and $R^X$ is independently selected from H, $C_1$-$C_6$ acyl, $C_1$-$C_6$ alkyl, $C_6$-aromatic group and 5 or 6 membered heteroaromatic group, wherein each of the foregoing R and $R^X$ groups are independently optionally substituted with 1-3 halo atoms, $C_1$-$C_6$ alkyl and $C_1$-$C_6$ alkoxy;

$R^1$ is H, $C_1$-$C_6$ alkyl, $C_3$-$C_8$ cycloalkyl, substituted bicycloalkyl, 5 to 8 membered cycloalkenyl, 6 to 10 membered aromatic group, 5 to 13 membered heteroaromatic group, 3 to 8 membered heterocycloalkyl group, and heterobicycloalkyl group, and each of the foregoing $R^1$ groups is optionally substituted with 1 to 5 $R^{10}$ groups;

$R^2$ is H, halo, $C_1$-$C_6$ alkyl, $C_3$-$C_8$ cycloalkyl, 6 to 10 membered aromatic group, 5 to 13 membered heteroaromatic group, 3 to 8 membered heterocycloalkyl, —$(CH_2)_{0-3}NR^6R^7$, and —$(CH_2)_{0-3}C(O)NR^6R^7$, and each of the foregoing $R^2$ groups is optionally substituted with 1 to 5 $R^5$ groups;

$R^3$ is H, $C_1$-$C_6$ alkyl, $C_3$-$C_8$ cycloalkyl, —$(CH_2)_t C_6$-$C_{10}$ aromatic group, —$(CH_2)_t$(5 to 13 membered heteroaromatic group), and 3 to 8 membered heterocycloalkyl, and each of the foregoing $R^3$ groups is optionally substituted with 1 to 5 $R^5$ groups;

each $R^5$ is independently selected from the group consisting of halo, cyano, trifluoromethoxy, trifluoromethyl, —C(O)$R^8$, —$NR^6C(O)R^7$, —C(O)$NR^6R^7$, —$NR^5R^7$, —$OR^9$, —SO$_2NR^6R^7$, —SO$_2R^6$, —$NR^6SO_2R^7$, $C_1$-$C_6$ alkyl, $C_2$-$C_6$ alkenyl, $C_1$-$C_6$ alkynyl, —$(CH_2)_jO(CH_2)_qNR^6R^7$, —$(CH_2)_jO(CH_2)_qOR^9$, —$(CH_2)_jOR^9$, —S(O)$_j(C_1$-$C_6$ alkyl), —$(CH_2)_t(C_6$-$C_{10}$ aryl), —$(CH_2)_t$(5 to 10 membered heterocyclic), —$(CH_2)_jO(CH_2)_q$ (5 to 10 membered heterocyclic), —C(O)$(CH_2)_t$(5 to 10 membered heterocyclic), —$(CH_2)_jNR^7(CH_2)_qNR^6R^7$, —$(CH_2)_jNR^7CH_2C(O)NR^6R^7$, —$(CH_2)_jNR^7(CH_2)_qNR^9C(O)R^8$, —$(CH_2)_jNR^7(CH_2)_tO(CH_2)_qOR^9$, —$(CH_2)_jNR^7(CH_2)_qS(O)_j(C_1$-$C_6$ alkyl), —$(CH_2)_jNR^7(CH_2)_tR^6$, —SO$_2(CH_2)_t(C_6$-$C_{10}$ aryl), and —SO$_2(CH_2)_t$(5 to 10 membered heterocyclic), wherein j is an integer from 0 to 2, t is an integer from 0 to 6, q is an integer from 2 to 6, the —$(CH_2)_q$— and —$(CH_2)_t$— moieties of the foregoing $R^5$ groups optionally include a carbon-carbon double or triple bond where t is an integer from 2 to 6, and the alkyl, aryl and heterocyclic moieties of the foregoing $R^5$ groups are optionally substituted by 1 to 3 substituents independently selected from halo, cyano, trifluoromethyl, —$C(O)R^8$, —$NR^6C(O)R^7$, —$C(O)NR^6R^7$, —$(CH_2)_tNR^6R^7$, —$SO_2R^6$, —$SO_2NR^6R^7$, $C_1$-$C_6$ alkyl, —$(CH_2)_t$(5 to 10 membered heterocyclic), —$(CH_2)_tO(CH_2)_qOR^9$, and —$(CH_2)_tOR^9$, wherein t is an integer from 0 to 6 and q is an integer from 2 to 6;

each $R^6$ and $R^7$ is independently selected from H, $C_1$-$C_6$ alkyl, —$(CH_2)_t(C_6$-$C_{10}$ aryl), —$(CH_2)_t$(5 to 10 membered heterocyclic), —$(CH_2)_tO(CH_2)_qOR^9$, and —$(CH_2)_tOR^9$, wherein t is an integer from 0 to 6 and q is an integer from 2 to 6, and the alkyl, aryl and heterocyclic moieties of the foregoing $R^6$ and $R^7$ groups are optionally substituted by 1 to 3 substituents independently selected from halo, cyano, trifluoromethyl, —$C(O)R^8$, —$NR^9C(O)R^{10}$, —$C(O)NR^9R^{10}$, —$NR^9R^{10}$, $C_1$-$C_6$ alkyl, —$(CH_2)_t(C_8$-$C_{10}$ aryl), —$(CH_2)_t$(5 to 10 membered heterocyclic), —$(CH_2)_tO(CH_2)_qOR^9$, and —$(CH_2)_tOR^9$, wherein t is an integer from 0 to 6 and q is an integer from 2 to 6, with the proviso that where $R^6$ and $R^7$ are both attached to the same nitrogen, then $R^6$ and $R^7$ are not both bonded to the nitrogen directly through an oxygen;

each $R^8$ is independently selected from H, $C_1$-$C_{10}$ alkyl, —$(CH_2)_t(C_6$-$C_{10}$ aryl), and —$(CH_2)_t$(5 to 10 membered heterocyclic), wherein t is an integer from 0 to 6;

each $R^9$ and $R^{10}$ is independently selected from H and $C_1$-$C_6$ alkyl; and $R^{11}$ and $R^{12}$ are independently selected from the group consisting of H, $C_1$-$C_6$ alkyl, $C_3$-$C_6$ cycloalkyl, $C_1$-$C_6$ alkoxy or $R^{11}$ and $R^{12}$ taken together form a 3 to 7 membered alkyl or heteroalkyl ring, which comprises treating a compound of the formula 9 wherein Z is halo

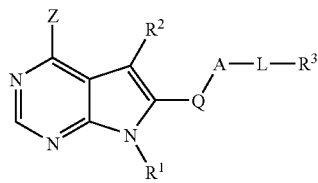

9 with a compound of the formula $H_3N$.

58. The process of claim 57, wherein Z is Cl.

59. A compound according to claims 28, wherein each $R^5$ is independently selected from the group consisting of halo, cyano, trifluoromethoxy, trifluoromethyl, —$C(O)R^8$, —$NR^6C(O)R^7$, —$C(O)NR^6R^7$, —$NR^6R^7$, —$OR^9$, $SO_2NR^6R^7$, —$SO_2R^6$, —$NR^6SO_2R^7$, $C_1$-$C_6$ alkyl, —$(CH_2)_tOR^9$, —$(CH_2)_jNR^7(CH_2)_qNR^6R^7$, —$(CH_2)_jNR^7CH_2C(O)NR^6R^7$, $(CH_2)_jNR^7(CH_2)_qNR^9C(O)R^8$, —$(CH_2)_jNR^7(CH_2)_tO(CH_2)_qOR^9$, —$(CH_2)_jNR^7(CH_2)_tR^6$, wherein j is an integer from 0 to 2, t is an integer from 0 to 6, q is an integer from 2 to 6, the —$(CH_2)_q$— and —$(CH_2)_t$— moieties of the foregoing $R^5$ groups optionally include a carbon-carbon double or triple bond where t is an integer from 2 to 6, and the alkyl, aryl and heterocyclic moieties of the foregoing $R^5$ groups are optionally substituted by 1 to 3 substituents independently selected from halo, cyano, trifluoromethyl, —$C(O)R^8$, —$NR^6C(O)R^7$, —$C(O)NR^6R^7$, —$(CH_2)_tNR^6R^7$, —$SO_2R^6$, —$SO_2NR^6R^7$, $C_1$-$C_6$ alkyl, —$(CH_2)_t$(5 to 10 membered heterocyclic), —$(CH_2)_tO(CH_2)_qOR^9$, and —$(CH_2)_tOR^9$, wherein t is an integer from 0 to 6 and q is an integer from 2 to 6.

60. A compound according to claims 29, wherein each $R^5$ is independently selected from the group consisting of halo, cyano, trifluoromethoxy, trifluoromethyl, —$C(O)R^8$, —$NR^6C(O)R^7$, —$C(O)NR^6R^7$, —$NR^6R^7$, —$OR^9$, $SO_2NR^6R^7$, —$SO_2R^6$, —$NR^6SO_2R^7$, $C_1$-$C_6$ alkyl, —$(CH_2)_tOR^9$, —$(CH_2)_jNR^7(CH_2)_qNR^6R^7$, —$(CH_2)_jNR^7CH_2C(O)NR^6R^7$, $(CH_2)_jNR^7(CH_2)_qNR^9C(O)R^8$, —$(CH_2)_jNR^7(CH_2)_tO(CH_2)_qOR^9$, —$(CH_2)_jNR^7(CH_2)_tR^6$, wherein j is an integer from 0 to 2, t is an integer from 0 to 6, q is an integer from 2 to 6, the —$(CH_2)_q$— and —$(CH_2)_t$— moieties of the foregoing $R^5$ groups optionally include a carbon-carbon double or triple bond where t is an integer from 2 to 6, and the alkyl, aryl and heterocyclic moieties of the foregoing $R^5$ groups are optionally substituted by 1 to 3 substituents independently selected from halo, cyano, trifluoromethyl, —$C(O)R^8$, —$NR^6C(O)R^7$, —$C(O)NR^6R^7$, —$(CH_2)_tNR^6R^7$, —$SO_2R^6$, —$SO_2NR^6R^7$, $C_1$-$C_6$ alkyl, —$(CH_2)_t$(5 to 10 membered heterocyclic), —$(CH_2)_tO(CH_2)_qOR^9$, and —$(CH_2)_tOR^9$, wherein t is an integer from 0 to 6 and q is an integer from 2 to 6.

61. A compound according to claims 8, wherein each $R^5$ is independently selected from the group consisting of halo, cyano, trifluoromethoxy, trifluoromethyl, —$C(O)R^8$, —$NR^6C(O)R^7$, —$C(O)NR^6R^7$, —$NR^6R^7$, —$OR^9$, $SO_2NR^6R^7$, —$SO_2R^6$, —$NR^6SO_2R^7$, $C_1$-$C_6$ alkyl, —$(CH_2)_tOR^9$, —$(CH_2)_jNR^7(CH_2)_qNR^6R^7$, —$(CH_2)_jNR^7CH_2C(O)NR^6R^7$, $(CH_2)_jNR^7(CH_2)_qNR^9C(O)R^8$, —$(CH_2)_jNR^7(CH_2)_tO(CH_2)_qOR^9$, —$(CH_2)_jNR^7(CH_2)_tR^6$, wherein j is an integer from 0 to 2, t is an integer from 0 to 6, q is an integer from 2 to 6, the —$(CH_2)_q$— and —$(CH_2)_t$— moieties of the foregoing $R^5$ groups optionally include a carbon-carbon double or triple bond where t is an integer from 2 to 6, and the alkyl, aryl and heterocyclic moieties of the foregoing $R^5$ groups are optionally substituted by 1 to 3 substituents independently selected from halo, cyano, trifluoromethyl, —$C(O)R^8$, —$NR^6C(O)R^7$, —$C(O)NR^6R^7$, —$(CH_2)_tNR^6R^7$, —$SO_2R^6$, —$SO_2NR^6R^7$, $C_1$-$C_6$ alkyl, —$(CH_2)_t$(5 to 10 membered heterocyclic), —$(CH_2)_tO(CH_2)_qOR^9$, and —$(CH_2)_tOR^9$, wherein t is an integer from 0 to 6 and q is an integer from 2 to 6.

* * * * *